United States Patent [19]

Jacobson

[11] Patent Number: 4,863,947

[45] Date of Patent: Sep. 5, 1989

[54] N-ARYL-3-ARYL-4,5-DIHYDRO-1H-PYRAZOLE-1-CARBOXAMIDES AND METHODS OF THEIR PRODUCTION

[75] Inventor: Richard M. Jacobson, Chalfont, Pa.

[73] Assignee: Rohm and Haas, Philadelphia, Pa.

[21] Appl. No.: 894,981

[22] Filed: Aug. 11, 1986

Related U.S. Application Data

[63] Continuation-in-part of Ser. No. 689,671, Jan. 11, 1985, Pat. No. 4,663,341, which is a continuation-in-part of Ser. No. 580,963, Feb. 15, 1984, abandoned.

[51] Int. Cl.$^4$ .................... A01N 43/56; A01N 43/54; C07D 231/06; C07D 417/14
[52] U.S. Cl. ................. 514/403; 514/256; 514/269; 514/272; 514/274; 514/275; 514/333; 514/341; 514/365; 514/369; 514/372; 514/374; 514/376; 514/377; 514/378; 514/380; 514/397; 514/406; 514/407; 514/401; 544/296; 544/297; 544/298; 544/300; 544/310; 544/315; 544/316; 544/317; 544/318; 544/319; 544/320; 544/321; 544/322; 544/324; 544/327; 544/328; 544/331; 544/333; 546/256; 546/277; 546/278; 546/279; 548/182; 548/183; 548/184; 548/185; 548/186; 548/187; 548/188; 548/189; 548/190; 548/191; 548/192; 548/193; 548/194; 548/195; 548/196; 548/197; 548/198; 548/199; 548/200; 548/201; 548/202; 548/203; 548/205; 548/206; 548/213; 548/214; 548/225; 548/226; 548/227; 548/228; 548/229; 548/230; 548/231; 548/232; 548/233; 548/234; 548/235; 548/236; 548/243; 548/244; 548/245; 548/246; 548/247; 548/248; 548/249; 548/336; 548/374

[58] Field of Search ............... 548/329, 182, 183, 184, 548/185, 186, 187, 188, 189, 190, 191, 192, 193, 194, 195, 196–203, 205, 206, 213, 214, 225–236, 243–249, 336, 374; 514/401, 408, 256, 269, 272, 274, 275, 333, 341, 365, 369–372, 374, 376–378, 380, 397, 403, 406, 407; 544/296, 297, 298, 300, 310, 315–322, 324, 327, 328, 331, 333; 546/256, 277, 278, 279

[56] References Cited

U.S. PATENT DOCUMENTS 4,070,365  1/1978  Van Daalen et al. ............... 548/379
4,174,393  11/1979  Van Daalen et al. ............... 548/379
4,407,813  10/1983  Ozawa et al. ........................ 548/379
4,439,440  3/1984  Van Hes et al. ...................... 548/379

Primary Examiner—Mary C. Lee
Assistant Examiner—Mary Sue Howard
Attorney, Agent, or Firm—John C. Demeter; Barbara V. Maurer

[57]  ABSTRACT

This invention relates to novel N-aryl-3-aryl-4,5-dihydro-1H-pyrazole-1-carboxamide compounds which are useful as pesticides, compositions containing those compounds, methods of controlling pests and processes for preparing these compounds.

48 Claims, No Drawings

N-ARYL-3-ARYL-4,5-DIHYDRO-1H-PYRAZOLE-1-CARBOXAMIDES AND METHODS OF THEIR PRODUCTION

This application is a continuation-in-part of U.S. patent application Ser. No. 689,671, filed Jan. 11, 1985, now U.S. Pat. No. 4,663,341; which is a continuation-in-part of U.S. patent application Ser. No. 580,963, filed Feb. 15, 1984 now abandoned.

BACKGROUND OF THE INVENTION

This invention relates to novel N-aryl-3-aryl-4,5-dihydro-1H-pyrazole-1-carboxamides which are useful as pesticides, compositions containing those compounds, methods of controlling pests and processes for preparing the compounds of the present invention.

The search for pesticides which have a combination of excellent pesticidal activity and essentially no toxicity is a continuing one due to recognition of the possible toxicity to animals and humans of many known pesticides.

Certain pyrazoline derivatives have been disclosed as having insecticidal activity.

German Offenlegungsschrift No. 2,304,584 discloses pyrazoline compounds which are substituted in the 1,3 or 1,3,5 positions of the pyrazoline ring that exert biocidal activity. German Offenlegungsschrift No. 2,304,584 corresponds to U.S. Pat. Nos. 3,991,973; 4,095,026; and 4,101,271.

U.S. Pat. Nos. 4,156,007; 4,070,365; and 4,174,393 disclose pyrazoline compounds which are substituted in the 1,3 and 4 positions of the pyrazoline ring that have insecticidal activity.

U.S. Pat. Nos. 4,140,787 and 4,140,792 disclose pyrazoline compounds which are substituted in the 1,3,5 positions of the pyrazoline ring that possess arthropodicidal properties.

Presently known compounds are believed to be subject to problems with photostability and biodegradability. These compounds tend to degrade faster than is desirable when applied to the external parts of plants due to the action of sunlight on these compounds. Moreover, when known compounds are applied to the soil, they exhibit poor biodegradability causing an undesirable residue to remain in the soil.

The present invention discloses N-aryl-3-aryl-4,5-dihydro-1H-pyrazole-1-carboxamides (hereinafter at times referred to as 1-substituted-4-substituted-4,5-dihydro-1H-pyrazoles), including N-aryl-3-aryl-4,5-dihydro-1H-pyrazole-1-thiocarboxamides and including N-aryl-3-aryl-4,5-dihydro-1H-pyrazole-1-iminocarboxamides which are disubstituted at the 4 position or monosubstituted at the 4 position. When these compounds are monosubstituted at the 4 position, the substituent has, at the 4-position, 1-oxo, 1-thiono, 1-imino or 1-alkenyl functionality.

It is believed this 4,4-disubstitution greatly lessens photodegradation and metabolic pathway transformations in plants and insects by blocking hydrogen loss and subsequent aromatization of the dihydropyrazole moiety to a pyrazole moiety resulting in an inactivation of the compound as an insecticide.

Certain of the compounds, particularly the 4-carboalkoxy substituted compounds (4-monosubstituted and 4-disubstituted) of this invention exhibit enhanced rates of soil metabolism thus minimizing undesirable residues.

It is therefore an object of the invention to provide novel compounds, and compositions containing said compounds, which possess pesticidal activity. It is another object of the present invention to provide compounds which demonstrate improved photostability and biodegradability. It is a further object of the invention to provide methods for the synthesis of 1-substituted-4-substituted-4,5-dihydro-1H-pyrazoles.

It is still another object of the present invention to provide methods for controlling pests and insects using the novel compounds.

These and other objects of the invention will become apparent to those skilled in the art from the following description.

SUMMARY OF THE INVENTION

In accordance with the present invention, there are provided compounds having the formula:

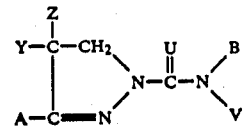

wherein
A is unsubstituted or substituted aryl;
B is unsubstituted or substituted aryl;
U is O, S or N—Q
V is ($C_3$–$C_6$)cycloalkyl, or $R^4$—Q;
Y is
  lower ($C_1$–$C_6$) straight or branched chain unsubstituted or substituted alkyl where the alkyl substituent(s) is selected from Q, unsubstituted or substituted aryl where the substituent(s) is selected from W (hereinafter at times referred to as Group A); or
  a group having the formula

where X is O, S, N—$R^1$, or $CR^1R^2$ and G is as defined below (hereinafter at times referred to as Group B);
when
  Y is Group A,
  Z is cycloalkyl($C_3$–$C_6$), or $R^4$—Q provided that Z is not hydrogen and Z is not methyl when Y is methyl;
when
  Y is Group B,
  Z is cycloalkyl($C_3$–$C_6$), or $R^4$—Q;
  Q is hydrogen, halogen, cyano, nitro, —$OR^1$, —$R^4OR^1$, —$CO_2R^1$, —$OR^4OR^1$, —$CR^1R^2R^3$, —$CONR^1R^2$, —$NR^1R^2$, —$NR^1COR^2$, —$N(COR^1)COR^2$, —$CSR^1$, —$SR^1$, —$SOR^1$, —$SO_2R^1$, —$NR^1SOR^2$, —$R^4SR^1$, —$OR^4SR^1$, —$SR^4SR^1$, —$SNHSR^1$, —$SNHSO_2R^1$, —$CONHSR^1$, —$OCOR^1$, —$R^1$, —$C(=NR^1)R^2$, —$COR^1$, —$N_3$, —$OSO_2R^1$, —$NR^1SO_2R^2$, —$NR^1CSR^2$, alkenyl (—$CR^1=CR^2R^3$), alkynyl (—C≡$CR^1$), unsubstituted or substituted aryl, pyrrolidin-1-yl, piperidin-1-yl, morpholin-1-yl, or 4,4-dimethyloxazolin-2-yl;
  $R^1$, $R^2$ and $R^3$ are, independently, hydrogen, halogen, cyano, nitro, hydroxy, an alkoxy group (—OR)

having up to four carbon atoms, an aryloxy group, an amino group (—NH$_2$), an alkylamino group (—NHR) having up to six carbon atoms, a dialkylamino group (—NR$_2$) having, independently, up to six carbon atoms in each alkyl moiety, a carboxy group (—CO$_2$H), a carbalkoxy group (—CO$_2$R) having up to six carbon atoms, an alkylcarbonyl group (—COR) having up to six carbon atoms, a formyl group (—CHO), an alkanoyloxy group (—OCOR) having up to six carbon atoms, a formate group (—OCHO), a carboxamido group (—CONH$_2$), an N-alkylcarboxamido group (—CONHR) having up to six carbon atoms, an N,N-dialkylcarboxamido group (—CONR$_2$) having independently, up to six carbon atoms in each alkyl moiety, a carbamoyloxy group (—O-CONH$_2$), an N-alkylcarbamoyloxy group (—O-CONHR) having up to six carbon atoms, an N,N-dialkylcarbamoyloxy group (—OCONR$_2$) having, independently, up to six carbon atoms in each alkyl moiety, a sulfhydril group (—SH), an alkylsulfinyl group (—SOR) having up to six carbon atoms, an alkylsulfonyl group (—SO$_2$R) having up to six carbon atoms, an alkysulfonato group (—OSO$_2$R) having up to six carbon atoms, an alkylthio group (—SR) having up to six carbon atoms, a sulfonamido group (—SO$_2$NH$_2$), an N-alkylsulfonamido group (—SO$_2$NHR), having up to six carbon atoms, an N,N-dialkylsulfonamido group (—SO$_2$NR$_2$) having, independently, up to six carbon atoms in each alkyl moiety, an acylamino group (—NHCOR) having up to six carbon atoms, an N-alkyl-N-acylamino group (—NRCOR) having independently, up to six carbon atoms in each alkyl moiety, an alkylsulfonamido group (—NHSO$_2$R) having up to six carbon atoms, an N-alkyl-N-alkylsulfonamino group (—NRSO$_2$R) having independently, up to six carbon atoms in each alkyl moiety, a thioformyl group (—CHS), an alkylthiocarbonyl group (—CSR) having up to six carbon atoms, a thioformamido group (—NHCHS), an N-N-alkyl-N-thioformylamino group (—NRCHS) having up to six carbon atoms, a thioacylamino group (—NHCSR) having up to six carbon atoms, an N-alkyl-N-thioacylamino group (—NRCSR) having independently, up to six carbon atoms in each alkyl moiety, an alkylsulfinamido group (—NHSOR) having up to six carbon atoms, an N-alkyl-N-alkylsulfinylamino group (—NRSOR) having independently, up to six carbon atoms in each alkyl moiety, an N,N-diacylamino group (—N(COR)COR) having, independently, up to six carbon atoms in each alkyl moiety, an unsubstituted or substituted straight or branched chain lower (C$_1$-C$_6$)alkyl, (C$_3$-C$_6$)cycloalkyl or aryl where the substituent on the alkyl moiety can be one or more of the same or different halogen, cyano, nitro, hydroxy, an alkoxy group (—OR) having up to four carbon atoms, an amino group (—NH$_2$), an alkylamino group (—NHR) having up to six carbon atoms, a dialkylamino group (—NR$_2$) having, independently, up to six carbon atoms in each alkyl moiety, a carboxy group (—CO$_2$H), a carbalkoxy group (—CO$_2$R) having up to six carbon atoms, an alkylcarbonyl group (—COR) having up to six carbon atoms, a formyl group (—CHO), an alkanoyloxy group (—OCOR) having up to six carbon atoms, a formate group (—O-CHO), a carboxamido group (—CONH$_2$), an N-alkylcarboxamido group (—CONHR) having up to six carbon atoms, an N,N-dialkylcarboxamido group (—CONR$_2$) having independently, up to six carbon atoms in each alkyl moiety, a carbamoyloxy group (—OCONH$_2$), an N-alkylcarbamoyloxy group (—OCONHR) having up to six carbon atoms, an N,N-dialkylcarbamoyloxy group (—OCONR$_2$) having, independently, up to six carbon atoms in each alkyl moiety, a sulfhydril group (—SH), an alkylsulfinyl group (—SOR) having up to six carbon atoms, an alkylsulfonyl group (—SO$_2$R) having up to six carbon atoms, an alkylsulfonato group (—OSO$_2$R) having up to six carbon atoms, an alkylthio group (—SR) having up to six carbon atoms, a sulfonamido group (—SO$_2$NH$_2$), an N-alkylsulfonamido group (—SO$_2$NHR), having up to six carbon atoms, an N,N-dialkylsulfonamido group (—SO$_2$NR$_2$) having, independently, up to six carbon atoms in each alkyl moiety, an acylamino group (—NHCOR) having up to six carbon atoms, an N-alkyl-N-acylamino group (—NRCOR) having independently, up to six carbon atoms in each alkyl moiety, an alkylsulfonamido group (—NHSO$_2$R) having up to six carbon atoms, an N-alkyl-N-alkylsulfonylamino group (—NRSO$_2$R) having independently, up to six carbon atoms in each alkyl moiety, a thioformyl group (—CHS), an alkylthiocarbonyl group (—CSR) having up to six carbon atoms, a thioformamido group (—NHCHS), an N-alkylthioformanido group (—NRCHS) having up to six carbon atoms, a thioacylamino group (—NHCSR) having up to six carbon atoms, an N-alkyl-N-thioacylamino group (—NRCSR) having independently, up to six carbon atoms in each alkyl moiety, an alkylsulfinamido group (—NHSOR) having up to six carbon atoms, an N-alkyl-N-alkylsulfinylamino group (—NRSOR) having independently, up to six carbon atoms in each alkyl moiety, an N,N-diacylamino group (—N(COR)COR) having, independently, up to six carbon atoms in each alkyl moiety, or an aryl group, where R is an alkyl group having the stated number of carbon atoms;

R$^4$ is

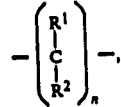

where R$^1$ and R$^2$ are independent for each carbon atom of a chain;

G is (C$_3$-C$_6$)cycloalkyl, or R$^4$—Q;

n is from 0 to 10;

and agronomically acceptable salts thereof.

Halogen can be chosen from fluorine, chlorine, bromine, or iodine;

Cycloalkyl can be chosen from cyclopropyl, cyclobutyl, cyclopentyl, cyclohexyl, cycloheptyl, cyclooctyl, cyclononyl, cyclodecyl, cycloundecyl, and cyclododecyl.

Aryl can be chosen from phenyl, optionally substituted with 1-5 substituents independently chosen from W; methylenedioxyphenyl; naphthyl, optionally substituted with 1-7 substituents independently chosen from W; a 5 membered heterocycle containing up to 3 nitrogen atoms, up to 2 oxygen atoms, up to 2 sulfur atoms and up to 4 nuclear carbon atoms, optionally substituted with 1-4 substituents independently chosen from W; or a 6 membered heterocycle containing up to 3 nitrogen atoms, up to 2 oxygen atoms, up to 2 sulfur atoms and 1-5 nuclear carbon atoms optionally substituted with 1-4 substituents independently chosen from W. Representative examples of 5 and 6 membered heterocycles include pyrryl, furyl, thienyl, imidazolyl, oxazolyl, thiazolyl, pyrazolyl, pyridyl, pyrimidyl and the like.

W is halogen, cyano, isocyano, nitro, $R^1$, $CO_2R^1$, $CONR^1R^2$, $CR^1=CR^2R^3$, $C\equiv CR^1$, $SR^1$, $OR^1$, $NR^1R^2$, $SOR^1$, $SO_2R^1$, $OSO_2R^1$, $NR^1COR^2$, $SF_5$, $CF_3$, $OCF_3$, $OCF_2H$, $SCF_3$, $OCF_2Br$, $SCF_2Br$, $SCF_2Cl$, $SCF_2H$, $NR^1SO_2R^2$ or $N(COR^1)COR^2$.

Further, in accordance with the present invention, there are provided compositions containing compounds of the present invention and processes for preparing 1-substituted-4-substituted-4,5-dihydro-1H-pyrazoles of the present invention. One process comprises dissolving a 1-substituted-4,5-dihydro-1H-pyrazole in an aprotic solvent, mixing a strong base with the resulting solution, allowing deprotonation to take place at the 4 position of the pyrazole ring, and then adding an alkylating or acylating agent, wherein the 1-substituted-4,5-dihydro-1H-pyrazole dissolved in the aprotic solvent must be a 1-substituted-4-monosubstituted-4,5-dihydro-1H-pyrazole when the desired end product is a 1-substituted-4,4-disubstituted-4,5-dihydro-1H-pyrazole.

A second process for preparing compounds of the present invention where Y is a group having the formula

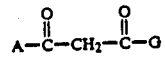

comprises treating a beta-dicarbonyl compound of the formula:

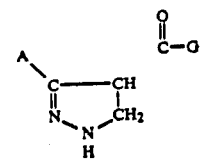  II where A, X and G are as defined above with a mixture of hydrazine and formaldehyde to produce a 3-aryl-4-monosubstituted-4,5-dihydropyrazole having the formula:

III

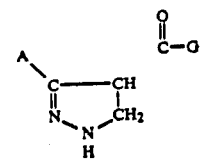

where A and G are as defined above.

Treatment of the dihydropyrazole of Formula III with an aryl isocyante affords the N-aryl-3-aryl-4-monosubstituted-4,5-dihydropyrazole-1-carboxamides of this invention.

Further treatment of this 1-substituted-4-monosubstituted-4,5-dihydropyrazole-1-carboxamide with a base, followed by an alkylating agent or acylating agent will yield the N-aryl-3-aryl-4,4-disubstituted-4,5-dihydropyrazole-1-carboxamides of this invention.

DETAILED DESCRIPTION OF THE INVENTION

The compounds of the instant invention are N-aryl-3-aryl-4,5-dihydro-1H-pyrazole-1-carboxamides which are disubstituted at the 4 position of the pyrazole ring and 4,5-dihydro-1H-pyrazole-1-carboxamides which are monosubstituted at the 4 position of the pyrazole ring, said monosubstituted compounds having 1-oxo, 1-thiono, 1-imino, or 1-alkenyl functionality at the 4 position of the pyrazole ring. The substituents that may be covalently bonded at the 4 position of the pyrazole ring, whether monosubstituted or disubstituted, are defined by Y and Z in Formula I. It should be appreciated that certain compounds of the present invention can exist as geometric isomers; that is enantiomers or diastereomers. The present invention includes compounds and compositions as disclosed herein comprising substantially pure dextrorotatory, levorotatory or racemic mixtures of said compounds.

The 4,5-dihydro-1H-pyrazole-1-carboxamides of the instant invention are deemed to include 4,5-dihydro-1H-pyrazole-1-thiocarboxamides and 4,5-dihydro-1H-pyrazole-1-iminocarboxamides. When U in Formula I is oxygen, the compound is an oxocarboxamide and when U is sulfur in Formula I, the compounds is a thiocarboxamide and when U is N—$R^1$ the compound is an iminocarboxamide. The preferred U substituent is oxygen.

The relationship between Y and Z is such that when Y is lower ($C_1$–$C_6$) straight or branched chain unsubstituted or substituted alkyl, unsubstituted or substituted aryl, (Group A), Z can be cycloalkyl ($C_3$–$C_6$), unsubstituted or substituted aryl or $R^4$—Q provided that Z is not hydrogen and Z is not methyl when Y is methyl. When Y is

(Group B) where X and G are as defined above for Formula I, Z can be hydrogen, cycloalkyl ($C_3$–$C_6$), unsubstituted substituted aryl or $R^4$—Q.

The only compounds of the invention which can be monosubstituted at the four position of the pyrazole ring (i.e., where Z is hydrogen) are those where Y is

and these monosubstituted compounds have, necessarily, 1-oxo

1-thiono

1-imino

or 1 alkenyl

functionality at the 4 position of the pyrazole ring. Otherwise, the compounds of the present invention are disubstituted at the 4 position of the pyrazole ring.

Possible Z substituents, when Y is Group A include, but are not limited to: alkyl, aryl, aralkyl, haloalkyl, alkoxyalkyl, alkylthioalkyl, alkylsulfinylalkyl, cyanoalkyl, carboalkoxy, carboalkoxyalkyl, carboxamido, carboxyamidoalkyl, N-alkylcarboxamido, N-alkylcarboxamidoalkyl, N,N-dialkylcarboxamido, N,N-dialkylcarboxamidoalkyl, hydroxyalkyl, ketoalkyl, ketoaryl, thionoalkyl, thionoaryl, iminoalkyl, iminoaryl, halo, hydroxy, carboxy, dithiocarboxy, dithiocarboxyalkyl or dithiocarboalkoxy.

Preferred Z substituents when Y is Group A are phenyl, 4-chlorophenyl, carbomethoxy, carboethoxy, dimethylcarbamoyl, acetyl, propionyl, benzoyl, butyl, 2-methylthioethyl, 3-cyanopropyl, 2-methylsulfonylethyl, carbomethoxymethyl, 2,2-dichlorovinyl and 2,2-dibromovinyl.

Possible Z substituents when Y has 1-oxo, 1-thiono, 1-imino or 1-alkenyl functionality (Group B), as defined in Formula I include, but are not limited to: hydrogen, alkyl, aryl, aralkyl, haloalkyl, alkoxyalkyl, alkylthioalkyl, alkylsulfinylalkyl, cyanoalkyl, carboalkoxy, carboalkoxyalkyl, dichlorovinyl, dibromovinyl, carboxamido, carboxamidoalkyl, N-alkylcarboxamido, N-alkylcarboxamidoalkyl, N,N-dialkylcarboxamido, N,N-dialkylcarboxamidoalkyl, hydroxyalkyl, ketoalkyl, ketoaryl, thionoalkyl, thionoaryl, iminoalkyl, iminoaryl, halo, hydroxy, carboxy, dithiocarboxy, dithiocarboxyalkyl, or dithiocarboalkoxy.

Preferred Z substituents when Y has 1-oxo, 1-thiono, 1-imino, or 1-alkenyl functionality (Group B) are hydrogen, methyl, dichlorovinyl, dibromovinyl, phenyl, 4-chlorophenyl, 4-trifluromethylphenyl, 4-trifluoromethoxyphenyl, 4-trifluorothiomethoxyphenyl, 4-difluoromethoxyphenyll or 4-difluorobromothiomethoxyphenyl. The most preferred substituent is methyl.

When the compounds of the present invention are monosubstituted at the 4 position (Group B), those compounds having 1-oxo functionality at the Y substituent are preferred.

Examples of substituents for G include hydrogen, alkoxy, thioalkoxy, alkyl, hydroxy, alkoxyalkyl, thioalkoxyalkyl, alkoxyalkoxy, thioalkoxyalkoxy, amino, alkylamino, dialkylamino, carbalkoxy, cyano, ketoalkyl and alkyl substituted with alkoxy, thioalkoxy, carbalkoxy, cyano or alkylheteroalkyl. Preferred G substituents include methyl, ethyl, methoxy, ethoxy, hydroxy, dimethylamino and phenyl. Most preferred are methoxy, ethoxy or dimethylamino.

Substituent A may be aryl or substituted aryl. The preferred A substituent is unsubstituted or substituted phenyl and most preferred is substituted phenyl. While the phenyl group may be substituted with up to five substituents, it is preferred that it be unsubstituted, or monosubstituted or disubstituted with the same or different substituents and most preferred that the phenyl group be monosubstituted with the substituent located in the para position. Preferred phenyl substituents include fluoro, chloro, bromo, 2-propoxy, isopropoxy, ethoxy, methoxy, n-butoxy, tetrafluoroethoxy, trifluoromethyl, trifluoromethoxy, difluoromethoxy or methyl. Most preferred substituents are chloro, bromo, n-propoxy, isopropoxy, trifluoromethyl, triflurormethoxy or difluoromethoxy at the 4 position on the phenyl ring.

Substituent B may be aryl or substituted aryl. The preferred B substituent is unsubstituted or substituted phenyl and most preferred is substituted phenyl having up to two of the same or different substituents located in the 3 and/or 4 positions. When substituent B is monosubstituted, it is preferred the phenyl group be substituted in the para position. Preferred substituents include fluoro, chloro, bromo, trifluoromethyl, trifluoromethoxy, tetrafluorethoxy, difluoromethoxy, carbomethoxy, carboethoxy, carboisopropoxy, methylthio or methylsulfonyl. Most preferred substituents include chloro, bromo, carbomethoxy, carboethoxy, carboisopropoxy, difluoromethoxy, trifluoromethoxy, trifluoromethyl, tetrafluoroethoxy, methylthio or methylsulfonyl.

Representative examples of substituent V include alkyl, branched alkyl, cycloalkyl, aryl or $R^4$—Q where Q and $R^4$ are as defined above for Formula I. Preferably, V is hydrogen, lower ($C_1$-$C_6$) straight or branched chain unsubstituted or substituted alkyl, lower ($C_1$-$C_6$)alkoxy, lower ($C_1$-$C_6$)alkylsulfenyl, unsubstituted or substituted arylsulfenyl, lower ($C_1$-$C_6$)carboalkoxy, cyano, lower ($C_1$-$C_6$)alkylheteroalkyl, wherein the substituent on the akyl moiety is lower ($C_1$-$C_4$)alkoxy, lower ($C_1$-$C_4$)alkylsulfenyl, lower ($C_1$-$C_4$)carboalkoxy, cyano or lower ($C_1$-$C_4$)heteroalkyl. Most preferred are hydrogen, methyl, methylsulfenyl, 2-nitrophenylsulfenyl, carbomethoxy, acetyl, trifluoroacetyl, formyl or methoxalyl.

Aryl can be chosen from phenyl, optionally substituted with 1-5 substituents independently chosen from W; methylenedioxyphenyl, naphthyl, optionally substituted with 1-7 substituents independently chosen from W; a 5 membered heterocycle containing up to 3 nitrogen atoms, up to 2 oxygen atoms, up to 2 sulfur atoms and up to 4 nuclear carbon atoms, optionally substituted with 1-4 substituents independently chosen from W; or a 6 membered heterocycle containing up to 3 nitrogen atoms, up to 2 oxygen atoms, up to 2 sulfur atoms and 1-5 nuclear carbon atoms optionally substituted with 1-4 substituents independently chosen from W. Representative examples of 5 and 6 membered heterocycles include pyrryl, furyl, thienyl, imidazolyl, oxazolyl, thiazolyl, pyrazolyl, pyridyl, triazolyl, pyrimidyl and the like.

W is halogen, cyano, nitro, $R^1$, $CO_2R^1$, $CONR^1R^2$, $CR^1=CR^2R^3$, $C=CR^1$, $SR^1$, $OR^1$, $NR^1R^2$, $SOR^1$, $SO_2R^1$, $OSO_2R^1$, $NR^1COR^2$, $SF_5$, $CF_3$, $OCF_3$, $OCF_2H$, $SCF_3$, $OCF_2Br$, $SCF_2Br$, $SCF_2Cl$, $SCF_2H$, $NR^1SO_2R^2$ or $N(COR^1)COR^2$.

Since the 1-substituted-4-substituted-4,5-dihydro-1H-pyrazoles of Formula I may possess acidic or basic functional groups, they may form novel salts with appropriate bases or acids which also exhibit pesticidal activity. Typical salts are the agronomically acceptable metal salts, ammonium salts and acid addition salts. Among the metal salts are those in which the metal cation is an alkali metal cation such as sodium, potassium, lithium or the like; alkaline earth metal cation such as calcium, magnesium, barium, strontium or the like; or heavy metal cation such as zinc, manganese, cupric, cuprous, ferric, ferrous, titanium, aluminum or the like. Among the ammonium salts are those in which the ammonium cation has the formula $NR^5R^6R^7R^8$ wherein each of $R^5$, $R^6$, $R^7$ and $R^8$ are independently a hydrogen atom, a hydroxy group, a $(C_1-C_4)$alkoxy group, a $(C_1-C_{20})$alkyl group, a $(C_3-C_8)$-alkenyl group, a $(C_3-C_8)$alkynyl group, a $(C_2-C_8)$hydroxyalkyl group, a $(C_2-C_8)$alkoxyalkyl group, a $(C_2-C_6)$aminoalkyl group, a $(C_2-C_6)$haloalkyl group, an amino group, a $(C_1-C_4)$alkyl group or $(C_1-C_4)$dialkylamino group, a substituted or unsubstituted phenyl group, a substituted or unsubstituted phenylalkyl group, having up to four carbon atoms in the alkyl moiety, or any two of $R^5$, $R^6$, $R^7$ or $R^8$ can be taken together to form with the nitrogen atom a 5- or 6-membered heterocyclic ring, optionally having up to one additional hetero atom (e.g., oxygen, nitrogen, or sulfur) in the ring, and preferably saturated, such as piperidino, morpholino, pyrrolidino, piperazino or the like, or any three of $R^5$, $R^6$, $R^7$ or $R^8$ can be taken together to form with the nitrogen atom a 5- or 6-membered aromatic heterocyclic ring, such as piperazole or pyridine. When the ammonium group contains a substituted phenyl or substituted phenylalkyl group, the substituents will generally be selected from halogen atoms, $(C_1-C_8)$alkyl groups, $(C_1-C_4)$alkoxy groups, hydroxy group, nitro groups, trifluoromethyl groups, cyano groups, amino groups, $(C_1-C_4)$alkylthio groups, and the like. Such substituted phenyl groups preferably have up to two such substituents. Representative ammonium cations include ammonium, dimethylammonium, 2-ethylehexylammonium, bis(2-hydroxyethyl)ammonium, tris(2-hydroxyethyl)ammonium, dicyclohexylammonium, t-octylammonium, 2-hydroxyethylammonium, morpholinium, piperidinium, 2-phenethylammonium, 2-methylbenzylammonium, n-hexylammonium, triethylammonium, trimethylammonium, tri(n-butyl)-ammonium, methoxyethylammonium, diisopropylammonium, pyridinium, dialkylammonium, pyrazolium, propargylammonium, dimethylhydrazinium, octadecylammonium, 4-dichlorophenylammonium, 4-nitrobenzylammonium, benzyltrimethylammonium, 2-hydroxyethyldimethyloctadecylammonium, 2-hydroxyethyldiethyloctylammonium, decyltrimethylammonium, hexyltriethylammonium, 4-methylbenzyltrimethylammonium, and the like. Among the acid addition salts are those in which the anion is an agronomically acceptable anion such as hydrochloride, hydrobromide, sulfate, nitrate, perchlorate, acetate, oxalate or the like.

Certain of the compounds of the present invention have been detected as complexing with ethanol or ether, such as the compound of Example 137 which is the alcoholate of Example 77. The present invention includes compounds as defined by Formula I complexed as agronomically acceptable hydrates, etherates and alcoholates; and compositions containing said complexes as active ingredient.

Representative examples of the compounds of the invention embraced by Formula I are listed below.

Those examples listed under Group A include compounds where Y is a Group A substituent as defined above for Formula I. Those examples listed under Group B include compounds where Y is a Group B substituent as defined above for Formula I.

GROUP A

N,3,4-tris-(4-chlorophenyl)-4-methyl-4,5-dihydro-1H-pyrazole-1-carboxamide
N,3,4-tris-(4-chlorophenyl)-N,4-dimethyl-4,5-dihydro-1H-pyrazole-1-carboxamide
N,3-bis-(4-bromophenyl)-4-carbomethoxy-4-methyl-4,5-dihydro-1H-pyrazole-1-carboxamide
N,3-bis-(4-chlorophenyl)-4-(1-ethylpropyl)-4-methyl-4,5-dihydro-1H-pyrazole-1-carboxamide
N,3-bis-(4-chlorophenyl)-4-(1-hydroxy-1-(4-fluorophenyl)-methyl)-4-methyl-4,5-dihydro-1H-pyrazole-1-carboxamide
N,3-bis-(4-chlorophenyl)-4-(1-hydroxyethyl)-4-methyl-4,5-dihydro-1H-pyrazole-1-carboxamide
N,3-bis-(4-chlorophenyl)-4-(1-methylethyl)-4-methyl-4,5-dihydro-1H-pyrazole-1-carboxamide
N,3-bis-(4-chlorophenyl)-4-(1-methylpropyl)-4-methyl-4,5-dihydro-1H-pyrazole-1-carboxamide
N,3-bis-(4-chlorophenyl)-4-(2,3-dibromopropyl)-4-methyl-4,5-dihydro-1H-pyrazole-1-carboxamide
N,3-bis-(4-chlorophenyl)-4-(2,3-dichloropropyl)-4-methyl-4,5-dihydro-1H-pyrazole-1-carboxamide
N,3-bis-(4-chlorophenyl)-4-(2-acetoxyethyl)-4-methyl-4,5-dihydro-1H-pyrazole-1-carboxamide
N,3-bis-(4-chlorophenyl)-4-(2-ethylthioethyl)-4-methyl-4,5-dihydro-1H-pyrazole-1-carboxamide
N,3-bis-(4-chlorophenyl)-4-(2-hydroxyethyl)-4-methyl-4,5-dihydro-1H-pyrazole-1-carboxamide
N,3-bis-(4-chlorophenyl)-4-(2-hydroxypropyl)-4-methyl-4,5-dihydro-1H-pyrazole-1-carboxamide
N,3-bis-(4-chlorophenyl)-4-(2-methoxyethoxymethyl)-4-methyl-4,5-dihydro-1H-pyrazole-1-carboxamide
N,3-bis-(4-chlorophenyl)-4-(2-methoxyethyl)-4-methyl-4,5-dihydro-1H-pyrazole-1-carboxamide
N,3-bis-(4-chlorophenyl)-4-(2-methylpropyl)-4-methyl-4,5-dihydro-1H-pyrazole-1-carboxamide
N,3-bis-(4-chlorophenyl)-4-(2-methylpropyl)-N,4-dimethyl-4,5-dihydro-1H-pyrazole-1-carboxamide
N,3-bis-(4-chlorophenyl)-4-(2-methylsulfonylethyl)-4-methyl-4,5-dihydro-1H-pyrazole-1-carboxamide
N,3-bis-(4-chlorophenyl)-4-(2-methylsulfoxylethyl)-4-methyl-4,5-dihydro-1H-pyrazole-1-carboxamide
N,3-bis-(4-chlorophenyl)-4-(2-methylthioethyl)-4-methyl-4,5-dihydro-1H-pyrazole-1-carboxamide
N,3-bis-(4-chlorophenyl)-4-(2-phenylthioethyl)-4-methyl-4,5-dihydro-1H-pyrazole-1-carboxamide
N,3-bis-(4-chlorophenyl)-4-(3-azidopropyl)-4-methyl-4,5-dihydro-1H-pyrazole-1-carboxamide
N,3-bis-(4-chlorophenyl)-4-(3-butenyl)-4-methyl-4,5-dihydro-1H-pyrazole-1-carboxamide
N,3-bis-(4-chlorophenyl)-4-(3-chloropropyl)-4-methyl-4,5-dihydro-1H-pyrazole-1-carboxamide
N,3-bis-(4-chlorophenyl)-4-(3-cyanopropyl)-4-methyl-4,5-dihydro-1H-pyrazole-1-carboxamide
N,3-bis-(4-chlorophenyl)-4-(4-chlorobenzoyl)-4-methyl-4,5-dihydro-1H-pyrazole-1-carboxamide
N,3-bis-(4-chlorophenyl)-4-(4-chlorobutyl)-4-methyl-4,5-dihydro-1H-pyrazole-1-carboxamide
N,3-bis-(4-chlorophenyl)-4-(4-methoxybutyl)-4-methyl-4,5-dihydro-1H-pyrazole-1-carboxamide
N,3-bis-(4-chlorophenyl)-4-(5-hexenyl)-4-methyl-4,5-dihydro-1H-pyrazole-1-carboxamide
N,3-bis-(4-chlorophenyl)-4-acetyl-4-methyl-4,5-dihydro-1H-pyrazole-1-carboxamide
N,3-bis-(4-chlorophenyl)-4-allyl-4-methyl-4,5-dihydro-1H-pyrazole-1-carboxamide N,3-bis-(4-chlorophenyl)-4-benzoyl-4-methyl-4,5-dihydro-1H-pyrazole-1-carboxamide
N,3-bis-(4-chlorophenyl)-4-benzyl-4-methyl-4,5-dihydro-1H-pyrazole-1-carboxamide
N,3-bis-(4-chlorophenyl)-4-butyl-4-methyl-4,5-dihydro-1H-pyrazole-1-carboxamide
N,3-bis-(4-chlorophenyl)-4-butyl-N,4-dimethyl-4,5-dihydro-1H-pyrazole-1-carboxamide
N,3-bis-(4-chlorophenyl)-4-carbo(2-dimethylaminoethoxy)-4-methyl-4,5-dihydro-1H-pyrazole-1-carboxamide
N,3-bis-(4-chlorophenyl)-4-carbo(2-dimethylaminoethoxy)-4-methyl-4,5-dihydro-1H-pyrazole-1-carboxamide hydrochloride salt
N,3-bis-(4-chlorophenyl)-4-carbo(2-methylsulfonylethoxy)-4-methyl-4,5-dihydro-1H-pyrazole-1-carboxamide
N,3-bis-(4-chlorophenyl)-4-carbo(2-methylthioethoxy)-4-methyl-4,5-dihydro-1H-pyrazole-1-carboxamide
N,3-bis-(4-chlorophenyl)-4-carbobutoxy-4-methyl-4,5-dihydro-1H-pyrazole-1-carboxamide
N,3-bis-(4-chlorophenyl)-4-carboethoxy-4-methyl-4,5-dihydro-1H-pyrazole-1-carboxamide
N,3-bis-(4-chlorophenyl)-4-carboisopropoxy-4-methyl-4,5-dihydro-1H-pyrazole-1-carboxamide
N,3-bis-(4-chlorophenyl)-4-carbomenthyloxy-4-methyl-4,5-dihydro-1H-pyrazole-1-carboxamide
N,3-bis-(4-chlorophenyl)-4-carbomethoxy-4-ethyl-4,5-dihydro-1H-pyrazole-1-carboxamide
N,3-bis-(4-chlorophenyl)-4-carbomethoxy-4-methyl-4,5-dihydro-1H-pyrazole-1-carboxamide
N,3-bis-(4-chlorophenyl)-4-carbomethoxy-4-methyl-N-acetyl-4,5-dihydro-1H-pyrazole-1-carboxamide
N,3-bis-(4-chlorophenyl)-4-carbomethoxy-N,4-dimethyl-4,5-dihydro-1H-pyrazole-1-carboxamide
N,3-bis-(4-chlorophenyl)-4-carbomethoxy-N-(1-carbomethoxy-prop-2-yl-thio)-4-methyl-4,5-dihydro-1H-pyrazole-1-carboxamide
N,3-bis-(4-chlorophenyl)-4-carbomethoxy-N-(2-nitrophenylsulfenyl)-4-methyl-4,5-dihydro-1H-pyrazole-1-carboxamide
N,3-bis-(4-chlorophenyl)-4-carbomethoxy-N-(3-cyanopropylthio)-4-methyl-4,5-dihydro-1H-pyrazole-1-carboxamide
N,3-bis-(4-chlorophenyl)-4-carbomethoxy-N-acetyl-4-methyl-4,5-dihydro-1H-pyrazole-1-carboxthioamide
N,3-bis-(4-chlorophenyl)-4-carbomethoxy-N-carboethoxy-4-methyl-4,5-dihydro-1H-pyrazole-1-carboxamide
N,3-bis-(4-chlorophenyl)-4-carbomethoxy-N-carbomethoxythio-4-methyl-4,5-dihydro-1H-pyrazole-1-carboxamide
N,3-bis-(4-chlorophenyl)-4-carbomethoxy-N-carbophenoxy-4-methyl-4,5-dihydro-1H-pyrazole-1-carboxamide
N,3-bis-(4-chlorophenyl)-4-carbomethoxy-N-carbovinyloxy-4-methyl-4,5-dihydro-1H-pyrazole-1-carboxamide
N,3-bis-(4-chlorophenyl)-4-carbomethoxy-N-dimethylcarbamoyl-4-methyl-4,5-dihydro-1H-pyrazole-1-carboxamide
N,3-bis-(4-chlorophenyl)-4-carbomethoxy-N-formyl-4-methyl-4,5-dihydro-1H-pyrazole-1-carboxamide
N,3-bis-(4-chlorophenyl)-4-carbomethoxy-N-methoxymethyl-4-methyl-4,5-dihydro-1H-pyrazole-1-carboxamide
N,3-bis-(4-chlorophenyl)-4-carbomethoxy-N-methyloxallyl-4-methyl-4,5-dihydro-1H-pyrazole-1-carboxamide
N,3-bis-(4-chlorophenyl)-4-carbomethoxy-N-methylthio-4-methyl-4,5-dihydro-1H-pyrazole-1-carboxamide
N,3-bis-(4-chlorophenyl)-4-carbomethoxy-N-phenylthio-4-methyl-4,5-dihydro-1H-pyrazole-1-carboxamide
N,3-bis-(4-chlorophenyl)-4-carbomethoxy-N-propylthio-4-methyl-4,5-dihydro-1H-pyrazole-1-carboxamide
N,3-bis-(4-chlorophenyl)-4-carbomethoxy-N-trifluoroacetyl-4-methyl-4,5-dihydro-1H-pyrazole-1-carboxamide
N,3-bis-(4-chlorophenyl)-4-carbomethoxymethyl-4-methyl-4,5-dihydro-1H-pyrazole-1-carboxamide
N,3-bis-(4-chlorophenyl)-4-carbomethylthiomethoxy-4-methyl-4,5-dihydro-1H-pyrazole-1-carboxamide
N,3-bis-(4-chlorophenyl)-4-carbopropoxy-4-methyl-4,5-dihydro-1H-pyrazole-1-carboxamide
N,3-bis-(4-chlorophenyl)-4-carboxy-4-methyl-4,5-dihydro-1H-pyrazole-1-carboxamide
N,3-bis-(4-chlorophenyl)-4-carboxy-4-methyl-4,5-dihydro-1H-pyrazole-1-carboxamide sodium salt
N,3-bis-(4-chlorophenyl)-4-cyano-4-methyl-4,5-dihydro-1H-pyrazole-1-carboxamide
N,3-bis-(4-chlorophenyl)-4-cyclohexyl-4-methyl-4,5-dihydro-1H-pyrazole-1-carboxamide
N,3-bis-(4-chlorophenyl)-4-diethylcarboxamido-4-methyl-4,5-dihydro-1H-pyrazole-1-carboxamide
N,3-bis-(4-chlorophenyl)-4-dimethylcarboxamido-4-methyl-4,5-dihydro-1H-pyrazole-1-carboxamide
N,3-bis-(4-chlorophenyl)-4-dimethylthiocarbamoyl-4-methyl-4,5-dihydro-1H-pyrazole-1-carboxamide
N,3-bis-(4-chlorophenyl)-4-ethyl-4-methyl-4,5-dihydro-1H-pyrazole-1-carboxamide
N,3-bis-(4-chlorophenyl)-4-hexyl-4-methyl-4,5-dihydro-1H-pyrazole-1-carboxamide
N,3-bis-(4-chlorophenyl)-4-isobutyryl-4-methyl-4,5-dihydro-1H-pyrazole-1-carboxamide
N,3-bis-(4-chlorophenyl)-4-methoxymethyl-4-methyl-4,5-dihydro-1H-pyrazole-1-carboxamide
N,3-bis-(4-chlorophenyl)-4-methylthiomethyl-4-methyl-4,5-dihydro-1H-pyrazole-1-carboxamide
N,3-bis-(4-chlorophenyl)-4-methylthiothiocarbonyl-4-methyl-4,5-dihydro-1H-pyrazole-1-carboxamide
N,3-bis-(4-chlorophenyl)-4-pentyl-4-methyl-4,5-dihydro-1H-pyrazole-1-carboxamide
N,3-bis-(4-chlorophenyl)-4-phenyl-4-methyl-4,5-dihydro-1H-pyrazole-1-carboxamide
N,3-bis-(4-chlorophenyl)-4-Phenyl-N,4-methyl-4,5-dihydro-1H-pyrazole-1-carboxamide
N,3-bis-(4-chlorophenyl)-4-phenyl-N-acetyl-4-methyl-4,5-dihydro-1H-pyrazole-1-carboxamide
N,3-bis-(4-chlorophenyl)-4-phenyl-N-benzoyl-4-methyl-4,5-dihydro-1H-pyrazole-1-carboxamide
N,3-bis-(4-chlorophenyl)-4-phenyl-N-carbomethoxy-4-methyl-4,5-dihydro-1H-pyrazole-1-carboxamide
N,3-bis-(4-chlorophenyl)-4-phenyl-N-carbomethoxythio-4-methyl-4,5-dihydro-1H-pyrazole-1-carboxamide
N,3-bis-(4-chlorophenyl)-4-phenyl-N-cyano-4-methyl-4,5-dihydro-1H-pyrazole-1-carboxamide
N,3-bis-(4-chlorophenyl)-4-phenyl-N-methoxymethyl-4-methyl-4,5-dihydro-1H-pyrazole-1-carboxamide
N,3-bis-(4-chlorophenyl)-4-phenyl-N-propionyl-4-methyl-4,5-dihydro-1H-pyrazole-1-carboxamide N,3-bis-(4-chlorophenyl)-4-phenyl-N-trimethylacetyl-4-methyl-4,5-dihydro-1H-pyrazole-1-carboxamide
N,3-bis-(4-chlorophenyl)-4-pivaloyl-4-methyl-4,5-dihydro-1H-pyrazole-1-carboxamide
N,3-bis-(4-chlorophenyl)-4-propionyl-4-methyl-4,5-dihydro-1H-pyrazole-1-carboxamide
N,3-bis-(4-chlorophenyl)-4-propyl-4-methyl-4,5-dihydro-1H-pyrazole-1-carboxamide
N,3-bis-(4-chlorophenyl)-4-phenyl-4-methyl-4,5-dihydro-1H-pyrazole-1-carboxamide
N,3-bis-(4-fluorophenyl)-4-butyl-4-methyl-4,5-dihydro-1H-pyrazole-1-carboxamide
N,3-bis-(4-trifluoromethylphenyl)-4-carbomethoxy-4-methyl-4,5-dihydro-1H-pyrazole-1-carboxamide
N-(1-naphthyl)-3-(4-chlorophenyl)-4-carbomethoxy-4,5-dihydro-1H-pyrazole-1-carboxamide
N-(2,4-dinitrophenyl)-3-(4-chlorophenyl)-4-carbomethoxy-4,5-dihydro-1H-pyrazole-1-carboxamide
N-(2-fluoro-4-trifluoromethylphenyl)-3-(3-chloro-4-trifluoromethylphenyl)-4-(3-methylthiopropyl)-4-methyl-4,5-dihydro-1H-pyrazole-1-carboxamide
N-(2-fluoro-4-trifluoromethylphenyl)-3-(3-chloro-4-trifluoromethylphenyl)-4-carboethoxy-4-methyl-4,5-dihydro-1H-pyrazole-1-carboxamide
N-(2-fluoro-4-trifluoromethylphenyl)-3-(3-chloro-4-trifluoromethylphenyl)-4-phenyl-4-methyl-4,5-dihydro-1H-pyrazole-1-carboxamide
N-(2-fluoro-4-trifluoromethylphenyl)-3-(4-chlorophenyl)-4-(3-methylthiopropyl)-4-methyl-4,5-dihydro-1H-pyrazole-1-carboxamide
N-(2-fluoro-4-trifluoromethylphenyl)-3-(4-chlorophenyl)-4-carboethoxy-4-methyl-4,5-dihydro-1H-pyrazole-1-carboxamide
N-(2-fluoro-4-trifluoromethylphenyl)-3-(4-chlorophenyl)-4-phenyl-4-methyl-4,5-dihydro-1H-pyrazole-1-carboxamide
N-(2-methyl-4-trifluoromethylphenyl)-3-(3-chloro-4-trifluoromethylphenyl)-4-(3-methylthiopropyl-4-methyl-4,5-dihydro-1H-pyrazole-1-carboxamide
N-(2-methyl-4-trifluoromethylphenyl)-3-(3-chloro-4-trifluoromethylphenyl)-4-carboethoxy-4-methyl-4,5-dihydro-1H-pyrazole-1-carboxamide
N-(2-methyl-4-trifluoromethylphenyl)-3-(3-chloro-4-trifluoromethylphenyl)-4-phenyl-4-methyl-4,5-dihydro-1H-pyrazole-1-carboxamide
N-(2-methyl-4-trifluoromethylphenyl)-3-(4-chlorophenyl)-4-(3-methylthiopropyl-4-methyl-4,5-dihydro-1H-pyrazole-1-carboxamide
N-(2-methyl-4-trifluoromethylphenyl)-3-(4-chlorophenyl)-4-carboethoxy-4-methyl-4,5-dihydro-1H-pyrazole-1-carboxamide
N-(2-methyl-4-trifluoromethylphenyl)-3-(4-chlorophenyl)-4-phenyl-4-methyl-4,5-dihydro-1H-pyrazole-1-carboxamide
N-(3,4-dichlorophenyl)-3-(4-chlorophenyl)-4-carbomethoxy-4-methyl-4,5-dihydro-1H-pyrazole-1-carboxamide
N-(3,4-dichlorophenyl)-3-(4-chlorophenyl)-4-phenyl-4-methyl-4,5-dihydro-1H-pyrazole-1-carboxamide
N-(3,4-dichlorophenyl)-3-phenyl-4-carbomethoxy)-4-methyl-4,5-dihydro-1H-pyrazole-1-carboxamide
N-(3-bromo-4-trifluoromethylphenyl)3-(3-chloro-4-trifluoromethylphenyl-4-(3-methylthiopropyl)-4-methyl-4,5-dihydro-1H-pyrazole-1-carboxamide
N-(3-bromo-4-trifluoromethylphenyl)3-(3-chloro-4-trifluoromethylphenyl-4-carboethoxy-4-methyl-4,5-dihydro-1H-pyrazole-1-carboxamide
N-(3-bromo-4-trifluoromethylphenyl)3-(3-chloro-4-trifluoromethylphenyl-4-phenyl-4-methyl-4,5-dihydro-1H-pyrazole-1-carboxamide
N-(3-bromo-4-trifluoromethylphenyl)3-(4-chlorophenyl-4-(3-methylthiopropyl)-4-methyl-4,5-dihydro-1H-pyrazole-1-carboxamide
N-(3-bromo-4-trifluoromethylphenyl)-3-(4-chlorophenyl-4-carboethoxy-4-methyl-4,5-dihydro-1H-pyrazole-1-carboxamide
N-(3-bromo-4-trifluoromethylphenyl)-3-(4-chlorophenyl-4-phenyl-4-methyl-4,5-dihydro-1H-pyrazole-1-carboxamide
N-(3-bromophenyl)-3-(3-chloro-4-trifluoromethylphenyl)-4-(3-methylthiopropyl)-4-methyl-4,5-dihydro-1H-pyrazole-1-carboxamide
N-(3-bromophenyl)-3-(3-chloro-4-trifluoromethylphenyl)4-carboethoxy-4-methyl-4,5-dihydro-1H-pyrazole-1-carboxamide
N-(3-bromophenyl)-3-(3-chloro-4-trifluoromethylphenyl)-4-phenyl-4-methyl-4,5-dihydro-1H-pyrazole-1-carboxamide
N-(3-bromophenyl)-3-(4-chlorophenyl)-4-(3-methylthiopropyl)-4-methyl-4,5-dihydro-1H-pyrazole-1-carboxamide
N-(3-bromophenyl)-3-(4-chlorophenyl)-4-carboethoxy-4-methyl-4,5-dihydro-1H-pyrazole-1-carboxamide
N-(3-bromophenyl)-3-(4-chlorophenyl)-4-phenyl-4-methyl-4,5-dihydro-1H-pyrazole-1-carboxamide
N-(3-carboethoxyphenyl)-3-(3-chloro-4-trifluoromethylphenyl)-4-(3-methylthiopropyl-4-methyl-4,5-dihydro-1H-pyrazole-1-carboxamide
N-(3-carboethoxyphenyl)-3-(3-chloro-4-trifluoromethylphenyl)-4-carboethoxy-4-methyl-4,5-dihydro-1H-pyrazole-1-carboxamide
N-(3-carboethoxyphenyl)-3-(3-chloro-4-trifluoromethylphenyl)-4-phenyl-4-methyl-4,5-dihydro-1H-pyrazole-1-carboxamide
N-(3-carboethoxyphenyl)-3-(4-chlorophenyl)-4-(3-methylthiopropyl-4-methyl-4,5-dihydro-1H-pyrazole-1-carboxamide
N-(3-carboethoxyphenyl)-3-(4-chlorophenyl)-4-carboethoxy-4-methyl-4,5-dihydro-1H-pyrazole-1-carboxamide
N-(3-carboethoxyphenyl)-3-(4-chlorophenyl)-4-phenyl-4-methyl-4,5-dihydro-1H-pyrazole-1-carboxamide
N-(3-carboisopropoxyphenyl)-3-(3-chloro-4-trifluoromethylphenyl)-4-(3-methylthiopropyl)-4-methyl-4,5-dihydro-1H-pyrazole-1-carboxamide
N-(3-carboisopropoxyphenyl)-3-(3-chloro-4-trifluoromethylphenyl)-4-carboethoxy-4-methyl-4,5-dihydro-1H-pyrazole-1-carboxamide
N-(3-carboisopropoxyphenyl)-3-(3-chloro-4-trifluoromethylphenyl)-4-phenyl-4-methyl-4,5-dihydro-1H-pyrazole-1-carboxamide
N-(3-carboisopropoxyphenyl)-3-(4-chlorophenyl)-4-(3-methylthiopropyl)-4-methyl-4,5-dihydro-1H-pyrazole-1-carboxamide
N-(3-carboisopropoxyphenyl)-3-(4-chlorophenyl)-4-carboethoxy-4-methyl-4,5-dihydro-1H-pyrazole-1-carboxamide
N-(3-carboisopropoxyphenyl)-3-(4-chlorophenyl)-4-phenyl-4-methyl-4,5-dihydro-1H-pyrazole-1-carboxamide
N-(3-carboimethoxyphenyl)-3-(3-chloro-4-trifluoromethylphenyl)-4-(3-methylthiopropyl)-4-methyl-4,5-dihydro-1H-pyrazole-1-carboxamide N-(3-carboimethoxyphenyl)-3-(3-chloro-4-trifluoromethylphenyl)-4-carboethoxy-4-methyl-4,5-dihydro-1H-pyrazole-1-carboxamide N-(3-carboimethoxyphenyl)-3-(3-chloro-4-trifluoromethylphenyl)-4-phenyl-4-methyl-4,5-dihydro-1H-pyrazole-1-carboxamide N-(3-carboimethoxyphenyl)-3-(4-chlorophenyl)-4-(3-methylthiopropyl)-4-methyl-4,5-dihydro-1H-pyrazole-1-carboxamide N-(3-carboimethoxyphenyl)-3-(4-chlorophenyl)-4-carboethoxy-4-methyl-4,5-dihydro-1H-pyrazole-1-carboxamide N-(3-carboimethoxyphenyl)-3-(4-chlorophenyl)-4-phenyl-4-methyl-4,5-dihydro-1H-pyrazole-1-carboxamide N-(3-chloro-4-trifluoromethylphenyl)-3-(3-chloro-4-trifluoromethylphenyl)-4-(3-methylthiopropyl)-4-methyl-4,5-dihydro-1H-pyrazole-1-carboxamide N-(3-chloro-4-trifluoromethylphenyl)-3-(3-chloro-4-trifluoromethylphenyl)-4-carboethoxy-4-methyl-4,5-dihydro-1H-pyrazole-1-carboxamide N-(3-chloro-4-trifluoromethylphenyl)-3-(3-chloro-4-trifluoromethylphenyl)-4-phenyl-4-methyl-4,5-dihydro-1H-pyrazole-1-carboxamide N-(3-chloro-4-trifluoromethylphenyl)-3-(4-chlorophenyl)-4-(3-methylthiopropyl)-4-methyl-4,5-dihydro-1H-pyrazole-1-carboxamide N-(3-chloro-4-trifluoromethylphenyl)-3-(4-chlorophenyl)-4-carboethoxy-4-methyl-4,5-dihydro-1H-pyrazole-1-carboxamide N-(3-chloro-4-trifluoromethylphenyl)-3-(4-chlorophenyl)-4-phenyl-4-methyl-4,5-dihydro-1H-pyrazole-1-carboxamide N-(3-chlorophenyl)-3-(4-chlorophenyl)-4-carbomethoxy-4-methyl-4,5-dihydro-1H-pyrazole-1-carboxamide N-(3-chlorophenyl)-3-(4-chlorophenyl)-4-phenyl-4-methyl-4,5-dihydro-1H-pyrazole-1-carboxamide N-(3-cyano-4-trifluoromethylphenyl)-3-(3-chloro-4-trifluoromethylphenyl)-4-(3-methylthiopropyl)-4-methyl-4,5-dihydro-1H-pyrazole-1-carboxamide N-(3-cyano-4-trifluoromethylphenyl)-3-(3-chloro-4-trifluoromethylphenyl)-4-carboethoxy-4-methyl-4,5-dihydro-1H-pyrazole-1-carboxamide N-(3-cyano-4-trifluoromethylphenyl)-3-(3-chloro-4-trifluoromethylphenyl)-4-phenyl-4-methyl-4,5-dihydro-1H-pyrazole-1-carboxamide N-(3-cyano-4-trifluoromethylphenyl)-3-(4-chlorophenyl)-4-(3-methylthiopropyl)-4-methyl-4,5-dihydro-1H-pyrazole-1-carboxamide N-(3-cyano-4-trifluoromethylphenyl)-3-(4-chlorophenyl)-4-carboethoxy-4-methyl-4,5-dihydro-1H-pyrazole-1-carboxamide N-(3-cyano-4-trifluoromethylphenyl)-3-(4-chlorophenyl)-4-phenyl-4-methyl-4,5-dihydro-1H-pyrazole-1-carboxamide N-(3-difluoromethoxy-4-trifluoromethylphenyl)-3-(3-chloro-4-trifluoromethylphenyl)-4-(3-methylthiopropyl)-4-methyl-4,5-dihydro-1H-pyrazole-1-carboxamide N-(3-difluoromethoxy-4-trifluoromethylphenyl)-3-(3-chloro-4-trifluoromethylphenyl)-4-carboethoxy-4-methyl-4,5-dihydro-1H-pyrazole-1-carboxamide N-(3-difluoromethoxy-4-trifluoromethylphenyl)-3-(3-chloro-4-trifluoromethylphenyl)-4-phenyl-4-methyl-4,5-dihydro-1H-pyrazole-1-carboxamide N-(3-difluoromethoxy-4-trifluoromethylphenyl)-3-(4-chlorophenyl)-4-(3-methylthiopropyl)-4-methyl-4,5-dihydro-1H-pyrazole-1-carboxamide N-(3-difluoromethoxy-4-trifluoromethylphenyl)-3-(4-chlorophenyl)-4-carboethoxy-4-methyl-4,5-dihydro-1H-pyrazole-1-carboxamide N-(3-difluoromethoxy-4-trifluoromethylphenyl)-3-(4-chlorophenyl)-4-phenyl-4-methyl-4,5-dihydro-1H-pyrazole-1-carboxamide N-(3-difluoromethoxyphenyl)-3-(3-chloro-4-trifluoromethylphenyl)-4-(3-methylthiopropyl)-4-methyl-4,5-dihydro-1H-pyrazole-1-carboxamide N-(3-difluoromethoxyphenyl)-3-(3-chloro-4-trifluoromethylphenyl)-4-carboethoxy-4-methyl-4,5-dihydro-1H-pyrazole-1-carboxamide N-(3-difluoromethoxyphenyl)-3-(3-chloro-4-trifluoromethylphenyl)-4-phenyl-4-methyl-4,5-dihydro-1H-pyrazole-1-carboxamide N-(3-difluoromethoxyphenyl)-3-(4-chlorophenyl)-4-(3-methylthiopropyl)-4-methyl-4,5-dihydro-1H-pyrazole-1-carboxamide N-(3-difluoromethoxyphenyl)-3-(4-chlorophenyl)-4-carboethoxy-4-methyl-4,5-dihydro-1H-pyrazole-1-carboxamide N-(3-difluoromethoxyphenyl)-3-(4-chlorophenyl)-4-phenyl-4-methyl-4,5-dihydro-1H-pyrazole-1-carboxamide N-(3-dimethylsulfonamidophenyl)-3-(3-chloro-4-trifluoromethylphenyl)-4-(3-methylthiopropyl)-4-methyl-4,5-dihydro-1H-pyrazole-1-carboxamide N-(3-dimethylsulfonamidophenyl)-3-(3-chloro-4-trifluoromethylphenyl)-4-carboethoxy-4-methyl-4,5-dihydro-1H-pyrazole-1-carboxamide N-(3-dimethylsulfonamidophenyl)-3-(3-chloro-4-trifluoromethylphenyl)-4-phenyl-4-methyl-4,5-dihydro-1H-pyrazole-1-carboxamide N-(3-dimethylsulfonamidophenyl)-3-(4-chlorophenyl)-4-(3-methylthiopropyl)-4-methyl-4,5-dihydro-1H-pyrazole-1-carboxamide N-(3-dimethylsulfonamidophenyl)-3-(4-chlorophenyl)-4-carboethoxy-4-methyl-4,5-dihydro-1H-pyrazole-1-carboxamide N-(3-dimethylsulfonamidophenyl)-3-(4-chlorophenyl)-4-phenyl-4-methyl-4,5-dihydro-1H-pyrazole-1-carboxamide N-(3-fluoro-4-trifluromethylphenyl)-3-(3-chloro-4-trifluoromethylphenyl)-4-(3-methylthiopropyl)-4-methyl-4,5-dihydro-1H-pyrazole-1-carboxamide N-(3-fluoro-4-trifluoromethylphenyl)-3-(3-chloro-4-trifluoromethylphenyl)-4-carboethoxy-4-methyl-4,5-dihydro-1H-pyrazole-1-carboxamide N-(3-fluoro-4-trifluoromethylphenyl)-3-(3-chloro-4-trifluoromethylphenyl)-4-phenyl-4-methyl-4,5-dihydro-1H-pyrazole-1-carboxamide N-(3-fluoro-4-trifluoromethylphenyl)-3-(4-chlorophenyl)-4-(3-methylthiopropyl)-4-methyl-4,5-dihydro-1H-pyrazole-1-carboxamide N-(3-fluoro-4-trifluoromethylphenyl)-3-(4-chlorophenyl)-4-carboethoxy-4-methyl-4,5-dihydro-1H-pyrazole-1-carboxamide N-(3-fluoro-4-trifluoromethylphenyl)-3-(4-chlorophenyl)-4-phenyl-4-methyl-4,5-dihydro-1H-pyrazole-1-carboxamide N-(3-methoxy-4-trifluromethylphenyl)-3-(3-chloro-4-trifluoromethylphenyl)-4-(3-methylthiopropyl)-4-methyl-4,5-dihydro-1H-pyrazole-1-carboxamide N-(3-methoxy-4-trifluoromethylphenyl)-3-(3-chloro-4-trifluoromethylphenyl)-4-carboethoxy-4-methyl-4,5-dihydro-1H-pyrazole-1-carboxamide N-(3-methoxy-4-trifluoromethylphenyl)-3-(3-chloro-4-trifluoromethylphenyl)-4-phenyl-4-methyl-4,5-dihydro-1H-pyrazole-1-carboxamide N-(3-methoxy-4-trifluoromethylphenyl)-3-(4-chlorophenyl)-4-(3-methylthiopropyl)-4-methyl-4,5-dihydro-1H-pyrazole-1-carboxamide N-(3-methoxy-4-trifluoromethylphenyl)-3-(4-chlorophenyl)-4-carboethoxy-4-methyl-4,5-dihydro-1H-pyrazole-1-carboxamide N-(3-methoxy-4-trifluoromethylphenyl)-3-(4-chlorophenyl)-4-phenyl-4-methyl-4,5-dihydro-1H-pyrazole-1-carboxamide N-(3-methyl-4-trifluromethylphenyl)-3-(3-chloro-4-trifluoromethylphenyl)-4-(3-methylthiopropyl)-4-methyl-4,5-dihydro-1H-pyrazole-1-carboxamide N-(3-methyl-4-trifluoromethylphenyl)-3-(3-chloro-4-trifluoromethylphenyl)-4-carboethoxy-4-methyl-4,5-dihydro-1H-pyrazole-1-carboxamide N-(3-methyl-4-trifluoromethylphenyl)-3-(3-chloro-4-trifluoromethylphenyl)-4-phenyl-4-methyl-4,5-dihydro-1H-pyrazole-1-carboxamide N-(3-methyl-4-trifluoromethylphenyl)-3-(4-chlorophenyl)-4-(3-methylthiopropyl)-4-methyl-4,5-dihydro-1H-pyrazole-1-carboxamide N-(3-methyl-4-trifluoromethylphenyl)-3-(4-chlorophenyl)-4-carboethoxy-4-methyl-4,5-dihydro-1H-pyrazole-1-carboxamide N-(3-methyl-4-trifluoromethylphenyl)-3-(4-chlorophenyl)-4-phenyl-4-methyl-4,5-dihydro-1H-pyrazole-1-carboxamide N-(3-methylsulfonyl-4-trifluromethylphenyl)-3-(3-chloro-4-trifluoromethylphenyl)-4-(3-methylthiopropyl)-4-methyl-4,5-dihydro-1H-pyrazole-1-carboxamide N-(3-methylsulfonyl-4-trifluoromethylphenyl)-3-(3-chloro-4-trifluoromethylphenyl)-4-carboethoxy-4-methyl-4,5-dihydro-1H-pyrazole-1-carboxamide N-(3-methylsulfonyl-4-trifluoromethylphenyl)-3-(3-chloro-4-trifluoromethylphenyl)-4-phenyl-4-methyl-4,5-dihydro-1H-pyrazole-1-carboxamide N-(3-methylsulfonyl-4-trifluoromethylphenyl)-3-(4-chlorophenyl)-4-(3-methylthiopropyl)-4-methyl-4,5-dihydro-1H-pyrazole-1-carboxamide N-(3-methylsulfonyl-4-trifluoromethylphenyl)-3-(4-chlorophenyl)-4-carboethoxy-4-methyl-4,5-dihydro-1H-pyrazole-1-carboxamide N-(3-methylsulfonyl-4-trifluoromethylphenyl)-3-(4-chlorophenyl)-4-phenyl-4-methyl-4,5-dihydro-1H-pyrazole-1-carboxamide N-(3-methylsulfonylphenyl)-3-(3-chloro-4-trifluoromethylphenyl)-4-(3-methylthiopropyl)-4-methyl-4,5-dihydro-1H-pyrazole-1-carboxamide N-(3-methylsulfonylphenyl)-3-(3-chloro-4-trifluoromethylphenyl)-4-carboethoxy-4-methyl-4,5-dihydro-1H-pyrazole-1-carboxamide N-(3-methylsulfonylphenyl)-3-(3-chloro-4-trifluoromethylphenyl)-4-phenyl-4-methyl-4,5-dihydro-1H-pyrazole-1-carboxamide N-(3-methylsulfonylphenyl)-3-(4-chlorophenyl)-4-(3-methylthiopropyl)-4-methyl-4,5-dihydro-1H-pyrazole-1-carboxamide N-(3-methylsulfonylphenyl)-3-(4-chlorophenyl)-4-carboethoxy-4-methyl-4,5-dihydro-1H-pyrazole-1-carboxamide N-(3-methylsulfonylphenyl)-3-(4-chlorophenyl)-4-carbomethoxy-4-methyl-4,5-dihydro-1H-pyrazole-1-carboxamide N-(3-methylsulfonylphenyl)-3-(4-chlorophenyl)-4-phenyl-4-methyl-4,5-dihydro-1H-pyrazole-1-carboxamide N-(3-methylthio-4-trifluromethylphenyl)-3-(3-chloro-4-trifluoromethylphenyl)-4-(3-methylthiopropyl)-4-methyl-4,5-dihydro-1H-pyrazole-1-carboxamide N-(3-methylthio-4-trifluoromethylphenyl)-3-(3-chloro-4-trifluoromethylphenyl)-4-carboethoxy-4-methyl-4,5-dihydro-1H-pyrazole-1-carboxamide N-(3-methylthio-4-trifluoromethylphenyl)-3-(3-chloro-4-trifluoromethylphenyl)-4-phenyl-4-methyl-4,5-dihydro-1H-pyrazole-1-carboxamide N-(3-methylthio-4-trifluoromethylphenyl)-3-(4-chlorophenyl)-4-(3-methylthiopropyl)-4-methyl-4,5-dihydro-1H-pyrazole-1-carboxamide N-(3-methylthio-4-trifluoromethylphenyl)-3-(4-chlorophenyl)-4-carboethoxy-4-methyl-4,5-dihydro-1H-pyrazole-1-carboxamide N-(3-methylthio-4-trifluoromethylphenyl)-3-(4-chlorophenyl)-4-phenyl-4-methyl-4,5-dihydro-1H-pyrazole-1-carboxamide N-(3-methyltiophenyl)-3-(3-chloro-4-trifluoromethylphenyl)-4-(3-methylthiopropyl)-4-methyl-4,5-dihydro-1H-pyrazole-1-carboxamide N-(3-methylthiophenyl)-3-(3-chloro-4-trifluoromethylphenyl)-4-carboethoxy-4-methyl-4,5-dihydro-1H-pyrazole-1-carboxamide N-(3-methylthiophenyl)-3-(3-chloro-4-trifluoromethylphenyl)-4-phenyl-4-methyl-4,5-dihydro-1H-pyrazole-1-carboxamide N-(3-methylthiophenyl)-3-(4-chlorophenyl)-4-(3-methylthiopropyl)-4-methyl-4,5-dihydro-1H-pyrazole-1-carboxamide N-(3-methylthiophenyl)-3-(4-chlorophenyl)-4-carboethoxy-4-methyl-4,5-dihydro-1H-pyrazole-1-carboxamide N-(3-methylthiophenyl)-3-(4-chlorophenyl)-4-carbomethoxy-4-methyl-4,5-dihydro-1H-pyrazole-1-carboxamide N-(3-methylthiophenyl)-3-(4-chlorophenyl)-4-phenyl-4-methyl-4,5-dihydro-1H-pyrazole-1-carboxamide N-(3-nitro-4-trifluromethylphenyl)-3-(3-chloro-4-trifluoromethylphenyl)-4-(3-methylthiopropyl)-4-methyl-4,5-dihydro-1H-pyrazole-1-carboxamide N-(3-nitro-4-trifluoromethylphenyl)-3-(3-chloro-4-trifluoromethylphenyl)-4-carboethoxy-4-methyl-4,5-dihydro-1H-pyrazole-1-carboxamide N-(3-nitro-4-trifluoromethylphenyl)-3-(3-chloro-4-trifluoromethylphenyl)-4-phenyl-4-methyl-4,5-dihydro-1H-pyrazole-1-carboxamide N-(3-nitro-4-trifluoromethylphenyl)-3-(4-chlorophenyl)-4-(3-methylthiopropyl)-4-methyl-4,5-dihydro-1H-pyrazole-1-carboxamide N-(3-nitro-4-trifluoromethylphenyl)-3-(4-chlorophenyl)-4-carboethoxy-4-methyl-4,5-dihydro-1H-pyrazole-1-carboxamide N-(3-nitro-4-trifluoromethylphenyl)-3-(4-chlorophenyl)-4-phenyl-4-methyl-4,5-dihydro-1H-pyrazole-1-carboxamide N-(3-trifluoromethoxy-4-trifluromethylphenyl)-3-(3-chloro-4-trifluoromethylphenyl)-4-(3-methylthiopropyl)-4-methyl-4,5-dihydro-1H-pyrazole-1-carboxamide N-(3-trifluoromethoxy-4-trifluoromethylphenyl)-3-(3-chloro-4-trifluoromethylphenyl)-4-carboethoxy-4-methyl-4,5-dihydro-1H-pyrazole-1-carboxamide N-(3-trifluoromethoxy-4-trifluoromethylphenyl)-3-(3-chloro-4-trifluoromethylphenyl)-4-phenyl-4-methyl-4,5-dihydro-1H-pyrazole-1-carboxamide N-(3-trifluoromethoxy-4-trifluoromethylphenyl)-3-(4-chlorophenyl)-4-(3-methylthiopropyl)-4-methyl-4,5-dihydro-1H-pyrazole-1-carboxamide N-(3-trifluoromethoxy-4-trifluoromethylphenyl)-3-(4-chlorophenyl)-4-carboethoxy-4-methyl-4,5-dihydro-1H-pyrazole-1-carboxamide N-(3-trifluoromethoxy-4-trifluoromethylphenyl)-3-(4-chlorophenyl)-4-phenyl-4-methyl-4,5-dihydro-1H-pyrazole-1-carboxamide N-(3-trifluoromethoxyphenyl)-3-(3-chloro-4-trifluoromethylphenyl)-4-(3-methylthiopropyl)-4-methyl-4,5-dihydro-1H-pyrazole-1-carboxamide N-(3-trifluoromethoxyphenyl)-3-(3-chloro-4-trifluoromethylphenyl)-4-carboethoxy-4-methyl-4,5-dihydro-1H-pyrazole-1-carboxamide N-(3-trifluoromethoxyphenyl)-3-(3-chloro-4-trifluoromethylphenyl)-4-phenyl-4-methyl-4,5-dihydro-1H-pyrazole-1-carboxamide N-(3-trifluoromethoxyphenyl)-3-(4-chlorophenyl)-4-(3-methylthiopropyl)-4-methyl-4,5-dihydro-1H-pyrazole-1-carboxamide N-(3-trifluoromethoxyphenyl)-3-(4-chlorophenyl)-4-carboethoxy-4-methyl-4,5-dihydro-1H-pyrazole-1-carboxamide N-(3-trifluoromethoxyphenyl)-3-(4-chlorophenyl)-4-phenyl-4-methyl-4,5-dihydro-1H-pyrazole-1-carboxamide N-(3-trifluoromethylphenyl)-3-(3-chloro-4-trifluoromethylphenyl)-4-(3-methylthiopropyl)-4-methyl-4,5-dihydro-1H-pyrazole-1-carboxamide N-(3-trifluoromethylphenyl)-3-(3-chloro-4-trifluoromethylphenyl)-4-carboethoxy-4-methyl-4,5-dihydro-1H-pyrazole-1-carboxamide N-(3-trifluoromethylphenyl)-3-(3-chloro-4-trifluoromethylphenyl)-4-phenyl-4-methyl-4,5-dihydro-1H-pyrazole-1-carboxamide N-(3-trifluoromethylphenyl)-3-(4-chlorophenyl)-4-(3-methylthiopropyl)-4-methyl-4,5-dihydro-1H-pyrazole-1-carboxamide N-(3-trifluoromethylphenyl)-3-(4-chlorophenyl)-4-carboethoxy-4-methyl-4,5-dihydro-1H-pyrazole-1-carboxamide N-(3-trifluoromethylphenyl)-3-(4-chlorophenyl)-4-carbomethoxy-4-methyl-4,5-dihydro-1H-pyrazole-1-carboxamide N-(3-trifluoromethylphenyl)-3-(4-chlorophenyl)-4-phenyl-4-methyl-4,5-dihydro-1H-pyrazole-1-carboxamide N-(4-(3-methylthiopropyl)phenyl)-3-(3-chloro-4-trifluoromethylphenyl)-4-(3-methylthiopropyl)-4-methyl-4,5-dihydro-1H-pyrazole-1-carboxamide N-(4-(3-methylthiopropyl)phenyl)-3-(4-chlorophenyl)-4-(3-methylthiopropyl)-4-methyl-4,5-dihydro-1H-pyrazole-1-carboxamide N-(4-bromophenyl)-3-(3-chloro-4-trifluoromethylphenyl)-4-(3-methylthiopropyl)-4-acetyl-4,5-dihydro-1H-pyrazole-1-carboxamide N-(4-bromophenyl)-3-(3-chloro-4-trifluoromethylphenyl)-4-(3-methylthiopropyl)-4-carbomethoxy-4,5-dihydro-1H-pyrazole-1-carboxamide N-(4-bromophenyl)-3-(3-chloro-4-trifluoromethylphenyl)-4-(3-methylthiopropyl)-4-ethyl-4,5-dihydro-1H-pyrazole-1-carboxamide N-(4-bromophenyl)-3-(3-chloro-4-trifluoromethylphenyl)-4-(3-methylthiopropyl)-4-methyl-4,5-dihydro-1H-pyrazole-1-carboxamide N-(4-bromophenyl)-3-(3-chloro-4-trifluoromethylphenyl)-4-(3-methylthiopropyl)-4-methyl-N-(2-methoxyethylsulfenyl)-4,5-dihydro-1H-pyrazole-1-carboxamide N-(4-bromophenyl)-3-(3-chloro-4-trifluoromethylphenyl)-4-(3-methylthiopropyl)-4-methyl-N-(2-nitrophenylsulfenyl)-4,5-dihydro-1H-pyrazole-1-carboxamide N-(4-bromophenyl)-3-(3-chloro-4-trifluoromethylphenyl)-4-(3-methylthiopropyl)-4-methyl-N-acetyl-4,5-dihydro-1H-pyrazole-1-carboxamide N-(4-bromophenyl)-3-(3-chloro-4-trifluoromethylphenyl)-4-(3-methylthiopropyl)-4-methyl-N-carboethoxy-4,5-dihydro-1H-pyrazole-1-carboxamide N-(4-bromophenyl)-3-(3-chloro-4-trifluoromethylphenyl)-4-(3-methylthiopropyl)-4-methyl-N-carbomethoxy-4,5-dihydro-1H-pyrazole-1-carboxamide N-(4-bromophenyl)-3-(3-chloro-4-trifluoromethylphenyl)-4-(3-methylthiopropyl)-4-methyl-N-carbomethoxycarbonyl-4,5-dihydro-1H-pyrazole-1-carboxamide N-(4-bromophenyl)-3-(3-chloro-4-trifluoromethylphenyl)-4-(3-methylthiopropyl)-4-methyl-N-carbomethoxysulfenyl-4,5-dihydro-1H-pyrazole-1-carboxamide N-(4-bromophenyl)-3-(3-chloro-4-trifluoromethylphenyl)-4-(3-methylthiopropyl)-4-methyl-N-dimethylcarbamoyl-4,5-dihydro-1H-pyrazole-1-carboxamide N-(4-bromophenyl)-3-(3-chloro-4-trifluoromethylphenyl)-4-(3-methylthiopropyl)-4-methyl-N-formyl-4,5-dihydro-1H-pyrazole-1-carboxamide N-(4-bromophenyl)-3-(3-chloro-4-trifluoromethylphenyl)-4-(3-methylthiopropyl)-4-methyl-N-methoxymethyl-4,5-dihydro-1H-pyrazole-1-carboxamide N-(4-bromophenyl)-3-(3-chloro-4-trifluoromethylphenyl)-4-(3-methylthiopropyl)-4-methyl-N-methyl-4,5-dihydro-1H-pyrazole-1-carboxamide N-(4-bromophenyl)-3-(3-chloro-4-trifluoromethylphenyl)-4-(3-methylthiopropyl)-4-methyl-N-methylsulfenyl-4,5-dihydro-1H-pyrazole-1-carboxamide N-(4-bromophenyl)-3-(3-chloro-4-trifluoromethylphenyl)-4-(3-methylthiopropyl)-4-methyl-N-trifluoroacetyl-4,5-dihydro-1H-pyrazole-1-carboxamide N-(4-bromophenyl)-3-(3-chloro-4-trifluoromethylphenyl)-4-carboethoxy-4-(2-chloroallyl)-4,5-dihydro-1H-pyrazole-1-carboxamide N-(4-bromophenyl)-3-(3-chloro-4-trifluoromethylphenyl)-4-carboethoxy-4-(2-methylthioethyl)-4,5-dihydro-1H-pyrazole-1-carboxamide N-(4-bromophenyl)-3-(3-chloro-4-trifluoromethylphenyl)-4-carboethoxy-4-(3-cyanopropyl)-4,5-dihydro-1H-pyrazole-1-carboxamide N-(4-bromophenyl)-3-(3-chloro-4-trifluoromethylphenyl)-4-carboethoxy-4-(4-chlorophenyl)-4,5-dihydro-1H-pyrazole-1-carboxamide N-(4-bromophenyl)-3-(3-chloro-4-trifluoromethylphenyl)-4-carboethoxy-4-(4-difluoromethoxyphenyl)-4,5-dihydro-1H-pyrazole-1-carboxamide N-(4-bromophenyl)-3-(3-chloro-4-trifluoromethylphenyl)-4-carboethoxy-4-(4-trifluoromethoxyphenyl)-4,5-dihydro-1H-pyrazole-1-carboxamide N-(4-bromophenyl)-3-(3-chloro-4-trifluoromethylphenyl)-4-carboethoxy-4-(4-trifluoromethylphenyl)-4,5-dihydro-1H-pyrazole-1-carboxamide N-(4-bromophenyl)-3-(3-chloro-4-trifluoromethylphenyl)-4-carboethoxy-4-acetyl-4,5-dihydro-1H-pyrazole-1-carboxamide N-(4-bromophenyl)-3-(3-chloro-4-trifluoromethylphenyl)-4-carboethoxy-4-allyl-4,5-dihydro-1H-pyrazole-1-carboxamide N-(4-bromophenyl)-3-(3-chloro-4-trifluoromethylphenyl)-4-carboethoxy-4-benzyl-4,5-dihydro-1H-pyrazole-1-carboxamide N-(4-bromophenyl)-3-(3-chloro-4-trifluoromethylphenyl)-4-carboethoxy-4-carbomethoxy-4,5-dihydro-1H-pyrazole-1-carboxamide N-(4-bromophenyl)-3-(3-chloro-4-trifluoromethylphenyl)-4-carboethoxy-4-ethyl-4,5-dihydro-1H-pyrazole-1-carboxamide N-(4-bromophenyl)-3-(3-chloro-4-trifluoromethylphenyl)-4-carboethoxy-4-methallyl-4,5-dihydro-1H-pyrazole-1-carboxamide N-(4-bromophenyl)-3-(3-chloro-4-trifluoromethylphenyl)-4-carboethoxy-4-methoxymethyl-4,5-dihydro-1H-pyrazole-1-carboxamide N-(4-bromophenyl)-3-(3-chloro-4-trifluoromethylphenyl)-4-carboethoxy-4-methyl-4,5-dihydro-1H-pyrazole-1-carboxamide N-(4-bromophenyl)-3-(3-chloro-4-trifluoromethylphenyl)-4-carboethoxy-4-methyl-N-(2-methoxyethylsulfenyl)-4,5-dihydro-1H-pyrazole-1-carboxamide N-(4-bromophenyl)-3-(3-chloro-4-trifluoromethylphenyl)-4-carboethoxy-4-methyl-N-(2-nitrophenylsulfenyl)-4,5-dihydro-1H-pyrazole-1-carboxamide N-(4-bromophenyl)-3-(3-chloro-4-trifluoromethylphenyl)-4-carboethoxy-4-methyl-N-acetyl-4,5-dihydro-1H-pyrazole-1-carboxamide N-(4-bromophenyl)-3-(3-chloro-4-trifluoromethylphenyl)-4-carboethoxy-4-methyl-N-carboethoxy-4,5-dihydro-1H-pyrazole-1-carboxamide N-(4-bromophenyl)-3-(3-chloro-4-trifluoromethylphenyl)-4-carboethoxy-4-methyl-N-carbomethoxy-4,5-dihydro-1H-pyrazole-1-carboxamide N-(4-bromophenyl)-3-(3-chloro-4-trifluoromethylphenyl)-4-carboethoxy-4-methyl-N-carbomethoxycarbonyl-4,5-dihydro-1H-pyrazole-1-carboxamide N-(4-bromophenyl)-3-(3-chloro-4-trifluoromethylphenyl)-4-carboethoxy-4-methyl-N-carbomethoxysulfenyl-4,5-dihydro-1H-pyrazole-1-carboxamide N-(4-bromophenyl)-3-(3-chloro-4-trifluoromethylphenyl)-4-carboethoxy-4-methyl-N-dimethylcarbamoyl-4,5-dihydro-1H-pyrazole-1-carboxamide N-(4-bromophenyl)-3-(3-chloro-4-trifluoromethylphenyl)-4-carboethoxy-4-methyl-N-formyl-4,5-dihydro-1H-pyrazole-1-carboxamide N-(4-bromophenyl)-3-(3-chloro-4-trifluoromethylphenyl)-4-carboethoxy-4-methyl-N-methoxymethyl-4,5-dihydro-1H-pyrazole-1-carboxamide N-(4-bromophenyl)-3-(3-chloro-4-trifluoromethylphenyl)-4-carboethoxy-4-methyl-N-methyl-4,5-dihydro-1H-pyrazole-1-carboxamide N-(4-bromophenyl)-3-(3-chloro-4-trifluoromethylphenyl)-4-carboethoxy-4-methyl-N-methylsulfenyl-4,5-dihydro-1H-pyrazole-1-carboxamide N-(4-bromophenyl)-3-(3-chloro-4-trifluoromethylphenyl)-4-carboethoxy-4-methyl-N-trifluoroacetyl-4,5-dihydro-1H-pyrazole-1-carboxamide N-(4-bromophenyl)-3-(3-chloro-4-trifluoromethylphenyl)-4-carboethoxy-4-methylthiomethyl-4,5-dihydro-1H-pyrazole-1-carboxamide N-(4-bromophenyl)-3-(3-chloro-4-trifluoromethylphenyl)-4-carboethoxy-4phenyl-4,5-dihydro-1H-pyrazole-1-carboxamide N-(4-bromophenyl)-3-(3-chloro-4-trifluoromethylphenyl)-4-methyl-4-(2chloroallyl)-4,5-dihydro-1H-pyrazole-1-carboxamide N-(4-bromophenyl)-3-(3-chloro-4-trifluoromethylphenyl)-4-methyl-4-(2-methylthioethyl)-4,5-dihydro-1H-pyrazole-1-carboxamide N-(4-bromophenyl)-3-(3-chloro-4-trifluoromethylphenyl)-4-methyl-4-(3-cyanopropyl)-4,5-dihydro-1H-pyrazole-1-carboxamide N-(4-bromophenyl)-3-(3-chloro-4-trifluoromethylphenyl)-4-methyl-4-(4-chlorophenyl)-4,5-dihydro-1H-pyrazole-1-carboxamide N-(4-bromophenyl)-3-(3-chloro-4-trifluoromethylphenyl)-4-methyl-4-(4-difluoromethoxyphenyl)-4,5-dihydro-1H-pyrazole-1-carboxamide N-(4-bromophenyl)-3-(3-chloro-4-trifluoromethylphenyl)-4-methyl-4-(4-trifluoromethoxyphenyl)-4,5-dihydro-1H-pyrazole-1-carboxamide N-(4-bromophenyl)-3-(3-chloro-4-trifluoromethylphenyl)-4-methyl-4-(4-trifluoromethylphenyl)-4,5-dihydro-1H-pyrazole-1-carboxamide N-(4-bromophenyl)-3-(3-chloro-4-trifluoromethylphenyl)-4-methyl-4-acetyl-4,5-dihydro-1H-pyrazole-1-carboxamide N-(4-bromophenyl)-3-(3-chloro-4-trifluoromethylphenyl)-4-methyl-4-allyl-4,5-dihydro-1H-pyrazole-1-carboxamide N-(4-bromophenyl)-3-(3-chloro-4-trifluoromethylphenyl)-4-methyl-4-benzyl-4,5-dihydro-1H-pyrazole-1-carboxamide N-(4-bromophenyl)-3-(3-chloro-4-trifluoromethylphenyl)-4-methyl-4-carboethoxy-4,5-dihydro-1H-pyrazole-1-carboxamide N-(4-bromophenyl)-3-(3-chloro-4-trifluoromethylphenyl)-4-methyl-4-ethyl-4,5-dihydro-1H-pyrazole-1-carboxamide N-(4-bromophenyl)-3-(3-chloro-4-trifluoromethylphenyl)-4-methyl-4-methallyl-4,5-dihydro-1H-pyrazole-1-carboxamide N-(4-bromophenyl)-3-(3-chloro-4-trifluoromethylphenyl)-4-methyl-4-methoxymethyl-4,5-dihydro-1H-pyrazole-1-carboxamide N-(4-bromophenyl)-3-(3-chloro-4-trifluoromethylphenyl)-4methyl-4-methylthiomethyl-4,5-dihydro-1H-pyrazole-1-carboxamide N-(4-bromophenyl)-3-(3-chloro-4-trifluoromethylphenyl)-4-methyl-4-phenyl-4,5-dihydro-1H-pyrazole-1-carboxamide N-(4-bromophenyl)-3-(3-chloro-4-trifluoromethylphenyl)-4-phenyl-4-(2-chloroallyl)-4,5-dihydro-1H-pyrazole-1-carboxamide N-(4-bromophenyl)-3-(3-chloro-4-trifluoromethylphenyl)-4-phenyl-4-(2-methylthioethyl)-4,5-dihydro-1H-pyrazole-1-carboxamide N-(4-bromophenyl)-3-(3-chloro-4-trifluoromethylphenyl)-4-phenyl-4-(3-cyanopropyl)-4,5-dihydro-1H-pyrazole-1-carboxamide N-(4-bromophenyl)-3-(3-chloro-4-trifluoromethylphenyl)-4-phenyl-4-(4-chlorophenyl)-4,5-dihydro-1H-pyrazole-1-carboxamide N-(4-bromophenyl)-3-(3-chloro-4-trifluoromethylphenyl)-4-phenyl-4-(4-difluoromethoxyphenyl)-4,5-dihydro-1H-pyrazole-1-carboxamide N-(4-bromophenyl)-3-(3-chloro-4-trifluoromethylphenyl)-4-phenyl-4-(4-trifluoromethoxyphenyl)-4,5-dihydro-1H-pyrazole-1-carboxamide N-(4-bromophenyl)-3-(3-chloro-4-trifluoromethylphenyl)-4-phenyl-4-(4-trifluoromethylphenyl)-4,5-dihydro-1H-pyrazole-1-carboxamide N-(4-bromophenyl)-3-(3-chloro-4-trifluoromethylphenyl)-4-phenyl-4-acetyl-4,5-dihydro-1H-pyrazole-1-carboxamide N-(4-bromophenyl)-3-(3-chloro-4-trifluoromethylphenyl)-4-phenyl-4-allyl-4,5-dihydro-1H-pyrazole-1-carboxamide N-(4-bromophenyl)-3-(3-chloro-4-trifluoromethylphenyl)-4-phenyl-4-benzyl-4,5-dihydro-1H-pyrazole-1-carboxamide N-(4-bromophenyl)-3-(3-chloro-4-trifluoromethylphenyl)-4-phenyl-4-carbomethoxy-4,5-dihydro-1H-pyrazole-1-carboxamide N-(4-bromophenyl)-3-(3-chloro-4-trifluoromethylphenyl)-4-phenyl-4-ethyl-4,5-dihydro-1H-pyrazole-1-carboxamide N-(4-bromophenyl)-3-(3-chloro-4-trifluoromethylphenyl)-4-phenyl-4-methallyl-4,5-dihydro-1H-pyrazole-1-carboxamide N-(4-bromophenyl)-3-(3-chloro-4-trifluoromethylphenyl)-4-phenyl-4-methoxymethyl-4,5-dihydro-1H-pyrazole-1-carboxamide N-(4-bromophenyl)-3-(3-chloro-4-trifluoromethylphenyl)-4-phenyl-4-methyl-4,5-dihydro-1H-pyrazole-1-carboxamide N-(4-bromophenyl)-3-(3-chloro-4-trifluoromethylphenyl)-4-phenyl-4-methyl-N-(2-methoxyethylsulfenyl)-4,5-dihydro-1H-pyrazole-1-carboxamide N-(4-bromophenyl)-3-(3-chloro-4-trifluoromethylphenyl)-4-phenyl-4-methyl-N-(2-nitrophenylsulfenyl)-4,5-dihydro-1H-pyrazole-1-carboxamide N-(4-bromophenyl)-3-(3-chloro-4-trifluoromethylphenyl)-4-phenyl-4-methyl-N-acetyl-4,5-dihydro-1H-pyrazole-1-carboxamide N-(4-bromophenyl)-3-(3-chloro-4-trifluoromethylphenyl)-4-phenyl-4-methyl-N-carboethoxy-4,5-dihydro-1H-pyrazole-1-carboxamide N-(4-bromophenyl)-3-(3-chloro-4-trifluoromethylphenyl)-4-phenyl-4-methyl-N-carbomethoxy-4,5-dihydro-1H-pyrazole-1-carboxamide N-(4-bromophenyl)-3-(3-chloro-4-trifluoromethylphenyl)-4-phenyl-4-methyl-N-carbomethoxycarbonyl-4,5-dihydro-1H-pyrazole-1-carboxamide N-(4-bromophenyl)-3-(3-chloro-4-trifluoromethylphenyl)-4-phenyl-4-methyl-N-carbomethoxysulfenyl-4,5-dihydro-1H-pyrazole-1-carboxamide N-(4-bromophenyl)-3-(3-chloro-4-trifluoromethylphenyl)-4-phenyl-4-methyl-N-dimethylcarbamoyl-4,5-dihydro-1H-pyrazole-1-carboxamide N-(4-bromophenyl)-3-(3-chloro-4-trifluoromethylphenyl)-4-phenyl-4-methyl-N-formyl-4,5-dihydro-1H-pyrazole-1-carboxamide N-(4-bromophenyl)-3-(3-chloro-4-trifluoromethylphenyl)-4-phenyl-4-methyl-N-methoxymethyl-4,5-dihydro-1H-pyrazole-1-carboxamide N-(4-bromophenyl)-3-(3-chloro-4-trifluoromethylphenyl)-4-phenyl-4-methyl-N-methyl-4,5-dihydro-1H-pyrazole-1-carboxamide N-(4-bromophenyl)-3-(3-chloro-4-trifluoromethylphenyl)-4-phenyl-4-methyl-N-methylsulfenyl-4,5-dihydro-1H-pyrazole-1-carboxamide N-(4-bromophenyl)-3-(3-chloro-4-trifluoromethylphenyl)-4-phenyl-4-methyl-N-trifluoroacetyl-4,5-dihydro-1H-pyrazole-1-carboxamide N-(4-bromophenyl)-3-(3-chloro-4-trifluoromethylphenyl)-4-phenyl-4-methylthiomethyl-4,5-dihydro-1H-pyrazole-1-carboxamide N-(4-bromophenyl)-3-(4-chlorophenyl)-4-(3-methylthiopropyl)-4-acetyl-4,5-dihydro-1H-pyrazole-1-carboxamide N-(4-bromophenyl)-3-(4-chlorophenyl)-4-(3-methylthiopropyl)-4-carbomethoxy-4,5-dihydro-1H-pyrazole-1-carboxamide N-(4-bromophenyl)-3-(4-chlorophenyl)-4-(3-methylthiopropyl)-4-ethyl-4,5-dihydro-1H-pyrazole-1-carboxamide N-(4-bromophenyl)-3-(4-chlorophenyl)-4-(3-methylthiopropyl)-4-methyl-4,5-dihydro-1H-pyrazole-1-carboxamide N-(4-bromophenyl)-3-(4-chlorophenyl)-4-(3-methylthiopropyl)-4-methyl-N-(2-methoxyethylsulfenyl)-4,5-dihydro-1H-pyrazole-1-carboxamide N-(4-bromophenyl)-3-(4-chlorophenyl)-4-(3-methylthiopropyl)-4-methyl-N-(2-nitrophenylsulfenyl)-4,5-dihydro-1H-pyrazole-1-carboxamide N-(4-bromophenyl)-3-(4-chlorophenyl)-4-(3-methylthiopropyl)-4-methyl-N-acetyl-4,5-dihydro-1H-pyrazole-1-carboxamide N-(4-bromophenyl)-3-(4-chlorophenyl)-4-(3-methylthiopropyl)-4-methyl-N-carboethoxy-4,5-dihydro-1H-pyrazole-1-carboxamide N-(4-bromophenyl)-3-(4-chlorophenyl)-4-(3-methylthiopropyl)-4-methyl-N-carbomethoxy-4,5-dihydro-1H-pyrazole-1-carboxamide N-(4-bromophenyl)-3-(4-chlorophenyl)-4-(3-methylthiopropyl)-4-methyl-N-carbomethoxysulfenyl-4,5-dihydro-1H-pyrazole-1-carboxamide N-(4-bromophenyl)-3-(4-chlorophenyl)-4-(3-methylthiopropyl)-4-methyl-N-dimethylcarbamoyl-4,5-dihydro-1H-pyrazole-1-carboxamide N-(4-bromophenyl)-3-(4-chlorophenyl)-4-(3-methylthiopropyl)-4-methyl-N-formyl-4,5-dihydro-1H-pyrazole-1-carboxamide N-(4-bromophenyl)-3-(4-chlorophenyl)-4-(3-methylthiopropyl)-4-methyl-N-methoxymethyl-4,5-dihydro-1H-pyrazole-1-carboxamide N-(4-bromophenyl)-3-(4-chlorophenyl)-4-(3-methylthiopropyl)-4-methyl-N-methyl-4,5-dihydro-1H-pyrazole-1-carboxamide N-(4-bromophenyl)-3-(4-chlorophenyl)-4-(3-methylthiopropyl)-4-methyl-N-methylsulfenyl-4,5-dihydro-1H-pyrazole-1-carboxamide N-(4-bromophenyl)-3-(4-chlorophenyl)-4-(3-methylthiopropyl)-4-methyl-N-trifluoroacetyl-4,5-dihydro-1H-pyrazole-1-carboxamide N-(4-bromophenyl)-3-(4-chlorophenyl)-4-(3-methylthiopropyl)-4-methylthiomethyl-4,5-dihydro-1H-pyrazole-1-carboxamide N-(4-bromophenyl)-3-(4-chlorophenyl)-4-(3-methylthiopropyl)-4-phenyl-4,5-dihydro-1H-pyrazole-1-carboxamide N-(4-bromophenyl)-3-(4-chlorophenyl)-4-carboethoxy-4-(2-chloroallyl)-4,5-dihydro-1H-pyrazole-1-carboxamide
N-(4-bromophenyl)-3-(4-chlorophenyl)-4-carboethoxy-4-(2-methylthioethyl)-4,5-dihydro-1H-pyrazole-1-carboxamide
N-(4-bromophenyl)-3-(4-chlorophenyl)-4-carboethoxy-4-(3-cyanopropyl)-4,5-dihydro-1H-pyrazole-1-carboxamide
N-(4-bromophenyl)-3-(4-chlorophenyl)-4-carboethoxy-4-(4-chlorophenyl)-4,5-dihydro-1H-pyrazole-1-carboxamide
N-(4-bromophenyl)-3-(4-chlorophenyl)-4-carboethoxy-4-(difluoromethoxyphenyl)-4,5-dihydro-1H-pyrazole-1-carboxamide
N-(4-bromophenyl)-3-(4-chlorophenyl)-4-carboethoxy-4-(4-trifluoromethoxyphenyl)-4,5-dihydro-1H-pyrazole-1-carboxamide
N-(4-bromophenyl)-3-(4-chlorophenyl)-4-carboethoxy-4-(4-trifluoromethylphenyl)-4,5-dihydro-1H-pyrazole-1-carboxamide
N-(4-bromophenyl)-3-(4-chlorophenyl)-4-carboethoxy-4-acetyl-4,5-dihydro-1H-pyrazole-1-carboxamide
N-(4-bromophenyl)-3-(4-chlorophenyl)-4-carboethoxy-4-allyl-4,5-dihydro-1H-pyrazole-1-carboxamide
N-(4-bromophenyl)-3-(4-chlorophenyl)-4-carboethoxy-4-benzyl-4,5-dihydro-1H-pyrazole-1-carboxamide
N-(4-bromophenyl)-3-(4-chlorophenyl)-4-carboethoxy-4-carbomethoxy-4,5-dihydro-1H-pyrazole-1-carboxamide
N-(4-bromophenyl)-3-(4-chlorophenyl)-4-carboethoxy-4-ethyl-4,5-dihydro-1H-pyrazole-1-carboxamide
N-(4-bromophenyl)-3-(4-chlorophenyl)-4-carboethoxy-4-methallyl-4,5-dihydro-1H-pyrazole-1-carboxamide
N-(4-bromophenyl)-3-(4-chlorophenyl)-4-carboethoxy-4-methoxymethyl-4,5-dihydro-1H-pyrazole-1-carboxamide
N-(4-bromophenyl)-3-(4-chlorophenyl)-4-carboethoxy-4-methyl-4,5-dihydro-1H-pyrazole-1-carboxamide
N-(4-bromophenyl)-3-(4-chlorophenyl)-4-carboethoxy-4-methyl-N-(2-methoxyethylsulfenyl)-4,5-dihydro-1H-pyrazole-1-carboxamide
N-(4-bromophenyl)-3-(4-chlorophenyl)-4-carboethoxy-4-methyl-N-(2-nitrophenylsulfenyl)-4,5-dihydro-1H-pyrazole-1-carboxamide
N-(4-bromophenyl)-3-(4-chlorophenyl)-4-carboethoxy-4-methyl-N-acetyl-4,5-dihydro-1H-pyrazole-1-carboxamide
N-(4-bromophenyl)-3-(4-chlorophenyl)-4-carboethoxy-4-methyl-N-carboethoxy-4,5-dihydro-1H-pyrazole-1-carboxamide
N-(4-bromophenyl)-3-(4-chlorophenyl)-4-carboethoxy-4-methyl-N-carbomethoxy-4,5-dihydro-1H-pyrazole-1-carboxamide
N-(4-bromophenyl)-3-(4-chlorophenyl)-4-carboethoxy-4-methyl-N-carbomethoxycarbonyl-4,5-dihydro-1H-pyrazole-1-carboxamide
N-(4-bromophenyl)-3-(4-chlorophenyl)-4-carboethoxy-4-methyl-N-carbomethoxysulfenyl-4,5-dihydro-1H-pyrazole-1-carboxamide
N-(4-bromophenyl)-3-(4-chlorophenyl)-4-carboethoxy-4-methyl-N-dimethylcarbamoyl-4,5-dihydro-1H-pyrazole-1-carboxamide
N-(4-bromophenyl)-3-(4-chlorophenyl)-4-carboethoxy-4-methyl-N-formyl-4,5-dihydro-1H-pyrazole-1-carboxamide
N-(4-bromophenyl)-3-(4-chlorophenyl)-4-carboethoxy-4-methyl-N-methoxymethyl-4,5-dihydro-1H-pyrazole-1-carboxamide
N-(4-bromophenyl)-3-(4-chlorophenyl)-4-carboethoxy-4-methyl-N-methyl-4,5-dihydro-1H-pyrazole-1-carboxamide
N-(4-bromophenyl)-3-(4-chlorophenyl)-4-carboethoxy-4-methyl-N-methylsulfenyl-4,5-dihydro-1H-pyrazole-1-carboxamide
N-(4-bromophenyl)-3-(4-chlorophenyl)-4-carboethoxy-4-methyl-N-trifluoroacetyl-4,5-dihydro-1H-pyrazole-1-carboxamide
N-(4-bromophenyl)-3-(4-chlorophenyl)-4-carboethoxy-4-methylthiomethyl-4,5-dihydro-1H-pyrazole-1-carboxamide
N-(4-bromophenyl)-3-(4-chlorophenyl)-4-carboethoxy-4-phenyl-4,5-dihydro-1H-pyrazole-1-carboxamide
N-(4-bromophenyl)-3-(4-chlorophenyl)-4-carbomethoxy-4-methyl-4,5-dihydro-1H-pyrazole-1-carboxamide
N-(4-bromophenyl)-3-(4-chlorophenyl)-4-methyl-4-(2-chloroallyl)-4,5-dihydro-1H-pyrazole-1-carboxamide
N-(4-bromophenyl)-3-(4-chlorophenyl)-4-methyl-4-(2-methylthioethyl)-4,5-dihydro-1H-pyrazole-1-carboxamide
N-(4-bromophenyl)-3-(4-chlorophenyl)-4-methyl-4-(3-cyanopropyl)-4,5-dihydro-1H-pyrazole-1-carboxamide
N-(4-bromophenyl)-3-(4-chlorophenyl)-4-methyl-4-(4-chlorophenyl)-4,5-dihydro-1H-pyrazole-1-carboxamide
N-(4-bromophenyl)-3-(4-chlorophenyl)-4-methyl-4-(4-difluoromethoxyphenyl)-4,5-dihydro-1H-pyrazole-1-carboxamide
N-(4-bromophenyl)-3-(4-chlorophenyl)-4-methyl-4-(4-trifluoromethoxyphenyl)-4,5-dihydro-1H-pyrazole-1-carboxamide
N-(4-bromophenyl)-3-(4-chlorophenyl)-4-methyl-4-(4-trifluoromethylphenyl)-4,5-dihydro-1H-pyrazole-1-carboxamide
N-(4-bromophenyl)-3-(4-chlorophenyl)-4-methyl-4-acetyl-4,5-dihydro-1H-pyrazole-1-carboxamide
N-(4-bromophenyl)-3-(4-chlorophenyl)-4-methyl-4-allyl-4,5-dihydro-1H-pyrazole-1-carboxamide
N-(4-bromophenyl)-3-(4-chlorophenyl)-4-methyl-4-benzyl-4,5-dihydro-1H-pyrazole-1-carboxamide
N-(4-bromophenyl)-3-(4-chlorophenyl)-4-methyl-4-carbomethoxy-4,5-dihydro-1H-pyrazole-1-carboxamide
N-(4-bromophenyl)-3-(4-chlorophenyl)-4-methyl-4-ethyl-4,5-dihydro-1H-pyrazole-1-carboxamide
N-(4-bromophenyl)-3-(4-chlorophenyl)-4-methyl-4-methallyl-4,5-dihydro-1H-pyrazole-1-carboxamide
N-(4-bromophenyl)-3-(4-chlorophenyl)-4-methyl-4-methoxymethyl-4,5-dihydro-1H-pyrazole-1-carboxamide
N-(4-bromophenyl)-3-(4-chlorophenyl)-4-methyl-4-methylthiomethyl-4,5-dihydro-1H-pyrazole-1-carboxamide
N-(4-bromophenyl)-3-(4-chlorophenyl)-4-methyl-4-phenyl-4,5-dihydro-1H-pyrazole-1-carboxamide
N-(4-bromophenyl)-3-(4-chlorophenyl)-4-phenyl-4-(2-chloroallyl)-4,5-dihydro-1H-pyrazole-1-carboxamide
N-(4-bromophenyl)-3-(4-chlorophenyl)-4-phenyl-4-(2-methylthioethyl)-4,5-dihydro-1H-pyrazole-1-carboxamide
N-(4-bromophenyl)-3-(4-chlorophenyl)-4-phenyl-4-(3-cyanopropyl)-4,5-dihydro-1H-pyrazole-1-carboxamide N-(4-bromophenyl)-3-(4-chlorophenyl)-4-phenyl-4-(4-chlorophenyl)-4,5-dihydro-1H-pyrazole-1-carboxamide
N-(4-bromophenyl)-3-(4-chlorophenyl)-4-phenyl-4-(4-difluoromethoxyphenyl)-4,5-dihydro-1H-pyrazole-1-carboxamide
N-(4-bromophenyl)-3-(4-chlorophenyl)-4-phenyl-4-(4-trifluoromethoxyphenyl)-4,5-dihydro-1H-pyrazole-1-carboxamide
N-(4-bromophenyl)-3-(4-chlorophenyl)-4-phenyl-4-(4-trifluoromethylphenyl)-4,5-dihydro-1H-pyrazole-1-carboxamide
N-(4-bromophenyl)-3-(4-chlorophenyl)-4-phenyl-4-acetyl-4,5-dihydro-1H-pyrazole-1-carboxamide
N-(4-bromophenyl)-3-(4-chlorophenyl)-4-phenyl-4-allyl-4,5-dihydro-1H-pyrazole-1-carboxamide
N-(4-bromophenyl)-3-(4-chlorophenyl)-4-phenyl-4-benzyl-4,5-dihydro-1H-pyrazole-1-carboxamide
N-(4-bromophenyl)-3-(4-chlorophenyl)-4-phenyl-4-carbomethoxy-4,5-dihydro-1H-pyrazole-1-carboxamide
N-(4-bromophenyl)-3-(4-chlorophenyl)-4-phenyl-4-ethyl-4,5-dihydro-1H-pyrazole-1-carboxamide
N-(4-bromophenyl)-3-(4-chlorophenyl)-4-phenyl-4-methallyl-4,5-dihydro-1H-pyrazole-1-carboxamide
N-(4-bromophenyl)-3-(4-chlorophenyl)-4-phenyl-4-methoxymethyl-4,5-dihydro-1H-pyrazole-1-carboxamide
N-(4-bromophenyl)-3-(4-chlorophenyl)-4-phenyl-4-methyl-4,5-dihydro-1H-pyrazole-1-carboxamide
N-(4-bromophenyl)-3-(4-chlorophenyl)-4-phenyl-4-methyl-N-(2-methoxyethylsulfenyl)-4,5-dihydro-1H-pyrazole-1-carboxamide
N-(4-bromophenyl)-3-(4-chlorophenyl)-4-phenyl-4-methyl-N-(2-nitrophenylsulfenyl)-4,5-dihydro-1H-pyrazole-1-carboxamide
N-(4-bromophenyl)-3-(4-chlorophenyl)-4-phenyl-4-methyl-N-acetyl-4,5-dihydro-1H-pyrazole-1-carboxamide
N-(4-bromophenyl)-3-(4-chlorophenyl)-4-phenyl-4-methyl-N-carboethoxy-4,5-dihydro-1H-pyrazole-1-carboxamide
N-(4-bromophenyl)-3-(4-chlorophenyl)-4-phenyl-4-methyl-N-carbomethoxy-4,5-dihydro-1H-pyrazole-1-carboxamide
N-(4-bromophenyl)-3-(4-chlorophenyl)-4-phenyl-4-methyl-N-carbomethoxycarbonyl-4,5-dihydro-1H-pyrazole-1-carboxamide
N-(4-bromophenyl)-3-(4-chlorophenyl)-4-phenyl-4-methyl-N-carbomethoxysulfenyl-4,5-dihydro-1H-pyrazole-1-carboxamide
N-(4-bromophenyl)-3-(4-chlorophenyl)-4-phenyl-4-methyl-N-dimethylcarbamoyl-4,5-dihydro-1H-pyrazole-1-carboxamide
N-(4-bromophenyl)-3-(4-chlorophenyl)-4-phenyl-4-methyl-N-formyl-4,5-dihydro-1H-pyrazole-1-carboxamide
N-(4-bromophenyl)-3-(4-chlorophenyl)-4-phenyl-4-methyl-N-methoxymethyl-4,5-dihydro-1H-pyrazole-1-carboxamide
N-(4-bromophenyl)-3-(4-chlorophenyl)-4-phenyl-4-methyl-N-methyl-4,5-dihydro-1H-pyrazole-1-carboxamide
N-(4-bromophenyl)-3-(4-chlorophenyl)-4-phenyl-4-methyl-N-methylsulfenyl-4,5-dihydro-1H-pyrazole-1-carboxamide
N-(4-bromophenyl)-3-(4-chlorophenyl)-4-phenyl-4-methyl-N-trifluoroacetyl-4,5-dihydro-1H-pyrazole-1-carboxamide
N-(4-bromophenyl)-3-(4-chlorophenyl)-4-phenyl-4-methylthiomethyl-4,5-dihydro-1H-pyrazole-1-carboxamide
N-(4-bromophenyl)-3-(4-fluorophenyl)-4-butyl-4-methyl-4,5-dihydro-1H-pyrazole-1-carboxamide
N-(4-bromophenyl)-3-(4-fluorophenyl)-4-carbomethoxy-4-methyl-4,5-dihydro-1H-pyrazole-1-carboxamide
N-(4-bromophenyl)-3-phenyl-4-carbomethoxy-4-methyl-4,5-dihydro-1H-pyrazole-1-carboxamide
N-(4-carboethoxyphenyl)-3-(3-chloro-4-trifluoromethylphenyl)-4-carboethoxy-4-methyl-4,5-dihydro-1H-pyrazole-1-carboxamide
N-(4-carboethoxyphenyl)-3-(4-chlorophenyl)-4-carboethoxy-4-methyl-4,5-dihydro-1H-pyrazole-1-carboxamide
N-(4-carboethoxyphenyl)-3-(4-chlorophenyl)-4-phenyl-4-methyl-4,5-dihydro-1H-pyrazole-1-carboxamide
N-(4-carboisopropoxyphenyl)-3-(3-chloro-4-trifluoromethylphenyl)-4-(3-methylthiopropyl)-4-methyl-4,5-dihydro-1H-pyrazole-1-carboxamide
N-(4-carboisopropoxyphenyl)-3-(3-chloro-4-trifluoromethylphenyl)-4-carboethoxy-4-methyl-4,5-dihydro-1H-pyrazole-1-carboxamide
N-(4-carboisopropoxyphenyl)-3-(3-chloro-4-trifluoromethylphenyl)-4-phenyl-4-methyl-4,5-dihydro-1H-pyrazole-1-carboxamide
N-(4-carboisopropoxyphenyl)-3-(4-chlorophenyl)-4-(3-methylthiopropyl)-4-methyl-4,5-dihydro-1H-pyrazole-1-carboxamide
N-(4-carboisopropoxyphenyl)-3-(4-chlorophenyl)-4-carboethoxy-4-methyl-4,5-dihydro-1H-pyrazole-1-carboxamide
N-(4-carboisopropoxyphenyl)-3-(4-chlorophenyl)-4-phenyl-4-methyl-4,5-dihydro-1H-pyrazole-1-carboxamide
N-(4-carbomethoxyphenyl)-3-(3-chloro-4-trifluoromethylphenyl)-4-(3-methylthiopropyl)-4-methyl-4,5-dihydro-1H-pyrazole-1-carboxamide
N-(4-carbomethoxyphenyl)-3-(3-chloro-4-trifluoromethylphenyl)-4-carboethoxy-4-methyl-4,5-dihydro-1H-pyrazole-1-carboxamide
N-(4-carbomethoxyphenyl)-3-(3-chloro-4-trifluoromethylphenyl)-4-phenyl-4-methyl-4,5-dihydro-1H-pyrazole-1-carboxamide
N-(4-carbomethoxyphenyl)-3-(4-chlorophenyl)-4-(3-methylthiopropyl)-4-methyl-4,5-dihydro-1H-pyrazole-1-carboxamide
N-(4-carbomethoxyphenyl)-3-(4-chlorophenyl)-4-carboethoxy-4-methyl-4,5-dihydro-1H-pyrazole-1-carboxamide
N-(4-carbomethoxyphenyl)-3-(4-chlorophenyl)-4-phenyl-4-methyl-4,5-dihydro-1H-pyrazole-1-carboxamide
N-(4-bromo-3-methylphenyl)-3-(4-chlorophenyl)-4-carbomethoxy-4-methyl-4,5-dihydro-1H-pyrazole-1-carboxamide
N-(4-chloro-3-trifluoromethylphenyl)-3-(4-chlorophenyl)-4-carbomethoxy-4-methyl-4,5-dihydro-1H-pyrazole-1-carboxamide
N-(4-chlorophenyl)-3-(3,4-dichlorophenyl)-4-phenyl-4-methyl-4,5-dihydro-1H-pyrazole-1-carboxamide
N-(4-chlorophenyl)-3-(4-bromophenyl)-4-butyl-4-methyl-4,5-dihydro-1H-pyrazole-1-carboxamide
N-(4-chlorophenyl)-3-(4-bromophenyl)-4-butyl-4-methyl-N-(1-methylethyl)-4,5-dihydro-1H-pyrazole-1-carboxamide N-(4-chlorophenyl)-3-(4-bromophenyl)-4-carbomethoxy-4-methyl-4,5-dihydro-1H-pyrazole-1-carboxamide
N-(4-chlorophenyl)-3-(4-fluorophenyl)-4-butyl-4-methyl-4,5-dihydro-1H-pyrazole-1-carboxamide
N-(4-chlorophenyl)-3-(4-fluorophenyl)-4-carbomethoxy-4-methyl-4,5-dihydro-1H-pyrazole-1-carboxamide
N-(4-chlorophenyl)-3-(4-methylphenyl)-4-carbomethoxy-4-methyl-4,5-dihydro-1H-pyrazole-1-carboxamide
N-(4-chlorophenyl)-3-(4-methoxyphenyl)-4-carbomethoxy-4-methyl-4,5-dihydro-1H-pyrazole-1-carboxamide
N-(4-chlorophenyl)-3-(4-methylsulfonylphenyl)-4-carbomethoxy-4-methyl-4,5-dihydro-1H-pyrazole-1-carboxamide
N-(4-chlorophenyl)-3-(4-methylthiophenyl)-4-carbomethoxy-4-methyl-4,5-dihydro-1H-pyrazole-1-carboxamide
N-(4-chlorophenyl)-3-(4-trifluoromethylphenyl)-4-carbomethoxy-4-methyl-4,5-dihydro-1H-pyrazole-1-carboxamide
N-(4-chlorophenyl)-3-phenyl-4-carboethoxy-4-methyl-4,5-dihydro-1H-pyrazole-1-carboxamide
N-(4-chlorophenyl)-3-phenyl-4-carbomethoxy-4-methyl-4,5-dihydro-1H-pyrazole-1-carboxamide
N-(4-chlorophenyl)-3-phenyl-4-dimethylcarboxamido-4-methyl-4,5-dihydro-1H-pyrazole-1-carboxamide
N-(4-chlorophenyl)-3-phenyl-N,4-bis-carbomethoxy-4-methyl-4,5-dihydro-1H-pyrazole-1-carboxamide
N-(4-chlorophenyl)-4-methyl-3,4-diphenyl-4,5-dihydro-1H-pyrazole-1-carboxamide
N-(4-difluoromethoxyphenyl)-3-(3-chloro-4-trifluoromethylphenyl)-4-(3-methylthiopropyl)-4-methyl-4,5-dihydro-1H-pyrazole-1-carboxamide
N-(4-difluoromethoxyphenyl)-3-(3-chloro-4-trifluoromethylphenyl)-4-carboethoxy-4methyl-4,5-dihydro-1H-pyrazole-1-carboxamide
N-(4-difluoromethoxyphenyl)-3-(3-chloro-4-trifluoromethylphenyl)-4-phenyl-4-methyl-4,5-dihydro-1H-pyrazole-1-carboxamide
N-(4-difluoromethoxyphenyl)-3-(4-chlorophenyl)-4-(3-methylthiopropyl)-4-methyl-4,5-dihydro-1H-pyrazole-1-carboxamide
N-(4-difluoromethoxyphenyl)-3-(4-chlorophenyl)-4-carboethoxy-4-methyl-4,5-dihydro-1H-pyrazole-1-carboxamide
N-(4-difluoromethoxyphenyl)-3-(4-chlorophenyl)-4-phenyl-4-methyl-4,5-dihydro-1H-pyrazole-1-carboxamide
N-(4-dimethylaminoxyphenyl)-3-(4chlorophenyl)-4-carbomethoxy-4-methyl-4,5-dihydro-1H-pyrazole-1-carboxamide
N-(4-dimethylsulfonamidophenyl)-3-(3-chloro-4-trifluoromethylphenyl)-4-(3-methylthiopropyl)-4-methyl-4,5-dihydro-1H-pyrazole-1-carboxamide
N-(4-dimethylsulfonamidophenyl)-3-(3-chloro-4-trifluoromethylphenyl)-4-carboethoxy-4-methyl-4,5-dihydro-1H-pyrazole-1-carboxamide
N-(4-dimethylsulfonamidophenyl)-3-(3-chloro-4-trifluoromethylphenyl)-4-phenyl-4-methyl-4,5-dihydro-1H-pyrazole-1-carboxamide
N-(4-dimethylsulfonamidophenyl)-3-(4-chlorophenyl)-4-(3-methylthiopropyl)-4-methyl-4,5-dihydro-1H-pyrazole-1-carboxamide
N-(4-dimethylsulfonamidophenyl)-3-(4-chlorophenyl)-4-carboethoxy-4-methyl-4,5-dihydro-1H-pyrazole-1-carboxamide
N-(4-dimethylsulfonamidophenyl)-3-(4-chlorophenyl)-4-phenyl-4-methyl-4,5-dihydro-1H-pyrazole-1-carboxamide
N-(4-fluorophenyl)-3-(4-bromophenyl)-4-carbomethoxy-4-methyl-4,5-dihydro-1H-pyrazole-1-carboxamide
N-(4-fluorophenyl)-3-(4-chlorophenyl)-4-carbomethoxy-4-methyl-4,5-dihydro-1H-pyrazole-1-carboxamide
N-(4-fluorophenyl)-3-(4-fluorophenyl)-4-carbomethoxy-4-methyl-4,5-dihydro-1H-pyrazole-1-carboxamide
N-(4-fluorophenyl)-3-phenyl-4-carbomethoxy-4-methyl-4,5-dihydro-1H-pyrazole-1-carboxamide
N-(4-iodophenyl)-3-(4-chlorophenyl)-4-carbomethoxy-4-methyl-4,5-dihydro-1H-pyrazole-1-carboxamide
N-(4-methoxyphenyl)-3-(4-chlorophenyl)-4-carbomethoxy-4-methyl-4,5-dihydro-1H-pyrazole-1-carboxamide
N-(4-methylphenyl)-3-(4-chlorophenyl)-4-carbomethoxy-4-methyl-4,5-dihydro-1H-pyrazole-1-carboxamide
N-(4-methylsulfonylphenyl)-3-(3-chloro-4-trifluoromethylphenyl)-4-(3-methylthiopropyl)-4-methyl-4,5-dihydro-1H-pyrazole-1-carboxamide
N-(4-methylsulfonylphenyl)-3-(3-chloro-4-trifluoromethylphenyl)-4-carboethoxy-4-methyl-4,5-dihydro-1H-pyrazole-1-carboxamide
N-(4-methylsulfonylphenyl)-3-(3-chloro-4-trifluoromethylphenyl)-4-phenyl-4-methyl-4,5-dihydro-1H-pyrazole-1-carboxamide
N-(4-methylsulfonylphenyl)-3-(4-chlorophenyl)-4-(3-methylthiopropyl)-4-methyl-4,5-dihydro-1H-pyrazole-1-carboxamide
N-(4-methylsulfonylphenyl)-3-(4-chlorophenyl)-4-carboethoxy-4-methyl-4,5-dihydro-1H-pyrazole-1-carboxamide
N-(4-methylsulfonylphenyl)-3-(4-chlorophenyl)-4-carbomethoxy-4-methyl-4,5-dihydro-1H-pyrazole-1-carboxamide
N-(4-methylsulfonylphenyl)-3-(4-chlorophenyl)-4-phenyl-4-methyl-4,5-dihydro-1H-pyrazole-1-carboxamide
N-(4-methylsulfonylphenyl)-3-(4-chlorophenyl)-4-carbomethoxy-4-methyl-4,5-dihydro-1H-pyrazole-1-carboxamide
N-(4-methylthiophenyl)-3-(3-chloro-4-trifluoromethylphenyl)-4-(3-methylthiopropyl)-4-methyl-4,5-dihydro-1H-pyrazole-1-carboxamide
N-(4-methylthiophenyl)-3-(3-chloro-4-trifluoromethylphenyl)-4-carboethoxy-4-methyl-4,5-dihydro-1H-pyrazole-1-carboxamide
N-(4-methylthiophenyl)-3-(3-chloro-4-trifluoromethylphenyl)-4-phenyl-4-methyl-4,5-dihydro-1H-pyrazole-1-carboxamide
N-(4-methylthiophenyl)-3-(4-chlorophenyl)-4-(3-methylthiopropyl)-4-methyl-4,5-dihydro-1H-pyrazole-1-carboxamide
N-(4-methylthiophenyl)-3-(4-chlorophenyl)-4-carboethoxy-4-methyl-4,5-dihydro-1H-pyrazole-1-carboxamide
N-(4-methylthiophenyl)-3-(4-chlorophenyl)-4-carbomethoxy-4-methyl4,5-dihydro-1H-pyrazole-1-carboxamide N-(4-methylthiophenyl)-3-(4-chlorophenyl)-4-phenyl-4-methyl-4,5-dihydro-1H-pyrazole-1-carboxamide
N-(4-nitrophenyl)-3-(3-chloro-4-trifluoromethylphenyl)-4-(3-methylthiopropyl)-4methyl-4,5-dihydro-1H-pyrazole-1-carboxamide
N-(4-nitrophenyl)-3-(3-chloro-4-trifluoromethylphenyl)-4carboethoxy-4-methyl-4,5-dihydro-1H-pyrazole-1-carboxamide
N-(4-nitrophenyl)-3-(3-chloro-4-trifluoromethylphenyl)-4-phenyl-4-methyl-4,5-dihydro-1H-pyrazole-1-carboxamide
N-(4-nitrophenyl)-3-(4-chlorophenyl)-4-(3-methylthiopropyl)-4-methyl-4,5-dihydro-1H-pyrazole-1-carboxamide
N-(4-nitrophenyl)-3-(4-chlorophenyl)-4-carboethoxy-4-methyl-4,5-dihydro-1H-pyrazole-1-carboxamide
N-(4-nitrophenyl)-3-(4-chlorophenyl)-4-carbomothoxy-4,5-dihydro-1H-pyrazole-1-carboxamide
N-(4-nitrophenyl)-3-(4-chlorophenyl)-4-phenyl-4-methyl-4,5-dihydro-1H-pyrazole-1-carboxamide
N-(4-phenylphenyl)-3-(3-chloro-4-trifluoromethylphenyl)-4-phenyl-4-methyl-4,5-dihydro-1H-pyrazole-1-carboxamide
N-(4-phenylphenyl)-3-(4-chlorophenyl)-4-phenyl-4-methyl-4,5-dihydro-1H-pyrazole-1-carboxamide
N-(4-trifluoromethoxyphenyl)-3-(3-chloro-4-trifluoromethylphenyl)-4-(3-methylthiopropyl(-4-methyl-4,5-dihydro-1H-pyrazole-1-carboxamide
N-(4-trifluoromethoxyphenyl)-3-(3-chloro-4-trifluoromethylphenyl)-4-carboethoxy-4-methyl-4,5-dihydro-1H-pyrazole-1-carboxamide
N-(4-trifluoromethoxyphenyl)-3-(3-chloro-4-trifluoromethylphenyl)-4-phenyl-4-methyl-4,5-dihydro-1H-pyrazole-1-carboxamide
N-(4-trifluoromethoxyphenyl)-3-(4-chlorophenyl)-4-(3-methylthiopropyl)-4-methyl-4,5-dihydro-1H-pyrazole-1-carboxamide
N-(4-trifluoromethoxyphenyl)-3-(4-chlorophenyl)-4-carboethoxy-4-methyl-4,5-dihydro-1H-pyrazole-1-carboxamide
N-(4-trifluoromethoxyphenyl)-3-(4-chlorophenyl)-4-carbomethoxy-4-methyl-4,5-dihydro-1H-pyrazole-1-carboxamide
N-(4-trifluoromethoxyphenyl)-3-(4-chlorophenyl)-4-phenyl-4-methyl-4,5-dihydro-1H-pyrazole-1-carboxamide
N-(trimethylammoniumphenyl)-3-(4-chlorophenyl)-4-carbomethoxy-4-methyl-4,5-dihydro-1H-pyrazole-1-carboxamide iodide
N-(4-trifluoromethoxyphenyl)-3-(3-chloro-4-trifluoromethylphenyl)-4-(3-methylthiopropyl)-4-acetyl-4,5-dihydro-1H-pyrazole-1-carboxamide
N-(4-trifluoromethoxyphenyl)-3-(3-chloro-4-trifluoromethylphenyl)-4-(3-methylthiopropyl)-4-carbomethoxy-4,5-dihydro-1H-pyrazole-1-carboxamide
N-(4-trifluoromethoxyphenyl)-3-(3-chloro-4-trifluoromethylphenyl)-4-(3-methylthiopropyl)-4-4,5-dihydro-1H-pyrazole-1-carboxamide
N-(4-trifluoromethoxyphenyl)-3-(3-chloro-4-trifluoromethylphenyl)-4-(3-methylthiopropyl)-4-methyl-4,5-dihydro-1H-pyrazole-1-carboxamide
N-(4-trifluoromethoxyphenyl)-3-(3-chloro-4-trifluoromethylphenyl)-4-(3-methylthiopropyl)-4-methyl-N-(2-methoxyethylsulfenyl)-4,5-dihydro-1H-pyrazole-1-carboxamide
N-(4-trifluoromethoxyphenyl)-3-(3-chloro-4-trifluoromethylphenyl)-4-(3-methylthiopropyl)-4-methyl-N-(2-nitrophenysulfenyl)-4,5-dihydro-1H-pyrazole-1-carboxamide
N-(4-trifluoromethoxyphenyl)-3-(3-chloro-4-trifluoromethylphenyl)-4-(3-methylthiopropyl)-4-methyl-N-acetyl-4,5-dihydro-1H-pyrazole-1-carboxamide
N-(4-trifluoromethoxyphenyl)-3-(3-chloro-4-trifluoromethylphenyl)-4-(3-methylthiopropyl)-4-methyl-N-carboethoxy-4,5-dihydro-1H-pyrazole-1-carboxamide
N-(4-trifluoromethoxyphenyl)-3-(3-chloro-4-trifluoromethylphenyl)-4-(3-methylthiopropyl)-4-methyl-N-carbomethoxy-4,5-dihydro-1H-pyrazole-1-carboxamide
N-(4-trifluoromethoxyphenyl)-3-(3-chloro-4-trifluoromethylphenyl)-4-(3-methylthiopropyl)-4-methyl-N-carbomethoxycarbonyl-4,5-dihydro-1H-pyrazole-1-carboxamide
N-(4-trifluoromethoxyphenyl)-3-(3-chloro-4-trifluoromethylphenyl)-4-(3-methylthiopropyl)-4-methyl-N-carbomethoxysulfenyl-4,5-dihydro-1H-pyrazole-1-carboxamide
N-(4-trifluoromethoxyphenyl)-3-(3-chloro-4-trifluoromethylphenyl)-4-(3-methylthiopropyl)-4-methyl-N-dimethylcarbamoyl-4,5-dihydro-1H-pyrazole-1-carboxamide
N-(4-trifluoromethoxyphenyl)-3-(3-chloro-4-trifluoromethylphenyl)-4-(3-methylthiopropyl)-4-methyl-N-formyl-4,5-dihydro-1H-pyrazole-1-carboxamide
N-(4-trifluoromethoxyphenyl)-3-(3-chloro-4-trifluoromethylphenyl)-4-(3-methylthiopropyl)-4-methyl-N-methoxymethyl-4,5-dihydro-1H-pyrazole-1-carboxamide
N-(4-trifluoromethoxyphenyl)-3-(3-chloro-4-trifluoromethylphenyl)-4-(3-methylthiopropyl)-4-methyl-N-methyl-4,5-dihydro-1H-pyrazole-1-carboxamide
N-(4-trifluoromethoxyphenyl)-3-(3-chloro-4-trifluoromethylphenyl)-4-(3-methylthiopropyl)-4-methyl-N-methysulfenyl-4,5-dihydro-1H-pyrazole-1-carboxamide
N-(4-trifluoromethoxyphenyl)-3-(3-chloro-4-trifluoromethylphenyl)-4-(3-methylthiopropyl)-4-methyl-N-trifluoroacetyl-4,5-dihydro-1H-pyrazole-1-carboxamide
N-(4-trifluoromethoxyphenyl)-3-(3-chloro-4-trifluoromethylphenyl)-4-carboethoxy-4-(2-chloroallyl)-4,5-dihydro-1H-pyrazole-1-carboxamide
N-(4-trifluoromethoxyphenyl)-3-(3-chloro-4-trifluoromethylphenyl)-4-carboethoxy-4-(2-methylthioethyl)-4,5-dihydro-1H-pyrazole-1-carboxamide
N-(4-trifluoromethoxyphenyl)-3-(3-chloro-4-trifluoromethylphenyl)-4-carboethoxy-4-(3-cyanopropyl)-4,5-dihydro-1H-pyrazole-1-carboxamide
N-(4-trifluoromethoxyphenyl)-3-(3-chloro-4-trifluoromethylphenyl)-4-carboethoxy-4-(4-chlorophenyl)-4,5-dihydro-1H-pyrazole-1-carboxamide
N-(4-trifluoromethoxyphenyl)-3-(3-chloro-4-trifluoromethylphenyl)-4-carboethoxy-4-(4-difluoromethoxyphenyl)-4,5-dihydro-1H-pyrazole-1-carboxamide
N-(4-trifluoromethoxyphenyl)-3-(3-chloro-4-trifluoromethylphenyl)-4-carboethoxy-4-(4-trifluoromethoxyphenyl)-4,5-dihydro-1H-pyrazole-1-carboxamide
N-(4-trifluoromethoxyphenyl)-3-(3-chloro-4-trifluoromethylphenyl)-4-carboethoxy-4-(4-trifluoromethylphenyl)-4,5-dihydro-1H-pyrazole-1-carboxamide N-(4-trifluoromethoxyphenyl)-3-(3-chloro-4-trifluoromethylphenyl)-4-carboethoxy-4-acetyl-4,5-dihydro-1H-pyrazole-1-carboxamide N-(4-trifluoromethoxyphenyl)-3-(3-chloro-4-trifluoromethylphenyl)-4-carboethoxy-4-allyl-4,5-dihydro-1H-pyrazole-1-carboxamide N-(4-trifluoromethoxyphenyl)-3-(3-chloro-4-trifluoromethylphenyl)-4-carboethoxy-4-benzyl-4,5-dihydro-1H-pyrazole-1-carboxamide N-(4-trifluoromethoxyphenyl)-3-(3-chloro-4-trifluoromethylphenyl)-4-carboethoxy-4-carbomethoxy-4,5-dihydro-1H-pyrazole-1-carboxamide N-(4-trifluoromethoxyphenyl)-3-(3-chloro-4-trifluoromethylphenyl)-4-carboethoxy-4-ethyl-4,5-dihydro-1H-pyrazole-1-carboxamide N-(4-trifluoromethoxyphenyl)-3-(3-chloro-4-trifluoromethylphenyl)-4-carboethoxy-4-methallyl-4,5-dihydro-1H-pyrazole-1-carboxamide N-(4-trifluoromethoxyphenyl)-3-(3-chloro-4-trifluoromethylphenyl)-4-carboethoxy-4-methoxymethyl-4,5-dihydro-1H-pyrazole-1-carboxamide N-(4-trifluoromethoxyphenyl)-3-(3-chloro-4-trifluoromethylphenyl)-4-carboethoxy-4-methyl-4,5-dihydro-1H-pyrazole-1-carboxamide N-(4-trifluoromethoxyphenyl)-3-(3-chloro-4-trifluoromethylphenyl)-4-carboethoxy-4-methyl-N-(2-methoxyethylsulfenyl)-4,5-dihydro-1H-pyrazole-1-carboxamide N-(4-trifluoromethoxyphenyl)-3-(3-chloro-4-trifluoromethylphenyl)-4-carboethoxy-4-methyl-N-(2-nitrophenylsulfenyl)-4,5-dihydro-1H-pyrazole-1-carboxamide N-(4-trifluoromethoxyphenyl)-3-(3-chloro-4-trifluoromethylphenyl)-4-carboethoxy-4-methyl-N-acetyl-4,5-dihydro-1H-pyrazole-1-carboxamide N-(4-trifluoromethoxyphenyl)-3-(3-chloro-4-trifluoromethylphenyl)-4-carboethoxy-4-methyl-N-carboethoxy-4,5-dihydro-1H-pyrazole-1-carboxamide N-(4-trifluoromethoxyphenyl)-3-(3-chloro-4-trifluoromethylphenyl)-4-carboethoxy-4-methyl-N-carbomethoxy-4,5-dihydro-1H-pyrazole-1-carboxamide N-(4-trifluoromethoxyphenyl)-3-(3-chloro-4-trifluoromethylphenyl)-4-carboethoxy-4-methyl-N-carbomethoxycarbonyl-4,5-dihydro-1H-pyrazole-1-carboxamide N-(4-trifluoromethoxyphenyl)-3-(3-chloro-4-trifluoromethylphenyl)-4-carboethoxy-4-methyl-N-carbomethoxysulfenyl-4,5-dihydro-1H-pyrazole-1-carboxamide N-(4-trifluoromethoxyphenyl)-3-(3-chloro-4-trifluoromethylphenyl)-4-carboethoxy-4-methyl-N-dimethylcarbamoyl-4,5-dihydro-1H-pyrazole-1-carboxamide N-(4-trifluoromethoxyphenyl)-3-(3-chloro-4-trifluoromethylphenyl)-4-carboethoxy-4-methyl-N-formyl-4,5-dihydro-1H-pyrazole-1-carboxamide N-(4-trifluoromethoxyphenyl)-3-(3-chloro-4-trifluoromethylphenyl)-4-carboethoxy-4-methyl-N-methoxymethyl-4,5-dihydro-1H-pyrazole-1-carboxamide N-(4-trifluoromethoxyphenyl)-3-(3-chloro-4-trifluoromethylphenyl)-4-carboethoxy-4-methyl-N-methyl-4,5-dihydro-1H-pyrazole-1-carboxamide N-(4-trifluoromethoxyphenyl)-3-(3-chloro-4-trifluoromethylphenyl)-4-carboethoxy-4-methyl-N-methylsulfenyl-4,5-dihydro-1H-pyrazole-1-carboxamide N-(4-trifluoromethoxyphenyl)-3-(3-chloro-4-trifluoromethylphenyl)-4-carboethoxy-4-methyl-N-trifluoroacetyl-4,5-dihydro-1H-pyrazole-1-carboxamide N-(4-trifluoromethoxyphenyl)-3-(3-chloro-4-trifluoromethylphenyl)-4-carboethoxy-4-methylthiomethyl-4,5-dihydro-1H-pyrazole-1-carboxamide N-(4-trifluoromethoxyphenyl)-3-(3-chloro-4-trifluoromethylphenyl)-4-carboethoxy-4-phenyl-4,5-dihydro-1H-pyrazole-1-carboxamide N-(4-trifluoromethoxyphenyl)-3-(3-chloro-4-trifluoromethylphenyl)-4-methyl-4-(2-chloroally)-4,5-dihydro-1H-pyrazole-1-carboxamide N-(4-trifluoromethoxyphenyl)-3-(3-chloro-4-trifluoromethylphenyl)-4-methyl-4-(2-methylthioethyl)-4,5-dihydro-1H-pyrazole-1-carboxamide N-(4-trifluoromethoxyphenyl)-3-(3-chloro-4-trifluoromethylphenyl)-4-methyl-4-(3-cyanopropyl)-4,5-dihydro-1H-pyrazole-1-carboxamide N-(4-trifluoromethoxyphenyl)-3-(3-chloro-4-trifluoromethylphenyl)-4-methyl-4-(4-chlorophenyl)-4,5-dihydro-1H-pyrazole-1-carboxamide N-(4-trifluoromethoxyphenyl)-3-(3-chloro-4-trifluoromethylphenyl)-4-methyl-4-(4-difluoromethoxyphenyl)-4,5-dihydro-1H-pyrazole-1-carboxamide N-(4-trifluoromethoxyphenyl)-3-(3-chloro-4-trifluoromethylphenyl)-4-methyl-4-(4-trifluoromethoxyphenyl)-4,5-dihydro-1H-pyrazole-1-carboxamide N-(4-trifluoromethoxyphenyl)-3-(3-chloro-4-trifluoromethylphenyl)-4-methyl-4-(4-trifluoromethylphenyl)-4,5-dihydro-1H-pyrazole-1-carboxamide N-(4-trifluoromethoxyphenyl)-3-(3-chloro-4-trifluoromethylphenyl)-4-methyl-4-acetyl-4,5-dihydro-1H-pyrazole-1-carboxamide N-(4-trifluoromethoxyphenyl)-3-(3-chloro-4-trifluoromethylphenyl)-4-methyl-4-allyl-4,5-dihydro-1H-pyrazole-1-carboxamide N-(4-trifluoromethoxyphenyl)-3-(3-chloro-4-trifluoromethylphenyl)-4-methyl-4-benzyl-4,5-dihydro-1H-pyrazole-1-carboxamide N-(4-trifluoromethoxyphenyl)-3-(3-chloro-4-trifluoromethylphenyl)-4-methyl-4-carbomethoxy-4,5-dihydro-1H-pyrazole-1-carboxamide N-(4-trifluoromethoxyphenyl)-3-(3-chloro-4-trifluoromethylphenyl)-4-methyl-4-ethyl-4,5-dihydro-1H-pyrazole-1-carboxamide N-(4-trifluoromethoxyphenyl)-3-(3-chloro-4-trifluoromethylphenyl)-4-methyl-4-methallyl-4,5-dihydro-1H-pyrazole-1-carboxamide N-(4-trifluoromethoxyphenyl)-3-(3-chloro-4-trifluoromethylphenyl)-4-methyl-4-methoxymethyl-4,5-dihydro-1H-pyrazole-1-carboxamide N-(4-trifluoromethoxyphenyl)-3-(3-chloro-4-trifluoromethylphenyl)-4-methyl-4-methylthiomethyl-4,5-dihydro-1H-pyrazole-1-carboxamide N-(4-trifluoromethoxyphenyl)-3-(3-chloro-4-trifluoromethylphenyl)-4-methyl-4-phenyl-4,5-dihydro-1H-pyrazole-1-carboxamide N-(4-trifluoromethoxyphenyl)-3-(3-chloro-4-trifluoromethylphenyl)-4-phenyl-4-(2-chloroally)-4,5-dihydro-1H-pyrazole-1-carboxamide N-(4-trifluoromethoxyphenyl)-3-(3-chloro-4-trifluoromethylphenyl)-4-phenyl-4-(2-methylthioethyl)-4,5-dihydro-1H-pyrazole-1-carboxamide N-(4-trifluoromethoxyphenyl)-3-(3-chloro-4-trifluoromethylphenyl)-4-phenyl-4-(3-cyanopropyl)-4,5-dihydro-1H-pyrazole-1-carboxamide N-(4-trifluoromethoxyphenyl)-3-(3-chloro-4-trifluoromethylphenyl)-4-phenyl-4-(4-chlorophenyl)-4,5-dihydro-1H-pyrazole-1-carboxamide N-(4-trifluoromethoxyphenyl)-3-(3-chloro-4-trifluoromethylphenyl)-4-phenyl-4-(4-difluoromethoxyphenyl)-4,5-dihydro-1H-pyrazole-1-carboxamide N-(4-trifluoromethoxyphenyl)-3-(3-chloro-4-trifluoromethylphenyl)-4-phenyl-4-(4-trifluoromethoxyphenyl)-4,5-dihydro-1H-pyrazole-1-carboxamide N-(4-trifluoromethoxyphenyl)-3-(3-chloro-4-trifluoromethylphenyl)-4-phenyl-4-(4-trifluoromethylphenyl)-4,5-dihydro-1H-pyrazole-1-carboxamide N-(4-trifluoromethoxyphenyl)-3-(3-chloro-4-trifluoromethylphenyl)-4-phenyl-4-acetyl-4,5-dihydro-1H-pyrazole-1-carboxamide N-(4-trifluoromethoxyphenyl)-3-(3-chloro-4-trifluoromethylphenyl)-4-phenyl-4-allyl-4,5-dihydro-1H-pyrazole-1-carboxamide N-(4-trifluoromethoxyphenyl)-3-(3-chloro-4-trifluoromethylphenyl)-4-phenyl-4-benzyl-4,5-dihydro-1H-pyrazole-1-carboxamide N-(4-trifluoromethoxyphenyl)-3-(3-chloro-4-trifluoromethylphenyl)-4-phenyl-4-carbomethoxy-4,5-dihydro-1H-pyrazole-1-carboxamide N-(4-trifluoromethoxyphenyl)-3-(3-chloro-4-trifluoromethylphenyl)-4-phenyl-4-ethyl-4,5-dihydro-1H-pyrazole-1-carboxamide N-(4-trifluoromethoxyphenyl)-3-(3-chloro-4-trifluoromethylphenyl)-4-phenyl-4-methallyl-4,5-dihydro-1H-pyrazole-1-carboxamide N-(4-trifluoromethoxyphenyl)-3-(3-chloro-4-trifluoromethylphenyl)-4-phenyl-4-methoxymethyl-4,5-dihydro-1H-pyrazole-1-carboxamide N-(4-trifluoromethoxyphenyl)-3-(3-chloro-4-trifluoromethylphenyl)-4-phenyl-4-methyl-4,5-dihydro-1H-pyrazole-1-carboxamide N-(4-trifluoromethoxyphenyl)-3-(3-chloro-4-trifluoromethylphenyl)-4-phenyl-4-methyl-N-(2-methoxyethylsulfenyl)-4,5-dihydro-1H-pyrazole-1-carboxamide N-(4-trifluoromethoxyphenyl)-3-(3-chloro-4-trifluoromethylphenyl)-4-phenyl-4-methyl-N-(2-nitrophenylsulfenyl)-4,5-dihydro-1H-pyrazole-1-carboxamide N-(4-trifluoromethoxyphenyl)-3-(3-chloro-4-trifluoromethylphenyl)-4-phenyl-4-methyl-N-acetyl-4,5-dihydro-1H-pyrazole-1-carboxamide N-(4-trifluoromethoxyphenyl)-3-(3-chloro-4-trifluoromethylphenyl)-4-phenyl-4-methyl-N-carboethoxy-4,5-dihydro-1H-pyrazole-1-carboxamide N-(4-trifluoromethoxyphenyl)-3-(3-chloro-4-trifluoromethylphenyl)-4-phenyl-4-methyl-N-carbomethoxy-4,5-dihydro-1H-pyrazole-1-carboxamide N-(4-trifluoromethoxyphenyl)-3-(3-chloro-4-trifluoromethylphenyl)-4-phenyl-4-methyl-N-carbomethoxycarbonyl-4,5-dihydro-1H-pyrazole-1-carboxamide N-(4-trifluoromethoxyphenyl)-3-(3-chloro-4-trifluoromethylphenyl)-4-phenyl-4-methyl-N-carbomethoxysulfenyl-4,5-dihydro-1H-pyrazole-1-carboxamide N-(4-trifluoromethoxyphenyl)-3-(3-chloro-4-trifluoromethylphenyl)-4-phenyl-4-methyl-N-dimethylcarbamoyl-4,5-dihydro-1H-pyrazole-1-carboxamide N-(4-trifluoromethoxyphenyl)-3-(3-chloro-4-trifluoromethylphenyl)-4-phenyl-4-methyl-N-formyl-4,5-dihydro-1H-pyrazole-1-carboxamide N-(4-trifluoromethoxyphenyl)-3-(3-chloro-4-trifluoromethylphenyl)-4-phenyl-4-methyl-N-methoxymethyl-4,5-dihydro-1H-pyrazole-1-carboxamide N-(4-trifluoromethoxyphenyl)-3-(3-chloro-4-trifluoromethylphenyl)-4-phenyl-4-methyl-N-methyl-4,5-dihydro-1H-pyrazole-1-carboxamide N-(4-trifluoromethoxyphenyl)-3-(3-chloro-4-trifluoromethylphenyl)-4-phenyl-4-methyl-N-methysulfenyl-4,5-dihydro-1H-pyrazole-1-carboxamide N-(4-trifluoromethoxyphenyl)-3-(3-chloro-4-trifluoromethylphenyl)-4-phenyl-4-methyl-N-trifluoroacetyl-4,5-dihydro-1H-pyrazole-1-carboxamide N-(4-trifluoromethoxyphenyl)-3-(3-chloro-4-trifluoromethylphenyl)-4-phenyl-4-methylthiomethyl-4,5-dihydro-1H-pyrazole-1-carboxamide N-(4-trifluoromethoxyphenyl)-3-(4-chlorophenyl)-4-(3-methylthiopropyl)-4-acetyl-4,5-dihydro-1H-pyrazole-1-carboxamide N-(4-trifluoromethoxyphenyl)-3-(4-chlorophenyl)-4-(3-methylthiopropyl)-4-carbomethoxy-4,5-dihydro-1H-pyrazole-1-carboxamide N-(4-trifluoromethoxyphenyl)-3-(4-chlorophenyl)-4-(3-methylthiopropyl)-4-ethyl-4,5-dihydro-1H-pyrazole-1-carboxamide N-(4-trifluoromethoxyphenyl)-3-(4-chlorophenyl)-4-(3-methylthiopropyl)-4-methyl-4,5-dihydro-1H-pyrazole-1-carboxamide N-(4-trifluoromethoxyphenyl)-3-(4-chlorophenyl)-4-(3-methylthiopropyl)-4-methyl-N-(2-methoxyethylsulfenyl)-4,5-dihydro-1H-pyrazole-1-carboxamide N-(4-trifluoromethoxyphenyl)-3-(4-chlorophenyl)-4-(3-methylthiopropyl)-4-methyl-N-(2-nitrophenylsulfenyl)-4,5-dihydro-1H-pyrazole-1-carboxamide N-(4-trifluoromethoxyphenyl)-3-(4-chlorophenyl)-4-(3-methylthiopropyl)-4-methyl-N-acetyl-4,5-dihydro-1H-pyrazole-1-carboxamide N-(4-trifluoromethoxyphenyl)-3-(4-chlorophenyl)-4-(3-methylthiopropyl)-4-methyl-N-carboethoxy-4,5-dihydro-1H-pyrazole-1-carboxamide N-(4-trifluoromethoxyphenyl)-3-(4-chlorophenyl)-4-(3-methylthiopropyl)-4-methyl-N-carbomethoxy-4,5-dihydro-1H-pyrazole-1-carboxamide N-(4-trifluoromethoxyphenyl)-3-(4-chlorophenyl)-4-(3-methylthiopropyl)-4-methyl-N-carbomethoxycarbonyl-4,5-dihydro-1H-pyrazole-1-carboxamide N-(4-trifluoromethoxyphenyl)-3-(4-chlorophenyl)-4-(3-methylthiopropyl)-4-methyl-N-carbomethoxysulfenyl-4,5-dihydro-1H-pyrazole-1-carboxamide N-(4-trifluoromethoxyphenyl)-3-(4-chlorophenyl)-4-(3-methylthiopropyl)-4-methyl-N-dimethylcarbamoyl-4,5-dihydro-1H-pyrazole-1-carboxamide N-(4-trifluoromethoxyphenyl)-3-(4-chlorophenyl)-4-(3-methylthiopropyl)-4-methyl-N-formyl-4,5-dihydro-1H-pyrazole-1-carboxamide N-(4-trifluoromethoxyphenyl)-3-(4-chlorophenyl)-4-(3-methylthiopropyl)-4-methyl-N-methoxymethyl-4,5-dihydro-1H-pyrazole-1-carboxamide N-(4-trifluoromethoxyphenyl)-3-(4-chlorophenyl)-4-(3-methylthiopropyl)-4-methyl-N-methyl-4,5-dihydro-1H-pyrazole-1-carboxamide N-(4-trifluoromethoxyphenyl)-3-(4-chlorophenyl)-4-(3-methylthiopropyl)-4-methyl-N-methylsulfenyl-4,5-dihydro-1H-pyrazole-1-carboxamide N-(4-trifluoromethoxyphenyl)-3-(4-chlorophenyl)-4-(3-methylthiopropyl)-4-methyl-N-trifluoroacetyl-4,5-dihydro-1H-pyrazole-1-carboxamide N-(4-trifluoromethoxyphenyl)-3-(4-chlorophenyl)-4-carboethoxy-4-(2-chloroallyl)-4,5-dihydro-1H-pyrazole-1-carboxamide N-(4-trifluoromethoxyphenyl)-3-(4-chlorophenyl)-4-carboethoxy-4-(2-methylthioethyl)-4,5-dihydro-1H-pyrazole-1-carboxamide N-(4-trifluoromethoxyphenyl)-3-(4-chlorophenyl)-4-carboethoxy-4-(3-cyanopropyl)-4,5-dihydro-1H-pyrazole-1-carboxamide N-(4-trifluoromethoxyphenyl)-3-(4-chlorophenyl)-4-carboethoxy-4-(4-chlorophenyl)-4,5-dihydro-1H-pyrazole-1-carboxamide N-(4-trifluoromethoxyphenyl)-3-(4-chlorophenyl)-4-carboethoxy-4-(4-difluoromethoxyphenyl)-4,5-dihydro-1H-pyrazole-1-carboxamide N-(4-trifluoromethoxyphenyl)-3-(4-chlorophenyl)-4-carboethoxy-4-(4-trifluoromethoxyphenyl)-4,5-dihydro-1H-pyrazole-1-carboxamide N-(4-trifluoromethoxyphenyl)-3-(4-chlorophenyl)-4-carboethoxy-4-(4-trifluoromethylphenyl)-4,5-dihydro-1H-pyrazole-1-carboxamide N-(4-trifluoromethoxyphenyl)-3-(4-chlorophenyl)-4-carboethoxy-4-acetyl-4,5-dihydro-1H-pyrazole-1-carboxamide N-(4-trifluoromethoxyphenyl)-3-(4-chlorophenyl)-4-carboethoxy-4-allyl-4,5-dihydro-1H-pyrazole-1-carboxamide N-(4-trifluoromethoxyphenyl)-3-(4-chlorophenyl)-4-carboethoxy-4-benzyl-4,5-dihydro-1H-pyrazole-1-carboxamide N-(4-trifluoromethoxyphenyl)-3-(4-chlorophenyl)-4-carboethoxy-4-carbomethoxy-4,5-dihydro-1H-pyrazole-1-carboxamide N-(4-trifluoromethoxyphenyl)-3-(4-chlorophenyl)-4-carboethoxy-4-ethyl-4,5-dihydro-1H-pyrazole-1-carboxamide N-(4-trifluoromethoxyphenyl)-3-(4-chlorophenyl)-4-carboethoxy-4-methallyl-4,5-dihydro-1H-pyrazole-1-carboxamide N-(4-trifluoromethoxyphenyl)-3-(4-chlorophenyl)-4-carboethoxy-4-methoxymethyl-4,5-dihydro-1H-pyrazole-1-carboxamide N-(4-trifluoromethoxyphenyl)-3-(4-chlorophenyl)-4-carboethoxy-4-methyl-4,5-dihydro-1H-pyrazole-1-carboxamide N-(4-trifluoromethoxyphenyl)-3-(4-chlorophenyl)-4-carboethoxy-4-methyl-N-(2-methoxyethylsulfenyl)-4,5-dihydro-1H-pyrazole-1-carboxamide N-(4-trifluoromethoxyphenyl)-3-(4-chlorophenyl)-4-carboethoxy-4-methyl-N-(2-nitrophenysulfenyl)-4,5-dihydro-1H-pyrazole-1-carboxamide N-(4-trifluoromethoxyphenyl)-3-(4-chlorophenyl)-4-carboethoxy-4-methyl-N-acetyl-4,5-dihydro-1H-pyrazole-1-carboxamide N-(4-trifluoromethoxyphenyl)-3-(4-chlorophenyl)-4-carboethoxy-4-methyl-N-carboethoxy-4,5-dihydro-1H-pyrazole-1-carboxamide N-(4-trifluoromethoxyphenyl)-3-(4-chlorophenyl)-4-carboethoxy-4-methyl-N-carnomethoxy-4,5-dihydro-1H-pyrazole-1-carboxamide N-(4-trifluoromethoxyphenyl)-3-(4-chlorophenyl)-4-carboethoxy-4-methyl-N-carbomethoxycarbonyl-4,5-dihydro-1H-pyrazole-1-carboxamide N-(4-trifluoromethoxyphenyl)-3-(4-chlorophenyl)-4-carboethoxy-4-methyl-N-carbomethoxysulfenyl-4,5-dihydro-1H-pyrazole-1-carboxamide N-(4-trifluoromethoxyphenyl)-3-(4-chlorophenyl)-4-carboethoxy-4-methyl-N-dimethylcarbamoyl-4,5-dihydro-1H-pyrazole-1-carboxamide N-(4-trifluoromethoxyphenyl)-3-(4-chlorophenyl)-4-carboethoxy-4-methyl-N-formyl-4,5-dihydro-1H-pyrazole-1-carboxamide N-(4-trifluoromethoxyphenyl)-3-(4-chlorophenyl)-4-carboethoxy-4-methyl-N-methoxymethyl-4,5-dihydro-1H-pyrazole-1-carboxamide N-(4-trifluoromethoxyphenyl)-3-(4-chlorophenyl)-4-carboethoxy-4-methyl-N-methyl-4,5-dihydro-1H-pyrazole-1-carboxamide N-(4-trifluoromethoxyphenyl)-3-(4-chlorophenyl)-4-carboethoxy-4-methyl-N-methysulfenyl-4,5-dihydro-1H-pyrazole-1-carboxamide N-(4-trifluoromethoxyphenyl)-3-(4-chlorophenyl)-4-carboethoxy-4-methyl-N-trifluoroacetyl-4,5-dihydro-1H-pyrazole-1-carboxamide N-(4-trifluoromethoxyphenyl)-3-(4-chlorophenyl)-4-carboethoxy-4-methylthiomethyl-4,5-dihydro-1H-pyrazole-1-carboxamide N-(4-trifluoromethoxyphenyl)-3-(4-chlorophenyl)-4-carboethoxy-4-phenyl-4,5-dihydro-1H-pyrazole-1-carboxamide N-(4-trifluoromethoxyphenyl)-3-(4-chlorophenyl)-4-carboethoxy-4-methyl-4,5-dihydro-1H-pyrazole-1-carboxamide N-(4-trifluoromethoxyphenyl)-3-(4-chlorophenyl)-4-dimethylcarbamoyl-4-methyl-4,5-dihydro-1H-pyrazole-1-carboxamide N-(4-trifluoromethoxyphenyl)-3-(4-chlorophenyl)-4-methyl-4-(2-chloroallyl)-4,5-dihydro-1H-pyrazole-1-carboxamide N-(4-trifluoromethoxyphenyl)-3-(4-chlorophenyl)-4-methyl-4-(2-methylthioethyl)-4,5-dihydro-1H-pyrazole-1-carboxamide N-(4-trifluoromethoxyphenyl)-3-(4-chlorophenyl)-4-methyl-4-(3-cyanopropyl)-4,5-dihydro-1H-pyrazole-1-carboxamide N-(4-trifluoromethoxyphenyl)-3-(4-chlorophenyl)-4-methyl-4-(4-chlorophenyl)-4,5-dihydro-1H-pyrazole-1-carboxamide N-(4-trifluoromethoxyphenyl)-3-(4-chlorophenyl)-4-methyl-4-(4-difluoromethoxyphenyl)-4,5-dihydro-1H-pyrazole-1-carboxamide N-(4-trifluoromethoxyphenyl)-3-(4-chlorophenyl)-4-methyl-4-(4-trifluoromethoxyphenyl)-4,5-dihydro-1H-pyrazole-1-carboxamide N-(4-trifluoromethoxyphenyl)-3-(4-chlorophenyl)-4-methyl-4-(4-trifluoromethylphenyl)-4,5-dihydro-1H-pyrazole-1-carboxamide N-(4-trifluoromethoxyphenyl)-3-(4-chlorophenyl)-4-methyl-4-acetyl-4,5-dihydro-1H-pyrazole-1-carboxamide N-(4-trifluoromethoxyphenyl)-3-(4-chlorophenyl)-4-methyl-4-allyl-4,5-dihydro-1H-pyrazole-1-carboxamide N-(4-trifluoromethoxyphenyl)-3-(4-chlorophenyl)-4-methyl-4-benzyl-4,5-dihydro-1H-pyrazole-1-carboxamide N-(4-trifluoromethoxyphenyl)-3-(4-chlorophenyl)-4-methyl-4-carbomethoxy-4,5-dihydro-1H-pyrazole-1-carboxamide N-(4-trifluoromethoxyphenyl)-3-(4-chlorophenyl)-4-methyl-4-ethyl-4,5-dihydro-1H-pyrazole-1-carboxamide N-(4-trifluoromethoxyphenyl)-3-(4-chlorophenyl)-4-methyl-4-methallyl-4,5-dihydro-1H-pyrazole-1-carboxamide N-(4-trifluoromethoxyphenyl)-3-(4-chlorophenyl)-4-methyl-4-methoxymethyl-4,5-dihydro-1H-pyrazole-1-carboxamide N-(4-trifluoromethoxyphenyl)-3-(4-chlorophenyl)-4-methyl-4-methylthiomethyl-4,5-dihydro-1H-pyrazole-1-carboxamide N-(4-trifluoromethoxyphenyl)-3-(4-chlorophenyl)-4-methyl-4-phenyl-4,5-dihydro-1H-pyrazole-1-carboxamide N-(4-trifluoromethoxyphenyl)-3-(4-chlorophenyl)-4-phenyl-4-(2-chloroallyl)-4,5-dihydro-1H-pyrazole-1-carboxamide N-(4-trifluoromethoxyphenyl)-3-(4-chlorophenyl)-4-phenyl-4-(2-methylthioethyl)-4,5-dihydro-1H-pyrazole-1-carboxamide N-(4-trifluoromethoxyphenyl)-3-(4-chlorophenyl)-4-phenyl-4-(3-cyanopropyl)-4,5-dihydro-1H-pyrazole-1-carboxamide N-(4-trifluoromethoxyphenyl)-3-(4-chlorophenyl)-4-phenyl-4-(4-chlorophenyl)-4,5-dihydro-1H-pyrazole-1-carboxamide N-(4-trifluoromethoxyphenyl)-3-(4-chlorophenyl)-4-phenyl-4-(4-difluoromethoxyphenyl)-4,5-dihydro-1H-pyrazole-1-carboxamide N-(4-trifluoromethoxyphenyl)-3-(4-chlorophenyl)-4-phenyl-4-(4-trifluoromethoxyphenyl)-4,5-dihydro-1H-pyrazole-1-carboxamide N-(4-trifluoromethoxyphenyl)-3-(4-chlorophenyl)-4-phenyl-4-(4-trifluoromethylphenyl)-4,5-dihydro-1H-pyrazole-1-carboxamide N-(4-trifluoromethoxyphenyl)-3-(4-chlorophenyl)-4-phenyl-4-acetyl-4,5-dihydro-1H-pyrazole-1-carboxamide N-(4-trifluoromethoxyphenyl)-3-(4-chlorophenyl)-4-phenyl-4-allyl-4,5-dihydro-1H-pyrazole-1-carboxamide N-(4-trifluoromethoxyphenyl)-3-(4-chlorophenyl)-4-phenyl-4-benzyl-4,5-dihydro-1H-pyrazole-1-carboxamide N-(4-trifluoromethoxyphenyl)-3-(4-chlorophenyl)-4-phenyl-4-carbomethoxy-4,5-dihydro-1H-pyrazole-1-carboxamide N-(4-trifluoromethoxyphenyl)-3-(4-chlorophenyl)-4-phenyl-4-ethyl-4,5-dihydro-1H-pyrazole-1-carboxamide N-(4-trifluoromethoxyphenyl)-3-(4-chlorophenyl)-4-phenyl-4-methallyl-4,5-dihydro-1H-pyrazole-1-carboxamide N-(4-trifluoromethoxyphenyl)-3-(4-chlorophenyl)-4-phenyl-4-methoxymethyl-4,5-dihydro-1H-pyrazole-1-carboxamide N-(4-trifluoromethoxyphenyl)-3-(4-chlorophenyl)-4-phenyl-4-methyl-4,5-dihydro-1H-pyrazole-1-carboxamide N-(4-trifluoromethoxyphenyl)-3-(4-chlorophenyl)-4-phenyl-4-methyl-N-(2-methoxyethylsulfenyl)-4,5-dihydro-1H-pyrazole-1-carboxamide N-(4-trifluoromethoxyphenyl)-3-(4-chlorophenyl)-4-phenyl-4-methyl-N-(2-nitrophenysulfenyl)-4,5-dihydro-1H-pyrazole-1-carboxamide N-(4-trifluoromethoxyphenyl)-3-(4-chlorophenyl)-4-phenyl-4-methyl-N-acetyl-4,5-dihydro-1H-pyrazole-1-carboxamide N-(4-trifluoromethoxyphenyl)-3-(4-chlorophenyl)-4-phenyl-4-methyl-N-carboethoxy-4,5-dihydro-1H-pyrazole-1-carboxamide N-(4-trifluoromethoxyphenyl)-3-(4-chlorophenyl)-4-phenyl-4-methyl-N-carbomethoxy-4,5-dihydro-1H-pyrazole-1-carboxamide N-(4-trifluoromethoxyphenyl)-3-(4-chlorophenyl)-4-phenyl-4-methyl-N-carbomethoxycarbonyl-4,5-dihydro-1H-pyrazole-1-carboxamide N-(4-trifluoromethoxyphenyl)-3-(4-chlorophenyl)-4-phenyl-4-methyl-N-carbomethoxysulfenyl-4,5-dihydro-1H-pyrazole-1-carboxamide N-(4-trifluoromethoxyphenyl)-3-(4-chlorophenyl)-4-phenyl-4-methyl-N-dimethylcarbamoyl-4,5-dihydro-1H-pyrazole-1-carboxamide N-(4-trifluoromethoxyphenyl)-3-(4-chlorophenyl)-4-phenyl-4-methyl-N-formyl-4,5-dihydro-1H-pyrazole-1-carboxamide N-(4-trifluoromethoxyphenyl)-3-(4-chlorophenyl)-4-phenyl-4-methyl-N-methoxymethyl-4,5-dihydro-1H-pyrazole-1-carboxamide N-(4-trifluoromethoxyphenyl)-3-(4-chlorophenyl)-4-phenyl-4-methyl-N-methyl-4,5-dihydro-1H-pyrazole-1-carboxamide N-(4-trifluoromethoxyphenyl)-3-(4-chlorophenyl)-4-phenyl-4-methyl-N-methylsulfenyl-4,5-dihydro-1H-pyrazole-1-carboxamide N-(4-trifluoromethoxyphenyl)-3-(4-chlorophenyl)-4-phenyl-4-methyl-N-trifluoroacetyl-4,5-dihydro-1H-pyrazole-1-carboxamide N-(4-trifluoromethoxyphenyl)-3-(4-chlorophenyl)-4-phenyl-4-methylthiomethyl-4,5-dihydro-1H-pyrazole-1-carboxamide N-(4-trifluoromethoxyphenyl)-3-phenyl-4-carboethoxy-4,5-dihydro-1H-pyrazole-1-carboxamide N-(4-trifluoromethoxyphenyl)-3-phenyl-4-carbomethoxy-4-methyl-4,5-dihydro-1H-pyrazole-1-carboxamide N-(4-trifluoromethoxyphenyl)-3-phenyl-4-dimethylcarbamoyl-4,5-dihydro-1H-pyrazole-1-carboxamide N-phenyl-3-(3-chloro-4-trifluoromethylphenyl)-4-(3-methylthiopropyl)-4-methyl-4,5-dihydro-1H-pyrazole-1-carboxamide N-phenyl-3-(3-chloro-4-trifluoromethylphenyl)-4-carboethoxy-4-methyl-4,5-dihydro-1H-pyrazole-1-carboxamide N-phenyl-3-(3-chloro-4-trifluoromethylphenyl)-4-phenyl-4-methyl-4,5-dihydro-1H-pyrazole-1-carboxamide N-phenyl-3-(4-chlorophenyl)-4-(3-methylthiopropyl)-4-methyl-4,5-dihydro-1H-pyrazole-1-carboxamide N-phenyl-3-(4-chlorophenyl)-4-carboethoxy-4-methyl-4,5-dihydro-1H-pyrazole-1-carboxamide N-phenyl-3-(4-chlorophenyl)-4-carbomethoxy-4-methyl-4,5-dihydro-1H-pyrazole-1-carboxamide N-phenyl-3-(4-chlorophenyl)-4-phenyl-4-methyl-4,5-dihydro-1H-pyrazole-1-carboxamide

GROUP B

N-(3,4-dichlorophenyl)-3-(4-chlorophenyl)-4-carbomethoxy-4-methyl-4,5-dihydro-1H-pyrazole N-(3,4-dichlorophenyl)-3-phenyl-4-carbomethoxy-4-methyl-4,5-dihydro-1H-pyrazole-1-carboxamide N,3-bis-(4-bromophenyl)-4-carbomethoxy-4-methyl-4,5-dihydro-1H-pyrazole-1-carboxamide N,3-bis-(4-chlorophenyl)-4-(4-chlorobenzoyl)-4-methyl-4,5-dihydro-1H-pyrazole-1-carboxamide N,3-bis-(4-chlorophenyl)-4-acetyl-4-methyl-4,5-dihydro-1H-pyrazole-1-carboxamide
N,3-bis-(4-chlorophenyl)-4-acetyl-4-phenyl-4,5-dihydro-1H-pyrazole-1-carboxamide
N,3-bis-(4-chlorophenyl)-4-benzoyl-4-methyl-4,5-dihydro-1H-pyrazole-1-carboxamide
N,3-bis-(4-chlorophenyl)-4-carbo(2-dimethylaminoethoxy)-4-methyl-4,5-dihydro-1H-pyrazole-1-carboxamide
N,3-bis-(4-chlorophenyl)-4-carbo(2-dimethylaminoethoxy)-4-methyl-4,5-dihydro-1H-pyrazole-1-carboxamide hydrochloride salt
N,3-bis-(4-chlorophenyl)-4-carbo(2-methylsulfonylethoxy)-4-methyl-4,5-dihydro-1H-pyrazole-1-carboxamide
N,3-bis-(4-chlorophenyl)-4-carbo(2-methylthioethoxy)-4-methyl-4,5-dihydro-1H-pyrazole-1-carboxamide
N,3-bis-(4-chlorophenyl)-4-carbobutoxy-4-methyl-4,5-dihydro-1H-pyrazole-1-carboxamide
N,3-bis-(4-chlorophenyl)-4-carboethoxy-4,5-dihydro-1H-pyrazole-1-carboxamide
N,3-bis-(4-chlorophenyl)-4-carboethoxy-4-methyl-4,5-dihydro-1H-pyrazole-1-carboxamide
N,3-bis-(4-chlorophenyl)-4-carboisopropoxy-4-methyl-4,5-dihydro-1H-pyrazole-1-carboxamide
N,3bis-(4-chlorophenyl)-4-carbomethyloxy-4-methyl-4,5-dihydro-1H-pyrazole-1-carboxamide
N,3-bis-(4-chlorophenyl)-4-carbomethoxy-4,5-dihydro-1H-pyrazole-1-carboxamide
N,3-bis-(4-chlorophenyl)-4-carbomethoxy-4-ethyl-4,5-dihydro-1H-pyrazole-1-carboxamide
N,3-bis-(4-chlorophenyl)-4-carbomethoxy-4-methyl-4,5-dihydro-1H-pyrazole-1-carboxamide
N,3-bis-(4-chlorophenyl)-4-carbomethoxy-4-methyl-4,5-dihydro-1H-pyrazole-1-carboxthioamide
N,3-bis-(4-chlorophenyl)-4-carbomethoxy-4-methyl-N-acetyl-4,5-dihydro-1H-pyrazole-1-carboxamide
N,3-bis-(4-chlorophenyl)-4-carbomethoxy-4-phenyl-4,5-dihydro-1H-pyrazole-1-carboxamide
N,3-bis-(4-chlorophenyl)-4-carbomethoxy-N,4,-dimethyl-4,5-dihydro-1H-pyrazole-1-carboxamide
N,3-bis-(4-chlorophenyl)-4-carbomethoxy-N-(1-carbomethoxy-prop-2-yl-thio)-4-methyl-4,5-dihydro-1H-pyrazole-1-carboxamide
N,3-bis-(4-chlorophenyl)-4-carbomethoxy-N-(2-nitrophenylsulfenyl)-4-methyl-4,5-dihydro-1H-pyrazole-1-carboxamide
N,3-bis-(4-chlorophenyl)-4-carbomethoxy-N-(3-cyanopropylthio)-4-methyl-4,5-dihydro-1H-pyrazole-1-carboxamide
N,3-bis-(4-chlorophenyl)-4-carbomethoxy-N-acetyl-4-methyl-4,5-dihydro-1H-pyrazole-1-carboxthioamide
N,3-bis-(4-chlorophenyl)-4-carbomethoxy-N-carboethoxy-4-methyl-4,5-dihydro-1H-pyrazole-1-carboxamide
N,3-bis-(4-chlorophenyl)-4-carbomethoxy-N-carbomethoxythio-4-methyl-4,5-dihydro-1H-pyrazole-1-carboxamide
N,3-bis-(4-chlorophenyl)-4-carbomethoxy-N-carbophenoxy-4-methyl-4,5-dihydro-1H-pyrazole-1-carboxamide
N,3-bis-(4-chlorophenyl)-4-carbomethoxy-N-carbovinyloxy-4-methyl-4,5-dihydro-1H-pyrazole-1-carboxamide
N,3-bis-(4-chlorophenyl)-4-carbomethoxy-N-dimethylcarbamoyl-4-methyl-4,5-dihydro-1H-pyrazole-1-carboxamide
N,3-bis-(4-chlorophenyl)-4-carbomethoxy-N-formyl-4-methyl-4,5-dihydro-1H-pyrazole-1-carboxamide
N,3-bis-(4-chlorophenyl)-4-carbomethoxy-N-methoxymethyl-4-methyl-4,5-dihydro-1H-pyrazole-1-carboxamide
N,3-bis-(4-chlorophenyl)-4-carbomethoxy-N-methyloxallyl-4-methyl-4,5-dihydro-1H-pyrazole-1-carboxamide
N,3-bis-(4-chlorophenyl)-4-carbomethoxy-N-methylthio-4-methyl-4,5-dihydro-1H-pyrazole-1-carboxamide
N,3-bis-(4-chlorophenyl)-4-carbomethoxy-N-phenylthio-4-methyl-4,5-dihydro-1H-pyrazole-1-carboxamide
N,3-bis-(4-chlorophenyl)-4-carbomethoxy-N-propylthio-4-methyl-4,5-dihydro-1H-pyrazole-1-carboxamide
N,3-bis-(4-chlorophenyl)-4-carbomethoxy-N-trifluoroacetyl-4-methyl-4,5-dihydro-1H-pyrazole-1-carboxamide
N,3-bis-(4-chlorophenyl)-4-carbomethylthiomethoxy-4-methyl-4,5-dihydro-1H-pyrazole-1-carboxamide
N,3-bis-(4-chlorophenyl)-4-carbopropoxy-4-methyl-4,5-dihydro-1H-pyrazole-1-carboxamide
N,3-bis-(4-chlorophenyl)-4-carboxy-4,5-dihydro-1H-pyrazole-1-carboxamide
N,3-bis-(4-chlorophenyl)-4-carboxy-4-methyl-4,5-dihydro-1H-pyrazole-1-carboxamide
N,3-bis-(4-chlorophenyl)-4-carboxy-4-methyl-4,5-dihydro-1H-pyrazole-1-carboxamide sodium salt
N,3-bis-(4-chlorophenyl)-4-carboxy-4-phenyl-4,5-dihydro-1H-pyrazole-1-carboxamide   N,3-bis-(4-chlorophenyl)-4-diethylcarboxamido-4-methyl-4,5-dihydro-1H-pyrazole-1-carboxamide
N,3-bis-(4-chlorophenyl)-4-dimethylcarbamoyl-4,5-dihydro-1H-pyrazole-1-carboxamide
N,3-bis-(4-chlorophenyl)-4-dimethylcarboxamido-4-methyl-4,5-dihydro-1H-pyrazole-1-carboxamide
N,3-bis-(4-chlorophenyl)-4-dimethylthiocarbamoyl-4-methyl-4,5-dihydro-1H-pyrazole-1-carboxamide
N,3-bis-(4-chlorophenyl)-4-isobutyryl-4-methyl-4,5-dihydro-1H-pyrazole-1-carboxamide
N,3-bis-(4-chlorophenyl)-4-methylthiothiocarbonyl-4-methyl-4,5-dihydro-1H-pyrazole-1-carboxamide
N,3-bis-(4-chlorophenyl)-4-pivaloyl-4-methyl-4,5-dihydro-1H-pyrazole-1-carboxamide
N,3-bis-(4-chlorophenyl)-4-propionyl-4-methyl-4,5-dihydro-1H-pyrazole-1-carboxamide
N,3-bis-(4-trifluoromethylphenyl)-4-carbomethoxy-4-methyl-4,5-dihydro-1H-pyrazole-1-carboxamide
N-(1-naphthyl)-3-(4-chlorophenyl)-4-carbomethoxy-4,5-dihydro-1H-pyrazole-1carboxamide
N-(2,4-dinitrophenyl)-3-(4-chlorophenyl)-4-carbomethoxy-4,5-dihydro-1H-pyrazole-1carboxamide
N-(2-fluoro-4-trifluoromethylphenyl)-3-(3-chloro-4-trifluoromethylphenyl)-4-carboethoxy-4-methyl-4,5-dihydro-1H-pyrazole-1-carboxamide
N-(2-fluoro-4-trifluoromethylphenyl)-3-(4-chlorophenyl-4-carboethoxy-4-methyl-4,5-dihydro-1H-pyrazole-1-carboxamide
N-(2-methyl-4-trifluoromethylphenyl)-3-(3-chloro-4-trifluoromethylphenyl)-4-carboethoxy-4-methyl-4,5-dihydro-1H-pyrazole-1-carboxamide
N-(2-methyl-4-trifluoromethylphenyl)-3-(4-chlorophenyl-4-carboethoxy-4-methyl-4,5-dihydro-1H-pyrazole-1-carboxamide N-(3-bromo-4-trifluoromethylphenyl)-3-(3-chloro-4-trifluoromethylphenyl)-4-carboethoxy-4-methyl-4,5-dihydro-1H-pyrazole-1-carboxamide N-(3-bromo-4-trifluoromethylphenyl)-3-(4-chlorophenyl)-4-carboethoxy-4-methyl-4,5-dihydro-1H-pyrazole-1-carboxamide N-(3-bromophenyl)-3-(3-chloro-4-trifluoromethylphenyl)-4-carboethoxy-4-methyl-4,5-dihydro-1H-pyrazole-1-carboxamide N-(3-bromophenyl)-3-(4-chlorophenyl-4-carboethoxy-4-methyl-4,5-dihydro-1H-pyrazole-1-carboxamide N-(3-carboethoxyphenyl)-3-(3-chloro-4-trifluoromethylphenyl)-4-carboethoxy-4-methyl-4,5-dihydro-1H-pyrazole-1-carboxamide N-(3-carboethoxyphenyl)-3-(4-chlorophenyl)-4-carboethoxy-4-methyl-4,5-dihydro-1H-pyrazole-1-carboxamide N-(3-carboisopropoxyphenyl)-3-(3-chloro-4-trifluoromethylphenyl)-4-carboethoxy-4-methyl-4,5-dihydro-1H-pyrazole-1-carboxamide N-(3-carboisopropoxyphenyl)-3-(4-chlorophenyl)-4-carboethoxy-4-methyl-4,5-dihydro-1H-pyrazole-1-carboxamide N-(3-carbomethoxyphenyl)-3-(3-chloro-4-trifluoromethylphenyl)-4-carboethoxy-4-methyl-4,5-dihydro-1H-pyrazole-1-carboxamide N-(3-carbomethoxyphenyl)-3-(4-chlorophenyl)-4-carboethoxy-4-methyl-4,5-dihydro-1H-pyrazole-1-carboxamide N-(3-chloro-4-trifluoromethylphenyl)-3-(3-chloro-4-trifluoromethylphenyl)-4-carboethoxy-4-methyl-4,5-dihydro-1H-pyrazole-1-carboxamide N-(3-chloro-4-trifluoromethylphenyl)-3-(4-chlorophenyl-carboethoxy-4-methyl-4,5-dihydro-1H-pyrazole-1-carboxamide N-(3-chlorophenyl)-3-(4-chlorophenyl)-4-carboethoxy-4-methyl-4,5-dihydro-1H-pyrazole-1-carboxamide N-(3-cyano-4-trifluoromethylphenyl)-3-(3-chloro-4-trifluoromethylphenyl)-4-carboethoxy-4-methyl-4,5-dihydro-1H-pyrazole-1-carboxamide N-(3-cyano-4-trifluoromethylphenyl)-3-(4-chlorophenyl)-4-carboethoxy-4-methyl-4,5-dihydro-1H-pyrazole-1-carboxamide N-(3-difluoromethoxy-4-trifluoromethylphenyl)-3-(3-chloro-4-trifluoromethylphenyl)-4-carboethoxy-4-methyl-4,5-dihydro-1H-pyrazole-1-carboxamide N-(3-difluoromethoxy-4-trifluoromethylphenyl)-3-(4-chlorophenyl)-4-carboethoxy-4-methyl-4,5-dihydro-1H-pyrazole-1-carboxamide N-(3-difluoromethoxyphenyl)-3-(3-chloro-4-trifluoromethylphenyl)-4-carboethoxy-4-methyl-4,5-dihydro-1H-pyrazole-1-carboxamide N-(3-difluoromethoxyphenyl)-3-(4-chlorophenyl)-4-carboethoxy-4-methyl-4,5-dihydro-1H-pyrazole-1-carboxamide N-(3-dimethylsulfonamidophenyl)-3-(3-chloro-4-trifluoromethylphenyl)-4-carboethoxy-4-methyl-4,5-dihydro-1H-pyrazole-1-carboxamide N-(3-dimethylsulfonamidophenyl)-3-(4-chlorophenyl)-4-carboethoxy-4-methyl-4,5-dihydro-1H-pyrazole-1-carboxamide N-(3-fluoro-4-trifluoromethylphenyl)-3-(3-chloro-4-trifluoromethylphenyl)-4-carboethoxy-4-methyl-4,5-dihydro-1H-pyrazole-1-carboxamide N-(3-fluoro-4-trifluoromethylphenyl)-3-(4-chlorophenyl)-4-carboethoxy-4-methyl-4,5-dihydro-1H-pyrazole-1-carboxamide N-(3-methoxy-4-trifluoromethylphenyl)-3-(3-chloro-4-trifluoromethylphenyl)-4-carboethoxy-4-methyl-4,5-dihydro-1H-pyrazole-1-carboxamide N-(3-methoxy-4-trifluoromethylphenyl)-3-(4-chlorophenyl)-4-carboethoxy-4-methyl-4,5-dihydro-1H-pyrazole-1-carboxamide N-(3-methyl-4-trifluoromethylphenyl)-3-(3-chloro-4-trifluoromethylphenyl)-4-carboethoxy-4-methyl-4,5-dihydro-1H-pyrazole-1-carboxamide N-(3-methyl-4-trifluoromethylphenyl)-3-(4-chlorophenyl)-4-carboethoxy-4-methyl-4,5-dihydro-1H-pyrazole-1-carboxamide N-(3-methylthiophenyl)-3-(4-chlorophenyl)-4-carbomethoxy-4-methyl-4,5-dihydro-1H-pyrazole-1-carboxamide N-(3-methylsulfonyl-4-trifluoromethylphenyl)-3-(3-chloro-4-trifluoromethylphenyl)-4-carboethoxy-4-methyl-4,5-dihydro-1H-pyrazole-1-carboxamide N-(3-methylsulfonyl-4-trifluoromethylphenyl)-3-(4-chlorophenyl)-4-carboethoxy-4-methyl-4,5-dihydro-1H-pyrazole-1-carboxamide N-(3-methylsulfonylphenyl)-3-(3-chloro-4-trifluoromethylphenyl)-4-carboethoxy-4-methyl-4,5-dihydro-1H-pyrazole-1-carboxamide N-(3-methylsulfonylphenyl)-3-(4-chlorophenyl)-4-carboethoxy-4-methyl-4,5-dihydro-1H-pyrazole-1-carboxamide N-(3-methylsulfonylphenyl)-3-(4-chlorophenyl)-4-carbomethoxy-4-methyl-4,5-dihydro-1H-pyrazole-1-carboxamide N-(3-methylthio-4-trifluoromethylphenyl)-3-(3-chloro-4-trifluoromethylphenyl)-4-carboethoxy-4-methyl-4,5-dihydro-1H-pyrazole-1-carboxamide N-(3-methylthio-4-trifluoromethylphenyl)-3-(4-chlorophenyl)-4-carboethoxy-4-methyl-4,5-dihydro-1H-pyrazole-1-carboxamide N-(3-methylthiophenyl)-3-(3-chloro-4-trifluoromethylphenyl)-4-carboethoxy-4-methyl-4,5-dihydro-1H-pyrazole-1-carboxamide N-(3-methylthiophenyl)-3-(4-chlorophenyl)-4-carboethoxy-4-methyl-4,5-dihydro-1H-pyrazole-1-carboxamide N-(3-nitro-4-trifluoromethylphenyl)-3-(3-chloro-4-trifluoromethylphenyl)-4-carboethoxy-4-methyl-4,5-dihydro-1H-pyrazole-1-carboxamide N-(3-nitro-4-trifluoromethylphenyl)-3-(4-chlorophenyl)-4-carboethoxy-4-methyl-4,5-dihydro-1H-pyrazole-1-carboxamide N-(3-trifluoromethoxy-4-trifluoromethylphenyl)-3-(3-chloro-4-trifluoromethylphenyl)-4-carboethoxy-4-methyl-4,5-dihydro-1H-pyrazole-1-carboxamide N-(3-trifluoromethoxy-4-trifluoromethylphenyl)-3-(4-chlorophenyl)-4-carboethoxy-4-methyl-4,5-dihydro-1H-pyrazole-1-carboxamide N-(3-trifluoromethoxyphenyl)-3-(3-chloro-4-trifluoromethylphenyl)-4-carboethoxy-4-methyl-4,5-dihydro-1H-pyrazole-1-carboxamide N-(3-trifluoromethoxyphenyl)-3-(4-chlorophenyl)-4-carboethoxy-4-methyl-4,5-dihydro-1H-pyrazole-1-carboxamide N-(3-trifluoromethylphenyl)-3-(chloro-4-trifluoromethylphenyl)-4-carboethoxy-4-methyl-4,5-dihydro-1H-pyrazole-1-carboxamide N-(3-trifluoromethylphenyl)-3-(4-chlorophenyl)-4-carboethoxy-4-methyl-4,5-dihydro-1H-pyrazole-1-carboxamide N-(3-trifluoromethylphenyl)-3-(4-chlorophenyl)-4-carbomethoxy-4-methyl-4,5-dihydro-1H-pyrazole-1-carboxamide N-(3-bromo-3-methylphenyl)-3-(4-chlorophenyl)-4-carbomethoxy-4-methyl-4,5-dihydro-1H-pyrazole-1-carboxamide N-(4-bromophenyl)-3-(3-chloro-4-trifluoromethylphenyl)-4-(3-methylthiopropyl)-4-acetyl-4,5-dihydro-1H-pyrazole-1-carboxamide N-(4-bromophenyl)-3-(3-chloro-4-trifluoromethylphenyl)-4-(3-methylthiopropyl)-4-carbomethoxy-4,5-dihydro-1H-pyrazole-1-carboxamide N-(4-bromophenyl)-3-(3-chloro-4-trifluoromethylphenyl)-4-carboethoxy-4-(2-chloroallyl)-4,5-dihydro-1H-pyrazole-1-carboxamide N-(4-bromophenyl)-3-(3-chloro-4-trifluoromethylphenyl)-4-carboethoxy-4-(2-methylthioethyl)-4,5-dihydro-1H-pyrazole-1-carboxamide N-(4-bromophenyl)-3-(3-chloro-4-trifluoromethylphenyl)-4-carboethoxy-4-(3-cyanopropyl)-4,5-dihydro-1H-pyrazole-1-carboxamide N-(4-bromophenyl)-3-(3-chloro-4-trifluoromethylphenyl)-4-carboethoxy-4-(4-chlorophenyl)-4,5-dihydro-1H-pyrazole-1-carboxamide N-(4-bromophenyl)-3-(3-chloro-4-trifluoromethylphenyl)-4-carboethoxy-4-(4-difluoromethoxyphenyl)-4,5-dihydro-1H-pyrazole-1-carboxamide N-(4-bromophenyl)-3-(3-chloro-4-trifluoromethylphenyl)-4-carboethoxy-4-(4-trifluoromethoxyphenyl)-4,5-dihydro-1H-pyrazole-1-carboxamide N-(4-bromophenyl)-3-(3-chloro-4-trifluoromethylphenyl)-4-carboethoxy-4-(4-trifluoromethylphenyl)-4,5-dihydro-1H-pyrazole-1-carboxamide N-(4-bromophenyl)-3-(3-chloro-4-trifluoromethylphenyl)-4-carboethoxy-4-acetyl-4,5-dihydro-1H-pyrazole-1-carboxamide N-(4-bromophenyl)-3-(3-chloro-4-trifluoromethylphenyl)-4-carboethoxy-4-allyl-4,5-dihydro-1H-pyrazole-1-carboxamide N-(4-bromophenyl)-3-(3-chloro-4-trifluoromethylphenyl)-4-carboethoxy-4-benzyl-4,5-dihydro-1H-pyrazole-1-carboxamide N-(4-bromophenyl)-3-(3-chloro-4-trifluoromethylphenyl)-4-carboethoxy-4-carbomethoxy-4,5-dihydro-1H-pyrazole-1-carboxamide N-(4-bromophenyl)-3-(3-chloro-4-trifluoromethylphenyl)-4-carboethoxy-4-ethyl-4,5-dihydro-1H-pyrazole-1-carboxamide N-(4-bromophenyl)-3-(3-chloro-4-trifluoromethylphenyl)-4-carboethoxy-4-methallyl-4,5-dihydro-1H-pyrazole-1-carboxamide N-(4-bromophenyl)-3-(3-chloro-4-trifluoromethylphenyl)-4-carboethoxy-4-methoxymethyl-4,5-dihydro-1H-pyrazole-1-carboxamide N-(4-bromophenyl)-3-(3-chloro-4-trifluoromethylphenyl)-4-carboethoxy-4-methyl-4,5-dihydro-1H-pyrazole-1-carboxamide N-(4-bromophenyl)-3-(3-chloro-4-trifluoromethylphenyl)-4-carboethoxy-4-methyl-N-(2-methoxyethylsulfenyl)-4,5-dihydro-1H-pyrazole-1-carboxamide N-(4-bromophenyl)-3-(3-chloro-4-trifluoromethylphenyl)-4-carboethoxy-4-methyl-N-(2-nitrophenylsulfenyl)-4,5-dihydro-1H-pyrazole-1-carboxamide N-(4-bromophenyl)-3-(3-chloro-4-trifluoromethylphenyl)-4-carboethoxy-4-methyl-N-acetyl-4,5-dihydro-1H-pyrazole-1-carboxamide N-(4-bromophenyl)-3-(3-chloro-4-trifluoromethylphenyl)-4-carboethoxy-4-methyl-N-carboethoxy-4,5-dihydro-1H-pyrazole-1-carboxamide N-(4-bromophenyl)-3-(3-chloro-4-trifluoromethylphenyl)-4-carboethoxy-4-methyl-N-carbomethoxy-4,5-dihydro-1H-pyrazole-1-carboxamide N-(4-bromophenyl)-3-(3-chloro-4-trifluoromethylphenyl)-4-carboethoxy-4-methyl-N-carbomethoxycarbonyl-4,5-dihydro-1H-pyrazole-1-carboxamide N-(4-bromophenyl)-3-(3-chloro-4-trifluoromethylphenyl)-4-carboethoxy-4-methyl-N-carbomethoxysulfenyl-4,5-dihydro-1H-pyrazole-1-carboxamide N-(4-bromophenyl)-3-(3-chloro-4-trifluoromethylphenyl)-4-carboethoxy-4-methyl-N-dimethylcarbamoyl-4,5-dihydro-1H-pyrazole-1-carboxamide N-(4-bromophenyl)-3-(3-chloro-4-trifluoromethylphenyl)-4-carboethoxy-4-methyl-N-formyl-4,5-dihydro-1H-pyrazole-1-carboxamide N-(4-bromophenyl)-3-(3-chloro-4-trifluoromethylphenyl)-4-carboethoxy-4-methyl-N-methoxymethyl-4,5-dihydro-1H-pyrazole-1-carboxamide N-(4-bromophenyl)-3-(3-chloro-4-trifluoromethylphenyl)-4-carboethoxy-4-methyl-N-methyl-4,5-dihydro-1H-pyrazole-1-carboxamide N-(4-bromophenyl)-3-(3-chloro-4-trifluoromethylphenyl)-4-carboethoxy-4-methyl-N-methylsulfenyl-4,5-dihydro-1H-pyrazole-1-carboxamide N-(4-bromophenyl)-3-(3-chloro-4-trifluoromethylphenyl)-4-carboethoxy-4-methyl-N-trifluoracetyl-4,5-dihydro-1H-pyrazole-1-carboxamide N-(4-bromophenyl)-3-(3-chloro-4-trifluoromethylphenyl)-4-carboethoxy-4-methylthiomethyl-4,5-dihydro-1H-pyrazole-1-carboxamide N-(4-bromophenyl)-3-(3-chloro-4-trifluoromethylphenyl)-4-carboethoxy-4-phenyl-4,5-dihydro-1H-pyrazole-1-carboxamide N-(4-bromophenyl)-3-(3-chloro-4-trifluoromethylphenyl)-4-methyl-4-acetyl-4,5-dihydro-1H-pyrazole-1-carboxamide N-(4-bromophenyl)-3-(3-chloro-4-trifluoromethylphenyl)-4-methyl-4-carbomethoxy-4,5-dihydro-1H-pyrazole-1-carboxamide N-(4-bromophenyl)-3-(3-chloro-4-trifluoromethylphenyl)-4-phenyl-4-acetyl-4,5-dihydro-1H-pyrazole-1-carboxamide N-(4-bromophenyl)-3-(3-chloro-4-trifluoromethylphenyl)-4-phenyl-4-carbomethoxy-4,5-dihydro-1H-pyrazole-1-carboxamide N-(4-bromophenyl)-3-(4-chlorophenyl)-4-(3-methylthiopropyl)-4-acetyl-4,5-dihydro-1H-pyrazole-1-carboxamide N-(4-bromophenyl)-3-(4-chlorophenyl)-4-(3-methylthiopropyl)-4-carbomethoxy-4,5-dihydro-1H-pyrazole-1-carboxamide N-(4-bromophenyl)-3-(4-chlorophenyl)-4-carboethoxy-4-(2-chloroally)-4,5-dihydro-1H-pyrazole-1-carboxamide N-(4-bromophenyl)-3-(4-chlorophenyl)-4-carboethoxy-4-(2-methylthioethyl)-4,5-dihydro-1H-pyrazole-1-carboxamide N-(4-bromophenyl)-3-(4-chlorophenyl)-4-carboethoxy-4-(3-cyanopropyl)-4,5-dihydro-1H-pyrazole-1-carboxamide N-(4-bromophenyl)-3-(4-chlorophenyl)-4-carboethoxy-4-(4-chlorophenyl)-4,5-dihydro-1H-pyrazole-1-carboxamide N-(4-bromophenyl)-3-(4-chlorophenyl)-4-carboethoxy-4-(4-difluoromethoxyphenyl)-4,5-dihydro-1H-pyrazole-1-carboxamide
N-(4-bromophenyl)-3-(4-chlorophenyl)-4-carboethoxy-4-(4-trifluoromethoxyphenyl)-4,5-dihydro-1H-pyrazole-1-carboxamide
N-(4-bromophenyl)-3-(4-chlorophenyl)-4-carboethoxy-4-(4-trifluoromethylphenyl)-4,5-dihydro-1H-pyrazole-1-carboxamide
N-(4-bromophenyl)-3-(4-chlorophenyl)-4-carboethoxy-4-acetyl-4,5-dihydro-1H-pyrazole-1-carboxamide
N-(4-bromophenyl)-3-(4-chlorophenyl)-4-carboethoxy-4-allyl-4,5-dihydro-1H-pyrazole-1-carboxamide
N-(4-bromophenyl)-3-(4-chlorophenyl)-4-carboethoxy-4-benzyl-4,5-dihydro-1H-pyrazole-1-carboxamide
N-(4-bromophenyl)-3-(4-chlorophenyl)-4-carboethoxy-4-carbomethoxy-4,5-dihydro-1H-pyrazole-1-carboxamide
N-(4-bromophenyl)-3-(4-chlorophenyl)-4-carboethoxy-4-ethyl-4,5-dihydro-1H-pyrazole-1-carboxamide
N-(4-bromophenyl)-3-(4-chlorophenyl)-4-carboethoxy-4-methallyl-4,5-dihydro-1H-pyrazole-1-carboxamide
N-(4-bromophenyl)-3-(4-chlorophenyl)-4-carboethoxy-4-methoxymethyl-4,5-dihydro-1H-pyrazole-1-carboxamide
N-(4-bromophenyl)-3-(4-chlorophenyl)-4-carboethoxy-4-methyl-4,5-dihydro-1H-pyrazole-1-carboxamide
N-(4-bromophenyl)-3-(4-chlorophenyl)-4-carboethoxy-4-methyl-N-(2-methoxyethylsulfenyl)-4,5-dihydro-1H-pyrazole-1-carboxamide
N-(4-bromophenyl)-3-(4-chlorophenyl)-4-carboethoxy-4-methyl-N-(2-nitrophenylsulfenyl)-4,5-dihydro-1H-pyrazole-1-carboxamide
N-(4-bromophenyl)-3-(4-chlorophenyl)-4-carboethoxy-4-methyl-N-acetyl-4,5-dihydro-1H-pyrazole-1-carboxamide
N-(4-bromophenyl)-3-(4-chlorophenyl)-4-carboethoxy-4-methyl-N-carboethoxy-4,5-dihydro-1H-pyrazole-1-carboxamide
N-(4-bromophenyl)-3-(4-chlorophenyl)-4-carboethoxy-4-methyl-N-carbomethoxy-4,5-dihydro-1H-pyrazole-1-carboxamide
N-(4-bromophenyl)-3-(4-chlorophenyl)-4-carboethoxy-4-methyl-N-carbomethoxycarbonyl-4,5-dihydro-1H-pyrazole-1-carboxamide
N-(4-bromophenyl)-3-(4-chlorophenyl)-4-carboethoxy-4-methyl-N-carbomethoxysulfenyl-4,5-dihydro-1H-pyrazole-1-carboxamide
N-(4-bromophenyl)-3-(4-chlorophenyl)-4-carboethoxy-4-methyl-N-dimethylcarbamoyl-4,5-dihydro-1H-pyrazole-1-carboxamide
N-(4-bromophenyl)-3-(4-chlorophenyl)-4-carboethoxy-4-methyl-N-formyl-4,5-dihydro-1H-pyrazole-1-carboxamide
N-(4-bromophenyl)-3-(4-chlorophenyl)-4-carboethoxy-4-methyl-N-methoxymethyl-4,5-dihydro-1H-pyrazole-1-carboxamide
N-(4-bromophenyl)-3-(4-chlorophenyl)-4-carboethoxy-4-methyl-N-methyl-4,5-dihydro-1H-pyrazole-1-carboxamide
N-(4-bromophenyl)-3-(4-chlorophenyl)-4-carboethoxy-4-methyl-N-methylsulfenyl-4,5-dihydro-1H-pyrazole-1-carboxamide
N-(4-bromophenyl)-3-(4-chlorophenyl)-4-carboethoxy-4-methyl-N-trifluoroacetyl-4,5-dihydro-1H-pyrazole-1-carboxamide
N-(4-bromophenyl)-3-(4-chlorophenyl)-4-carboethoxy-4-methylthiomethyl-4,5-dihydro-1H-pyrazole-1-carboxamide
N-(4-bromophenyl)-3-(4-chlorophenyl)-4-carboethoxy-4-phenyl-4,5-dihydro-1H-pyrazole-1-carboxamide
N-(4-bromophenyl)-3-(4-chlorophenyl)-4-carbomethoxy-4-methyl-4,5-dihydro-1H-pyrazole-1-carboxamide
N-(4-bromophenyl)-3-(4-chlorophenyl)-4-methyl-4-acetyl-4,5-dihydro-1H-pyrazole-1-carboxamide
N-(4-bromophenyl)-3-(4-chlorophenyl)-4-methyl-4-carbomethoxy-4,5-dihydro-1H-pyrazole-1-carboxamide
N-(4-bromophenyl)-3-(4-chlorophenyl)-4-phenyl-4-acetyl-4,5-dihydro-1H-pyrazole-1-carboxamide
N-(4-bromophenyl)-3-(4-chlorophenyl)-4-phenyl-4-carbomethoxy-4,5-dihydro-1H-pyrazole-1-carboxamide
N-(4-bromophenyl)-3-(4-chlorophenyl)-4-carbomethoxy-4-methyl-4,5-dihydro-1H-pyrazole-1-carboxamide
N-(4-bromophenyl)-3-phenyl-4-carbomethoxy-4-methyl-4,5-dihydro-1H-pyrazole-1-carboxamide
N-(4-carboethoxyphenyl)-3-(3-chloro-4-trifluoromethylphenyl)-4-carboethoxy-4-methyl-4,5-dihydro-1H-pyrazole-1-carboxamide
N-(4-carboethoxyphenyl)-3-(4-chlorophenyl)-4-carboethoxy-4-methyl-4,5-dihydro-1H-pyrazole-1-carboxamide
N-(4-carboethoxyphenyl)-3-(4-chlorophenyl)-4-carbomethoxy-4,5-dihydro-1H-pyrazole-1-carboxamide
N-(4-carboisopropoxyphenyl)-3-(3-chloro-4-trifluoromethylphenyl)-4-(3-methylthiopropyl)-4-methyl-4,5-dihydro-1H-pyrazole-1-carboxamide
N-(4-carboisopropoxyphenyl)-3-(3-chloro-4-trifluoromethylphenyl)-4-carboethoxy-4-methyl-4,5-dihydro-1H-pyrazole-1-carboxamide
N-(4-carboisopropoxyphenyl)-3-(3-chloro-4-trifluoromethylphenyl)-4-phenyl-4-methyl-4,5-dihydro-1H-pyrazole-1-carboxamide
N-(4-carboisopropoxyphenyl)-3-(4-chlorophenyl)-4-(3-methylthiopropyl)-4-methyl-4,5-dihydro-1H-pyrazole-1-carboxamide
N-(4-carboisopropoxyphenyl)-3-(4-chlorophenyl)-4-carboethoxy-4-methyl-4,5-dihydro-1H-pyrazole-1-carboxamide
N-(4-carboisopropoxyphenyl)-3-(4-chlorophenyl)-4-phenyl-4-methyl-4,5-dihydro-1H-pyrazole-1-carboxamide
N-(4-carbomethoxyphenyl)-3-(3-chloro-4-trifluoromethylphenyl)-4-(3-methylthiopropyl)-4-methyl-4,5-dihydro-1H-pyrazole-1-carboxamide
N-(4-carbomethoxyphenyl)-3-(3-chloro-4-trifluoromethylphenyl)-4-carboethoxy-4-methyl-4,5-dihydro-1H-pyrazole-1-carboxamide
N-(4-carbomethoxyphenyl)-3-(3-chloro-4-trifluoromethylphenyl)-4-phenyl-4-methyl-4,5-dihydro-1H-pyrazole-1-carboxamide
N-(4-carbomethoxyphenyl)-3-(4-chlorophenyl)-4-(3-methylthiopropyl)-4-methyl-4,5-dihydro-1H-pyrazole-1-carboxamide
N-(4-carbomethoxyphenyl)-3-(4-chlorophenyl)-4-carboethoxy-4-methyl-4,5-dihydro-1H-pyrazole-1-carboxamide
N-(4-carbomethoxyphenyl)-3-(4-chlorophenyl)-4-carbomethoxy-4,5-dihydro-1H-pyrazole-1-carboxamide
N-(4-carbomethoxyphenyl)-3-(4-chlorophenyl)-4-phenyl-4-methyl-4,5-dihydro-1H-pyrazole-1-carboxamide N-(4-chloro-3-trifluoromethylphenyl)3-(4-chlorophenyl)-4-carbomethoxy-4-methyl-4,5-dihydro-1H-pyrazole-1-carboxamide
N-(4-chlorophenyl)-3-(4-bromophenyl)-4-carbomethoxy-4-methyl-4,5-dihydro-1H-pyrazole-1-carboxamide
N-(4-chlorophenyl)-3-(4-fluorophenyl)-4-carbomethoxy-4-methyl-4,5-dihydro-1H-pyrazole-1-carboxamide
N-(4-chlorophenyl)-3-(4-methoxyphenyl)-4-carbomethoxy-4-methyl-4,5-dihydro-1H-pyrazole-1-carboxamide
N-(4-chlorophenyl)-3-(4-methylphenyl)-4-carbomethoxy-4-methyl-4,5-dihydro-1H-pyrazole-1-carboxamide
N-(4-chlorophenyl)-3-(4-methylsulfonylphenyl)-4-carbomethoxy-4-methyl-4,5-dihydro-1H-pyrazole-1-carboxamide
N-(4-chlorophenyl)-3-(4-methylthiophenyl)-4-carbomethoxy-4-methyl-4,5-dihydro-1H-pyrazole-1-carboxamide
N-(4-chlorophenyl)-3-(4-trifluoromethylphenyl)-4-carbomethoxy-4-methyl-4,5-dihydro-1H-pyrazole-1-carboxamide
N-(4-chlorophenyl)-3-phenyl-4-carboethoxy-4-methyl-4,5-dihydro-1H-pyrazole-1-carboxamide
N-(4-chlorophenyl)-3-phenyl-4-carbomethoxy-4-methyl-4,5-dihydro-1H-pyrazole-1-carboxamide
N-(4-chlorophenyl)-3-phenyl-4-dimethylcarboxamido-4-methyl-4,5-dihydro-1H-pyrazole-1-carboxamide
N-(4-chlorophenyl)-3-phenyl-N,4-bis-carbomethoxy-4-methyl-4,5-dihydro-1H-pyrazole-1-carboxamide
N-(4-difluoromethoxyphenyl)-3-(3-chloro-4-trifluoromethylphenyl)-4-carboethoxy-4-methyl-4,5-dihydro-1H-pyrazole-1-carboxamide
N-(4-difluoromethoxyphenyl)-3-(4-chlorophenyl)-4-carboethoxy-4-methyl-4,5-dihydro-1H-pyrazole-1-carboxamide
N-(4-difluoromethoxyphenyl)-3-(4-chlorophenyl)-4-carbomethoxy-4-methyl-4,5-dihydro-1H-pyrazole-1-carboxamide
N-(4-dimethylsulfonamidophenyl)-3-(3-chloro-4-trifluoromethylphenyl)-4-carboethoxy-4-methyl-4,5-dihydro-1H-pyrazole-1-carboxamide
N-(4-dimethylsulfonamidophenyl)-3-(4-chlorophenyl)-4-carboethoxy-4-methyl-4,5-dihydro-1H-pyrazole-1-carboxamide
N-(4-fluorophenyl)-3-(4-chlorophenyl)-4-carbomethoxy-4-methyl-4,5-dihydro-1H-pyrazole-1-carboxamide
N-(4-fluorophenyl)-3-(4-bromophenyl)-4-carbomethoxy-4-methyl-4,5-dihydro-1H-pyrazole-1-carboxamide
N-(4-fluorophenyl)-3-(4-fluorophenyl)-4-carbomethoxy-4-methyl-4,5-dihydro-1H-pyrazole-1-carboxamide
N-(4-fluorophenyl)-3-phenyl-4-carbomethoxy-4-methyl-4,5-dihydro-1H-pyrazole-1-carboxamide
N-(4-iodophenyl)-3-(4-chlorophenyl)-4-carbomethoxy-4-methyl-4,5-dihydro-1H-pyrazole-1-carboxamide
N-(4-methoxyphenyl)-3-(4-chlorophenyl)-4-carbomethoxy-4-methyl-4,5-dihydro-1H-pyrazole-1-carboxamide
N-(4-methylphenyl)-3-(4-chlorophenyl)-4-carbomethoxy-4-methyl-4,5-dihydro-1H-pyrazole-1-carboxamide
N-(4-methylsulfonylphenyl)-3-(3-chloro-4-trifluoromethylphenyl)-4-carboethoxy-4-methyl-4,5-dihydro-1H-pyrazole-1-carboxamide
N-(4-methylsulfonylphenyl)-3-(4-chlorophenyl)-4-carboethoxy-4-methyl-4,5-dihydro-1H-pyrazole-1-carboxamide
N-(4-methylsulfonylphenyl)-3-(4-chlorophenyl)-4-carbomethoxy-4-methyl-4,5-dihydro-1H-pyrazole-1-carboxamide
N-(4-methylsulfoxylphenyl)-3-(4-chlorophenyl)-4-carbomethoxy-4-methyl-4,5-dihydro-1H-pyrazole-1-carboxamide
N-(4-methylthiophenyl)-3-(3-chloro-4-trifluoromethylphenyl)-4-carboethoxy-4-methyl-4,5-dihydro-1H-pyrazole-1-carboxamide
N-(4-methylthiophenyl)-3-(4-chlorophenyl)-4-carboethoxy-4-methyl-4,5-dihydro-1H-pyrazole-1-carboxamide
N-(4-methylthiophenyl)-3-(4-chlorophenyl)-4-carbomethoxy-4-methyl-4,5-dihydro-1H-pyrazole-1-carboxamide
N-(4-nitrophenyl)-3-(3-chloro-4-trifluoromethylphenyl)-4-carboethoxy-4-methyl-4,5-dihydro-1H-pyrazole-1-carboxamide
N-(4-nitrophenyl)-3-(4-chlorophenyl)-4-carboethoxy-4-methyl-4,5-dihydro-1H-pyrazole-1-carboxamide
N-(4-nitrophenyl)-3-(4-chlorophenyl)-4-carbomethoxy-4,5-dihydro-1H-pyrazole-1-carboxamide
N-(4-trifluoromethoxyphenyl)-3-(3-chloro-4-trifluoromethylphenyl)-4-carboethoxy-4-methyl-4,5-dihydro-1H-pyrazole-1-carboxamide
N-(4-trifluoromethoxyphenyl)-3-(4-chlorophenyl)-4-carboethoxy-4-methyl-4,5-dihydro-1H-pyrazole-1-carboxamide
N-(4-trimethylammoniumphenyl)-3-(4-chlorophenyl)-4-carbomethoxy-4-methyl-4,5-dihydro-1H-pyrazole-1-carboxamide
N-(4-trifluoromethylphenyl)-3-(4-chlorophenyl)-4-dimethylcarbamoyl-4-methyl-4,5-dihydro-1H-pyrazole-1-carboxamide
N-(4-trifluoromethoxyphenyl)-3-(4-chlorophenyl)-4-carbomethoxy-4-methyl-4,5-dihydro-1H-pyrazole-1-carboxamide
N-(4-trifluoromethylphenyl)-3-(3-chloro-4-trifluoromethylphenyl)-4-(3-methylthiopropyl)-4-acetyl-4,5-dihydro-1H-pyrazole-1-carboxamide
N-(4-trifluoromethylphenyl)-3-(3-chloro-4-trifluoromethylphenyl)-4-(3-methylthiopropyl)-4-carbomethoxy-4,5-dihydro-1H-pyrazole-1-carboxamide
N-(4-trifluoromethylphenyl)-3-(3-chloro-4-trifluoromethylphenyl)-4-carboethoxy-4-(2-chloroallyl)-4,5-dihydro-1H-pyrazole-1-carboxamide
N-(4-trifluoromethylphenyl)-3-(3-chloro-4-trifluoromethylphenyl)-4-carboethoxy-4-(2-methylthioethyl)-4,5-dihydro-1H-pyrazole-1-carboxamide
N-(4-trifluoromethylphenyl)-3-(3-chloro-4-trifluoromethylphenyl)-4-carboethoxy-4-(3-cyanopropyl)-4,5-dihydro-1H-pyrazole-1-carboxamide
N-(4-trifluoromethylphenyl)-3-(3-chloro-4-trifluoromethylphenyl)-4-carboethoxy-4-(4-chlorophenyl)-4,5-dihydro-1H-pyrazole-1-carboxamide
N-(4-trifluoromethylphenyl)-3-(3-chloro-4-trifluoromethylphenyl)-4-carboethoxy-4-(4-difluoromethoxyphenyl)-4,5-dihydro-1H-pyrazole-1-carboxamide
N-(4-trifluoromethylphenyl)-3-(3-chloro-4-trifluoromethylphenyl)-4-carboethoxy-4-(4-trifluoromethoxyphenyl)-4,5-dihydro-1H-pyrazole-1-carboxamide N-(4-trifluoromethylphenyl)-3-(3-chloro-4-trifluoromethylphenyl)-4-carboethoxy-4-(4-trifluoromethylphenyl)-4,5-dihydro-1H-pyrazole-1-carboxamide
N-(4-trifluoromethylphenyl)-3-(3-chloro-4-trifluoromethylphenyl)-4-carboethoxy-4-acetyl-4,5-dihydro-1H-pyrazole-1-carboxamide
N-(4-trifluoromethylphenyl)-3-(3-chloro-4-trifluoromethylphenyl)-4-carboethoxy-4-allyl-4,5-dihydro-1H-pyrazole-1-carboxamide
N-(4-trifluoromethylphenyl)-3-(3-chloro-4-trifluoromethylphenyl)-4-carboethoxy-4-benzyl-4,5-dihydro-1H-pyrazole-1-carboxamide
N-(4-trifluoromethylphenyl)-3-(3-chloro-4-trifluoromethylphenyl)-4-carboethoxy-4-carbomethoxy-4,5-dihydro-1H-pyrazole-1-carboxamide
N-(4-trifluoromethylphenyl)-3-(3-chloro-4-trifluoromethylphenyl)-4-carboethoxy-4-ethyl-4,5-dihydro-1H-pyrazole-1-carboxamide
N-(4-trifluoromethylphenyl)-3-(3-chloro-4-trifluoromethylphenyl)-4-carboethoxy-4-methallyl-4,5-dihydro-1H-pyrazole-1-carboxamide
N-(4-trifluoromethylphenyl)-3-(3-chloro-4-trifluoromethylphenyl)-4-carboethoxy-4-methoxymethyl-4,5-dihydro-1H-pyrazole-1-carboxamide
N-(4-trifluoromethylphenyl)-3-(3-chloro-4-trifluoromethylphenyl)-4-carboethoxy-4-methyl-4,5-dihydro-1H-pyrazole-1-carboxamide
N-(4-trifluoromethylphenyl)-3-(3-chloro-4-trifluoromethylphenyl)-4-carboethoxy-4-methyl-N-(2-methoxyethylsulfenyl)-4,5-dihydro-1H-pyrazole-1-carboxamide
N-(4-trifluoromethylphenyl)-3-(3-chloro-4-trifluoromethylphenyl)-4-carboethoxy-4-methyl-N-(2-nitrophenylsulfenyl)-4,5-dihydro-1H-pyrazole-1-carboxamide
N-(4-trifluoromethylphenyl)-3-(3-chloro-4-trifluoromethylphenyl)-4-carboethoxy-4-methyl-N-acetyl-4,5-dihydro-1H-pyrazole-1-carboxamide
N-(4-trifluoromethylphenyl)-3-(3-chloro-4-trifluoromethylphenyl)-4-carboethoxy-4-methyl-N-carboethoxy-4,5-dihydro-1H-pyrazole-1-carboxamide
N-(4-trifluoromethylphenyl)-3-(3-chloro-4-trifluoromethylphenyl)-4-carboethoxy-4-methyl-N-carbomethoxy-4,5-dihydro-1H-pyrazole-1-carboxamide
N-(4-trifluoromethylphenyl)-3-(3-chloro-4-trifluoromethylphenyl)-4-carboethoxy-4-methyl-N-carbomethoxycarbonyl-4,5-dihydro-1H-pyrazole-1-carboxamide
N-(4-trifluoromethylphenyl)-3-(3-chloro-4-trifluoromethylphenyl)-4-carboethoxy-4-methyl-N-carbomethoxysulfenyl-4,5-dihydro-1H-pyrazole-1-carboxamide
N-(4-trifluoromethylphenyl)-3-(3-chloro-4-trifluoromethylphenyl)-4-carboethoxy-4-methyl-N-dimethylcarbamoyl-4,5-dihydro-1H-pyrazole-1-carboxamide
N-(4-trifluoromethylphenyl)-3-(3-chloro-4-trifluoromethylphenyl)-4-carboethoxy-4-methyl-N-formyl-4,5-dihydro-1H-pyrazole-1-carboxamide
N-(4-trifluoromethylphenyl)-3-(3-chloro-4-trifluoromethylphenyl)-4-carboethoxy-4-methyl-N-methoxymethyl-4,5-dihydro-1H-pyrazole-1-carboxamide
N-(4-trifluoromethylphenyl)-3-(3-chloro-4-trifluoromethylphenyl)-4-carboethoxy-4-methyl-N-methyl-4,5-dihydro-1H-pyrazole-1-carboxamide
N-(4-trifluoromethylphenyl)-3-(3-chloro-4-trifluoromethylphenyl)-4-carboethoxy-4-methyl-N-methylsulfenyl-4,5-dihydro-1H-pyrazole-1-carboxamide
N-(4-trifluoromethylphenyl)-3-(3-chloro-4-trifluoromethylphenyl)-4-carboethoxy-4-methyl-N-trifluoroacetyl-4,5-dihydro-1H-pyrazole-1-carboxamide
N-(4-trifluoromethylphenyl)-3-(3-chloro-4-trifluoromethylphenyl)-4-carboethoxy-4-methylthiomethyl-4,5-dihydro-1H-pyrazole-1-carboxamide
N-(4-trifluoromethylphenyl)-3-(3-chloro-4-trifluoromethylphenyl)-4-carboethoxy-4-phenyl-4,5-dihydro-1H-pyrazole-1-carboxamide
N-(4-trifluoromethylphenyl)-3-(3-chloro-4-trifluoromethylphenyl)-4-methyl-4-acetyl-4,5-dihydro-1H-pyrazole-1-carboxamide
N-(4-trifluoromethylphenyl)-3-(3-chloro-4-trifluoromethylphenyl)-4-methyl-4-carbomethoxy-4,5-dihydro-1H-pyrazole-1-carboxamide
N-(4-trifluoromethylphenyl)-3-(3-chloro-4-trifluoromethylphenyl)-4-phenyl-4-acetyl-4,5-dihydro-1H-pyrazole-1-carboxamide
N-(4-trifluoromethylphenyl)-3-(3-chloro-4-trifluoromethylphenyl)-4-phenyl-4-carbomethoxy-4,5-dihydro-1H-pyrazole-1-carboxamide
N-(4-trifluoromethylphenyl)-3-(4-chlorophenyl)-4-(3-methylthiopropyl)-4-acetyl-4,5-dihydro-1H-pyrazole-1-carboxamide
N-(4-trifluoromethylphenyl)-3-(4-chlorophenyl)-4-(3-methylthiopropyl)-4-carbomethoxy-4,5-dihydro-1H-pyrazole-1-carboxamide
N-(4-trifluoromethylphenyl)-3-(4-chlorophenyl)-4-carboethoxy-4-(2-chloroallyl)-4,5-dihydro-1H-pyrazole-1-carboxamide
N-(4-trifluoromethylphenyl)-3-(4-chlorophenyl)-4-carboethoxy-4-(2-methylthioethyl)-4,5-dihydro-1H-pyrazole-1-carboxamide
N-(4-trifluoromethylphenyl)-3-(4-chlorophenyl)-4-carboethoxy-4-(3-cyanopropyl)-4,5-dihydro-1H-pyrazole-1-carboxamide
N-(4-trifluoromethylphenyl)-3-(4-chlorophenyl)-4-carboethoxy-4-(4-chlorophenyl)-4,5-dihydro-1H-pyrazole-1-carboxamide
N-(4-trifluoromethylphenyl)-3-(4-chlorophenyl)-4-carboethoxy-4-(4-difluoromethoxyphenyl)-4,5-dihydro-1H-pyrazole-1-carboxamide
N-(4-trifluoromethylphenyl)-3-(4-chlorophenyl)-4-carboethoxy-4-(4-trifluoromethoxyphenyl)-4,5-dihydro-1H-pyrazole-1-carboxamide
N-(4-trifluoromethylphenyl)-3-(4-chlorophenyl)-4-carboethoxy-4-(4-trifluoromethylphenyl)-4,5-dihydro-1H-pyrazole-1-carboxamide
N-(4-trifluoromethylphenyl)-3-(4-chlorophenyl)-4-carboethoxy-4-acetyl-4,5-dihydro-1H-pyrazole-1-carboxamide
N-(4-trifluoromethylphenyl)-3-(4-chlorophenyl)-4-carboethoxy-4-allyl-4,5-dihydro-1H-pyrazole-1-carboxamide
N-(4-trifluoromethylphenyl)-3-(4-chlorophenyl)-4-carboethoxy-4-benzyl-4,5-dihydro-1H-pyrazole-1-carboxamide
N-(4-trifluoromethylphenyl)-3-(4-chlorophenyl)-4-carboethoxy-4-carbomethoxy-4,5-dihydro-1H-pyrazole-1-carboxamide
N-(4-trifluoromethylphenyl)-3-(4-chlorophenyl)-4-carboethoxy-4-ethyl-4,5-dihydro-1H-pyrazole-1-carboxamide
N-(4-trifluoromethylphenyl)-3-(4-chlorophenyl)-4-carboethoxy-4-methallyl-4,5-dihydro-1H-pyrazole-1-carboxamide N-(4-trifluoromethylphenyl)-3-(4-chlorophenyl)-4-carboethoxy-4-methoxymethyl-4,5-dihydro-1H-pyrazole-1-carboxamide
N-(4-trifluoromethylphenyl)-3-(4-chlorophenyl)-4-carboethoxy-4-methyl-4,5-dihydro-1H-pyrazole-1-carboxamide
N-(4-trifluoromethylphenyl)-3-(4-chlorophenyl)-4-carboethoxy-4-methyl-N-(2-methoxyethylsulfenyl)-4,5-dihydro-1H-pyrazole-1-carboxamide
N-(4-trifluoromethylphenyl)-3-(4-chlorophenyl)-4-carboethoxy-4-methyl-N-(2-nitrophenylsulfenyl)-4,5-dihydro-1H-pyrazole-1-carboxamide
N-(4-trifluoromethylphenyl)-3-(4-chlorophenyl)-4-carboethoxy-4-methyl-N-acetyl-4,5-dihydro-1H-pyrazole-1-carboxamide
N-(4-trifluoromethylphenyl)-3-(4-chlorophenyl)-4-carboethoxy-4-methyl-N-carboethoxy-4,5-dihydro-1H-pyrazole-1-carboxamide
N-(4-trifluoromethylphenyl)-3-(4-chlorophenyl)-4-carboethoxy-4-methyl-N-carbomethoxy-4,5-dihydro-1H-pyrazole-1-carboxamide
N-(4-trifluoromethylphenyl)-3-(4-chlorophenyl)-4-carboethoxy-4-methyl-N-carbomethoxycarbonyl-4,5-dihydro-1H-pyrazole-1-carboxamide
N-(4-trifluoromethylphenyl)-3-(4-chlorophenyl)-4-carboethoxy-4-methyl-N-carbomethoxysulfenyl-4,5-dihydro-1H-pyrazole-1-carboxamide
N-(4-trifluoromethylphenyl)-3-(4-chlorophenyl)-4-carboethoxy-4-methyl-N-dimethylcarbamoyl-4,5-dihydro-1H-pyrazole-1-carboxamide
N-(4-trifluoromethylphenyl)-3-(4-chlorophenyl)-4-carboethoxy-4-methyl-N-formyl-4,5-dihydro-1H-pyrazole-1-carboxamide
N-(4-trifluoromethylphenyl)-3-(4-chlorophenyl)-4-carboethoxy-4-methyl-N-methoxymethyl-4,5-dihydro-1H-pyrazole-1-carboxamide
N-(4-trifluoromethylphenyl)-3-(4-chlorophenyl)-4-carboethoxy-4-methyl-N-methyl-4,5-dihydro-1H-pyrazole-1-carboxamide
N-(4-trifluoromethylphenyl)-3-(4-chlorophenyl)-4-carboethoxy-4-methyl-N-methylsulfenyl-4,5-dihydro-1H-pyrazole-1-carboxamide
N-(4-trifluoromethylphenyl)-3-(4-chlorophenyl)-4-carboethoxy-4-methyl-N-trifluoroacetyl-4,5-dihydro-1H-pyrazole-1-carboxamide
N-(4-trifluoromethylphenyl)-3-(4-chlorophenyl)-4-carboethoxy-4-methylthiomethyl-4,5-dihydro-1H-pyrazole-1-carboxamide
N-(4-trifluoromethylphenyl)-3-(4-chlorophenyl)-4-carboethoxy-4-phenyl-4,5-dihydro-1H-pyrazole-1-carboxamide
N-(4-trifluoromethylphenyl)-3-(4-chlorophenyl)-4-carboethoxy-4-methyl-4,5-dihydro-1H-pyrazole-1-carboxamide
N-(4-trifluoromethylphenyl)-3-(4-chlorophenyl)-4-methyl-4-acetyl-4,5-dihydro-1H-pyrazole-1-carboxamide
N-(4-trifluoromethylphenyl)-3-(4-chlorophenyl)-4-methyl-4-carbomethoxy-4,5-dihydro-1H-pyrazole-1-carboxamide
N-(4-trifluoromethylphenyl)-3-(4-chlorophenyl)-4-phenyl-4-acetyl-4,5-dihydro-1H-pyrazole-1-carboxamide
N-(4-trifluoromethylphenyl)-3-(4-chlorophenyl)-4-phenyl-4-carbomethoxy-4,5-dihydro-1H-pyrazole-1-carboxamide
N-(4-trifluoromethylphenyl)-3-phenyl-4-carboethoxy-4,5-dihydro-1H-pyrazole-1-carboxamide
N-(4-trifluoromethylphenyl)-3-phenyl-4-carbomethoxy-4-methyl-4,5-dihydro-1H-pyrazole-1-carboxamide
N-(4-trifluoromethylphenyl)-3-phenyl-4-dimethylcarbamoyl-4,5-dihydro-1H-pyrazole-1-carboxamide
N-phenyl-3-(3-chloro-4-trifluoromethylphenyl)-4-carboethoxy-4-methyl-4,5-dihydro-1H-pyrazole-1-carboxamide
N-phenyl-3-(4-chlorophenyl)-4-carboethoxy-4-methyl-4,5-dihydro-1H-pyrazole-1-carboxamide
N-phenyl-3-(4-chlorophenyl)-4-carbomethoxy-4-methyl-4,5-dihydro-1H-pyrazole-1carboxamide.

The present invention includes unique processes for preparing 1-substituted-4-substituted-4,5-dihydro-1H-pyrazoles. One of these processes comprises dissolving a 1-substituted-4,5-dihydro-1H-pyrazole in an aprotic solvent, mixing a strong base with the resultant solution, allowing deprotonation to take place at the 4 position of the pyrazole ring, and then adding an alkylating or acylating agent, wherein the 1-substituted-4,5-dihydro-1H-pyrazole dissolved in the aprotic solvent must be a 1-substituted-4-monosubstituted-4,5-dihydro-1H-pyrazole when the desired end product is a 1-substituted-4,4-disubstituted-4,5-dihydro-1H-pyrazole. Processes for making 1-substituted-4-monosubstituted-4,5-dihydro-1H-pyrazole and 1-substituted-4-unsubstituted-4,5-dihydro-1H-pyrazole are known to those skilled in the art (See, e.g., U.S. Pat. No. 4,156,007) and are described in Examples A through J.

In carrying out the process, the 1-substituted-4,5-dihydro-1H-pyrazole which is dissolved in the aprotic solvent may be added to the base or the base may be added to the 1-substituted-4,5-dihydro-1H-pyrazole which has been dissolved in the aprotic solvent. Any 1-substituted-4,5-dihydro-1H-pyrazole may be dissolved in the aprotic solvent. Examples of 1-substituted-4,5-dihydro-1H-pyrazoles which may be employed in the process of this invention include, but are not limited to:

N,3,4-tris-(4-chlorophenyl)-4,5-dihydro-1H-pyrazole-1-carboxamide
N,3-bis-(3,4-dichlorophenyl)-4-phenyl-4,5-dihydro-1H-pyrazole-1-carboxamide
N,3-bis-(4-chlorophenyl)-4-methyl-4,5-dihydro-1H-pyrazole-1-carboxamide
N,3-bis-(4-chlorophenyl)-4-phenyl-4,5-dihydro-1H-pyrazole-1-carboxamide
N,3-bis-(4-chlorophenyl)-4-(2-methylethyl)-4,5-dihydro-1H-pyrazole-1-carboxamide
N,3-bis-(4-chlorophenyl)-4-(2-methylpropyl)-4,5-dihydro-1H-pyrazole-1-carboxamide
N,3-bis-(4-chlorophenyl)-4-(4-chlorobutyl)-4,5-dihydro-1H-pyrazole-1-carboxamide
N,3-bis-(4-chlorophenyl)-4-cyclohexyl-4,5-dihydro-1H-pyrazole-1-carboxamide
N,3-bis-(4-chlorophenyl)-4-ethyl-4,5-dihydro-1H-pyrazole-1-carboxamide
N,3-bis-(4-chlorophenyl)-4-phenyl-4,5-dihydro-1H-pyrazole-1-thiocarboxamide
N,(3-chlorophenyl)-3-(4-chlorophenyl)-4-phenyl-4,5-dihydro-1H-pyrazole-1-carboxamide
N-(4-bromophenyl)-3-(4-fluorophenyl)-4-methyl-4,5-dihydro-1H-pyrazole-1-carboxamide
N-(4-carboethoxyphenyl)-3-(4-chlorophenyl)-4-phenyl-4,5-dihydro-1H-pyrazole-1-carboxamide
N-(4-carboisopropoxyphenyl)-3-(4-chlorophenyl)-4-phenyl-4,5-dihydro-1H-pyrazole-1-carboxamide N-(2,4-dichlorophenyl)-3-(4-chlorophenyl)-4-phenyl-4,5-dihydro-1H-pyrazole-1-carboxamide
N-(2-pyridyl)-3-(4-chlorophenyl)-4-phenyl-4,5-dihydro-1H-pyrazole-1-carboxamide
N-(3,4-dichlorophenyl)-3,4-bis-(4-chlorophenyl)-4,5-dihydro-1H-pyrazole-1-carboxamide
N-(3,4-dichlorophenyl)-3-(4-difluoromethoxyphenyl)-4-phenyl-4,5-dihydro-1H-pyrazole-1-carboxamide
N-(3,5-dichlorophenyl)-3-(4-chlorophenyl)-4-phenyl-4,5-dihydro-1H-pyrazole-1-carboxamide
N-(3-chlorophenyl)-3-(4-chlorophenyl)-4-phenyl-4,5-dihydro-1H-pyrazole-1-carboxamide
N-(3-cyanophenyl)-3-(4-chlorophenyl)-4-phenyl-4,5-dihydro-1H-pyrazole-1-carboxamide
N-(3-phenoxyphenyl)-3-(4-chlorophenyl)-4-phenyl-4,5-dihydro-1H-pyrazole-1-carboxamide
N-(3-pyridyl)-3-(4-chlorophenyl)-4-phenyl-4,5-dihydro-1H-pyrazole-1-carboxamide
N-(3-trifluoromethylphenyl)-3-(4-chlorophenyl)-4-phenyl-4,5-dihydro-1H-pyrazole-1-carboxamide
N-(4-trifluoromethylphenyl)-3-(4-chlorophenyl)-4-phenyl-4,5-dihydro-1H-pyrazole-1-carboxamide
N,3-bis-(4-trifluoromethylphenyl)-4-phenyl-4,5-dihydro-1H-pyrazole-1-carboxamide
N-(4-trifluoromethylphenyl)-3-(4-chlorophenyl)-4-methyl-4,5-dihydro-1H-pyrazole-1-carboxamide
N,3-bis-(4-trifluoromethylphenyl)-4-methyl-4,5-dihydro-1H-pyrazole-1-carboxamide
N-(4-bromophenyl)-3-(4-chlorophenyl)-4-methyl-4,5-dihydro-1H-pyrazole-1-carboxamide
N-(4-bromophenyl)-3-(4-chlorophenyl)-4-phenyl-4,5-dihydro-1H-pyrazole-1-carboxamide
N-(4-carboethoxyphenyl)-3,4-diphenyl-4,5-dihydro-1H-pyrazole-1-carboxamide
N-(4-carboethoxyphenyl)-3-(4-chlorophenyl)-4-phenyl-4,5-dihydro-1H-pyrazole-1-carboxamide
N-(4-carboisopropoxyphenyl)-3,4-diphenyl-4,5-dihydro-1H-pyrazole-1-carboxamide
N-(4-carboisopropoxyphenyl)-3-(4-chlorophenyl)-4-phenyl-4,5-dihydro-1H-pyrazole-1-carboxamide
N-(4-carbomethoxyphenyl)-3-(4-chlorophenyl)-4-phenyl-4,5-dihydro-1H-pyrazole-1-carboxamide
N-(4-chlorophenyl)-3,4-diphenyl-4,5-dihydro-1H-pyrazole-1-carboxamide
N-(4-chlorophenyl)-3-(3,4-dichlorophenyl)-4-phenyl-4,5-dihydro-1H-pyrazole-1-carboxamide
N-(4-chlorophenyl)-3-(4-bromophenyl)-4-methyl-4,5-dihydro-1H-pyrazole-1-carboxamide
N-(4-chlorophenyl)-3-(4-difluoromethoxyphenyl)-4-phenyl-4,5-dihydro-1H-pyrazole-1-carboxamide
N-(4-chlorophenyl)-3-(4-fluorophenyl)-4-methyl-4,5-dihydro-1H-pyrazole-1-carboxamide
N-(4-chlorophenyl)-3-phenyl-4-methyl-4,5-dihydro-1H-pyrazole-1-carboxamide
N-(4-difluoromethoxyphenyl)-3-(4-chlorophenyl)-4-phenyl-4,5-dihydro-1H-pyrazole-1-carboxamide
N-(4-fluorophenyl)-3-(4-chlorophenyl)-4-phenyl-4,5-dihydro-1H-pyrazole-1-carboxamide
N-(4-nitrophenyl)-3-(4-chlorophenyl)-4-phenyl-4,5-dihydro-1H-pyrazole-1-carboxamide
N-(4-phenoxyphenyl)-3-(4-chlorophenyl)-4-phenyl-4,5-dihydro-1H-pyrazole-1-carboxamide
N-(4-phenyl)-3-(4-chlorophenyl)-4-phenyl-4,5-dihydro-1H-pyrazole-1-carboxamide
N-(4-pyridyl)-3-(4-chlorophenyl)-4-phenyl-4,5-dihydro-1H-pyrazole-1-carboxamide
N-(4-trifluoromethylphenyl)-3-(4-chlorophenyl)-4-methyl-4,5-dihydro-1H-pyrazole-1-carboxamide
N-(4-trifluoromethoxyphenyl)-3-(4-chlorophenyl)-4-methyl-4,5-dihydro-1H-pyrazole-1-carboxamide
N-(4-trifluoromethylphenyl)-3-(4-propoxyphenyl)-4-methyl-4,5-dihydro-1H-pyrazole-1-carboxamide
N-(4-trifluoromethoxyphenyl)-3-(4-propexyphenyl)-4-methyl-4,5-dihydro-1H-pyrazole-1-carboxamide
N-(4-trifluoromethylphenyl)-3-(4-chlorophenyl)-4-carbomethoxy-4,5-dihydro-1H-pyrazole-1-carboxamide Preferably, the base used is a strong base; that is, a base having sufficient strength to deprotonate the 4,5-dihydro-1H-pyrazole at the 4-position of the pyrazole ring. Therefore, a base, the conjugate acid of which has a pKa of at least about 10, is required.

Suitable bases for use in this process include, but are not limited to, alkali metal hydroxides, alkaline earth hydroxides, alkali metal alkoxides, alkaline earth alkoxides, alkali metal hydrides, alkaline earth hydrides, alkali metal oxides, alkaline earth oxides, alkali metal amides, alkaline earth amides, alkyl lithiums, aryl lithiums or such other strong bases as are known to those skilled in the art. The preferred bases are alkali metal amides. The most preferred base is lithium diisopropylamide.

The reaction must be carried out in the presence of an aprotic solvent. Suitable aprotic solvents are those not significantly deprotonated under reaction conditions. Aprotic solvents that are useful in carrying out the invention include, but are not limited to, dialkyl ethers, tetrahydrofuran, aliphatic hydrocarbons, aromatic hydrocarbons, aliphatic alcohols, amines, ammonia, dialkyl amides, dialkyl sulfoxides, dialkyl sulfones, polyalkyl phosphoric amides, and such other solvents that are known by those skilled in the art. Preferred solvents are dialkyl ethers, ammonia, tetrahydrofuran, and amines. The most preferred solvent is tetrahydrofuran.

Alkylating and/or acylating agents that are useful in carrying out the process of this invention vary with the particular compound being synthesized. For example, to effect a methylation, appropriate alkylating agents would include, but are not limited to, methyl chloride, methyl bromide, methyl iodide, methyl arylsulfonates, methyl alkylsulfonates, methyl sulfate, trimethyl oxonium salts, methyl halosulfonates, and such other methylating agents as are known to those skilled in the art. Preferred methylating agents are methyl chloride, methyl bromide, methyl iodide, and methyl sulfate. The most preferred methylating agent is methyl iodide. Examples of acylating agents include but are not limited to: alkanoyl chlorides, aroyl chlorides, alkyl chloroformates, aryl chloroformates, alkyl carbonates, aryl carbonates, alkyl isocyanates, aryl isocyanates, alkyl isothiocyanates, aryl isothiocyanates, dialkyl carbamoyl chlorides, alkyl chlorothioformates, aryl chlorothioformates, dialkyl carbodiimides, alkyl aryl carbodiimides, diaryl carbodiimides, carbon dioxide, and carbon disulfide. Those skilled in the art will be able to choose other appropriate alkylating and/or acylating agents to introduce other Y groups.

The reaction temperature can be varied within a substantial range. In general, the reaction is carried out at from about −120° C. to about 200° C., preferable at from about −78° C. to about 100° C. The reaction is allowed to take place under normal pressure. The most preferred temperature is −10° C. Yields may be improved by carrying out the reaction at temperatures from −80° C. to −30° C. when using acylating agents.

To carry out the process, the materials are preferably employed in stoichiometric amounts. An excess of one or the other component produces no significant advantages. After completion of the reaction, acetic acid is added to neutralize the reaction.

A second process for preparing compounds of the present invention where Y is a group having the formula

(Group B) comprises treating the beta-dicarbonyl compound of the Formula II

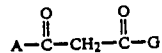

II where A, X and G are as defined above for Formula I with a mixture of hydrazine and formaldehyde to produce a 3-aryl-4-monosubstituted-4,5-dihydropyrazole having the formula

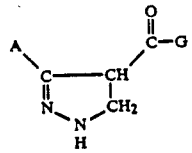

III

Where A and G are as defined above for Formula I. Treatment of the dihydropyrazole of Formula III with an aryl isocyanate gives the N-aryl-3-aryl-4-monosubstituted-4,5-dihydropyrazole-1-carboxamides of this invention.

Further treatment of this 1-substituted-4-mono-substituted-4,5-dihydropyrazole-1-carboxamide with a base, followed by an alkylating agent or acylating agent will yield the N-aryl-3-4,4-disubstituted-4,5-dihydropyrazole-1-carboxamides of this invention.

In carrying out the process, to produce a 3-aryl-4-monosubstituted-4,5-dihydropyrazole having the Formula III, any beta-dicarbonyl compound of Formula II may be used. Examples of beta-dicarbonyl compounds which may be employed in this process of the invention include, but are not limited to:

2-methylthioethyl 3-(3-methyl-4-trifluoromethylphenyl)-3-oxo-propanoate;
2-methylthioethyl 3-(4-chlorophenyl)-3-oxo-propanoate;
3'-trifluoromethylbenzyl 3-(3-chloro-4-difluoromethoxyphenyl)-3-oxo-propanoate;
3'-trifluoromethylbenzyl 3-(4-chlorophenyl)-3-oxo-propanoate;
3-(3-methyl-4-trifluoromethylphenyl)-3-oxo-propanamide;
N,N-diethyl 3-(3-fluoro-4-trifluoromethylphenyl)-3-oxo-propanamide;
N,N-dimethyl 3-(3-chloro-4-trifluoromethylphenyl)-3-oxo-propanamide;
N-cyclopentyl 3-(4-chloro-3-trifluoromethylphenyl)-3-oxo-propanamide;
N-ethyl-N-methyl 3-(3-chloro-4-difluoromethylphenyl)-3-oxo-propanamide;
N-methyl-N-phenyl 3-(3-chloro-4-trifluoromethoxyphenyl)-3-oxo-propanamide;
N-phenyl 3-(2-chloro-4-trifluoromethylphenyl)-3-oxo-propanamide;
N-propyl 3-(3-bromo-4-trifluoromethylphenyl)-3-oxo-propanamide;
allyl 3-(3-chloro-4-trifluoromethylphenyl)-3-oxo-propanoate;
allyl 3-(4-chlorophenyl)-3-oxo-propanoate;
cyclopentyl 3-(4-chloro-3-trifluoromethylphenyl)-3-oxo-propanoate;
cyclopentyl 3-(4-chlorophenyl)-3-oxo-propanoate;
ethyl 3-(3-fluoro-4-trifluoromethylphenyl)-3-oxo-dithiopropanoate;
ethyl 3-(3-fluoro-4-trifluoromethylphenyl)-3-oxo-propanoate;
ethyl 3-(4-chlorophenyl)-3-oxo-propanoate;
methyl 3-(3-chloro-4-trifluoromethylphenyl)-3-oxo-dithiopropanoate;
methyl 3-(3-chloro-4-trifluoromethylphenyl)-3-oxo-propanoate;
methyl 3-(4-chlorophenyl)-3-oxo-propanoate;
methyl 3-(4-propoxyphenyl)-3-oxo-propanoate;
phenyl 3-(2-chloro-4-trifluoromethylphenyl)-3-oxo-dithiopropanoate;
phenyl 3-(2-chloro-4-trifluoromethylphenyl)-3-oxo-propanoate;
phenyl 3-(4-chlorophenyl)-3-oxo-propanoate;
propyl 3-(3-bromo-4-trifluoromethylphenyl)-3-oxo-dithiopropanoate;
propyl 3-(3-bromo-4-trifluoromethylphenyl)-3-oxo-propanoate;
propyl 3-(4-chlorophenyl)-3-oxo-propanoate;
t-butyl 3-(3-chloro-4-trifluoromethoxyphenyl)-3-oxo-propanoate; or
t-butyl 3-(4-chlorophenyl)-3-oxo-propanoate.

Preferably, a substantially equimolar mixture of hydrazine and formaldehyde is used.

The reaction may be carried out in the presence or absence of a solvent. Suitable solvents are those that afford some solubility to the components of the reaction mixture. Suitable solvents that are useful in carrying out the invention include, but are not limited to, water, dialkyl ethers, tetrahydrofuran, aliphatic hydrocarbons, aromatic hydrocarbons, aliphatic alcohols, tertiary amines, dialkyl amides, dialkyl sulfoxides, dialkyl sulfones, polyalkyl phosphoric amides, and such other solvents that are known by those skilled in the art. Preferred solvents are aliphatic alcohols, tetrahydrofuran, and tertiary amines. The most preferred solvent is methanol.

Because of the basic nature of hydrazine, the reaction can be carried out in the presence or absence of additional base. Suitable additional bases for use in this process include, but are not limited to, alkali metal hydroxide, alkaline earth hydroxide, alkali metal alkoxide, alkaline earth alkoxide, alkali metal oxide, alkaline earth oxide, tertiary amines, amidines, guanidines, and such other bases that are known to those skilled in the art.

The reaction temperature can be varied within a substantial range. In general, the reaction is carried out at from about $-120°$ C. to about 200° C., preferably at from about $-78°$ C. to about 100° C. The reaction is allowed to take place under normal pressure. The most preferred temperature is about 20° C.

The beta-dicarbonyl compounds are generally commercially available or can be prepared by procedures well-known to those skilled in the art. For example a carboxyaryl compound is reacted with thionyl chloride to afford the corresponding acid chloride; which in turn is reacted with ammonia to afford the corresponding amide; which in turn is reacted to afford the corresponding cyano compound; which in turn is reacted with a suitable Grignard reagent to afford the corresponding alkylcarbonyl-aryl derivative. The alkylcarbonyl-aryl derivative is used to prepare compounds as described in Example E, below. Alternatively, an ethylcarbonyl-aryl is reacted with dimethyl carbonate to afford the the corresponding methyl 2-methyl-3-aryl-3-keto-propanoate (i.e. a keto-acetate) which may be used as described below. The ethylcarbonylaryl compound is used to prepare the claimed compounds as described beginning in Example E, below.

Suitable precursors for compounds of the present invention where G is aryl are generally commercially available or can be prepared by procedures well-known to those skilled in the art. For example an alkyl-aryl can be reacted with a methoxycarbonyl-aryl and used as described in Example B below; a carboxymethyl-aryl can be condensed with an aryl through a Friedel-Crafts reaction and used as described in Example B below; a cyanomethylaryl can be condensed with an aryl-Grignard reagent and used as described in Example B below.

Treatment of the dihydropyrazole of Formula III with an aryl isocyanate gives the N-aryl-3-aryl-4-monosubstituted-4,5-dihydropyrazole-1-carboxamides of this invention.

In carrying out the process, to produce a 3-aryl-4-monosubstituted-4,5-dihydropyrazole-1-carboxamide of this invention, any aryl isocyanate of the formula

B—N=C=O     IV

Where B is as defined in Formula I may be used. Examples of aryl isocyanates which may be employed in this process of this invention include, but are not limited to:
3,4-dichlorophenyl isocyanate;
3-bromo-4-dimethylaminophenyl isocyanate;
3-bromo-4-methylphenyl isocyanate;
3-bromo-4-methylphenyl isothiocyanate;
3-bromo-4-trifluoromethylphenyl isocyanate;
3-bromodifluoromethoxyphenyl isocyanate;
3-bromodifluorothiomethoxyphenyl isocyanate;
3-bromophenyl isocyanate;
3-carboethoxyphenyl isocyanate;
3-carboisopropoxyphenyl isocyanate;
3-carbomethoxyphenyl isocyanate;
3-chloro-4-bromodifluoromethoxyphenyl isocyanate;
3-chloro-4-bromodifluorothiomethoxyphenyl isocyanate;
3-chloro-4-bromophenyl isocyanate;
3-chloro-4-carboethoxyphenyl isocyanate;
3-chloro-4-carboisopropoxyphenyl isocyanate;
3-chloro-4-carbomethoxyphenyl isocyanate;
3-chloro-4-cyanophenyl isocyanate;
3-chloro-4-difluoromethoxyphenyl isocyanate;
3-chloro-4-dimethylaminophenyl isocyanate;
3-chloro-4-fluorophenyl isocyanate;
3-chloro-4-iodophenyl isocyanate;
3-chloro-4-methylphenyl isocyanate;
3-chloro-4-methylsulfinylphenyl isocyanate;
3-chloro-4-methylsulfonylphenyl isocyanate;
3-chloro-4-methylthiophenyl isocyanate;
3-chloro-4-nitrophenyl isocyanate;
3-chloro-4-trifluoromethoxyphenyl isocyanate;
3-chloro-4-trifluoromethylphenyl isocyanate;
3-chlorophenyl isocyanate;
3-cyano-4-carbomethoxyphenyl isocyanate;
3-cyano-4-carbomethoxyphenyl isothiocyanate;
3-cyanophenyl isocyanate;
3-difluoromethoxy-4-methylthiophenyl isocyanate;
3-difluoromethoxyphenyl isocyanate;
3-dimethylaminophenyl isocyanate;
3-fluoro-4-bromophenyl isocyanate;
3-fluoro-4-carboethoxyphenyl isocyanate;
3-fluoro-4-carboethoxyphenyl isothiocyanate;
3-fluoro-4-cyanophenyl isocyanate;
3-fluoro-4-cyanophenyl isothiocyanate;
3-fluorophenyl isocyanate;
3-iodo-4-difluoromethoxyphenyl isocyanate;
3-iodo-4-fluorophenyl isocyanate;
3-iodophenyl isocyanate;
3-methyl-4-trifluoromethoxyphenyl isocyanate;
3-methylphenyl isocyanate;
3-methylsulfinylphenyl isocyanate;
3-methylsulfonylphenyl isocyanate;
3-methylthio-4-methylsulfinylphenyl isocyanate;
3-methylthiophenyl isocyanate;
3-methylthio-4-bromodifluoromethoxyphenyl isocyanate;
3-nitro-4-bromodifluorothiomethoxyphenyl isocyanate;
3-nitro-4-bromodifluorothiomethoxyphenyl isothiocyanate;
3-nitrophenyl isocyanate;
3-trifluoromethoxy-4-methylsulfonylphenyl isocyanate;
3-trifluoromethoxy-4-nitrophenyl isocyanate;
3-trifluoromethoxy-4-nitrophenyl isothiocyanate;
3-trifluoromethoxyphenyl isocyanate;
3-trifluoromethyl-4-carboisopropoxyphenyl isocyanate;
3-trifluoromethyl-4-carboisothiopropoxyphenyl isothiocyanate;
3-trifluoromethyl-4-iodophenyl isocyanatel;
3-trifluoromethylphenyl isocyanate;
4-bromodifluoromethoxyphenyl isocyanate;
4-bromodifluorothiomethoxyphenyl isocyanate;
4-bromophenyl isocyanate;
4-bromophenyl isothiocyanate;
4-carboethoxyphenyl isocyanate;
4-carboisopropoxyphenyl isocyanate;
4-carbomethoxyphenyl isocyanate;
4-chlorophenyl isocyanate;
4-chlorophenyl isothiocyanate;
4-cyanophenyl isocyanate;
4-difluoromethoxyphenyl isocyanate;
4-difluoromethoxyphenyl isothiocyanate;
4-dimethylaminophenyl isocyanate;
4-fluorophenyl isocyanate;
4-iodophenyl isocyanate;
4-methylphenyl isocyanate;
4-methylsulfinylphenyl isocyanate;
4-methylsulfonylphenyl isocyanate;
4-methylthiophenyl isocyanate;
4-nitrophenyl isocyanate;
4-pentafluorosulfuranylphenyl isocyanate;
4-trifluoromethoxyphenyl isocyanate;
4-trifluoromethoxyphenyl isothiocyanate;
4-trifluoromethylphenyl isocyanate;
4-trifluoromethylphenyl isothiocyanate; or phenyl isocyanate.

The reaction may be carried out in the presence or absence of a solvent. Suitable solvents are those that afford some solubility to the components of the reaction mixture, and do not react with the aryl isocyanate at an appreciable rate. Suitable solvents that are useful in carrying out the invention include, but are not limited to, dialkyl ethers, chlorinated hydrocarbons, tetrahydrofuran, aliphatic hydrocarbons, aromatic hydrocarbons, aliphatic alcohols, tertiary amines, dialkyl amides, dialkyl sulfoxides, dialkyl sulfones, polyalkyl phosphoric amides, and such other solvents that are known by those skilled in the art. Preferred solvents are chlorinated hydrocarbons, tetrahydrofuran, and tertiary amines. The most preferred solvent is methylene chloride.

The reaction temperature can be varied within a substantial range. In general, the reaction is carried out at from about $-120°$ C. to about $200°$ C., preferably at from about $-78°$ C. to about $100°$ C. The reaction is allowed to take place under normal pressure. The most preferred temperature is about $45°$ C.

Further treatment of this 1-substituted-4-monosubstituted-4,5-dihydropyrazole-1-carboxamide with a base, followed by an alkylating agent or acylating agent will yield the N-aryl-3-aryl-4,4-disubstituted-4,5-dihydropyrazole-1-carboxamides of this invention.

The methods for effecting this reaction have been described above and are exemplified below in Example 77, Method C.

The isocyanates of Formula IV are generally commercially available, or can be prepared by techniques well-known to those skilled in the art. For example, reacting an amino-aryl compound with phosgene to afford the aryl isocyanate of Formula IV.; or reacting a carboxy-aryl compound to afford an acyl azide which is in turn reacted to afford the aryl isocyanate of Formula IV.

A preferred process for preparing compounds of the present invention where Z is methyl, Y is a group having the Formula

X is O which comprises:
(a) hydroxymethylation of a dicarbonyl having the Formula

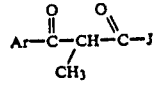
V where Ar is unsubstituted or substituted phenyl having one to three of the same or different halo, cyano, hydroxy, nitro, isocyano, ($C_1$–$C_4$) alkyl, ($C_1$–$C_4$) haloalkyl ($C_1$–$C_{10}$) alkoxy, ($C_1$–$C_4$) haloalkyenyl ($C_2$–$C_6$) alkenyloxy, ($C_2$–$C_6$) alkynyloxy, ($C_1$–$C_4$) alkoxyalkoxy having independently the stated number of carbon atoms in each alkyl group, ($C_1$–$C_4$) alkoxycarbonyl, methylendioxy, phenyl, phenoxy, or phen($C_1$–$C_4$)alkyloxy, naphthyl, furyl, or pyridyl; and J is ($C_1$–$C_6$) alkoxy, ($C_1$–$C_4$) haloalkyl, amino, ($C_1$–$C_4$) alkylamino or ($C_1$–$C_4$) dialkylamino having independently the stated number of carbon atoms in each alkyl group; with a source of formaldehyde such as formalin or paraformaldehyde in the presence of a base such as sodium hydroxide or triethylamine in an inert or substantially inert solvent or mixture of solvents such as toluene, pyridine, mthanol, methylene chloride or ethyl acetate, or depending on the selection of base, no solvent (i.e. neat), at a temperature of from about $25°$ C. to about $85°$ C. to afford a hydroxymethyl-dicarbonyl compound having the formula

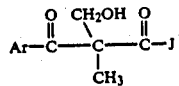
VI where A and J are as defined above; or
(b) halomethylation of a dicarbonyl having the Formula V as defined above by reacting said dicarbonyl with a dihalomethane such as $CH_2Br_2$ or $CH_2Cl_2$, in the presence of a base such as sodium hydreide in an inert or substantially inert solvent or mixture of solvents such as dimethyl sulfixide, dimethyl formamide or the like at a temperature of from about $20°$ C. to about $90°$ C. to afford a halomethyl-dicarbonyl compound having the formula

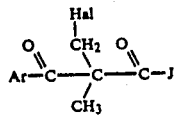
VII where Ar and J as defined above and Hal is chloro or bromo; and
(c) mesylation of the hydroxymethyl-dicarbonyl from (a) by treating with additional base followed by the addition of methanesulfonyl chloride in an inert or substantially inert solvent or mixture of solvents such as toluene, methanol, methylene chloride or ethyl acetate at a temperature of from about $0°$ C. to about $50°$ C. to afford a mesylate dicarbonyl having the formula

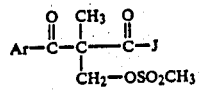
VIII where Ar and J are as defined above;
(c) halogenation of the methyl hydroxymethyl-dicarbonyl of Formula VI with thionyl chloride ($SOCL_2$) in the presence of a base such as pyridine, triethylamine or sodium hydroxide in an inert or substantially inert solvent or mixture of solvents such as pyridine, methylene bromide of methylene chloride at a temperature of from about $0°$ C. to about $50°$ C. to afford a chloromethyl-dicarbonyl compound of Formula VII; and
(d) cyclization of the mesyloxymethyl-dicarbonyl compound of Formula VIII or the halomethyl-dicarbonyl of Formula VII with a source of hydrazine such as hydrazine hydrate or hydrazine hydrochloride in the presence of a base such as potassium hydroxide or sodium hydride, or buffered conditions such as acetic acid and sodium acetate, in an inert or substantially inert solvent or mixture of solvents such as methanol, ethanol, dimethyl foramamide (DMF) or toluene at a temperature of from about $35°$ C. to about $85°$ C. to afford a 4,4-disubstituted-3-aryl-2-pyrazoline, and
(e) carbamoylation of the 4,4-disubstituted-3-aryl-2-pyrazoline with a compound of Formula IV as described above.

When the 4,4-disubstituted-3-aryl-2-pyrazolines prepared are not to be used immediately but are to be stored for subsequent use, it may be desirable to stabilize said compounds by preparing the corresponding acid addition salt. The acid addition salts can be prepared by any convenient art-recognized method such as by reacting hydrochloric, hydrobromic, sulfuric, nitric, phosphoric acetic, propionic, benzoic or other suitable acid with the 4,4disubstituted-3-aryl-2-pyrazolines in an inert or substantially inert solvent or mixture of solvents. Useful solvents include water, alchohols, ethers, esters, ketones, haloketones and the like. The particular choice of solvent will depend upon the relative solubilities of the starting materials and the resulting salts, and slurries rather than solutions of certain reagents may be used to obtain the salts. Generally, the salt-forming reaction is carried out at a temperature of from about $-20°$ C. to about 50° C., preferably between about 0° C. and about 25° C.

The several reactions of the present process are preferably carried out at about atmospheric pressure, although higher or lower pressures can be used if desired.

Unless otherwise stated, substantially equimolor amounts of reactants are preferably used although higher or lower amounts can be used if desired.

The dicarbonyl compounds of Formula V are prepared from commercially available starting materials by a variety to standard reactions well-known to those skilled in the art, such as, a standard Claisen condensation of appropriate esters. For example, the condensation of phenylethyl ketone with ethyl carbonate or methyl benzoate with methyl propanoate in the presence of a base. The preferred method of preparation of the dicarbonyl compounds of Formula V is by acylation of the anion of methyl acetoacetate with an aroyl acid chloride in the presence of a base; which is then deacetylated under acid or basic conditions; which is then alkylated using standard procedures well-known to these skilled in the art.

Examples of dicarbonyl compounds suitable for use in the above process include ethyl benzoylacetate; methyl 4-propoxybenzoylacetate; and methyl 4-chlorobenzoylacetate.

After preparing compounds embraced by Formula I by any of the above processes, the salts of the invention can be prepared by any convenient art-recognized method, such as by reacting a metal hydroxide, a metal hydride or an amine or ammonium salt, such as a halide, hydroxide or alkoxide with the free acid, or reacting a quaternary ammonium salt, such as chloride, a bromide, nitrate or the like with a metal salt of the invention in a suitable solvent. When metal hydroxides are used as reagents, useful solvents include water, glyme, dioxane, tetrahydrofuran, methanol, ethanol, isopropanol and the like. When metal hydrides are used as reagents, useful solvents include nonhydroxylic solvents such as dioxane, glyme, tetrahydrofuran, diethyl ether, hydrocarbons such as toluene, xylene, hexane, pentane, heptane, and octane, dimethylformamide, and the like. When amines are used as reagents, useful solvents include alcohols, such as methanol or ethanol, hydrocarbons, such as toluene, xylene, hexane and the like, tetrahydrofuran, glyme, dioxane, or water. When ammonium salts are used as reagents, useful solvents include water, alcohols, such as methanol or ethanol, glyme, tetrahydrofuran, or the like. When the ammonium salt is other than a hydroxide or alkoxide, an additional base, such as potassium or sodium hydroxide, hydride, or alkoxide is generally used. The particular choice of solvent will depend on the relative solubilities of the starting materials and the resultant salts, and slurries rather than solutions of certain reagents may be used to obtain the salts. Generally, equivalent amouints of the starting reagents are used and the salt-forming reaction is carried out at about 0° C. to about 100° C., preferably at about room temperature.

The acid addition salts of the present invention can be prepared by any convenient art-recognized method such as by reacting hydrochloric, hydrobromic, sulfuric, nitric, phosphoric, acetic, propionic, benzoic or other suitable acid with a compound of the present invention having a basic functionality in a suitable solvent. Useful solvents include water, alcohols, ethers, esters, ketones, haloalkanes and the like. The particular choice of solvent will depend on the relative solubilities of the starting materials and the resulting salts, and slurries rather than solutions of certain reagents may be used to obtain the salts. Generally, equivalent molar amounts of starting materials are used and the salt-forming reaction is carried out at from about $-100°$ C. to about 100° C., preferably at about room temperature.

The following examples will further illustrate this invention but are not intended to limit it in any way. In Table I, typical 1-substituted-4-substituted-4,5-dihydro-1H-pyrazoles of the present invention are listed. Structures were confirmed by NMR and in some cases by IR and/or elemental analysis. After Table I, preparation of representative precursors or intermediates are described as Examples A through P. Following Examples A through P, specific illustrative preparations of compounds of Examples 2, 5, 34, 51, 61, 74, 77, 92, 95, 98, 115, 130, 138, 145, 147, 150, 160, 224, 239, 261, 262, 264, 265, 383, 467 and 473 are described. It will be appreciated by those skilled in the art that except for those compounds where Z is hydrogen, the Y and Z substituents can be interchanged without departing from the spirit or scope of the present invention.

TABLE I $$Y-C-CH_2 \overset{Z}{\underset{N}{|}} \overset{U}{\underset{|}{C}}-N \overset{B}{\underset{V}{\diagdown}}$$
$$A-C\equiv N$$

| Example No. | A | B | Y | Z | V | U | Melting Point °C. |
|---|---|---|---|---|---|---|---|
| 1 | —C₆H₄Cl-4 | —C₆H₄Cl-4 | —CO₂CH₂CH₂SCH₃ | —CH₃ | H | O | Solid |
| 2 | —C₆H₄Cl-4 | —C₆H₄Cl-4 | —C₆H₅ | —CH₃ | H | O | 151-153 |
| 3 | —C₆H₄Cl-4 | —C₆H₄Cl-4 | —CH₂CH(CH₃)₂ | —CH₃ | H | O | 128-130 |
| 4 | —C₆H₄Cl-4 | —C₆H₄Cl-4 | —CH₂CH₃ | —CH₃ | H | O | 134-136 |
| 5 | —C₆H₄Cl-4 | —C₆H₄Cl-4 | —CH₃ | —CH₂C₆H₅ | H | O | Oil |
| 6 | —C₆H₄Cl-4 | —C₆H₄Cl-4 | —CH₂CH₃ | —C₆H₅ | H | O | Solid |
| 7 | —C₆H₄Cl-4 | —C₆H₄Cl-4 | —CH₂CH₂CH₃ | —C₆H₅ | H | O | Solid |
| 8 | —C₆H₄Cl-4 | —C₆H₄Cl-4 | —CH(CH₃)₂ | —C₆H₅ | H | O | Solid |
| 9 | —C₆H₄Cl-4 | —C₆H₄Cl-4 | —CH₂CH(CH₃)₂ | —C₆H₅ | H | O | Solid |
| 10 | —C₆H₄Cl-4 | —C₆H₄Cl-4 | —C₆H₅ | —CH₂C₆H₅ | H | O | Foam |
| 11 | —C₆H₄Cl-4 | —C₆H₄Cl-4 | —CH(CH₃)CH₂CH₃ | —CH₂CH₂CH₂Cl | H | O | Solid |
| 12 | —C₆H₄Cl-4 | —C₆H₄Cl-4 | —C₆H₅ | —C₆H₅ | H | O | Solid |
| 13 | —C₆H₄Cl-4 | —C₆H₄Cl-4 | —CH₂CH₂CH₂CH₃ | —CH₃ | H | O | Foam |
| 14 | —C₆H₄Cl-4 | —C₆H₄Cl-4 | —CH₂CH₂CH₃ | —CH₃ | H | O | Foam |
| 15 | —C₆H₄Cl-4 | —C₆H₄Cl-4 | —CH(CH₃)₂ | —CH₃ | H | O | 89-92 |
| 16 | —C₆H₄Cl-4 | —C₆H₄Cl-4 | —CH₂CH₂CH₃ | —CH₃ | H | O | Oil |
| 17 | —C₆H₄Cl-4 | —C₆H₄Cl-4 | —CH(CH₃)CH₂CH₃ | —CH₃ | H | O | Oil |
| 18 | —C₆H₄Cl-4 | —C₆H₄Cl-4 | —CH₂CH₂CH₂CH₂Cl | —CH₃ | H | O | 161-165 |
| 19 | —C₆H₄Cl-4 | —C₆H₄Cl-4 | —C₆H₅ | —CH₂CH=CH₂ | H | O | 138-142 |
| 20 | —C₆H₄Cl-4 | —C₆H₄Cl-4 | —C₆H₅ | —CH₂CO₂CH₂CH₃ | H | O | 156-158 |
| 21 | —C₆H₄Cl-4 | —C₆H₄Cl-4 | —C₆H₅ | —CH₂CN | H | O | 69-71 |
| 22 | —C₆H₄Cl-4 | —C₆H₄Cl-4 | —C₆H₅ | —CH₂SCH₃ | H | O | 88-93 |
| 23 | —C₆H₄Cl-4 | —C₆H₄Cl-4 | —C₆H₅ | —CH₂OCH₃ | H | O | 130-135 |
| 24 | —C₆H₄Cl-4 | —C₆H₄Cl-4 | —CH(CH₃)₂ | —C₆H₅ | —CH(CH₃)₂ | O | Oil |
| 25 | —C₆H₄Cl-4 | —C₆H₄Cl-4 | —CH₂CH₂CH₃ | —CH₃ | H | O | Oil |
| 26 | —C₆H₄Br-4 | —C₆H₄Cl-4 | —CH₂CH₂CH₃ | —CH₃ | H | O | Semisolid |
| 27 | —C₆H₄Cl-4 | —C₆H₄Cl-4 | —CH₂CH₂CH₂CH₃ | —CH₃ | H | O | Oil |
| 28 | —C₆H₄Cl-4 | —C₆H₄Cl-4 | —CH₂CH₂CH₂CH₂CH₃ | —CH₃ | H | O | Solid |
| 29 | —C₆H₄Cl-4 | —C₆H₄Cl-4 | —CH₃ | —CH₂CH=CH₂ | H | O | Oil |
| 30 | —C₆H₄Cl-4 | —C₆H₄Cl-4 | —CH(CH₃)₂ | —CH₃ | H | O | Foam |
| 31 | —C₆H₄Cl-4 | —C₆H₄Cl-4 | —CH(CH₃)₂ | —CH₃ | H | O | Oil |
| 32 | —C₆H₄Cl-4 | —C₆H₄Cl-4 | —CH₂SCH₃ | —CH₃ | H | O | Oil |
| 33 | —C₆H₄Cl-4 | —C₆H₄Cl-4 | —CH₂OCH₃ | —CH₃ | H | O | Solid |
| 34 | —C₆H₄Cl-4 | —C₆H₄Cl-4 | —CH₂CH₂CH₂CH₃ | —CH₃ | H | O | Solid |
| 35 | —C₆H₄F-4 | —C₆H₄Cl-4 | —CH₂CH₂CH₂CH₃ | —CH₃ | H | O | Oil |
| 36 | —C₆H₄F-4 | —C₆H₄Cl-4 | —CH₂CH₂CH₂OCH₃ | —CH₃ | H | O | Oil |
| 37 | —C₆H₄Cl-4 | —C₆H₄Cl-4 | —CH₃ | —CH₂CH₂OCH₃ | H | O | Oil |
| 38 | —C₆H₄Cl-4 | —C₆H₄Cl-4 | —CH₂CH₂CH₂CN | —CH₃ | H | O | Solid |
| 39 | —C₆H₄Cl-4 | —C₆H₄Cl-4 | —CH₃ | —CH₂CH=CH₂ | H | O | Oil |
| 40 | —C₆H₄Cl-4 | —C₆H₄Cl-4 | —CH₂CH₂OCOCH₃ | —CH₃ | H | O | 60-65 |
| 41 | —C₆H₄Cl-4 | —C₆H₄Cl-4 | —CH₂OCH₂CH₂OCH₃ | —CH₃ | H | O | Solid |
| 42 | —C₆H₄Cl-4 | —C₆H₄Cl-4 | —CH₃ | —CH₂CH₂CH₂CH=CH₂ | H | O | Solid |
| 43 | —C₆H₄Cl-4 | —C₆H₄Cl-4 | —CH₃ | —CH₂CH₂SC₆H₅ | H | O | 125-128 |
| 44 | —C₆H₄Cl-4 | —C₆H₄Cl-4 | —OCOCH₃ | —CH₃ | H | O | Solid |

TABLE I-continued

| Example No. | A | B | Y | Z | V | U | Melting Point °C |
|---|---|---|---|---|---|---|---|
| 45 | —C₆H₄Cl—4 | —C₆H₄Cl—4 | —CH₃ | —CH(OH)CH₃ | H | O | — |
| 46 | —C₆H₄Cl—4 | —C₆H₄Cl—4 | —C₆H₄Cl—4 | —CH₃ | H | O | Solid |
| 47 | —C₆H₄Cl—4 | —C₆H₄Cl—4 | —CH₂—CH₂—CH₂—CH₃ | —CH₃ | H | O | 179–181 |
| 48 | —C₆H₄Cl—4 | —C₆H₄Cl—2,4 | —C₆H₅ | —CH₃ | H | O | 110–114 |
| 49 | —C₆H₃Cl₂—3,4 | —C₆H₄Cl—4 | —C₆H₅ | —CH₃ | H | O | 102–104 |
| 50 | —C₆H₄Cl—4 | —C₆H₄Cl—4 | —CH₃ | —C₆H₁₁ | H | O | 132–135 |
| 51 | —C₆H₄Cl—4 | —C₆H₄Cl—4 | —C₆H₅ | —CH₃ | —CH₃ | O | Foam |
| 52 | —C₆H₄Cl—4 | —C₆H₄Cl—4 | —CH(OH)CH₃ | —C₆H₅ | H | O | Foam |
| 53 | —C₆H₄Cl—4 | —C₆H₄Cl—4 | —COCH₃ | —CH₃ | —CH₃ | O | Oil |
| 54 | —C₆H₄Cl—4 | —C₆H₄Cl—4 | —CH₂—CH(CH₃)₂ | —CH₃ | H | O | Solid |
| 55 | —C₆H₄Cl—4 | —C₆H₃Cl₂—3,4 | —C₆H₅ | —CH₃ | H | O | Solid |
| 56 | —C₆H₄Cl—4 | —C₆H₃Cl₂—3,5 | —C₆H₅ | —CH₃ | —CH₃ | O | Solid |
| 57 | —C₆H₄Cl—4 | —C₆H₄Cl—3 | —C₆H₅ | —CH₃ | H | O | Solid |
| 58 | —C₆H₄Cl—4 | —C₆H₄Cl—4 | —C₆H₄Cl—4 | —C₆H₅ | H | O | Solid |
| 59 | —C₆H₄Cl—4 | —C₆H₃Cl₂—3,5 | —C₆H₄Cl—4 | —CH₃ | —CH₃ | O | 163–164 |
| 60 | —C₆H₃Cl₂—3,4 | —C₆H₃Cl₂—3,5 | —CH₃ | —CH₃ | H | O | Oil |
| 61 | —C₆H₃(OCH₃)₂—3,4 | —C₆H₃Cl₂—3,4 | —C₆H₅ | —CH₃ | —CH₃ | O | 140–147 |
| 62 | —C₆H₃(OCH₃)₂—3,4 | —C₆H₄OCF₃—4 | —CO₂CH₃ | —CH₂—CH₂—CH₂—CH₃ | H | O | 146–150 |
| 63 | —C₆H₄Cl—4 | —C₆H₄Cl—4 | —CH₃ | —C₆H₅ | H | O | Solid |
| 64 | —C₆H₄Cl—4 | —C₆H₄Cl—4 | —CH₂OH | —CH₃ | H | O | Solid |
| 65 | —C₆H₄Cl—4 | —C₆H₄Cl—4 | —CH₂OCOCH₃ | —C₆H₅ | H | O | Solid |
| 66 | —C₆H₄Cl—4 | —C₆H₄Cl—4 | —CH₂CH₂Cl | —CH₃ | H | O | Solid |
| 67 | —C₆H₄Cl—4 | —C₆H₄Cl—4 | —CO₂H | —CH₃ | H | O | Solid |
| 68 | —C₆H₄Cl—4 | —C₆H₄Cl—4 | —CO₂H | —CH₃ | H | O | Oil |
| 69 | —C₆H₄Cl—4 | —C₆H₄Cl—4 | —CO₂Na | —CH₃ | H | O | Solid |
| 70 | —C₆H₄Cl—4 | —C₆H₄Cl—4 | —CH₂CH₂SCH₃ | —CH₂CH(OH)CH₃ | H | O | Solid |
| 71 | —C₆H₄Cl—4 | —C₆H₄Cl—4 | —CH₃ | —CH₃ | H | O | Oil |
| 72 | —C₆H₄Cl—4 | —C₆H₄Cl—4 | —CH₂SCH₂SCH₂CH₃ | —CH₂CH₂CH₂N₃ | H | O | Oil |
| 73 | —C₆H₄Cl—4 | —C₆H₄Cl—4 | —CH₃ | —CH₃ | H | O | 128–150 |
| 74 | —C₆H₄Cl—4 | —C₆H₄Cl—4 | —CO₂CH₃ | H | H | O | Solid |
| 75 | —C₆H₄Cl—4 | —C₆H₄Cl—4 | —C₆H₅ | —CH₂CO₂C₂H₅ | H | O | Solid |
| 76 | —C₆H₄Cl—4 | —C₆H₄Cl—4 | —CO₂CH₃ | —CH₃ | H | O | 125.5–126.5 |
| 77 | —C₆H₄Cl—4 | —C₆H₄Cl—4 | —CO₂CH₃ | —C₆H₅ | H | O | Solid |
| 78 | —C₆H₄Cl—4 | —C₆H₄Cl—4 | —CH₂CO₂H | —CH₃ | H | O | Solid |
| 79 | —C₆H₄Cl—4 | —C₆H₄Cl—4 | —C₆H₅ | —CH₂CH₂SO₂CH₃ | H | O | Solid |
| 80 | —C₆H₄Cl—4 | —C₆H₄Cl—4 | —CH₃ | —CH₂CH₃ | H | O | Solid |
| 81 | —C₆H₄Cl—4 | —C₆H₄Cl—4 | —CH₂CH₃ | —CH₃ | H | O | Solid |
| 82 | —C₆H₄Cl—4 | —C₆H₄Cl—4 | —CH₂CH₂SOCH₃ | —CH₃ | H | O | Solid |
| 83 | —C₆H₄Cl—4 | —C₆H₄Cl—4 | —CO₂CH₂CH₃ | —CH₃ | —CN | O | — |
| 84 | —C₆H₄Cl—4 | —C₆H₄Cl—4 | —C₆H₅ | —CH₃ | H | O | 175–176 |
| 85 | —C₆H₅ | —C₆H₄Cl—4 | —CH₂CO₂CH₃ | —CH₃ | H | O | Oil |
| 86 | —C₆H₄Cl—4 | —C₆H₄Cl—4 | —C₆H₅ | —CH₃ | H | O | Foam |
| 87 | —C₆H₄Cl—4 | —C₆H₄Cl—4 | —CH₃ | —SCH₃ | —COCH₃ | O | Oil |
| 88 | —C₆H₄Cl—4 | —C₆H₄Cl—4 | | | H | O | |

TABLE I-continued $$Y-CH_2 \overset{Z}{\underset{A-C=N}{\overset{|}{C}}} \overset{B}{\underset{|}{N}} \overset{U}{\underset{V}{N}}$$

| Example No. | A | B | Y | Z | U | V | Melting Point °C. |
|---|---|---|---|---|---|---|---|
| 89 | —C₆H₄Cl—4 | —C₆H₄Cl—4 | —CO₂CH₂SCH₃ | —CH₃ | O | H | Oil |
| 90 | —C₆H₄Cl—4 | —C₆H₄Cl—4 | —COCH₂CH₃ | —CH₃ | O | H | Solid |
| 91 | —C₆H₄Cl—4 | —C₆H₄(CO₂CH₂CH₃)—4 | —C₆H₅ | —CH₃ | O | H | 81-82 |
| 92 | —C₆H₄Cl—4 | —C₆H₄Cl—4 | —CON(CH₃)₂ | —CH₃ | O | H | 194-197 |
| 93 | —C₆H₄Cl—4 | —C₆H₄Cl—4 | —CH₃ | —CN | O | H | — |
| 94 | —C₆H₄Cl—4 | —C₆H₄Cl—4 | —CH₂CH₂OH | —CH₃ | O | H | Solid |
| 95 | —C₆H₄Cl—4 | —C₆H₄Cl—4 | —CO₂CH₂CH₃ | H | O | H | Solid |
| 96 | —C₆H₄Cl—4 | —C₆H₄Cl—4 | —C₆H₅ | —CH₃ | O | —CH₂OCH₃ | Oil |
| 97 | —C₆H₄Cl—4 | —C₆H₄Cl—4 | —CO₂CH₃ | —CH₃ | O | —CH₃ | 117-120 |
| 98 | —C₆H₄Cl—4 | —C₆H₄Cl—4 | —CS₂CH₃ | —CH₃ | O | H | Solid |
| 99 | —C₆H₄Cl—4 | —C₆H₄(CO₂CH(CH₃)₂)—4 | —C₆H₅ | —CH₃ | O | H | Foam |
| 100 | —C₆H₄Cl—4 | —C₆H₄Cl—4 | —CO₂CH₂CH₂CH₃ | —CH₃ | O | H | Foam |
| 101 | —C₆H₄Cl—4 | —C₆H₄Cl—4 | —CO₂CH₂CH₂CH₃ | —CH₃ | O | H | Solid |
| 102 | —C₆H₄Cl—4 | —C₆H₄Cl—4 | —CO₂CH(CH₃)₂ | —CH₃ | O | H | Solid |
| 103 | —C₆H₄Cl—4 | —C₆H₄Cl—4 | —CO₂CH₂CH₂N(CH₃)₂ | —CH₃ | O | H | Solid |
| 104 | —C₆H₄Cl—4 | —C₆H₄Cl—4 | —CO₂CH₂CH₂N(CH₃)₂·HCl | —CH₃ | O | H | 100-103 |
| 105 | —C₆H₄Cl—4 | —C₆H₄Cl—4 | —CO₂CH₃ | —CH₃ | O | —CO₂CH₃ | Solid |
| 106 | —C₆H₄Cl—4 | —C₆H₄Cl—4 | —CH₂CHBrCH₂Br | —CH₃ | O | H | Oil |
| 107 | —C₆H₅ | —C₆H₄Cl—4 | —CO₂CH₂CH₂SO₂CH₃ | —CH₃ | O | H | Foam |
| 108 | —C₆H₄Cl—4 | —C₆H₄Cl—4 | —CO₂C₆H₄Cl—4 | —CH₂CH₂CH₂Cl | O | H | Foam |
| 109 | —C₆H₄Cl—4 | —C₆H₄Cl—4 | —CH₃ | —CH₃ | O | H | Solid |
| 110 | —C₆H₄Cl—4 | —C₆H₄Cl—4 | —CO₂CH₂CH₃ | —CH₃ | O | H | Solid |
| 111 | —C₆H₄Cl—4 | —C₆H₄Cl—4 | —COCH₂CH₃ | —CH₃ | O | H | Foam |
| 112 | —C₆H₄Cl—4 | —C₆H₄Cl—4 | —COC₆H₅ | —CH₃ | O | H | Solid |
| 113 | —C₆H₄Cl—4 | —C₆H₄Cl—4 | —CON(CH₂CH₃)₂ | —CH₃ | O | H | 147-149 |
| 114 | —C₆H₄Cl—4 | —C₆H₄Cl—4 | —CO₂CH₃ | —CH₃ | O | —COCH₃ | Oil |
| 115 | —C₆H₄Cl—4 | —C₆H₄Cl—4 | —CO₂CH₂CH₃ | —CH₃ | O | —COCH₃ | Oil |
| 116 | —C₆H₅ | —C₆H₄Cl—4 | —CON(CH₃)₂ | —CH₃ | O | H | Solid |
| 117 | —C₆H₅ | —C₆H₄Cl—4 | —CON(CH₃)₂ | —CH₃ | O | —COCH₂CH₃ | Solid |
| 118 | —C₆H₄Cl—4 | —C₆H₄Cl—4 | —C₆H₅ | —CH₃ | O | —COC(CH₃)₃ | Solid |
| 119 | —C₆H₄Cl—4 | —C₆H₄Cl—4 | —C₆H₅ | —CH₃ | O | —CO₂CH₃ | Solid |
| 120 | —C₆H₄Cl—4 | —C₆H₄Cl—4 | —CON(CH₃)₂ | H | O | —CO₂CH₃ | Solid |
| 121 | —C₆H₄Cl—4 | —C₆H₄Cl—4 | —C₆H₅ | —CH₃ | O | —COC₆H₅ | Solid |
| 122 | —C₆H₄Cl—4 | —C₆H₄Cl—4 | —CO₂CH₃ | —CH₃ | O | —COCF₃ | Solid |
| 123 | —C₆H₄Cl—4 | —C₆H₄Cl—4 | —CO₂CH₃ | —CH₃ | O | —CHO | Oil |
| 124 | —C₆H₄Cl—4 | —C₆H₄Cl—4 | —CO₂CH₃ | —CH₃ | O | —CO₂OCH₃ | — |
| 125 | —C₆H₄Cl—4 | —C₆H₄Cl—4 | —CO₂CH₃ | —CH₃ | O | —CO₂CH₂CH₃ | Solid |
| 126 | —C₆H₄Cl—4 | —C₆H₄Cl—4 | —CO₂CH₃ | —CH₃ | O | —CO₂CH=CH₂ | Solid |
| 127 | —C₆H₄Cl—4 | —C₆H₄Cl—4 | —CO₂CH₃ | —CH₃ | O | —CO₂C₆H₅ | Solid |
| 128 | —C₆H₄Cl—4 | —C₆H₄Cl—4 | —CSN(CH₃)₂ | —CH₃ | O | H | Solid |
| 129 | —C₆H₄Cl—4 | —C₆H₄Cl—4 | —CO₂CH₃ | —CH₃ | O | H | 69-78 |
| 130 | —C₆H₄Cl—4 | —C₆H₄Cl—4 | —CO₂CH₃ | —CH₃ | S | —COCH₃ | 138-141 |
| 131 | —C₆H₄Cl—4 | —C₆H₄F—4 | —CO₂CH₃ | —CH₃ | O | H | 115-119 |
| 132 | —C₆H₅ | | | | | | |

TABLE I-continued

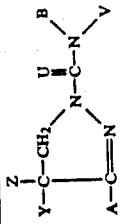

| Example No. | A | B | Y | Z | V | U | Melting Point °C |
|---|---|---|---|---|---|---|---|
| 133 | —C₆H₅ | —C₆H₄Br—4 | —CO₂CH₃ | —CH₃ | H | O | 130-136 |
| 134 | —C₆H₄F—4 | —C₆H₄Cl—4 | —CO₂CH₃ | —CH₃ | H | O | 168-173 |
| 135 | —C₆H₄F—4 | —C₆H₄Br—4 | —CO₂CH₃ | —CH₃ | H | O | 154-158 |
| 136 | —C₆H₄F—4 | —C₆H₄F—4 | —CO₂CH₃ | —CH₃ | H | O | 142-145 |
| 137 | —C₆H₄Cl—4 | —C₆H₄Cl—4 | —CO₂CH₃ | —CH₃ | —CO₂CH₃ | O | 100-103 |
| 138 | —C₆H₄Cl—4 | —C₆H₄Cl—4 | —CO₂CH₃ | —CH₃ | —CON(CH₃)₂ | O | Solid |
| 139 | —C₆H₅ | —C₆H₄Cl—4 | —CO₂CH₃ | —CH₃ | —CO₂CH₃ | O | Solid |
| 140 | —C₆H₄Br—4 | —C₆H₄Cl—4 | —CO₂CH₃ | —CH₃ | H | O | Oil |
| 141 | —C₆H₄Cl—4 | —C₆H₄Cl—4 | —CO₂CH₃ | —CH₃ | —COCO₂CH₃ | O | 78-87 |
| 142 | —C₆H₄Cl—4 | —C₆H₄F—4 | —CO₂CH₃ | —CH₃ | H | O | 148-151 |
| 143 | —C₆H₄Cl—4 | —C₆H₄Cl—4 | —CO₂CH₃ | —CH₃ | H | O | 105-110 |
| 144 | —C₆H₄F—4 | —C₆H₄F—4 | —CO₂CH₃ | —CH₃ | —SCO₂CH₃ | O | Foam |
| 145 | —C₆H₄Cl—4 | —C₆H₄Cl—4 | —CO₂CH₃ | —CH₃ | —SCO₂CH₃ | O | Foam |
| 146 | —C₆H₄Cl—4 | —C₆H₄Cl—4 | —C₆H₅ | —CH₃ | H | O | Oil |
| 147 | —C₆H₄Br—4 | —C₆H₄Br—4 | —CO₂CH₃ | —CH₃ | H | O | 114-117 |
| 148 | —C₆H₄CF₃—4 | —C₆H₄Cl—4 | —CO₂CH₃ | —CH₃ | H | O | 145-149 |
| 149 | —C₆H₄Cl—4 | —C₆H₄CF₃—4 | —CO₂CH₃ | —CH₃ | H | O | 143-146 |
| 150 | —C₆H₄Cl—4 | —C₆H₄Cl—4 | —CO₂CH₃ | —CH₃ | —SC₆H₄NO₂—2 | O | — |
| 151 | —C₆H₄Cl—4 | —C₆H₄Cl—4 | —CO₂CH₃ | —CH₃ | —SCH₂CH₂CH₃ | O | Oil |
| 152 | —C₆H₄CF₃—4 | —C₆H₄(CH(CH₃)₂)—4 | —CO₂CH₃ | —CH₃ | H | O | 165-167 |
| 153 | —C₆H₄Cl—4 | —C₆H₄OCH₃—4 | —CO₂CH₃ | —CH₃ | H | O | 58-60 |
| 154 | —C₆H₄Cl—4 | —C₆H₄SCH₃—4 | —CO₂CH₃ | —CH₃ | H | O | 120-122 |
| 155 | —C₆H₄Cl—4 | —C₆H₄SO₂CH₃—4 | —CO₂CH₃ | —CH₃ | H | O | 114-116 |
| 156 | —C₆H₄Cl—4 | —C₆H₄Cl—4 | —CO₂CH₃ | —CH₃ | —SC₆H₅ | O | 179-182 |
| 157 | —C₆H₄Cl—4 | —C₆H₄Cl—4 | —CO₂CH₃ | —CH₃ | —SCH₂CH₂CN | O | 122-125 |
| 158 | —C₆H₄Cl—4 | —C₆H₄Cl—4 | —CO₂CH₃ | —CH₃ | CH₃ | O | Solid |
| 159 | —C₆H₄Cl—4 | —C₆H₄Cl—4 | —CO₂CH₃ | —CH₃ | —SCH | O | Oil |
| 160 | —C₆H₄Cl—4 | —C₆H₄Cl—4 | —CO₂CH₃ | —CH₃ | CH₂CO₂CH₃ | O | — |
| 161 | —C₆H₄Cl—4 | —C₆H₄Cl—4 | —CO₂CH₃ | —CH₃ | —SCH₃ | O | — |
| 162 | —C₆H₄Cl—4 | —C₆H₄SOCH₃—4 | —CO₂CH₃ | —CH₃ | H | O | Oil |
| 163 | —C₆H₄Cl—4 | —C₆H₄I—4 | —CO₂CH₃ | —CH₃ | H | O | 120-123 |
| 164 | —C₆H₄Cl—4 | —C₆H₄N(CH₃)₂—4 | —COCH(CH₃)₂ | —CH₃ | H | O | 145-146 |
| 165 | —C₆H₄Cl—4 | —C₆H₄Cl—4 | —COC(CH₃)₃ | —CH₃ | H | O | 93-95 |
| 166 | —C₆H₄Cl—4 | —C₆H₄Cl—4 | —CO₂CH₃ | —CH₃ | H | O | 211-212 |
| 167 | —C₆H₄Cl—4 | —C₆H₄(N(CH₃)₃⁺I⁻)—4 | —CO₂CH₃ | —CH₃ | H | O | Oil |
| 168 | —C₆H₄Cl—4 | —C₆H₄(N(CH₃)₂O)—4 | —CO₂CH₃ | —CH₃ | H | O | Solid |
| 169 | —C₆H₄CF₃—4 | —C₆H₄Cl—4 | —CO₂CH₃ | —CH₃ | H | O | Solid |
| 170 | —C₆H₄Cl—4 | —C₆H₄CF₃—3 | —CO₂CH₃ | —CH₃ | H | O | Solid |
| 171 | —C₆H₄Cl—4 | —C₆H₄SCH₃—3 | —CO₂CH₃ | —CH₃ | H | O | Foam |
| 172 | —C₆H₄Cl—4 | —C₆H₄SO₂CH₃—3 | —CH₃ | —CH₃ | H | O | 186-187 |
| 173 | —C₆H₄Cl—4 | —C₆H₄Cl—4 | —CH₃ | —CHOHC₆H₄F—4 | H | O | |

TABLE I-continued $$Y-C-CH_2-N\overset{Z}{\underset{A-C=N}{\bigvee}}\overset{B}{\underset{U}{\bigvee}}N\overset{V}{\underset{}{\diagdown}}$$

| Example No. | A | B | Y | Z | V | U | Melting Point °C. |
|---|---|---|---|---|---|---|---|
| 174 | —C$_6$H$_4$CH$_3$—4 | —C$_6$H$_4$Cl—4 | —CO$_2$CH$_3$ | —CH$_3$ | H | O | 127–128 |
| 175 | —C$_6$H$_4$OCH$_3$—4 | —C$_6$H$_4$Cl—4 | —CO$_2$CH$_3$ | —CH$_3$ | H | O | 148–149 |
| 176 | —C$_6$H$_4$Cl—4 | —C$_6$H$_4$Cl—4 | —CO$_2$CH$_3$ | —CH$_2$CH$_3$ | H | O | 141–143 |
| 177 | —C$_6$H$_4$Cl—4 | —C$_6$H$_4$CF$_3$—4 | —CON(CH$_3$)$_2$ | —CH$_3$ | H | O | 152–155 |
| 178 | —C$_6$H$_4$SCH$_3$—4 | —C$_6$H$_4$Cl—4 | —CO$_2$CH$_3$ | —CH$_3$ | H | O | 131–133 |
| 179 | —C$_6$H$_5$ | —C$_6$H$_4$CF$_3$—4 | —CO$_2$CH$_3$ | —CH$_3$ | H | O | 133–135 |
| 180 | —C$_6$H$_5$ | —C$_6$H$_5$Cl$_2$—3,4 | —CO$_2$CH$_3$ | —CH$_3$ | H | O | 127–130 |
| 181 | —C$_6$H$_4$SO$_2$CH$_3$—4 | —C$_6$H$_4$Cl—4 | —CO$_2$CH$_3$ | —CH$_3$ | H | O | 205–207 |
| 182 | —C$_6$H$_4$Cl—4 | —C$_6$H$_5$ | —CO$_2$CH$_3$ | —CH$_3$ | H | O | 116–119 |
| 183 | —C$_6$H$_4$Cl—4 | —C$_6$H$_3$Cl$_2$—3,4 | —CO$_2$CH$_3$ | —CH$_3$ | H | O | 132–134 |
| 184 | —C$_6$H$_4$Cl—4 | —C$_6$H$_4$Cl—4 | ![cyclohexyl with CO$_2$ and CH(CH$_3$)$_2$ and CH$_3$] | —CH$_3$ | H | O | 176–178 |
| 185 | —C$_6$H$_4$Cl—4 | —C$_6$H$_4$CF$_3$—4 | —CO$_2$CH$_3$ | —CH$_3$ | H | O | Oil |
| 186 | —C$_6$H$_4$Cl—4 | —C$_6$H$_4$OCF$_3$—4 | —CO$_2$CH$_3$ | —CH$_3$ | H | O | 47–49 |
| 187 | —C$_6$H$_4$Cl—4 | —C$_6$H$_3$CF$_3$—3,Cl—4 | —CO$_2$CH$_3$ | —CH$_3$ | H | O | 154–155 |
| 188 | —C$_6$H$_4$Cl—4 | —C$_6$H$_3$CH$_3$—3,Br—4 | —CO$_2$CH$_3$ | —CH$_3$ | H | O | 127–130 |
| 189 | —C$_6$H$_4$Cl—4 | —C$_6$H$_4$CO$_2$CH$_2$CH$_3$—4 | —CO$_2$CH$_3$ | H | H | O | 138–140 |
| 190 | —C$_6$H$_4$Cl—4 | —C$_6$H$_4$CO$_2$CH$_3$—4 | —CO$_2$CH$_3$ | H | H | O | 138–140 |
| 191 | —C$_6$H$_4$Cl—4 | ![naphthyl] | —CO$_2$CH$_3$ | —CH$_3$ | H | O | 188–190 |
| 192 | —C$_6$H$_5$ | —C$_6$H$_4$CF$_3$—4 | —CO$_2$CH$_2$CH$_3$ | —CH$_3$ | H | O | 149–150 |
| 193 | —C$_6$H$_4$Cl—4 | —C$_6$H$_4$(NO$_2$)$_2$—2,4 | —CO$_2$CH$_3$ | —CH$_3$ | H | O | 196–198 |
| 194 | —C$_6$H$_4$Cl—4 | —C$_6$H$_4$NO$_2$—4 | —CON(CH$_3$)$_2$ | —CH$_3$ | H | O | 0135–140 |
| 195 | —C$_6$H$_5$ | —C$_6$H$_4$CF$_3$—4 | —CO$_2$CH$_3$ | —CH(CH$_3$)$_2$ | H | O | 186–188 |
| 196 | —C$_6$H$_4$Cl—4 | —C$_6$H$_4$Cl—4 | —COCH$_3$ | —CH$_3$ | H | H | Oil |
| 197 | —C$_6$H$_5$ | —C$_6$H$_4$CF$_3$—4 | —COCH$_3$ | —CH$_3$ | H | O | 137–138 |
| 198 | —C$_6$H$_4$Br—4 | —C$_6$H$_4$Cl—4 | —CON(CH$_3$)$_2$ | —CH$_3$ | H | O | 160–162 |
| 199 | —C$_6$H$_4$Br—4 | —C$_6$H$_4$CF$_3$4 | —CO$_2$CH$_3$ | —CH$_3$ | H | O | 131–132 |
| 200 | —C$_6$H$_4$Br—4 | —C$_6$H$_4$CF$_3$—4 | —CO$_2$CH$_2$CH$_3$ | —CH$_3$ | H | O | 74–77 |
| 201 | —C$_6$H$_4$Br—4 | —C$_6$H$_4$CF$_3$—4 | —COCH$_3$ | —CH$_3$ | H | O | 170–172 |
| 202 | —C$_6$H$_4$Br—4 | —C$_6$H$_4$CF$_3$—4 | —CO$_2$CH$_3$ | —CH$_3$ | H | O | 48–51 |
| 203 | —C$_6$H$_4$CF$_3$—4 | —C$_6$H$_4$OCF$_3$—4 | —CO$_2$CH$_3$ | —CH$_3$ | H | O | 113–118 |

TABLE I-continued $$Y-C-CH_2 \overset{Z}{\underset{A-C=N}{\overset{|}{C}}} \overset{U}{\underset{}{\overset{||}{C}}} \overset{B}{\underset{}{N}} \overset{}{\underset{}{V}}$$

| Example No. | A | B | Y | Z | U | V | Melting Point °C |
|---|---|---|---|---|---|---|---|
| 204 | —C₆H₄Cl—4 | —C₆H₄CF₃—4 | —COCF₃ | —CH₃ | O | H | 133-136 |
| 205 | —C₆H₄Cl—4 | —C₆H₄CF₃—4 | —CHO | —CH₃ | O | H | 160-165 |
| 206 | —C₆H₄Cl—4 | —C₆H₄CF₃—4 | —CHNN(CH₃)₂ | —CH₃ | O | H | Solid |
| 207 | —C₆H₄Cl—4 | —C₆H₄CF₃—4 | —CHNNH₂ | —CH₃ | O | H | Solid |
| 208 | —C₆H₄Cl—4 | —C₆H₄CF₃—4 | —CHNOH | —CH₃ | O | H | Solid |
| 209 | —C₆H₄Cl—4 | —C₆H₄CF₃—4 | —CHNOCH₃ | —CH₃ | O | H | 131-135 |
| 210 | —C₆H₄Cl—4 | —C₆H₄CF₃—4 | —CHNOC₆H₅ | —CH₃ | O | H | 116.5-118 |
| 211 | —C₆H₄OCH₃—4 | —C₆H₄CF₃—4 | —CH=CBr₂ | —CH₃ | O | H | 174-178 |
| 212 | —C₆H₄Cl—4 | —C₆H₄CF₃—4 | —CO₂CH₃ | —CH₃ | O | H | — |
| 213 | —C₆H₄Cl—4 | —C₆H₄CO₂CH₂CH₃—4 | —CO₂CH₃ | —CH₃ | O | H | 161-163 |
| 214 | —C₆H₄Cl—4 | —C₆H₄CN—4 | —CO₂CH₃ | —CH₃ | O | H | 120-123 |
| 215 | —C₆H₄Cl—4 | —C₆H₄CO₂CH(CH₃)₂—4 | —CO₂CH₃ | —CH₃ | O | H | 144-155 |
| 216 | —C₆H₄Cl—4 | —C₆H₄OCF₂H—4 | —CO₂CH₃ | —CH₃ | O | H | 145-155 |
| 217 | —C₆H₄Cl—4 | —C₆H₄CO₂CH₃—4 | —CH=CCl₂ | —CH₃ | O | H | 164-165 |
| 218 | —C₆H₄Cl—4 | —C₆H₄CF₃—4 | —C₆H₅ | —CH₃ | O | H | 137-139 |
| 219 | —C₆H₄Cl—4 | —C₆H₄CF₃—4 | —CO₂CH₃ | —CH₃ | O | H | 180-181 |
| 220 | —C₆H₄Cl—4 | —C₆H₄OCF₂Br—4 | —CO₂CH₃ | —CH₃ | O | H | |
| 221 | —C₆H₄Cl—4 | —C₆H₄OCO₂CH₃—4 | —CO₂CH₃ | —CH₃ | O | H | 135-137 |
| 222 | —C₆H₄Cl—4 | 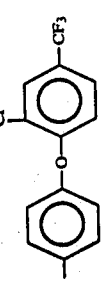 | —CO₂CH₃ | —CH₃ | O | H | 232-235 |
| 223 | —C₆H₄Cl—4 | 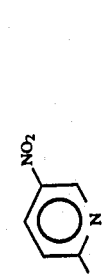 | —CO₂CH₃ | —CH₃ | O | H | 130-140 |
| 224 | —C₆H₄Cl—4 | 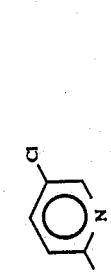 | —CO₂CH₃ | —CH₃ | O | H | |
| 225 | —C₆H₄Cl—4 | —C₆H₄CF₃—4 | —CH=CH₂ | —CH₃ | O | H | 126-131 |

TABLE I-continued

| Example No. | A | B | Y | Z | V | U | Melting Point °C. |
|---|---|---|---|---|---|---|---|
| 226 | —C₆H₄Cl-4 | (thiazole) | —CO₂CH₃ | —CH₃ | H | O | Solid |
| 227 | —C₆H₄Cl-4 | —C₆H₄OSO₂CH₃-4 | —CO₂CH₃ | —CH₃ | H | O | 171-172 |
| 228 | —C₆H₄Cl-4 | —C₆H₄OCOCH₃-4 | —CO₂CH₃ | —CH₃ | H | O | 151-152 |
| 229 | —C₆H₄Cl-4 | —C₆H₄CF₃-4 | —CO₂CH₃ | —CH₃ | H | O | 187-193 |
| 230 | —C₆H₄Cl-4 | —C₆H₄OSO₂CF₃-4 | —CO₂CH₃ | —CH₃ | H | O | 142-144 |
| 231 | —C₆H₄Cl-4 | —C₆H₃CF₃-3-Br-4 | —CO₂CH₃ | —CH₃ | H | O | Solid |
| 232 | —C₆H₄OSO₂CH₃-4 | —C₆H₄CF₃-4 | —CO₂CH₃ | —CH₃ | H | O | 113-118 |
| 234 | —C₆H₄Cl-4 | —C₆H₄CF₃-4 | —CONH₂ | —CH₃ | H | O | 233-235 |
| 235 | —C₆H₄Cl-4 | —C₆H₄CF₃-4 | —C(O)N(pyrrolidine) | —CH₃ | H | O | 127-130 |
| 236 | —C₆H₄Cl-4 | —C₆H₄CF₃-4 | —C(O)N(piperidine) | —CH₃ | H | O | 192-194 |
| 237 | —C₆H₄Cl-4 | —C₆H₄CF₃-4 | —C(O)N(morpholine) | —CH₃ | H | O | 191-193 |
| 238 | —C₆H₄Cl-4 | —C₆H₄CF₃-4 | —CH=CF₂ | —CH₃ | H | O | 120-129 |
| 239 | —C₆H₄Cl-4 | —C₆H₄OCF₃-4 | —CH=CF₂ | —CH₃ | H | O | 142-148 |
| 240 | —C₆H₄OSO₂CF₃-4 | —C₆H₄CF₃-4 | —CO₂CH₃ | —CH₃ | H | O | Oil |
| 241 | —C₆H₄Cl-4 | —C₆H₄Cl-4 | —CH=CF₂ | —CH₃ | H | O | 124-128 |
| 242 | —C₆H₄Cl-4 | —C₆H₄Cl-4 | —CH=CCl₂ | —CH₃ | H | O | Oil |
| 243 | —C₆H₄Cl-4 | —C₆H₄OCF₂CF₂H-4 | —CO₂CH₃ | —CH₃ | H | O | 98-100 |
| 244 | —C₆H₄Cl-4 | (4-CF₃-pyridyl-oxy-phenyl) | —CO₂CH₃ | —CH₃ | H | O | Solid |

TABLE I-continued $$Y-C-CH_2 \quad \underset{A-C=N}{\overset{Z}{\underset{N-C-N}{|}}}\overset{U\ B}{\underset{V}{\parallel}}$$

| Example No. | A | B | Y | Z | V | U | Melting Point °C. |
|---|---|---|---|---|---|---|---|
| 245 | —C₆H₄Cl—4 | 2,6-Cl₂-4-CH₃-C₆H₂-O-(5-CF₃-pyridin-2-yl) | —CO₂CH₃ | —CH₃ | H | O | 126-129 |
| 246 | —C₆H₄OCF₂H—4 | —C₆H₄CF₃—4 | —CO₂CH₃ | —CH₃ | H | O | 124-132 |
| 247 | —C₆H₄Cl—4 | —C₆H₄CF₃—4 | —CO₂CH₂CH₂OCH₂CH₂OCH₃ | —CH₃ | H | O | 100-102 |
| 248 | —C₆H₄OCF₂H—4 | —C₆H₄Cl—4 | —CO₂CH₃ | —CH₃ | H | O | 147-150 |
| 249 | —C₆H₄Cl—4 | —C₆H₄SO₂NH₂—4 | —CO₂CH₃ | —CH₃ | H | O | 213-215 |
| 250 | —C₆H₄Cl—4 | —C₆H₄CON(CH₃)₂—4 | —CO₂CH₃ | —CH₃ | H | O | 179-181 |
| 251 | —C₆H₄Cl—4 | —C₆H₄SO₂N(CH₃)₂—4 | —CO₂CH₃ | —CH₃ | H | O | 146-149 |
| 252 | —C₆H₄OCF₃—4 | —C₆H₄CF₃—4 | —CO₂CH₃ | —CH₃ | H | O | 128-131 |
| 253 | —C₆H₄OCF₃—4 | —C₆H₄OCF₃—4 | —CO₂CH₃ | —CH₃ | H | O | 86-90 |
| 254 | —C₆H₄C₆H₅—4 | —C₆H₄CF₃—4 | —CO₂CH₃ | —CH₃ | H | O | Solid |
| 255 | —C₆H₄C₆H₅—4 | —C₆H₄CF₃—4 | —CO₂CH₃ | —CH₃ | H | O | 158-161 |
| 256 | —C₆H₄OC₆H₅—4 | —C₆H₄CF₃—4 | —CO₂CH₃ | —CH₃ | H | O | 153-157 |
| 257 | —C₆H₄Cl—4 | —C₆H₄SCF₂CF₂H—4 | —CO₂CH₃ | —CH₃ | H | O | 125-131 |
| 258 | —C₆H₄Cl—4 | —C₆H₄SO₂CF₂CF₂H—4 | —CO₂CH₃ | —CH₃ | H | O | 178-181 |
| 259 | —C₆H₄Cl—4 | 4-Cl-C₆H₄-O-pyridin-2-yl | —CO₂CH₃ | —CH₃ | H | O | — |
| 260 | —C₆H₄Cl—4 | 4-methyl-C₆H₄-O-(3-CF₃-pyridin-2-yl) | —CO₂CH₃ | —CH₃ | H | O | Solid |
| 261 | —C₆H₄Cl—4 | 3,4-dimethylisoxazol-5-yl | —CO₂CH₃ | —CH₃ | H | O | 214-216 |
| 262 | —C₆H₄Cl—4 | —C₆H₄OCF₃—4 | —CHO | —CH₃ | H | O | — |
| 263 | —C₆H₄Cl—4 | —C₆H₃Cl—2-OCF₃—4 | —CH=CCl₂ | —CH₃ | H | O | Oil |

TABLE I-continued $$Y-C(Z)-CH_2-N(U)(B)-C(=V)-N(A)-C=N$$

| Example No. | A | B | Y | Z | V | U | Melting Point °C |
|---|---|---|---|---|---|---|---|
| 264 | —C₆H₄Cl—4 | —C₆H₄OCF₃—4 | —CH=CCl₂ | —CH₃ | H | O | 140-143 |
| 265 | —C₆H₄Cl—4 | —C₆H₄OCF₃—4 | —CH=CBr₂ | —CH₃ | H | O | — |
| 266 | —C₆H₄Cl—4 | —C₆H₄Cl—4 | —CHO | —CH₃ | H | O | 182-185 |
| 267 | —C₆H₄OH—4 | —C₆H₄CF₃—4 | —CO₂CH₃ | —CH₃ | H | O | 195-197 |
| 268 | —C₆H₄CH(CH₃)OCH₂CH₃—4 | —C₆H₄CF₃—4 | —CO₂CH₃ | —CH₃ | H | O | Oil |
| 269 | —C₆H₄Cl—4 | —C₆H₄Cl—4 | —CH=CBr₂ | —CH₃ | H | O | 67-70 |
| 270 | —C₆H₄Cl—4 | C₆H₄CF₃ | —CO₂H | —CH₃ | H | O | 142-143 |
| 271 | —C₆H₄Cl—4 | —C₆H₄C₆H₅ | —CO₂CH₃ | —CH₃ | H | O | Solid |
| 272 | —C₆H₄Cl—4 | —C₆H₃Cl—3F—4 | —CO₂CH₃ | —CH₃ | H | O | 148-148 |
| 273 | —C₆H₄Cl—4 | —C₆H₄(CF₃)₂—3,5 | —CO₂CH₃ | —CH₃ | H | O | 172.5-173.5 |
| 274 | —C₆H₄Cl—4 | —C₆H₃NO₂—2-Cl—4 | —CO₂CH₃ | —CH₃ | H | O | 163-164 |
| 275 | —C₆H₄Cl—4 | —C₆H₃NO₂—3-CH₃—4 | —CO₂CH₃ | —CH₃ | H | O | 181-180.5 |
| 276 | —C₆H₄Cl—4 | —C₆H₄OC₆H₅—4 | —CO₂CH₃ | —CH₃ | H | O | Solid |
| 277 | —C₆H₄Cl—4 | —C₆H₄CF₃—4 | —CO₂CH₃ | —CH₃ | H | O | 108-110 |
| 278 | —C₆H₄CH₂CH₃—4 | —C₆H₄N=NC₆H₅—4 | —CO₂CH₃ | —CH₃ | H | O | 181-189 |
| 279 | —C₆H₄CH₂CH₂CH₃—4 | —C₆H₄CF₃—4 | —CO₂CH₃ | —CH₃ | H | O | 116-120 |
| 280 | —C₆H₄Cl—4 | —C₆H₄CHCl₂—4 | —CO₂CH₃ | —CH₃ | H | O | 131-134 |
| 281 | —C₆H₄Cl—4 | —C₆H₄Cl | —CO₂CH₂CO₂CH₃ | —CH₃ | H | O | 148-150 |
| 282 | —C₆H₄Cl—4 | —C₆H₄CF₃ | —CO₂CH₂C₆H₃Cl₂—3,4 | —CH₃ | H | O | 155-156 |
| 283 | —C₆H₄Cl—4 | —C₆H₄CF₃ | —CO₂CH₃ | —CH₃ | H | O | 148-150 |
| 284 | —C₆H₄Cl—4 | —C₆H₃Cl—2-CF₃—4 | —CO₂CH₃ | —CH₃ | H | O | Solid |
| 285 | —C₆H₄Cl—4 | —C₆H₄COCH₃ | —CO₂CH₃ | —H | H | O | 151-153 |
| 286 | —C₆H₄Cl—4 | —C₆H₄CF₃—4 | —CH=CCl₂ | —CH₃ | H | O | — |
| 287 | —C₆H₄Cl—4 | —C₆H₄CF₃—4 | —COCH₂Cl | —H | H | O | 195-197 |
| 288 | —C₆H₄Cl—4 | —C₆H₄OCF₃—4 | —CH=CCl₂ | —H | H | O | Solid |
| 289 | —C₆H₄Cl—4 | —C₆H₄Cl—4 | —CH=CCl₂ | —H | H | O | 194-198 |
| 290 | —C₆H₄Cl—4 | —C₆H₄OCF₂CF₂H—4 | —CH=CCl₂ | —H | H | O | 183-190 |
| 291 | —C₆H₄Cl—4 | —C₆H₄COCH₃ | —CH₂CO₂C(CH₃)₃ | —CH₃ | H | O | 144-146 |
| 292 | —C₆H₄Cl—4 | —C₆H₄CF₃—4 | —CH(CH₂CN)₂ | —CH₃ | H | O | Solid |
| 293 | —C₆H₄Cl—4 | —C₆H₄CF₃—4 | —CH=C(CN)CO₂CH₃ | —CH₃ | H | O | Solid |
| 294 | —C₆H₄Cl—4 | —C₆H₄CH₃ | —CH=C(COCH₃)CO₂CH₃ | —CH₃ | H | O | — |
| 295 | —C₆H₄Cl—4 | —C₆H₄OCF₃—4 | —CH=NN(H)CSNH₂ | —CH₃ | H | O | — |
| 296 | —C₆H₄Cl—4 | —C₆H₄Cl—4 | —CH(CO₂CH₃)CH₂CO₂CH₃ | —CH₃ | H | O | 150-154 |
| 297 | —C₆H₄Cl—4 | —C₆H₄CF₃ | —CH₂CO₂CH₃ | —CH₃ | H | O | 111-115 |
| 298 | —C₆H₄Cl—4 | —C₆H₄CF₃ | —CH=C(CO₂CH₃)₂ | —CH₃ | H | O | — |
| 299 | —C₆H₄Cl—4 | —C₆H₄CF₃ | —COCH₃ | —CH₃ | H | O | 170-181 |
| 300 | —C₆H₄Cl—4 | —C₆H₄CF₃ | —CO₂CH₃ | —CH₃ | H | O | — |
| 301 | —C₆H₄Cl—4 | (4-methylphenoxy-3-chloro-5-trifluoromethylpyridinyl) | —CO₂CH₃ | —CH₃ | H | O | — |

TABLE I-continued

| Example No. | A | B | Y | Z | V | U | Melting Point °C. |
|---|---|---|---|---|---|---|---|
| 302 | —C₆H₄Cl—4 | —C₆H₄CF₃—4 | —CH=CHBr | —CH₃ | H | O | 154-161 |
| 303 | —C₆H₄Cl—4 | —C₆H₄CF₃—4 | —COCO₂CH₃ | —CH₃ | H | O | 139-141 |
| 304 | —C₆H₄Cl—4 | —C₆H₄CF₃—4 | —CO₂CH₃(+) | —CH₃ | H | O | Solid |
| 305 | —C₆H₄Cl—4 | —C₆H₄CF₃—4 | —CO₂CH₃(−) | —CH₃ | H | O | Solid |
| 306 | —C₆H₄C—4 | —C₆H₄CF₃—4 | —CHCH₂CO₂C(CH₃)₃<br>CO₂C(CH₃)₃ | —CH₃ | H | O | 93-95 |
| 307 | —C₆H₄Cl—4 | —C₆H₄OCH₂C≡CH—4 | —CO₂CH₃ | —CH₃ | H | O | Solid |
| 308 | —C₆H₄Cl—4 | —C₆H₄OCH₂CH=CH₂ | —CO₂CH₃ | —CH₃ | H | O | Oil |
| 309 | —C₆H₄Cl—4 | —C₆H₄OCH₂CH₂CH₃—4 | —CHO | —CH₃ | H | O | 125-139 |
| 310 | —C₆H₄Cl—4 | —C₆H₄SCH₃—4 | —CH=CCl₂ | —CH₃ | H | O | 177.5-179 |
| 311 | —C₆H₄Cl—4 | —C₆H₄SO₂CH₃—4 | —CH=CCl₂ | —CH₃ | H | O | 227-228 |
| 312 | —C₆H₄Cl—4 | —C₆H₄CF₃—4 | —CO₂CH₃ | —CH₃ | H | O | 122-128 |
| 313 | —C₆H₄C(CH₃)₃—4 | —C₆H₄CF₃—4 | —CO₂CH₃ | —CH₃ | H | O | 122-125 |
| 314 | —C₆H₄Cl—4 | —C₆H₄CF₃—4 | —CO₂CH₃ | —CH₃ | —COCH₃ | O | Oil |
| 315 | —C₆H₄Cl—4 | —C₆H₄CF₃—4 | —CO₂CH₃ | —CH₃ | —CO₂CH₃ | O | 130-134 |
| 316 | —C₆H₄Cl—4 | —C₆H₄CF₃—4 | —CO₂CH₃ | —CH₃ | —COCO₂CH₃ | O | — |
| 317 | —C₆H₄Cl—4 | naphthyl | —CO₂CH₃ | —CH₃ | H | O | Oil |
| 318 | —C₆H₄Cl—4 | —C₆H₄CF₃—4 | —CO₂CH₃ | —CH₃ | —SCO₂CH₃ | O | Oil |
| 319 | —C₆H₄Cl—4 | —C₆H₄CF₃—4 | —CO₂CH₃ | —CH₃ | —SCH₂CH₂CH₃ | O | Oil |
| 320 | —C₆H₄Cl—4 | —C₆H₄CF₃—4 | —CO₂CH₃ | —CH₃ | —SCH₃ | O | Oil |
| 321 | —C₆H₄Cl—4 | —C₆H₄CF₃—4 | —CO₂CH₃ | —CH₃ | —SCH₂CH₂CH₂CH₃ | O | 208-212 |
| 322 | —C₆H₄Cl—4 | —C₆H₄CF₃—4 | —COC₆H₄Cl—4 | —CH₃ | H | O | 196-201 |
| 323 | —C₆H₄Cl—4 | —C₆H₄CF₃—4 | —COC₆H₄CH₃—4 | —CH₃ | H | O | 194-196 |
| 324 | —C₆H₄Cl—4 | —C₆H₄CF₃—4 | —COC₆H₄CH₃—4 | —CH₃ | H | O | 122-125 |
| 325 | —C₆H₄Cl—4 | —C₆H₄CF₃—4 | —CO₂CH₃ | —CH₃ | —SC₆H₅ | O | |
| 326 | —C₆H₄Cl—4 | naphthyl | —CO₂C₂H₅ | —CH₃ | H | O | 171-173 |
| 327 | —C₆H₄Cl—4 | —C₆H₄CF₃—4 | —CH₂CH₂CH₂CH₃ | —CH₃ | H | O | 122-124 |

TABLE I-continued $$Y-\underset{A}{\overset{Z}{\underset{|}{C}}}-CH_2\underset{\underset{C}{\underset{\parallel}{C}}}{\overset{U}{\underset{\parallel}{\underset{N}{\overset{B}{\underset{|}{C}}}}}}-N\underset{V}{\overset{B}{\underset{|}{\underset{}{V}}}}$$

| Example No. | A | B | Y | Z | U | V | Melting Point °C. |
|---|---|---|---|---|---|---|---|
| 328 | (furan) | —C₆H₄CF₃-4 | —CO₂CH₃ | —CH(CH₃)₂ | O | H | 125–128 |
| 329 | (naphthalene) | —C₆H₄CF₃-4 | —CO₂CH₃ | —CH₃ | O | H | Oil |
| 330 | —C₂H₅ | —C₆H₄SCH₃-4 | —CO₂CH₃ | —CH₃ | O | H | 116–120 |
| 331 | —C₂H₅ | —C₆H₄OCF₂CF₂H-4 | —CO₂CH₃ | —CH₃ | O | H | 110–113 |
| 332 | —C₂H₅ | —C₆H₄OCF₂CF₂H-4 | —CO₂CH₃ | —CH₃ | O | H | 108–111 |
| 333 | —C₂H₅ | —C₆H₄CN-4 | —CO₂CH₃ | —CH₃ | O | H | 83–86 |
| 334 | —C₂H₅ | —C₆H₄CO₂CH(CH₃)₂-4 | —CO₂CH₃ | —CH₃ | O | H | 144–146 |
| 335 | —C₂H₅ | —C₆H₄CO₂CH₂CH₃-4 | —CO₂CH₃ | —CH₃ | O | H | 167–170 |
| 336 | —C₂H₅ | —C₆H₄SCF₂CF₂H | —CO₂CH₃ | —CH₃ | O | H | Oil |
| 337 | —C₂H₄Cl-4 | —C₆H₄CF₃-4 | —CO₂CH₃ | —CH₃ | O | —COCH₃ | Oil |
| 338 | —C₂H₄Cl-4 | —C₆H₄OCF₃-4 | —CO₂CH₃ | —CH₃ | O | —SCO₂CH₃ | Oil |
| 339 | —C₂H₄Cl-4 | —C₆H₄OCF₃-4 | —CO₂CH₃ | —CH₃ | O | —COCF₃ | Oil |
| 340 | —C₂H₄Cl-4 | —C₆H₄CF₃-4 | —CO₂CH₃ | —CH₃ | O | —SCH₂CH₃ | Oil |
| 341 | —C₂H₅ | —C₆H₄CF₃-4 | —CH=CH₂ | —CH₃ | O | H | 81–84 |
| 342 | —C₂H₄Cl-4 | —C₆H₄CF₃-4 | —CO₂CH₃ | —CH₃ | O | —S(CH₂)₁₁CH₃ | Oil |
| 343 | —C₂H₅ | —C₆H₄OCF₃-4 | CH=CC₂ | —CH₃ | O | H | Oil |
| 344 | —C₂H₄Cl-4 | —C₆H₄F₃-2,3,4 | —CO₂CH₃ | —CH₃ | O | —CHO | Solid |
| 345 | —C₂H₄Cl-4 | —C₆H₄CF₃-4 | —CO₂CH₃ | —CH₃ | O | H | 135–138 |
| 346 | —C₂H₄CO₂CH₃-4 | —C₆H₄CF₃-4 | —CO₂CH₃ | —CH₃ | O | —CHO | 138–140 |
| 347 | —C₂H₄CO₂CH₃-4 | —C₆H₄OCF₃-4 | —CO₂CH₃ | —CH₃ | O | H | Oil |
| 348 | —C₂H₄Cl-4 | —C₆H₄CF₃-4 | —CO₂CH₂C≡CH | —CH₃ | O | H | 130–132 |
| 349 | —C₂H₄Cl-4 | —C₆H₄CF₃-4 | —CO₂CH₂C=CH₂ | —CH₃ | O | H | 100–103 |
| 350 | —C₂H₄Cl-4 | —C₆H₄CF₃-4 | —CO₂CH₂CH₂CH₃ | —CH₃ | O | H | 95–102 |
| 351 | —C₂H₄Cl-4 | —C₆H₄CF₃ | —CO₂CH₂CF₃ | —CH₃ | O | H | 134–135 |
| 352 | —C₂H₄Cl-4 | —C₆H₄CF₃ | —CO₂CH₂C₆H₅ | —CH₃ | O | H | 142–146 |
| 353 | —C₂H₄Cl-4 | —C₆H₄CF₃ | —CO₂C₂H₅ | —CH₃ | O | H | 130–133 |
| 354 | —C₂H₄Cl-4 | —C₆H₄CF₃ | —CO₂CH₂CH=CHCl | —CH₃ | O | H | 119–120 |
| 355 | —C₂H₄Cl-4 | —C₆H₄CF₃ | —CO₂CH₂CCl=CH₂ | —CH₃ | O | H | 116–118 |
| 356 | —C₂H₄Cl-4 | —C₆H₄CF₃ | —CO₂CH₂C(CH₃)=CH₂ | —CH₃ | O | H | 180–182 |
| 357 | —C₂H₄Cl-4 | —C₆H₄CF₃ | —COSC₆H₄Cl-4 | —CH₃ | O | H | 158–161 |
| 358 | —C₂H₄Cl-4 | —C₆H₄CF₃ | —COSCH₃ | —CH₃ | O | H | 147–151 |
| 359 | —C₂H₄Cl-4 | —C₆H₄CF₃ | —COCl | —CH₃ | O | H | |
| 360 | —C₂H₄Cl-4 | —C₆H₄CF₃ | —CONHC(CH₃)₂CH₂OH | —CH₃ | O | H | |
| 361 | —C₂H₄Cl-4 | —C₆H₄CF₃ | | —CH₃ | O | H | 96–99 |

TABLE I-continued

| Example No. | A | B | Y | Z | V | U | Melting Point °C. |
|---|---|---|---|---|---|---|---|
| 362 | —C₆H₄Cl—4 | —C₆H₄CF₃—4 | —CO₂CH(CF₃)₂ | —CH₃ | H | O | 145-147 |
| 363 | —C₆H₄Cl—4 | —C₆H₄CF₃—4 | —CONHN(CH₃)₂ | —CH₃ | H | O | 206-210 |
| 364 | —C₆H₄Cl—4 | —C₆H₄CF₃—4 | —COSC₆H₅ | —CH₃ | H | O | 173-175 |
| 367 | —C₆H₄CH₃—4 | —C₆H₄CF₃—4 | —CO₂CH₃ | —CH₃ | H | O | Solid |
| 368 | —C₆H₄OCH₃—4 | —C₆H₄OCH₃—4 | —CO₂CH₃ | —CH₃ | H | O | Oil |
| 369 | —C₆H₄Cl—4 | —C₆H₄CF₃—4 | —CO₂CH₂CH(CH₃)₂ | —CH₃ | H | O | 78-72 |
| 370 | —C₆H₄Cl—4 | —C₆H₄CF₃—4 | —CONHCH₂CH₂OH | —CH₃ | H | O | 175-177 |
| 371 | —C₆H₄COCH₃—4 | —C₆H₄CF₃—4 | —CO₂H | —CH₃ | H | O | — |
| 372 | —C₆H₄COCH₃—4 | —C₆H₄CF₃—4 | —CO₂CO₂CH₃ | —CH₃ | H | O | Solid |
| 373 | —C₆H₄COCH₃—4 | —C₆H₄CF₃—4 | —CO₂CH₂CH₃ | —CH₃ | H | O | Solid |
| 374 | —C₆H₄CO₂CH(CH₃)₂—4 | —C₆H₄CF₃—4 | —CO₂CH(CH₃)₂ | —CH₃ | H | O | 97-101 |
| 375 | —C₆H₄Cl—4 | —C₆H₄CF₃—4 | —CO₂C(CH₃)₃ | —CH₃ | H | O | 171-174 |
| 376 | —C₆H₄Cl—4 | —C₆H₄CF₃—4 | —CONHC₆H₄OH—4 | —CH₃ | H | O | 183.5-185 |
| 377 | —C₆H₄Cl—4 | —C₆H₄CF₃—4 | (3,5-dimethylpyrazol-1-yl-carbonyl) | —CH₃ | H | O | |
| 378 | —C₆H₄Cl—4 | —C₆H₄CF₃—4 | —CO₂CH₂CN | —CH₃ | H | O | 146-149 |
| 379 | —C₆H₄Cl—4 | —C₆H₄CF₃—4 | —CO₂N=C(CH₃)₂ | —CH₃ | H | O | 128-131 |
| 380 | —C₆H₄OCONHCH₃—4 | —C₆H₄CF₃—4 | —CO₂CH₃ | —CH₃ | H | O | Solid |
| 381 | —C₆H₄OCON(CH₃)₂—4 | —C₆H₄CF₃—4 | —CO₂CH₃ | —CH₃ | H | O | Solid |
| 382 | —C₆H₄OCHCH₂(CH₃)₂—4 | —C₆H₄CF₃—4 | —CO₂CH₃ | —CH₃ | H | O | 134-137 |
| 383 | —C₆H₄OCH₂CH₂CH₃ | —C₆H₄CF₃—4 | —CO₂CH₃ | —CH₃ | H | O | Solid |
| 384 | —C₆H₄OCH₂C=CH₂—4 | —C₆H₄CF₃—4 | —CO₂CH₃ | —CH₃ | H | O | — |
| 385 | —C₆H₄OCH₂C≡CH—4 | —C₆H₄CF₃—4 | —CO₂CH₃ | —CH₃ | H | O | Solid |
| 386 | —C₆H₄NO₂—4 | —C₆H₄CF₃—4 | —CO₂CH₃ | —CH₃ | H | O | 218-221 |
| 387 | —C₆H₄Cl—4 | —C₆H₄CF₃—4 | —CO₂CH₃ | —CH₃ | —CH₃ | O | Oil |
| 388 | —C₆H₄Cl—4 | —C₆H₄CF₃—4 | —CO₂CH₃ | —CH₃ | H | | |
| 389 | (3-pyridyl) | —C₆H₄CF₃—4 | —CO₂CH₃ | —CH₃ | H | O | Oil |
| 365 | —C₆H₄Cl—4 | —C₆H₄CF₃—4 | (imidazol-1-yl-carbonyl) | —CH₃ | H | O | 203-206 |

TABLE I-continued

| Example No. | A | B | Y | Z | V | U | Melting Point °C |
|---|---|---|---|---|---|---|---|
| 366 | —C₆H₄Cl—4 | —C₆H₄CF₃—4 | | —CH₃ | H | O | 196-198 |
| 390 | —C₆H₄NH₂—4 | —C₆H₄CF₃—4 | —CO₂CH₃ | —CH₃ | H | O | Solid |
| 391 | —C₆H₄NHCOCH₃—4 | —C₆H₄CF₃—4 | —CO₂CH₃ | —CH₃ | H | O | — |
| 392 | —C₆H₄NHCO₂CH₃—4 | —C₆H₄CF₃—4 | —CO₂CH₃ | —CH₃ | H | O | Solid |
| 393 | —C₆H₄N(CH₃)₂— | —C₆H₄CF₃—4 | —CO₂CH₃ | —CH₃ | H | O | Oil |
| 394 | —C₆H₄Cl—4 | —C₆H₄CF₃—4 | (pyrazole-C(O)—) | —CH₃ | COCH=CH₂ | O | 189-192 |
| 395 | —C₆H₄Cl—4 | —C₆H₄CF₃—4 | —CONHCH₂CH₂SH | —CH₃ | H | O | Solid |
| 396 | —C₆H₄NHCONHCH₃—4 | —C₆H₄CF₃—4 | —CO₂CH₃ | —CH₃ | H | O | Solid |
| 397 | —C₆H₄NHCH₃—4 | —C₆H₄CF₃—4 | —CO₂CH₃ | —CH₃ | H | O | 116-119 |
| 398 | —C₆H₄OCH₂CH₃—4 | —C₆H₄CF₃—4 | —CO₂CH₃ | —CH₃ | H | O | 119-121 |
| 399 | —C₆H₄OCH₂CH₂CH₃—4 | —C₆H₄CF₃—4 | —CO₂CH₃ | —CH₃ | H | O | Solid |
| 400 | —C₆H₄OCH₂CH(CH₃)CH₃—4 | —C₆H₄CF₃—4 | —CO₂CH₃ | —CH₃ | H | O | — |
| 401 | —C₆H₄OCH(CH₃)₂—4 | —C₆H₄CF₃—4 | —CO₂CH₃ | —CH₃ | H | O | — |
| 402 | —C₆H₄OCH(CH₃)CH₂CH₃—4 | —C₆H₄CF₃—4 | —CO₂CH₃ | —CH₃ | H | O | Solid |
| 403 | —C₆H₄OCH₂CH₂CH₃—4 | —C₆H₄CF₃—4 | —CO₂CH₃ | —CH₃ | H | O | Oil |
| 404 | —C₆H₄OCH₂CH=CH₂ | —C₆H₄CF₃—4 | —CO₂CH₃ | —CH₃ | H | O | 148-152 |
| 405 | —C₆H₄OCH₂OCH₃—4 | —C₆H₄CF₃—4 | —CO₂CH₃ | —CH₃ | H | O | 152-154 |
| 406 | —C₆H₄OCH₂OC₆H₅—4 | —C₆H₄CF₃—4 | —CO₂CH₃ | —CH₃ | H | O | 108-109 |
| 407 | —C₆H₄Cl—4 | —C₆H₄CF₃—4 | —CO₂CH₃ | —CH₃ | H | O | 95-98 |
| 408 | —C₆H₄Cl—4 | —C₆H₄CF₃—4 | —CO₂CH₃ | —CH₃ | H | O | 108-110 |
| 409 | —C₆H₄Cl—4 | —C₆H₄OCF₃—4 | —CO₂CH₃ | —CH₃ | H | O | 105-108 |
| 410 | —C₆H₄OCH₂CH₃—4 | —C₆H₄Cl—4 | —CO₂CH₃ | —CH₃ | H | O | 114-115 |
| 411 | —C₆H₄OCH(CH₃)₂—4 | —C₆H₄Cl—4 | —CO₂CH₃ | —CH₃ | H | O | 103-105 |
| 412 | —C₆H₄OCH₂CH₂CH₃—3 | —C₆H₄Cl—4 | —CO₂CH₃ | —CH₃ | H | O | 111-113 |
| 413 | —C₆H₄OCH₂CH₂CH₃—3 | —C₆H₄OCF₃—4 | —CO₂CH₃ | —CH₃ | H | O | 142-144 |
| 414 | —C₆H₄OCH₂CH₂CH₃—3 | —C₆H₄Cl—4 | —CO₂CH₃ | —CH₃ | H | O | 109-112 |
| 415 | —C₆H₄OCH₂CH=CH₂ | —C₆H₄Cl—4 | —CO₂CH₃ | —CH₃ | H | O | Oil |
| 416 | —C₆H₄OCH₂CH₃—4 | —C₆H₄OCF₃—4 | —CO₂CH₃ | —CH₃ | H | O | 128-132 |
| 417 | —C₆H₄OCH₃—4 | —C₆H₄CF₃—4 | —CO₂CH₃ | —CH₃ | H | O | Oil |
| 418 | —C₆H₄CON(CH₃)₂—4 | —C₆H₄CF₃—4 | —CO₂CH₃ | —CH₃ | H | O | 90-94 |
| 419 | —C₆H₄CON(CH₃)₂—4 | —C₆H₄CF₃—4 | —CO₂CH₃ | —CH₃ | H | O | 84-88 |
| 420 | —C₆H₄OCH₂CH₂CH₂CH₃—4 | —C₆H₄OCF₃—4 | —CO₂CH₃ | —CH₃ | H | O | 85-95 |
| 421 | —C₆H₄OCH₂CH(CH₃)₂—4 | —C₆H₄Cl—4 | —CO₂CH₃ | —CH₃ | H | O | Oil |
| 422 | —C₆H₄OCH₂CH₂CH₂CH₃—4 | —C₆H₄Cl—4 | —CO₂CH₃ | —CH₃ | H | O | 90-93 |
| 423 | —C₆H₄OCH₂CH₂CH₃—4 | —C₆H₄CF₃—4 | —CO₂CH₃ | —CH₃ | H | O | 125-127 |
| 424 | —C₆H₄OCH₂CH₃—4 | —C₆H₄CF₃—4 | —CO₂CH₃ | —CH₃ | H | O | Oil |
| 425 | —C₆H₄OCH₂CH₃—4 | —C₆H₄Cl—4 | —CO₂CH₃ | —CH₃ | H | O | |
| 426 | —C₆H₄NHCOCH₃—4 | —C₆H₄CF₃—4 | —CO₂CH₃ | —CH₃ | H | O | |

TABLE I-continued

| Example No. | A | B | Y | Z | V | U | Melting Point °C. |
|---|---|---|---|---|---|---|---|
| 427 | —C₆H₄(NHCOC₆H₄Cl—4)—4 | —C₆H₄CF₃—4 | —CO₂CH₃ | —CH₃ | H | O | Oil |
| 428 | —C₆H₄Cl—4 | —C₆H₄CF₃—4 |  | —CH₃ | H | O | 101–103; and 189–191 |
| 429 | —C₆H₄Cl—4 | —C₆H₄CF₃—4 |  | —CH₃ | H | O | 203–206 |
| 430 | —C₆H₄Cl—4 | —C₆H₄CF₃—4 |  | —CH₃ | H | O | 213–216 |
| 431 | —C₆H₄Cl—4 | —C₆H₄CF₃—4 |  | —CH₃ | H | O | 144.5–146.6 |
| 432 | —C₆H₄OCH₂CH₂CH₃—4 | —C₆H₄CF₃—4 | —CH=CCl₂ | —CH₃ | H | O | 133–135 |
| 433 | —C₆H₄OCH₂CH₂CH₃—4 | —C₆H₄OCF₃—4 | —CH=CCl₂ | —CH₃ | H | O | 94–96 |
| 434 | —C₆H₄OCH₂CH₂CH₃—4 | —C₆H₄CF₃—4 | —CO₂CH₃ | —CH₃ | H | O | Oil |
| 435 | —C₆H₄C(O)N(CH₂CH₂CH₃)₂—4 | —C₆H₄OCF₃—4 | —CH=CCl₂ | —CH₃ | H | O | 138–139.5 |
| 436 | —C₆H₄OCH₂CH₂CH₃—4 | —C₆H₄Cl—4 | —CO₂CH₃ | —CH₃ | H | O | 91–96 |
| 437 | —C₆H₄OCH₂CH₂CH₃—4 | —C₆H₄CF₃—4 | —CO₂CH₃ | —CH₃ | —CHO | O | Oil |
| 438 | —C₆H₄OCH₂CH₂CH₃—4 | —C₆H₄CF₃—4 | —CO₂CH₃ | —CH₃ | —CHO | O | Oil |
| 439 | —C₆H₄OCH₂CH₂CH₃—4 | —C₆H₄CF₃—4 | —CO₂CH₃ | —CH₃ | —C(O)CH₃ | O | Oil |
| 440 | —C₆H₄OCH₂CH₂CH₃—4 | —C₆H₄OCF₃—4 | —CO₂CH₃ | —CH₃ | —C(O)CH₃ | O | 103–106 |
| 441 | —C₆H₄OCH₂CH₂CH₃—4 | —C₆H₄Cl—4 | —CH=CCl₂ | —CH₃ | H | O | 152–156 |
| 442 | —C₆H₄OCH₂CH₂CH₃—4 | —C₆H₄Cl—4 | —CH=CCl₂ | —CH₃ | H | O | 158–161 |
| 443 | —C₆H₄OCH₂CH₂CH₃—4 | —C₆H₄CF₃—4 | —CH=CCl₂ | —CH₃ | H | O | |

TABLE I-continued $$Y-\overset{Z}{\underset{A-C=N}{C}}-CH_2-\overset{U}{\underset{}{N}}-\overset{B}{\underset{V}{C}}$$

| Example No. | A | B | Y | Z | U | V | Melting Point °C. |
|---|---|---|---|---|---|---|---|
| 444 | —C$_6$H$_4$Cl—4 | —C$_6$H$_4$CF$_3$—4 | | —CO$_2$CH$_3$ | O | H | 185–187 |
| 445 | —C$_6$H$_4$Cl—4 | —C$_6$H$_4$NH$_2$—4 | | —CO$_2$CH$_3$ | O | H | Oil |
| 446 | —C$_6$H$_4$Cl—4 | —C$_6$H$_4$NHCHO—4 | | —CO$_2$CH$_3$ | O | H | 146–150 |
| 447 | —C$_6$H$_4$Cl—4 | —C$_6$H$_4$NC(O)CH$_3$—4 | | —CO$_2$CH$_3$ | O | H | 218–220 |
| 448 | —C$_6$H$_4$Cl—4 | —C$_6$H$_4$NHCO$_2$CH$_3$—4 | | —CO$_2$CH$_3$ | O | H | 215–219 |
| 449 | —C$_6$H$_4$Cl—4 | —C$_6$H$_4$OCF$_3$—4 | | —CH=CCl$_2$ | O | H | 210–215 |
| 450 | —C$_6$H$_4$OCH$_3$—4 | —C$_6$H$_4$OCF$_3$—4 | | —CH=CCl$_2$ | O | H | 133–135 |
| 451 | —C$_6$H$_4$OCH$_3$—4 | —C$_6$H$_4$OCF$_3$—4 | | —CH=CCl$_2$ | O | H | 161–163 |
| 452 | —C$_6$H$_4$OCH$_3$—4 | —C$_6$H$_4$Cl—4 | | —CO$_2$CH$_2$CH$_2$CH$_3$ | O | H | 146–149 |
| 453 | —C$_6$H$_4$OCH$_2$CH$_2$CH$_3$—4 | —C$_6$H$_4$CF$_3$—4 | | —CO$_2$CH(CH$_3$)$_2$ | O | H | 85–89 |
| 454 | —C$_6$H$_4$OCH$_2$CH$_2$CH$_3$—4 | —C$_6$H$_4$CF$_3$—4 | | —CO$_2$CH$_3$ | O | H | 122–127 |
| 455 | —C$_6$H$_4$Cl—4 | —C$_6$H$_4$NC—4 | | —CO$_2$CH$_3$ | O | H | 102–107 |
| 456 | —C$_6$H$_4$OCH$_2$CH(CH$_3$)$_2$CH$_3$—4 | —C$_6$H$_4$CF$_3$—4 | | —CO$_2$CH$_3$ | O | H | Oil |
| 457 | —C$_6$H$_4$OCH$_2$(CH$_3$)$_6$ | —C$_6$H$_4$CF$_3$—4 | | —CO$_2$CH$_3$ | O | H | Oil |
| 458 | —C$_6$H$_4$NHCHO—4 | —C$_6$H$_4$CF$_3$—4 | | —CO$_2$CH$_3$ | O | H | 198–200 |
| 459 | —C$_6$H$_4$NC—4 | —C$_6$H$_4$CF$_3$—4 | | —CO$_2$CH$_3$ | O | H | 190–192 |
| 460 | —C$_6$H$_4$NHC(O)OC$_3$ | —C$_6$H$_4$CF$_3$—4 | | —CO$_2$CH$_3$ | O | H | 226–228 |
| 461 | —C$_6$H$_4$NHC(O)C$_6$H$_5$ | —C$_6$H$_4$CF$_3$—4 | | —CO$_2$CH$_3$ | O | H | 195–197 |
| 462 | —C$_6$H$_4$OCH$_2$CH$_2$CH$_3$—4 | —C$_6$H$_4$Cl—4 | | —CO$_2$CH$_3$ | O | H | 078–81 |
| 463 | —C$_6$H$_4$OCH$_2$CH$_2$CH$_3$—4 | —C$_6$H$_4$CF$_3$—4 | | —CO$_2$CH$_3$ | O | H | 142–146 |
| 464 | —C$_6$H$_4$OCH$_2$CH$_2$CH$_3$—4 | —C$_6$H$_4$CF$_3$—4 | | —CO$_2$CH$_3$ | O | H | 133–136 |
| 465 | —C$_6$H$_4$OCH$_2$CH$_2$CH$_3$—4 | —C$_6$H$_4$CF$_3$—4 | | —CO$_2$CH$_3$ | O | H | Oil |
| 466 | —C$_6$H$_4$OCH$_2$CH$_2$CH$_3$—4 | —C$_6$H$_4$CF$_3$—4 | | —C(O)NH$_2$ | O | H | 154–157 |
| 467 | —C$_6$H$_4$Cl—4 | —C$_6$H$_4$CF$_3$—4 | | —CO$_2$CH$_3$ | O | H | Solid |
| 468 | —C$_6$H$_4$Cl—4 | —C$_6$H$_4$OCF$_2$CF$_2$H—4 | | —CH=Cl$_2$ | O | H | 142–143 |
| 469 | —C$_6$H$_4$Cl—4 | —C$_6$H$_4$OCF$_2$CF$_2$H—4 | | —CH=CBr$_2$ | O | H | 173–175 |
| 470 | —C$_6$H$_4$OCH$_2$CH$_2$CH$_3$—4 | —C$_6$H$_4$OCF$_2$CF$_2$H—4 | | —CO$_2$CH$_3$ | O | H | 124–125 |
| 471 | —C$_6$H$_4$OCH$_2$CH$_2$CH$_3$—4 | —C$_6$H$_4$OCF$_2$CF$_2$H—4 | | —CH=CCl$_2$ | O | H | Oil |
| 472 | | —C$_6$H$_4$CF$_3$—4 | (benzodioxole) | —CO$_2$CH$_3$ | O | H | 204–206 |
| 473 | —C$_6$H$_4$Cl—4 | —C$_6$H$_4$CF$_3$—4 | | —CH$_2$CH=CH$_2$ | O | H | 124–127 |
| 474 | —C$_6$H$_4$Cl—4 | —C$_6$H$_4$CF$_3$—4 | | —CO$_2$CH$_3$ | O | H | 155–161 |

TABLE I-continued

| Example No. | A | B | Y | Z | V | U | Melting Point °C |
|---|---|---|---|---|---|---|---|
| 475 | —C₆H₄OCH₃—4 | —C₆H₄CF₃—4 | —CHO | —CH₃ | H | O | 148-152 |
| 476 | —C₆H₅ | —C₆H₄CF₃—4 | —CHO | —CHO | —CH₃ | O | 145-148 |
| 477 | (4-piperidinocarbonyl-phenyl) | —C₆H₄CF₃—4 | —CO₂CH₃ | —CH₃ | H | O | 171-175 |
| 478 | (4-piperidinocarbonyl-phenyl) | —C₆H₄OCH₃—4 | —CO₂CH₃ | —CH₃ | H | O | 140-144 |
| 479 | —C₆H₄OCH₂CH₂CH₃—4 | —C₆H₄CF₃—4 | (pyrrolidinocarbonyl) | —CH₃ | H | O | 158-161 |
| 480 | —C₆H₄OCH₂CH₂CH₃—4 | —C₆H₄CF₃—4 | —CO₂CH₃ | —CH₃ | H | O | 175-178 |
| 481 | —C₆H₅ | —C₆H₄CF₃—4 | —CH=CO₂ | —C₂H₅ | H | O | 178-180 |
| 482 | —C₆H₅ | —C₆H₄CF₃—4 | —CON(CH₃)₂ | —C₂H₅ | H | O | 188-192 |
| 483 | —C₆H₄Cl—4 | —C₆H₄CF₃—4 | —CON(CH₃)₂ | —C₂H₅ | H | O | 185-190 |
| 484 | —C₆H₄Cl—2 | —C₆H₄OCF₃—4 | —CO₂CH₃ | —CH₃ | H | O | Oil |
| 485 | —C₆H₄Cl—4 | —C₆H₄CF₃—4 | —CH=CO₂ | —C₆H₅ | H | O | 179-181 |
| 486 | —C₆H₄Cl—4 | —C₆H₄CF₃—4 | —CO₂CH₃ | —CH₂CH₂CH₃ | H | O | 153-156 |
| 487 | —C₆H₄Cl—4 | —C₆H₄CF₃—4 | —CO₂CH₃ | —CH₂C≡CH | H | O | 158-161 |
| 488 | —C₆H₄Cl—4 | —C₆H₄CF₃—4 | —CO₂CH₃ | —CH₃ | H | O | Oil |
| 489 | —C₆H₄CF₂CFHCF₃ | —C₆H₄CF₃—4 | —CO₂CH₃ | —C(O)CH₃ | H | O | 156-162 |
| 490 | —C₆H₄Cl—4 | —C₆H₄CF₃—4 | —CO₂CH₃ | —CH₂CO₂CH₃ | H | O | 201-203 |
| 491 | —C₆H₄Cl—4 | —C₆H₄CF₃—4 | —CO₂CH₃ | —CH₂OCH₃ | H | O | 154-157 |
| 492 | —C₆H₄Cl—4 | —C₆H₄CF₃—4 | —CO₂CH₃ | —CO₂N(CH₃)₂ | H | O | 201-204 |
| 493 | —C₆H₃(OCH₃)₂—3,4 | —C₆H₄CF₃—4 | —CO₂CH₃ | —CH₃ | H | O | 175-177 |

EXAMPLE A

Preparation of 4-chlorophenyl benzyl ketone

To a 2 liter 4 necked flask equipped with a mechanical stirrer, thermometer, and reflux condensor was added 155 g (1.0 mole) of phenyl acetyl chloride and 500 ml (4.9 mole) of chlorobenzene. A total of 145 g (1.08 mole) of anhydrous aluminum chloride was added portionwise over 10 minutes. The mixture self warmed to 44° C. and evolved HCl gas over the course of the next 30 minutes The mixture was stirred at about 50° C. for an additional 30 minutes and then poured onto about 500 g of ice and 110 ml of concentrated aqueous HCl. The organic layer (lower) was separated and the aqueous layer was washed with ethyl ether. The combined organic layers were washed with water, dilute aqueous NaOH, and water and then concentrated in vacuo. The resulting crude solid was recrystalized from 2200 ml of hexane yielding 132 g of 4-chlorophenyl benzyl ketone, mp 85°-90° C. NMR data was consistent with the structure.

EXAMPLE B

Preparation of 2-phenyl 4'-chlorophenyl acrylophenone

In a 1000 ml round bottomed flask equipped with a reflux condensor was placed 100 g 4-chlorophenyl benzyl ketone (0.43 mole), 400 ml of methanol, 40 ml of 37% formalin (0.67 mole), 5 g of piperidine, and 5 g of acetic acid. The resulting mixture was refluxed for 2 hours, concentrated in vacuo, partitioned between ethyl ether and water, washed with water, dried over anhydrouis magnesium sulfate and concentrated in vacuo to yield 98 g of 2-phenyl 4'-chlorophenyl acrylophenone, an oil. NMR data was consistent with the structure.

EXAMPLE C

Preparation of 3-(4-chlorophenyl)-4-phenyl-4,5-dihydro-1H-pyrazole

In a 500 ml round bottomed flask equipped with a reflux condensor was mixed 98 g of 2-phenyl 4'-chlorophenyl acrylophenone (0.40 mole), 200 ml n-propanol, and 50 ml hydrazine monohydrate (1.0 mole). The mixture was refluxed for 1 hour, cooled slightly and 100 ml of methanol added. The resulting solution was cooled in an ice bath and the resulting solid filtered and washed twice with cold ethyl ether yielding 55 g of a white solid. mp 156°-162° C. NMR data was consistent with the structure.

EXAMPLE D

Preparation of N,3-bis-(4-chlorophenyl-4-phenyl-4,5dihydro-1H-pyrazole-1-carboxamide In a 500 ml round bottomed flask was suspended 55 g of 3-(4-chlorophenhyl)-4-phenyl-4,5-dihydro-1H-pyrazole in 250 ml of diethyl ether. The suspension was warmed to reflux and 33 g of 4-chlorophenyl isocyanate was added at a rate to maintain reflux. After cooling and standing overnight the precipitated product was filtered yielding 78 g of white solid. mp 173°-175° C. NMR data was consistent with the structure.

EXAMPLE E

Preparation of 3-dimethylamino-2-methyl-4'-chloropropiophenone

In a 500 ml round bottomed flask equipped with a reflux condensor was mixed 84 g of 4-chloropropiophenone (0.50 mole), 50 g of dimethylamine hydrochloride (0.61 mole), 20 g of paraformaldehyde (0.67 mole), 50 ml of ethanol, and 10 ml of concentrated aqueous hydrochloric acid. The mixture was refluxed for 18 hours, cooled and partitioned between ethyl and water. The ether layer was discarded and the aqueous layer was basified with sodium hydroxide and the resulting mixture extracted twice with fresh ethyl ether. The combined organic layers were washed with brine, dried over magnesium sulfate and concentrated in vacuo to yield 105 g of 3-dimethylamino-2-methyl-4'-chloropropiopenone, an oil. NMR data was consistent with the structure.

EXAMPLE F

Preparation of 3-(4-chlorophenyl-4-methyl-4,5-dihydro-1H-pyrazole

In a 500 ml round bottomed flask equipped with a reflux condensor was placed 100 g of 3-dimethylamino-2-methyl-4'-chloropropiophenone (0.47 mole), 200 ml of n-propanol, 48 g of hydrazine monohydrate (0.96 mole), and 5 g of 50% aqueous sodium hydroxide. The mixture was refluxed for 2 hours. The solvent was removed in vacuo and the product was partitioned between methylene chloride and water. The organic layer was washed 3 times with water and dried over anhydrous magnesium sulfate. The organic layer contains 82 g (0.42 mole) of 3-(4-chlorophenyl)-4-methyl-4,5-dihydro-1H-pyrazole an air sensitive solid. NMR data was consistent with the structure.

EXAMPLE G

Preparation of N,3-bis-(4-chlorophenyl)-4-methyl-4,5-dihydro-1H-pyrazole-1-carboxamide In a 500 ml round bottomed flask was placed 82 g (0.42 mole) of 3-(4-chlorophenyl)-4-methyl-4,5-dihydro-1H-pyrazole dissolved in 300 ml of methylene chloride and the solution was brought to boiling. A solution of 64.5 g of 4-chlorophenyl isocyanate (0.42 mole) in 100 ml of methylene chloride was added at a rate to maintain reflux. After stirring for an additional 30 minutes the solvent was removed in vacuo and the resulting oil was crystallized from ethyl ether yielding 140 g of N,3-bis-(4-chlorophenyl)-4-methyl-4,5-dihydro-1H-pyrazole-1-carboxamide. mp 139°-140° C. NMR data was consistent with the structure.

EXAMPLE H

Preparation of 3,4-dichlorophenyl benzyl carbinol

Into a 1000 ml three necked flask equiped with a reflux condenser and an addition funnel was placed 8.8 g of magnesium turnings (0.36 mole) and 400 ml of diethyl ether. After activation of the magnesium with 0.02 g of iodine, the mixture was heated to reflux and a solution of 44 g (0.35 mole) of benzyl chloride in ethyl ether was added at a rate to maintain the reflux. When the reaction had subsided, a solution of 50 g (0.29 mole) of 3,4-dichlorobenzaldehyde in 75 ml of diethyl ether was added at a rate to maintain reflux. After 15 minutes, the reaction was quenched with water and acidified with dilute hydrochloric acid. The organic layere was washed with brine, dried, and concentrated in vacuo yielding 75 g of 3,4-dichlorophenyl benzyl carbinol which was used without further purification. NMR data was consistent with the structure.

EXAMPLE I

Preparation of 3,4-dichlorophenyl benzyl ketone

In a 500 ml round bottomed flask was placed 75 g of crude 3,4-dichlorophenyl benzyl carbinol and 300 ml of acetone. The reaction mixture was cooled to 0° C. and a solution of 20 g of chromic anhydride and 17.25 ml of concentrated sulfuric acid in 60 ml of water was added at a rate to keep the internal temperature below 5° C. After stirring an additional 15 minutes, the reaction was quenched with 10 ml of isopropanol and partitioned between ethyl ether and water. The organic layer was washed with brine, dried, and concentrated. The resulting crude ketone was crystallized from hexane yielding 51 g of 3,4-dichlorophenyl benzyl ketone. NMR data was consistent with the structure.

EXAMPLE J

Preparation of Methyl 3-(4-chlorophenyl)-3-keto-propanoate

Into a 1000 ml three necked flask equipped with an additional funnel, and condenser was added 15.4 g of 60% sodium hydride (0.63 mole). The sodium hydride was washed twice with hexane and then suspended in 300 ml of tetrahydrofuran and 29 g of dimethyl carbonate (0.32 mole). The reaction mixture was brought to reflux and a solution of 50 g (0.32 mole) of 4-chloroacetophenone in 50 ml of tetrahydrofuran was added over 30 minutes. After hydrogen evolution had ceased the reaction was cooled and poured onto ice. The aqueous layer was acidified with hydrochloric acid and extracted with ethyl ether. The organic layer was dried, concentrated, and distilled at 15 torr bp 180°-205° C. to give 40 g of methyl 3-(4-chlorophenyl)-3-keto-propanoate. NMR data was consistent with the structure.

EXAMPLE K

Preparation of methyl 2-(4-chlorobenzoyl)-acetate (MCBA)

The sodium enolate of methyl acetoacetate (MAA) is prepared by adding 94 g of 50% NaOH (2 eq.) to a solution of 138 g MAA (2 eq.) in 405 g of xylene at 5°-10° C. The addition requires about one hour and is followed by a hold at 25° C. for two hours. Before or after the base addition, 7 g of LiCl (0.27 eq.) is added. This reaction forms a stirrable slurry of the anion which thickens at higher temperatures. This is treated over one hour with 106 g of 4-chlorobenzoyl chloride (1 eq.) with the temperature being held below 35° C. The pot becomes progressively more fluid throughout the addition as the bright yellow anion of MCBAA forms. The solution is warmed to 50° C. for two hours then cooled. The reaction is neutralized by addition of 35 g of acetic acid followed by 152 g of water. After separation the water is drawn off and about 30% of the xylene is stripped to remove all water from the solution.

MeOH, 100 g, is added to the MCBAA/xylene solution, followed by 2.8 g MgCl$_2$ (2 wt% of initial MAA). This mixture is warmed to 70° C. for 2 hrs., then cooled to room temperature. To this is added 100 g of salt solution, 50% of saturation, and after the extraction is complete the aqueous layer is drawn off. The xylene is then stripped to provide MCBA as a red oil.

Alternatively, MDBA may be prepared by the carbomethoxylation of a ketone. For example, 4-chloracetophenone reacts with excess dimethylcarbonate using sodium methoxide as a catalyst to produce methyl 4-chlorobenzoylacetate as described in U.S. Pat. No. 3,950,381. NMR data was consistent with the structure.

EXAMPLE L

Preparation of methyl 2-(4-chlorobenzoyl)-propionate (MCBP)

Method 1

To a suspension of 800 g (7.12 mole) of potassium t-butoxide in 2 liters of THF in a 5 liter RBF was added (all at once) 641 g (7.12 mole) of dimethyl carbonate with efficient mechanical stirring. The internal temperature rises to 50° C. To this suspension is added solution of 1000 g (5.93 mole) of 4-chloropropiophenone in 300 ml of THF. The addition takes 15 minutes. The reaction mixture is refluxed for 75 minutes. The mixture is then cooled to room temperature by the addition of 2 liters of cold water and transferred to a 12 liter separatory funnel. Two kgs of ice and 2 liters of ethyl ether are added before slowly neutralizing the mixture with 500 ml of conc. HCl. The organic phase is separated, washed with 2 liters of cold water, 2 liters of brine, dried over MgSO$_4$ and concentrated on a rotary evaporator to afford 1254 g of yellow oil. After 24 hours at room temperature, the precipitated 4-chlorobenzoic acid is separated by filtration and the low boiling impurities are removed from the filtrate by distillation at 1 torr up to a vapor temperature of 135° C. The material left in the pot is pure enough for subsequent use. Yield 858 g, 65% of methyl 2-(4-chlorobenzoyl)-propionate (MCBP). The compound afforded by this preparation may also be termed methyl 2-methyl-3-(4-chlorophenyl)-3-keto-propanoate. NMR data was consistent with the structure. See also Example J.

Method 2

The reactor is charged with 50 g MCBA and 50 g methanol and stirred. While at room temperature 45 g (2 eq.) methyl bromide are added and the system sealed. To this is added 1 eq., NaOMe (25% in MeOH as the reactor is warmed to 70°-75° C. After 1 hour the reaction is sampled and checked for pH and MCBP/MCBA ratio. When the reaction is over the system is cooled vented, and a sufficient amount, about 0.2 g, of concentrated HCl is added to lower the pH to about 2. About 75% of the methanol is then stripped off. After the extraction is complete the water is removed and a second extraction performed with sat. NaCl. The xylene is then stripped to give MCBP, which is also named methyl 2-methyl-3-(4-chlorophenyl)-3-keto-propanoate, as an oil. NMR data was consistent with the structure. See also Example J.

EXAMPLE M

Preparation of methyl 2-methyl-2-hydroxymethyl-3-(4-chlorophenyl)-3-keto-propanoate Into a 5 liter RBF is placed 1000 g (4.37 mole) of methyl 2-methyl-3-(4-chlorophenyl)-3-keto-propanoate, 157 g (5.25 mole) of paraformaldehyde, 1000 ml of pyridine, and 50 g of Triton B (40% in MeOH). The resulting mixture was heated 50° C. for 2 hours. After cooling to room temperature, the reaction mixture was transferred to a 12 liter separatory funnel and 1.5 liters of ether and 2 kgs of ice are added. The mixture is slowly acidified by 1.0 liters of conc HCl and the organic phase is separated, washed with 2 liters of brine and dried over MgSO4. On concentration, it affords 1100 g (100%) of a red oil, methyl 2-methyl-2-hydroxymethyl-3-(4-chlorophenyl)-3-keto-propanoate. NMR data was consistent with the structure.

EXAMPLE N

Preparation of methyl 2-methyl-2-mesyloxymethyl-3-(4-chlorophenyl)-3-ketopropanoate Into a 5 liter RBF is placed 100 g (4.37 mole) of methyl 2-methyl-2-hydroxymethyl-3-(4-chlorophenyl)-3-keto-propanoate, 473 g (4.25 mole) of triethylamine, and 2 liters of toluene. This mixture is cooled to −10° C. and methane sulfonyl chloride, 488 g (4.25 mole), is added over 30 minutes. The internal temperature rose to 40° C. by the end of the addition. After stirring at room temperature for 2 hours, the mixture is worked up with 4 liters of cold water and 1 liter methylene chloride. The resulting red semisolid (1400 g) is crystalized using 200 ml of hot ethyl acetate and adding 1500 ml of hexane. Yielding 1060 g (74%) of a light yellow solid mp 85°–86° C., methyl 2-methyl-2-mesyloxymethyl-3-(4-chlorophenyl)-3-keto-propanoate. NMR data was consistent with the structure.

EXAMPLE O

Preparation of 3-(4-chlorophenyl)-4-carbomethoxy-4-methyl-4,5-dihydro-1H-pyrazole Into a 5 liter RBF was added 700 g (2.07) mole) of methyl 2-methyl-2-mesyloxymethyl-3-(4-chlorophenyl)-3-keto-propanoate and 1700 ml of methanol. The slurry is warmed to 50° C. whereon, 248 g (4.14 mole) of acetic acid and 186 g (2.28 mole) of sodium acetate are added. Without further heating, 207 g (4.14 mole) of hydrazine hydrate is added over 20 minutes and the temperature is allowed to rise to reflux. After the addition, the mixture is allowed to stir for 45 minutes whereon the temperature has fallen 50° C. The mixture is worked up with 2 kgs of ice, 2 kgs of cold water and 5 liters of ethyl ether and neutralized using approximately 300 g of 50% NaOH to achieve pH 8. After separating the organic layer and washing it with brine the organic layer is thoroughly dried with MgSO4. The resulting solution of 3-(4-chlorophenyl)-4-carbomethoxy-4-methyl-4,5-dihydro-1H-pyrazole is used as is in the next reaction. NMR data was consistent with the structure.

EXAMPLE P

Preparation of 3-(4-chlorophenyl)-4-carbomethoxy-4-methyl-4,5-dihydro-1H-pyrazole hydrochloride To an ether solution containing approximately 14 g (55 mmole) of 3-(4-chlorophenyl)-4-carbomethoxy-4-methyl-4,5-dihydro-1H-pyrazole (Example O) was bubbled excess anhydrous hydrogen chloride. The precipitated solid was filtered, washed with ether and dried yielding 15.5 g (53.6 mmole) of 3-(4-chlorophenyl)-4-carbomethoxy-4-methyl-4,5-dihydro-1H-pyrazole hydrochloride. NMR data was consistent with the structure.

EXAMPLE 2

Preparation of N,3-bis-(4-chlorophenyl)-4-methyl-4-phenyl-4,5-dihydro-1H-pyrazole-1-carboxamide To 2.1 g of diisopropylamine dissolved in 15 ml of tetrahydrofuran and cooled in an ice salt bath was added 8.0 ml of a 2.7 molar solution of n-butyllithium in hexane. After stirring for 5 minutes a solution of 4.2 g of N,3-bis-(4-chlorophenyhl)-4-phenyl-4,5-dihydro-1H-pyrazole-1-carboxamide (Example D) in 15 ml of tetrahydrofuran was added and the resulting solution stirred for 15 minutes. To this solution was added 1.0 ml of iodomethane and, after 15 minutes 1.0 ml of acetic acid was added. The reaction mixture was partitioned between diethyl ether and water and the organic layer was dried over anhydrous magnesium sulfate. The resulting solution was filtered and evaporated in vacuo to give 4.3 g of N,3-bis-(4-chlorophenyl)-4-phenyl-4-methyl-4,5-dihydro-1H-pyrazole-1-carboxamide, melting point 151°–158° C. NMR and IR data were consistent with the structure.

EXAMPLE 5

Preparation of N,3-bis-(4chlorophenyl)-4-benzyl-4-methyl-4,5-dihydro-1H-pyrazole-1-carboxamide To 2.1 g of diisopropylamine dissolved in 15 ml of tetrahydrofuran and cooled in an ice salt bath was added 8.0 ml of a 2.7 molar solution of n-butyllithium in hexane. After stirring for 5 minutes a solution of 3.4 g of N,3-bis-(4-chlorophenyl)-4-methyl-4,5-dihydro-1H-pyrazole-1-carboxamide (Example G) in 15 ml of tetrahydrofuran was added and the resulting solution stirred for 15 minutes. To this solution was added 1.5 ml of benzyl bromide and, after 5 minutes 1.5 ml of acetic acid was added. The reaction mixture was partitioned between diethyl ether and water and the organic layer was dried over anhydrous magnesium sulfate. The resulting solution was filtered and evaporated in vacuo to give 3.90 g of N,3-bis-(4-chlorophenyl)-4-benzyl-4-methyl-4,5-dihydro-1H-pyrazole-1-carboxamide, an oil. NMR and IR data were consistent with the structure.

EXAMPLE 34

Preparation of N-(4-bromophenyl)-3-(4-fluorophenyl)-4-butyl-4-methyl-4,5-dihydro-1H-pyrazole-1-carboxamide To 2.1 g of diisopropylamine dissolved in 15 ml of tetrahydrofuran and cooled in an ice salt bath was added 8.0 ml of a 2.7 molar solution of n-butyllithium in hexane. After stirring for 5 minutes a solution of 3.7 g of N-(4-bromophenyl)-3-(4-fluorophenyl)-4-methyl-4,5-dihydro-1H-pyrazole-1-carboxamide (prepared from 4-fluoropropiophenone and 4-bromophenyl isocyanate by substantially following the procedures described in Examples E, F, and G) in 15 ml of tetrahydrofuran was added and the resulting solution stirred for 15 minutes. To this solution was added 1.5 ml of 1-iodobutane and, after 15 minutes 1.5 ml of acetic acid was added. The reaction mixture was partitioned between diethyl ether and water and the organic layer was dried over anhydrous magnesium sulfate. The resulting solution was filtered, evaporated in vacuo, and chromatographed to give 2.9 g of N-(4-bromophenyl)-3-(4-fluorophenyl)-4-butyl-4-methyl-4,5-dihydro-1H-pyrazole-1-carboxamide an oil that solidified on long standing. NMR and IR data were consistent with the structure.

EXAMPLE 51

Preparation of
N,3-bis-(4-chlorophenyl)-N,4-dimethyl-4-phenyl-4,5-dihydro-1H-pyrazole-1-carboxamide To a 100 ml round bottomed flask was added 0.40 g (0.01 mole) of 60% sodium hydride. The sodium hydride was washed twice with hexane and 10 ml of dimethylformamide was added. Then, 2.1 g (0.05 mole) N,3-bis-(4-chlorophenyl)-4-methyl-4-phenyl-4,5-dihydro-1H-pyrazole-1-carboxamide (Example 2) was added portionwise. After hydrogen evolution ceased 1 ml of iodomethane was added and the mixture was stirred for 1 hour. The reaction mixture was partitioned between ether and water and the organic layer dried, filtered, concentrated, and chromatographed yielding 1.5 g of N,3-bis-(4-chlorophenyl)-N,4-dimethyl-4-phenyl-4,5-dihydro-1H-pyrazole-1-carboxamide, mp 132°–135° C. NMR and IR data were consistent with the structure.

EXAMPLE 61

Preparation of
N,3-bis-(3,4-dichlorophenyl)-4-methyl-4-phenyl-4,5-dihydro-1H-pyrazole-1-carboxamide 3,4-dichlorophenyl benzyl ketone was used, by substantially following the procedures given in Examples B, C, and D, to prepare N,3-bis-(3,4-dichlorophenyl)-4-phenyl-4,5-dihydro-1H-pyrazole-1-carboxamide, which was used, by substantially following the procedures given in Example 2, to prepare N,3-bis-(3,4-dichlorophenyl)-4-methyl-4-phenyl-4,5-dihydro-1H-pyrazole-1-carboxamide, an oil that solidified on long standing. NMR and IR data were consistent with the structure.

EXAMPLE 74

Preparation of
N,3-bis-(4-chlorophenyl)-4-carbomethoxy-4,5-dihydro-1H-pyrazole

To 20.0 g of methyl 3-(4-chlorophenyl)-3-ketopropanoate in 100 ml of methanol was added a mixture of 4.7 g of hydrazine monohydrate and 7.6 g of 37% formalin in 50 ml of methanol. The reaction was stirred at room temperature for 18 hrs. The methanol was then removed in vacuo and the product was dissolved in 40 ml of methylene chloride and washed 5 times with 100 ml portions of water. The methylene chloride layer was dried over anhydrous magnesium sulfate and evaporated in vacuo to yield 22 g of 3-(4-chlorophenyl)-4-carbomethoxy-4,5-dihydro-1H-pyrazole which was used without further purification in the next reaction.

To 22 g of 3-(4chlorophenyl)-4-carbomethoxy-4,5-dihydro-1H-pyrazole obtained from previous reaction was added 200 ml of methylene chloride and the resulting solution was brought to reflux, whereon 14.5 g of 4-chlorophenyl isocyanate in 25 ml of methylene chloride was added at a rate to maintain a controlled reflux. After refluxing a further 15 minutes the mixture was cooled, filtered and evaporated in vacuo yielding 14 g of N,3-bis-(4-chlorophenyl)-4-carbomethoxy-4,5-dihydro-1H-pyrazole-1-carboxamide which was purified by column chromatography. NMR and IR data were consistent with the structure. NMR data was consistent with the structure.

EXAMPLE 77

Preparation of
N,3-bis-(4-chlorophenyl)-4-carbomethoxy-4-methyl-4,5-dihydro-1H-pyrazole-1-carboxamide

Method A

To 3.1 g of diisopropylamine dissolved in 15 ml of tetrahydrofuran and cooled in an ice salt bath was added 8.0 ml of a 2.7 molar solution of n-butyllithium in hexane. After stirring for 5 minutes a solution of 3.4 g of N,3-bis-(4-chlorophenyl)-4-methyl-4,5-dihydro-1H-pyrazole-1-carboxamide in 7 ml of tetrahydrofuran was added and the resulting solution stirred for 15 minutes. To this solution was added 1.5 ml of dimethylcarbonate and, after 15 minutes 1.5 ml of acetic acid was added. The reaction mixture was partitioned between diethyl ether and water and the organic layer was dried over anhydrous magnesium sulfate. The resulting solution was filtered and evaporated in vacuo to give 3.0 g of N,3-bis-(4-chlorophenyl)-4-carbomethoxy-4-methyl-4,5-dihydro-1H-pyrazole-1-carboxamide, mp 122° C. NMR and IR data were consistent with the structure.

Method B

To 3.4 g of N,3-bis-(4-chlorophenyl)-4-methyl-4,5-dihydro-1H-pyrazole-1-carboxamide and 1.1 g of diisopropylamine dissolved in 20 ml of tetrahydrofuran and cooled in an acetone bath maintained at −20° C., was added 8.0 ml of a 2.7 molar solution of butyllithium in hexane. The resulting solution was stirred for 20 minutes and then cooled to −70° C. To this solution was added 0.9 ml of methyl chloroformate. The reaction was allowed to stir of 10 minutes and then allowed to warm to room temperature over 10 minutes. The reaction was quenched with 1.0 ml of acetic acid and the reaction mixture was partitioned between diethyl ether and water and the organic layer was dried over anhydrous magnesium sulfate. The resulting solution was filtered evaporated in vacuo to give 2.9 g of N,3-bis-(4-chlorophenyl)-4-carbomethoxy-4-methyl-4,5-dihydro-1H-pyrazole-1-carboxamide. NMR and IR data were consistent with the structure.

Method C

To 0.9 ml of diisopropylamine in 10 ml of tetrahydrofuran under a nitrogen atmosphere and cooled to −30° C. was added 2.4 ml of a 2.6 molar solution of n-butyllithium in hexane. To this reaction mixture was added 1.0 g of 3-(4-chlorophenyl)-4-carbomethoxy-4,5-dihydro-1H-pyrazole (Example 74) in 5 ml of tetrahydrofuran. After stirring for 15 minutes, 0.6 ml of iodomethane was added and the mixture was warmed to room temperature and stirred for 1 hr. Quenching with 1.4 ml of 10% aqueous acetic acid and 5 ml of water and standard ether water workup gave 1.1 g of N,3-bis-(4-chlorophenyl)-4-carbomethoxy-4-methyl-4,5-dihydro-1H-pyrazole-1-carboxamide, mp 138°–150° C. NMR and IR data were consistent with the structure.

Method D

An ether solution of 3-(4-chlorophenyl)-4-carbomethoxy-4-methyl-4,5-dihydro-1H-pyrazole (Example O) (approximately 1.8 mole) is treated with 286 g (1.86 mole) of 4-chlorophenyl isocyanate at a rate sufficient to maintain a mild reflux. After stirring for 30 minutes solvent is removed to ⅓ of the volume to afford a semi-solid. After cooling in an ice bath solid product is filtered and washed with cold hexane and dried yielding 702 g (95%) of N,3-bis-(4-chlorophenyl)-4-carbomethoxy-4-methyl-4,5-dihydro-1H-pyrazole-1-carboxamide. NMR data was consistent with the structure.

EXAMPLE 92

Preparation of N,3-bis-(4-chlorophenyl)-4-dimethylcarbamoyl-4-methyl-4,5-dihydro-1H-pyrazole-1-carboxamide Into a 3000 ml three necked flask equipped with a mechanical stirrer, thermometer, and addition funnel was placed 65 ml (0.47 mole) of diisopropylamine, 155 g (0.45 mole) of N,3-bis-(4-chlorophenyl)-4-methyl-4,5-dihydro-1H-pyrazole-1-carboxamide and 1000 ml of tetrahydrofuran. The atmosphere was exchanged for nitrogen and the mixture was cooled to −20° C. internal. Then 375 ml of 2.6M n-butyllithium in hexane (0.97 mole) was added at a rate to maintain the internal temperature below −10° C. The mixture was stirred for an additional 30 minutes at −20° C. and then cooled to −60° C. whereon 45 ml of dimethylcarbamoyl chloride (0.49 mole) was added in one portion. After stirring for 15 minutes the reaction was quenched with 35 ml of acetic acid and 100 ml of water. After warming to room temperature, the organic layer was separated, dried over magnesium sulfate and concentrated in vacuo. Crystallization from ethyl ether gave 125 g of N,3-bis-(4-chlorophenyl)-4-dimethylcarbamoyl-4-methyl-4,5-dihydro-1H-pyrazole-1-carboxamide. Mp 194°–197° C. NMR and IR data were consistent with the structure.

EXAMPLE 95

Preparation of N,3-bis-(4-chlorophenyl)-4-carboethoxy-4,5-dihydro-1H-pyrazole-1-carboxamide To 3.2 g of N,3-bis-(4-chlorophenyl)-4,5-dihydro-1H-pyrazole-1-carboxamide dissolved in 20 ml of tetrahydrofuran and cooled in an acetone bath maintained at −20° C., was added 1.5 ml of diisopropyl amine and 8.0 ml of a 2.7 molar solution of butyllithium in hexane. The resulting solution was stirred for 20 minutes and then cooled to −70° C. To this solution was added 0.5 ml of ethyl chloroformate. The reaction was allowed to stir for 10 minutes and then allowed to warm to room temperature over 10 minutes. The reaction was quenched with 1.0 ml of acetic acid and the reaction mixture was partitioned between diethyl ether and water and the organic layer was dried over anhydrous magnesium sulfate. The resulting solution was filtered evaporated in vacuo to give 3.3 g of N,3-bis-(4-chlorophenyl)-4-carboethoxy-4,5-dihydro-1H-pyrazole-1-carboxamide. NMR and IR data were consistent with the structure.

EXAMPLE 98

Preparation of N,3-bis-(4-chlorophenyl)-4-dithiocarbomethoxy-4-methyl-4,5-dihydro-1H-pyrazole-1-carboxamide To 2.3 g of diisopropylamine dissolved in 15 ml of tetrahydrofuran and cooled in an ice salt bath was added 8.0 ml of a 2.7 molar solution of n-butyllithium in hexane. After stirring for 5 minutes a solution of 3.4 g of N,3-bis-(4-chlorophenyl)-4-methyl-4,5-dihydro-1H-pyrazole-1-carboxamide in 7 ml of tetrahydrofuran was added and the resulting solution stirred for 15 minutes. To this solution was added 1.5 ml of carbon disulfide and, after 15 minutes, 1.5 ml of methyl iodide was added. Stirring was continued for 1 hour. The reaction mixture was partitioned between diethyl ether and water and the organic layer was dried over anhydrous magnesium sulfate. The resulting solution was filtered and evaporated in vacuo to give 2.7 g of N,3-bis-(4-chlorophenyl)-4-dithiocarbomethoxy-4-methyl-4,5-dihydro-1H-pyrazole-1-carboxamide. NMR and IR data were consistent with the structure.

EXAMPLE 115

Preparation of N,3-bis-(4-chlorophenyl)-4-dimethyl-carbamoyl-4-methyl-N-acetyl-4,5-dihydro-1H-pyrazole-1-carboxamide In a 50 ml round bottomed flask was placed 0.45 g of 60% sodium hydride (0.011 mole). The sodium hydride was washed twice with hexane and suspended in 15 ml of tetrahydrofuran. A solution of 2.0 g (0.005 mole) of N,3-bis-(4-chlorophenyl)-4-dimethylcarbamoyl-4-methyl-4,5-dihydro-1H-pyrazole-1-carboxamide in 5 ml of tetrahydrofuran was added slowly. When hydrogen evolution ceased, 1 ml of acetic anhydride was added and the mixture was stirred for 5 minutes. The reaction was partitioned between ethyl ether and brine, dried, concentrated, and chromatographed yielding 1.6 g of N,3-bis-(4-chlorophenyl)-4-dimethylcarbamoyl-4-methyl-N-acetyl-4,5-dihydro-1H-pyrazole-1-carboxamide, an oil. NMR and IR data were consistent with the structure.

EXAMPLE 130

Preparation of N,3-bis-(4-chlorophenyl)-4-carbomethoxy-4-methyl-4,5-dihydro-1H-pyrazole-1-thiocarboxamide 4-chlorophenyl isothiocyanate and 3-(4-chlorophenyl)-4-methyl-4,5-dihydro-1H-pyrazole were used, by substantially following the procedures given in Example G, to prepare N,3-bis-(4-chlorophenyl)-4-methyl-4,5-dihydro-1H-pyrazole-1-thiocarboxamide, which was used, by substantially following the procedures given in Example 77 Method A, to prepare N,3-bis-(4-chlorophenyl)-4-carbomethoxy-4-methyl-4,5-dihydro-1H-pyrazole-1-thiocarboxamide, mp 69°–78° C. NMR and IR data were consistent with the structure.

EXAMPLE 138

Preparation of N,3-bis-(4-chlorophenyl)-4-carbomethoxy-4-methyl-N-dimethylcarbamoyl-4,5-dihydro-1H-pyrazole-1-carboxamide N,3-bis-(4-chlorophenyl)-4-carbomethoxy-4-methyl-4,5-dihydro-1H-pyrazole-1-carboxamide was treated with dimethylcarbamoyl chloride by substantially following the procedure given in Example 115 yielding N,3-bis-(4-chlorophenyl)-4-carbomethoxy-4-methyl-N-dimethylcarbamoyl-4,5-dihydro-1H-pyrazole-1-carboxamide, an oil which solidified on long standing. NMR and IR data were consistent with the structure.

EXAMPLE 145

Preparation of
N,3-bis-(4-chlorophenyl)-4-carbomethoxy-4-methyl-N-carbomethoxythio-4,5-dihydro-1H-pyrazole-1-carboxamide N,3-bis-(4-chlorophenyl)-4-carbomethoxy-4-methyl-4,5-dihydro-1H-pyrazole-1-carboxamide was treated with carbomethoxysulfenyl chloride by substantially following the procedure given in Example 115 yielding N,3-bis-(4-chlorophenyl)-4-carbomethoxy-4-methyl-N-carbomethoxythio-4,5-dihydro-1H-pyrazole-1-carboxamide, a foam. NMR and IR data were consistent with the structure.

EXAMPLE 149

Preparation of
N-(4-trifluoromethylphenyl)-3-(4-chlorophenyl)-4-carbomethoxy-4-methyl-4,5-dihydro-1H-pyrazole-1-carboxamide

Method A 4-trifluoromethylphenyl isocyanate and 3-(4-chlorophenyl)-4-methyl-4,5-dihydro-1H-pyrazole were used, by substantially following the procedures given in Example G, to prepare N-(4-trifluoromethylphenyl)-3-(4-chlorophenyl)-4-methyl-4,5-dihydro-1H-pyrazole-1-carboxamide which was used, by substantially following the procedures given in Example 77 Method A except that methyl chloroformate was used as the acylating agent, to prepare N-(4-trifluoromethylphenyl)-3-(4-chlorophenyl)-4-carbomethoxy-4-methyl-4,5-dihydro-1H-pyrazole-1-carboxamide, mp 143°–146° C. NMR and IR data were consistent with the structure.

Method B 3-(4-chlorophenyl)-4-carbomethoxy-4-methyl-4,5-dihydro-1H-pyrazole (Example O) and 4-trifluoromethylphenyl isocyanate were reacted by substantially following the procedure given in Example D to give a 95% yield of N-(4-trifluoromethylphenyl)-3-(4-chlorophenyl)-4-carbomethoxy-4-methyl-4,5-dihydro-1H-pyrazole-1-carboxamide. NMR data was consistent with the structure.

Method C 3-(4-chlorophenyl)-4-carbomethoxy-4-methyl-4,5-dihydro-1H-pyrazole hydrochloride (Example P) (10 mmole), triethylamine (20 mmole), methylene chloride (30 ml) were added together and stirred for 10 minutes, whereon 10 mmole of 4-trifluoromethylphenyl isocyanate was added and after 30 minutes the resulting mixture was washed twice with water, dried with magnesium sulfate and concentrated giving a 95% yield of N-(4-trifluoromethylphenyl)-3-(4-chlorophenyl)-4-carbomethoxy-4-methyl-4,5-dihydro-1H-pyrazole-1-carboxamide. NMR data was consistent with the structure.

EXAMPLE 150

Preparation of
N,3-bis-(4-chlorophenyl)-4-carbomethoxy-4-methyl-N-(2-nitrophenylsulfenyl)-4,5-dihydro-1H-pyrazole-1-carboxamide N,3-bis-(4-chlorophenyl)-4-carbomethoxy-4methyl-4,5-dihydro-1H-pyrazole-1-carboxamide was treated with 2-nitrophenylsulfenyl chloride by substantially following the procedure given in Example 115 yielding N,3-bis-(4-chlorophenyl)-4-carbomethoxy-4-methyl-N-(2-nitrophenylsulfenyl)-4,5-dihydro-1H-pyrazole-1-carboxamide. NMR and IR data were consistent with the structure.

EXAMPLE 160

Preparation of
N,3-bis-(4-chlorophenyl)-4-carbomethoxy-4-methyl-N-(1-carbomethoxy-prop-2-yl-thio)-4,5-dihydro-1H-pyrazole-1-carboxamide N,3-bis-(4-chlorophenyl)-4-carbomethoxy-4-methyl-4,5-dihydro-1H-pyrazole-1-carboxamide was treated with (1-carbomethoxy-prop-2-yl) disulfide by substantially following the procedure given in Example 115 yielding N,3-bis-(4-chlorophenyl)-4-carbomethoxy-4-methyl-N-(1-carbomethoxy-prop-2-yl-thio)-4,5-dihydro-1H-pyrazole-1-carboxamide. NMR and IR data were consistent with the structure.

EXAMPLE 224

Preparation of
N-(5-chloropyrid-2-yl)-3-(4-chlorophenyl)-4-carbomethoxy-4-methyl-4,5-dihydro-1H-pyrazole-1-carboxamide To 10 ml of acetonitrile containing 4.5 ml of 2.5M phosgene in ethyl acetate was added a slurry of 2.9 g (10 mmole) of 3-(4-chlorophenyl)-4-carbomethoxy-4-methyl-4,5-dihydro-1H-pyrazole hydrochloride 2.0 g (20 mmole) of triethylamine and 20 ml of acetonitrile. After stirring for 10 minutes the carbamoyl chloride was judged to have been formed and then 1.5 g (11 mmole) of 2-amino-5-chloropyridine was added with an additional 2 g of triethylamine. After stirring for 18 hours the mixture was partitioned between ether and water, washed with brine, dried over magnesium sulfate, filtered concentrated, and chromatographed yielding N-(5-chloropyrid-2-yl)-3-(4-chlorophenyl)-4-carbomethoxy-4-methyl-4,5-dihydro-1H-pyrazole-1-carboxamide, mp 130°–146° C. NMR data was consistent with the structure.

EXAMPLE 239

Preparation of
N-(4-trifluoromethoxyphenyl)-3-(4-chlorophenyl)-4-(2,2-difluorovinyl)-4,5-dihydro-1H-pyrazole-1-carboxamide To 2.0 g of N-(4-trifluoromethoxyphenyl)-3-(4-chlorophenyl)-4-formyl-4-methyl-4,5-dihydro-1H-pyrazole-1-carboxamide (5 mmole), was added 4 g of triphenylphosphine (15 mmole), 3 g of sodium chlorodifluoroacetate (20 mmole) and 15 ml of diglyme. The mixture was heated slowly to reflux over 1 hour. Gas evolved. After refluxing for 20 minutes the mixture was cooled, partitioned between ether and water, dried, rotovaped and chromatographed (ether/hexane) to yield 0.5 g of N-(4-trifluoromethoxyphenyl)-3-(4-chlorophenyl)-4-(2,2-difluorovinyl)-4-methyl-4,5-dihydro-1H-pyrazole-1-carboxamide mp 142°–8° C. NMR data was consistent with the structure.

EXAMPLE 261

Preparation of N-(3,5-dimethylisoxazol-4-yl)-3-(4-chlorophenyl)-4-carbomethoxy-4-methyl-4,5-dihydro-1H-pyrazole-1-carboxamide 3-(4-chlorophenyl)-4-carbomethoxy-4-methyl-4,5-dihydro-1H-pyrazole hydrochloride (10 mmole), triethylamine (20 mmole), methylene chloride (30 ml and 3,5-dimethylisoxazole-4-yl isocyanate (Maybridge Chemical Co. Ltd.) (10 mmole) were reacted by stirring at room temperature for 30 minutes. The reaction mixture was then washed twice with water, dried with magnesium sulfate concentrated giving a 95% yield of N-(3,5-dimethylisoxazol-4-yl)-3-(4-chlorophenyl)-4-carbomethoxy-4-methyl-4,5-dihydro-1H-pyrazole-1-carboxamide mp 214°–216° C. NMR data was consistent with the structure.

EXAMPLE 262

Preparation of N-(4-trifluoromethoxyphenyl)-3-(4-chlorophenyl)-4-formyl-4-methyl-4,5-dihydro-1H-pyrazole-1-carboxamide To 3.5 ml of diisopropylamine dissolved in 20 ml of tetrahydrofuran and cooled in a −20° C. bath was added 10.0 ml of a 2.5 molar solution n-butyllithium in hexane. After stirring for 5 minutes a solution of 4.0 g of N-(4-trifluoromethoxyphenyl)-3-(4-chlorophenyl)-4-methyl-4,5-dihydro-1H-pyrazole-1-carboxamide in 10 ml of tetrahydrofuran was added and the resulting solution stirred for 15 minutes and then cooled to −78° C. To this solution was added 2.0 ml of methyl formate and, after 5 minutes, 2 ml of acetic acid was added. The reaction mixture was partitioned between diethyl ether and water and the organic layer was dried over anhydrous magnesium sulfate. The resulting solution was filtered, evaporated in vacuo to give 3.9 g of N-(4-trifluoromethoxyphenyl)-3-(4-chlorophenyl)-4-formyl-4-methyl-4,5-dihydro-1H-pyrazole-1-carboxamide. NMR and IR data were consistent with the structure.

EXAMPLE 264

Preparation N-(4-trifluoromethoxyphenyl)-3-(4-chlorophenyl)-4-(2,2-dichlorovinyl)-4-methyl-4,5-dihydro-1H-pyrazole-1-carboxamide To 6.5 g of triphenyl phosphine and 2.5 g of potassium t-butoxide dissolved in 75 ml of THF and cooled to −70° C. was added 3.5 g of chloroform. After stirring for 5 minutes a solution of 3.9 g of N-(4-trifluoromethoxyphenyl)-3-(4-chlorophenyl)-4-formyl-4-methyl-4,5-dihydro-1H-pyrazole-1-carboxamide in 10 ml of THF is added and the mixture is allowed to warm to 10° C. over 1 hour. The resulting mixture is partitioned between ether and water, dried, rotovaped and chromatographed (ether/hexane) on silica gel yielding 3.1 g of N-(4-trifluoromethoxyphenyl)-3-(4-chlorophenyl)-4-(2,2-dichlorovinyl)-4-methyl-4,5-dihydro-1H-pyrazole-1-carboxamide mp 138°–141° C. NMR and IR data were consistent with the structure.

EXAMPLE 265

Preparation of N-(4-trifluoromethoxyphenyl)-3-(4-chlorophenyl)-4-(2,2-dibromovinyl)-4-methyl-4,5-dihydro-1H-pyrazole-1-carboxamide To 1.5 g of zinc dust (23.8 mmole) and 5.2 g of triphenylphosphine (20 mmole) in 20 ml of methylene chloride was added 6.8 g of carbon tetrabromide (20 mmole) after stirring for 90 minutes a solution of 3 g of N-(4-trifluoromethoxyphenyl)-3-(4-chlorophenyl)-4-formyl-4-methyl-4,5-dihydro-1H-pyrazole-1-carboxamide in 10 ml of MeCl$_2$ is added and the mixture is stirred an additional 60 minutes. The reaction is partitioned between ether and aqueous sodium thiosulfate, dried, rotovaped and chromatographed (ether/hexane) to yield 2.0 g of N-(4-trifluoromethoxyphenyl)-3-(4-chlorophenyl)-4-(2,2-dibromovinyl)-4-methyl-4,5-dihydro-1H-pyrazole-1-carboxamide an oil. NMR data was consistent with the structure.

EXAMPLE 383

Preparation of N-(4-trifluoromethylphenyl)-3-(4-propoxyphenyl)-4-carbomethoxy-4-methyl-4,5-dihydro-1H-pyrazole-1-carboxamide 3-(4-proxyphenyl)-4-carbomethoxy-4-methyl-4,5-dihydro-1H-pyrazole made from 4-proxypropiophenone by substantially following the procedures in Example L, Method 1; Example M; Example N; and Example O and 4-trifluoromethylphenyl isocyanate were reacted by substantially following the procedure in Example 149, Method B to afford a 95% yield of N-(4-trifluoromethylphenyl)-3-(4-propoxyphenyl)-4-carbomethoxy-4-methyl-4,5-dihydro-1H-pyrazole-1-carboxamide, m.p. 134°–137° C. NMR data was consistent with the structure.

EXAMPLE 467

Preparation of N-(4-trifluoromethylphenyl)-3-(4-chlorophenyl)-4-carbomethoxy-4,5-dihydro-1H-pyrazole-1-carboxamide To 60 g (282 mmole) of 3-(4-chlorophenyl)-3-ketopropanoate (MCBA) in 200 ml of methanol was added 75 ml (1312 mmole) of acetic acid. The reaction mixture was cooled to −10° C. and 45 ml (330 mmole) of N,N,N,N-tetramethyldiaminomethane was added while maintaining the internal temperature below 0° C. for 30 minutes and then 16 ml (330 mmole) of hydrazine monohydrate was added. The reaction was warmed to room temperature and stirred for 60 minutes. The methanol was then removed under vacuum and the residue dissolved in 400 ml of methylene chloride. The organic solution was washed three times with water and once with aqueous sodium bicarbonate and dried over MgSO$_4$. This solution of 3-(4-chlorophenyl)4-carbomethoxy-4,5-dihydro-1H-pyrazole was used without further purification in the next reaction.

To the methylene chloride solution of 3-(4-chlorophenyl)-4-carbomethoxy-4,5-dihydro-1H-pyrazole obtained in the previous reaction was added 20 ml of 4-trifluoromethylphenyl isocyanate and the resulting mixture was refluxed for 20 minutes. Upon evaporation of the methylene chloride, trituration with ethyl ether, and recrystalization from toluene was obtained 44 g (103 mmole) of N-(4-trifluoromethylphenyl)-3-(4-chlorophenyl)-4-carbomethoxy-4,5-dihydro-1H-pyrazole-1-carboxamide. NMR data was consistent with the structure.

EXAMPLE 473

Preparation of N-(4-trifluoromethylphenyl)-3-(4-chlorophenyl)-4-carbomethoxy-4-allyl-4,5-dihydro-1H-pyrazole-1-carboxamide N-(4-trifluoromethylphenyl)-3-(4-chlorophenyl)-4-carbomethoxy-4,5-dihydro-1H-pyrazole-1-carboxamide (Example 467) was alkylated by substantially following the procedures of Example 77 Method C and substituting allyl iodide for iodmethane afforded N-(4-trifluoromethylphenyl)-3-(4-chlorophenyl)-4-carbomethoxy-4-allyl-4,5-dihydro-1H-pyrazole-1-carboxamide. NMR data was consistent with the structure.

Surprisingly, many of the compounds of the present invention exhibit better pesticidal activity than the known dihydropyrazoles. Accordingly, compounds of the present invention represent a genuine enrichment of the art.

Certain of the 1-substituted-4-substituted-4,5-dihydro-1H-pyrazoles of the present invention show, for example, activity at a concentration of from about 2 ppm to about 15 ppm against Southern Armyworm; from about 0.1 ppm to about 10 ppm against Mexican Bean Beetle; and from about 1 ppm to about 10 ppm against Boll Weevil.

On the basis of their strong initial pesticidal activity and excellent residual pesticidal activity, compounds according to the invention may be used in low dosages in controlling pests. The amount of dosage depends on a variety of factors, for example, the substance used, the kind of pest, the formulation used, the state of the crop infected with the pest and the prevailing weather conditions. In general, for the control of pests in agriculture and horticulture, a dosage corresponding to from about 0.1 grams to about 1000 grams of the active substance per hectare may be used and from about 5 grams to about 200 grams per hectare of the active substance is preferred. The exact amount of dosage for a given situation can be routinely determined and depends on a variety of factors, for example, the substance used, the kind of pest, the formulation used, the state of the crop infested with the insect and the prevailing weather conditions. The term "pesticidal" as employed in the specification and claims of this application is to be construed as any means which adversely affects the existence or growth of the target pest. Such means can compromise a complete killing action, eradication, arresting in growth, inhibition, reducing in number of any combination thereof. The term "control" as employed in the specification and claims of this application is to be construed as meaning "pesticidal" and protecting plants from pest damage. By "pesticidally effective amount" is meant that dosage of active substance sufficient to exert the desired pest "control".

Representative pests which can be controlled by the compounds of the present invention include:
American Cockroach (*Periplanta americana*)
Bean Leaf Beetle (*Cerotoma trifurcata*)
Bean Leaf Roller (*Urbanus proteus*)
Black Carpenter Ant (*Camponotus Pennsylvanicus*)
Black Cutworm (*Agrotis ipsilon*)
Boll Weevil (*Anthonomus grandis grandis*)
Colorado Potato Beetle (*Lepitinotarsa decemlineata*)
Fall Armyworm (*Spodoptera frugiperda*)
German Cockroach (*Blatella germanica*)
Green June Beetle (*Cotinis nitida*)
House Cricket (*Ancheta domesticus*)
Housefly (*Musca domestica*)
Mexican Bean Beetle (*Epilachna varivestis*)
Potato Leaf Hopper (*Empoasca fabae*)
Red Harvester Ant (*Pogonomyrmex barbatus*)
Red Imported Fire Ant (*Solenopsis invicta*)
Redlegged Grasshopper (*Melanopus femurrubrum*)
Southern Armyworm (*Spodoptera eridania*)
Southern Corn Rootworm (*Diabrotica undecimpunctata howardi*)
Tobacco Budworm (*Heliothis virescens*).

The compounds of the present invention, for practical applications, can be utilized in the form of compositions or formulations. Examples of the preparation of compositions and formulations can be found in the American Chemical Society publication "Pesticidal Formulation Research," (1969), Advances in Chemistry Series No. 86, written by Wade Van Valkenburg; and the Marcel Dekker Inc. publication "Pesticide Formulations", (1973) edited by Wade Van Valkenburg. In these compositions and formulations, the active substance is mixed with conventional inert agronomically acceptable (i.e., plant compatible and/or pesticidally inert) pesticide diluents or extenders such as solid carrier material or liquid carrier material, of the type usable in conventional pesticide compositions or formulations. By "agronomically acceptable carrier" is meant any substance which can be used to dissolve, disperse of diffuse the active ingredient in the composition without impairing the active ingredients effectiveness and which by itself has no significant detrimental effect on the soil, equipment, desirable plants, or agronomic enviornment. If desired, adjuvants such as surfactants, stabilizers, antifoam agents and antidrift agents may also be combined.

Examples of compositions and formulations according to the invention are aqueous solutions and dispersions, oily solutions and oil dispersions, pastes, dusting powders, wettable powders, emulsifiable concentrates, flowables, granules, baits, invert emulsions, aerosol compositions and fumigating candles.

Wettable powders, pastes, flowables and emulsifiable concentrates are concentrated preparations which are diluted with water before or during use.

Baits are preparations generally comprising a food or other substance attractive to insets, that includes at least one lethal or non-lethal toxicant. Lethal toxicants kill insects upon ingesting the bait while non-lethal toxicants change the behavior and physiology of the insect for the purpose of control.

The invert emulsions are mainly used for air application, where large areas are treated with a comparatively small amount of preparation. The invert emulsion may be prepared in the spraying apparatus shortly before, or even during, the spraying operation by emulsifying water in an oil solution or an oil dispersion of the active substance.

Compositions and formulations are prepared in a known manner, for instance by extending the active compounds with conventional pesticide dispersible liquid diluent carriers and/or dispersible solid carriers optionally with the use of carrier vehicle assistants, e.g., conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons, e.g., dichlorodifluoromethane and trifluorochloromethane, as well as butane, propane, nitrogen and carbon dioxide; inert dispersible liquid diluent carriers, including inert organic solvents, such as aromatic hydrocarbons (e.g., benzene, toluene, xylene, alkyl naphthalenes, etc.), halogenated, especially chlorinated, aromatic hydrocarbons (e.g., chlorobenzenes, etc.), cycloalkanes, (e.g., cyclohexane, etc.), paraffins (e.g., petroleum or mineral oil fractions), chlorinated aliphatic hydrocarbons (e.g., methylene chloride, chloroethylenes, etc.), vegetable oils (e.g., soybean oil, cotton seed oil, corn oil, etc.), alcohols (e.g., methanol, ethanol, propanol, butanol, glycol, etc.) as well as ethers and esters thereof (e.g., glycol monomethyl ether, etc.), amines (e.g., ethanolamine, etc.), amides (e.g., dimethyl formamide, etc.), sulfoxides (e.g., dimethyl sulfoxide, etc.), acetonitrile, ketones (e.g., acetone, methyl ethyl ketone, methyl isobutyl ketone, cyclohexanone, isophorone, etc.), and/or water; solid carriers including ground natural minerals, such as kaolins, clays, talc, chalk, quartz, attapulgite, montmorillonite or diatomaceous earth, and ground synthetic minerals, such as highly-dispersed silicic acid, alumina and silicates; solid carriers for granules include crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. The following may be chiefly considered for use as conventional carrier vehicle assistants: emulsifying agents, such as cationic and/or non-ionic and/or anionic emulsifying agents (e.g., polyetehylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

If desired, it is possible to use colorants in compositions and formulations containing compounds of the present invention such as inorganic pigments, for example, iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The active compounds of the present invention may be employed alone or in the form of mixtures with one another and/or with such solid and/or liquid dispersible carrier vehicles and/or with other known compatible active agents, especially plant protection agents, such as other insecticides, arthropodicides, nematicides, fungicides, bactericides, rodenticides, herbicides, fertilizers, growth-regulating agents, synergists, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1-99% by weight, preferably between about 0.5-90% by weight, and more preferably between about 1-75% by weight of the mixture. Carrier composition mixtures suitable for direct application or field application generally contemplate those in which the active compound is present in an amount substantially between about 0.0001-95%, preferably between about 0.0005-90% by weight, and more preferably between about 0.001-75% by weight of the mixture. Thus the present invention contemplates overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, (e.g., a surfaceactive agent, such as an emulsifying agent and/or a dispersing agent), and an amount of the active compound generally between about 0.001% and about 99%, preferably between about 0.0005% and about 95%, and more preferably between about 0.001% about 75% by weight of the composition, which is effective for the purpose in question.

The active compounds can be applied as insecticide sprays by methods commonly employed, such as conventional high-gallonage hydraulic sprays, low gallonage sprays, ultra-low-volume sprays, airblast spray, aerial sprays, and dusts. If low volume applications are desired, a solution of the compound is usually used. In ultra-low-volume applications, a liquid composition containing the active compound is usually applied as a spray (e.g., mist by means of atomizing equipment in finely divided form (average particle size of from about 50 to about 100 microns or less) using airplane crop spraying techniques. Typically only a few liters per hectare are needed and often amounts up to about 15 to 1000 g/hectare, preferbly about 40 to 600 g/hectare are sufficient. With ultra-low-volume, it is possible to use highly concentrated liquid compositions with said liquid carrier vehicles containing from about 20 to about 95% by weight of the active compound.

Furthermore, the present invention contemplates methods of killing, combatting or controlling pests which compromises contacting pests with correspondively combative or toxic amount (i.e. a pesticidally effective amount) of at least one active compound of the invention alone or together with a carrier vehicle (composition or formulation) as noted above. The term "contacting" as employed in the specification and claims is to be construed as applying to at least one of (a) such pests and (b) the corresponding habit at thereof (i.e., the locus to be protected, for example, to a growing crop or to an area where a crop is to be grown) the active compound of this invention alone or as a constituent of a composition or formulation. The instant formulations or compositions are applied in the usual manner, for instance by spraying, atomizing, vaporizing, scattering, dusting, watering, squirting, sprinkling, pouring, fumigating, dry dressing, moist dressing, wet dressing, slurry dressing, encrusting and the like.

It will be realized, of course, that the concentration of the particular active compound utilized in admixture with the carrier vehicle will depend upon such factors as the type of equipment employed, method of application, area to be treated, types of pests to be controlled and degree of infestation. Therefore, in special cases it is possible to go above or below the aforementioned concentration ranges.

Granular preparations are produced for example, by taking up the active substance in a solvent and by using the resulting solution, as the case may be in the presence of a binder, to impregnate a granular carrier material, such as porous granules (for example pumice and attaclay), or mineral non-porous granules (for example dried coffee grounds and chopped tobacco stems).

A granular preparation (frequently termed a "pellet") may alternatively be produced by compressing the active substance together with powdered minerals in the presence of lubricants and binders and by disintegrating and straining the composite to the desired grain size.

Dusts are obtainable by intimately mixing the active substance with an inert solid carrier material in a concentration of from about 1 to about 50% by weight. Examples of suitable solid carrier materials are talc, kaolin, pipe clay, diatomaceous earth, dolomite, gypsum, chalk, bentonite, attapulgite and colloidal $SiO_2$ or mixtures of these and simular substances. Alternatively organic carrier materials such, for example, as ground walnut shells may be used.

Wettable powders and flowables are produced by mixing from about 10 to about 99 parts by weight of a solid inert carrier such, for example, as the aforementioned carrier materials with from about 1 to about 80 parts by weight of the active substance, from about 1 to about 5 parts by weight of a dispersing agent such, for example, as the lignosulfonates or alkylnaphthalene sulfonates known for this purpose and preferably also from about 0.5 to about 5 parts by weight of a wetting agent, such as fatty alcohol sulfates, or alkylarylsulfonates of fatty acid condensation products. In the case of flowables, a liquid inert carrier such as water is also included.

To produce emulsifiable concentrates the active compound is dissolved or finely divided in a suitable solvent which preferably is poorly miscible with water, an emulsifier being added to the resulting solution. Examples of suitable solvents are xylene, toluene, high-boiling aromatic petroleum distillates, for example solvent naphtha, distilled tar oil and mixtures of these liquids. Examples of suitable emulsifiers are alkylphenoxypolyglycol ethers, polyoxyethylene sorbitan esters of fatty acids or polyoxyethylene sorbitol esters of fatty acids. The concentration of the active compound in these emulsifiable concentrates is not restricted within narrow limits and may vary between about 2% and about 50% by weight. A suitable liquid highly concentrated primary composition other than an emulsifiable concentrate is a solution of the active substance in a liquid which is readily miscible with water, for example, acetone, to which solution a dispersent and, as the case may be, a wetting agent are added. When such a primary composition is diluted with water shortly before or during the spraying operation an aqueous dispersion of the active substance is obtained.

An aerosol preparation according to the invention is obtained in the usual manner by incorporating the active substance or a solution thereof in a suitable solvent in a volatile liquid suitable for use as a propellant such, for example, as a mixture of chlorine and fluorine derivatives of methane and ethane.

Fumigating candles or fumigating powders, i.e. preparations which when burning are capable of emitting a pesticidal smoke, are obtained by taking up the active substance in a combustible mixture which may, for example, comprise a sugar or a wood, preferably in the ground form, as a fuel, a substance to sustain combustion such, for example, as ammonium nitrate or potassium chlorate, and furthermore a substance for retarding combustion, for example kaolin, bentonite and/or colloidal silicic acid.

A bait preparation comprises a food or other substance attractive to pests, a carrier, the toxicant and may optionally include other substances commonly used in preparations of this kind, such as, a preservative to inhibit bacterial and fungal growth, a waterproofing agent to prevent disintegration under wet conditions and dyes or colorants as described above.

In addition to the aforementioned ingredients the preparations according to the invention may also contain other substances commonly used in preparations of this kind.

For example, a lubricant, such as calcium stearate or magnesium stearate, may be added to a wettable powder or to a mixture to be granulated. Furthermore there may, for example, be added "adhesives" such as polyvinylalcoholcellulose derivatives or other colloidal materials, such as casein, to improve the adherence of the pesticide to the surface to be protected.

Representative illustrative preparations of compositions and formulations including the compounds of the present invention are set forth below as Examples Q through Y.

EXAMPLE Q

| Granular | |
|---|---|
| Ingredient %/wt. | |
| Toxicant and toxicant impurities | 0.25 |
| Triton ® X-305 (binder) (Octylphenyl-30 ethylene oxide ethanol) | 0.25 |
| Agsorb ® 24/48 (diluent) (Montmorillonite clay) | 99.50 |

Preparation: The toxicant and Triton ® X-305 are dissolved into methylene chloride and the mixture is added to the Agsorb ® with continuous mixing. The methylene chloride is then allowed to evaporate.

EXAMPLE R

| Dust | |
|---|---|
| Ingredient %/wt. | |
| Toxicant and Toxicant impurities | 1.0 |
| Talc | 99.0 |

Preparation: Toxicant is dissolved in excess acetone and the mixture is impregnated onto the talc. The acetone is then permitted to evaporate.

EXAMPLE S

| Ingredient %/wt. | |
|---|---|
| Toxicant and toxicant impurities | 31.3 |
| Duponal ® WA Dry (wetter) (Sodium Lauryl Sulfate) | 2.0 |
| Reax ® 45A (dispersant) (Sodium Lignin Sulfonate) | 5.0 |
| Barden clay (diluent) | 31.7 |
| HiSil ® 233 (diluent) (Sodium Silica) | 30.0 |

Preparation: The toxicant is absorbed onto the Barden clay and HiSil® carriers. The Duponal® and Reax® are then added and the entire dry mixture blended until homogeneous. The composition is then micronized to a fine particle size.

EXAMPLE T Emulsifiable Concentrate

| Ingredient | %/wt. |
| --- | --- |
| Toxicant and toxicant impurities | 15.0 |
| Sponto® 232T (emulsifier) (Anionic and nonionic blend of the following Surfactants: calcium dodecyl benzene sulfonate; and ethoxylated alkylphenol) | 6.0 |
| Sponto® 234T (emulsifier) (Anionic and nonionic blend of the following surfactants: calcium dodecyl benzene sulfonate; and ethoxylated alkylphenol) | 4.0 |
| Cyclohexanone (solvent) | 22.5 |
| Tenneco® 500-100 (solvent) (Aromatic solvent mixture principally comprising xylene, cumene and ethyl benzene having a boiling point range of 290-345° F.) | 52.5 |

Preparation: All ingredients are mixed together with continuous agitation until a homogeneous clear solution is obtained.

EXAMPLE U Aerosol

| Ingredient | %/wt. |
| --- | --- |
| Toxicant and toxicant impurities | 0.5 |
| Freon 12 | 99.5 |

Preparation: The components are mixed and packaged under pressure in a suitable container equipped with a release spray valve.

EXAMPLE V

| Fumigating Candle or Fumigating Powder | |
| --- | --- |
| Ingredient | %/wt. |
| Toxicant and toxicant impurities | 1.0 |
| Wood dust | 96.0 |
| Starch | 3.0 |

Preparation: Toxicant, wood dust, and starch are blended together and then molded into a candle using a small amount of water to activate the starch.

EXAMPLE W

Bait

| Method A | |
| --- | --- |
| Ingredient | %/wt. |
| Toxicant and toxicant impurities | 1.00 |
| Wheat Bran (carrier and attractant) | 89.95 |
| Corn Syrup (attractant) | 7.00 |
| Corn Oil (attractant) | 2.00 |
| Kathon® 4200 (preservative) (2-n-Octyl-4-isothiazolin-3-one) | 0.05 |

Preparation: The corn oil and corn syrup are added to the wheat bran with adequate mixing. The toxicant and Kathon® are premixed with excess acetone and this solution is added to the wheat bran base with continued mixing. The acetone is then permitted to evaporate.

| Method B | |
| --- | --- |
| Ingredient | %/wt. |
| Toxicant and toxicant impurities | 0.06 |
| Granulated Sugar (carrier and attractant) | 99.94 |

EXAMPLE X

Pellet

Same as Example W, Method A, with this addition: the bait composition is formed into ¼" diameter by ½" long pellets using a suitable die and press apparatus.

EXAMPLE Y

| Flowable | |
| --- | --- |
| Ingredient | %/wt. |
| Toxicant and toxicant impurities | 13.3 |
| Duponal® WA Dry (wetter) (Sodium Lauryl Sulfate) | 2.0 |
| Reax® 45A (dispersant) (Sodium Lignin Sulfonate) | 5.0 |
| HiSil® 233 (diluent) (Sodium Silica) | 30.0 |
| Kelzan® (thickener) (Xanthan gum) | 0.5 |
| Water | 31.2 |

Preparation: The toxicant is absorbed onto the HiSil® carrier. The Duponal® and Reax® are then added and the entire dry mixture blended until homogeneous. The composition is then micronized to a fine particle size. The resulting powder is suspended in water and the Kelzan® added.

Compositions and formulations according to the present invention may also include known pesticidal compounds. This expands the spectrum of activity of the preparation and may give rise to synergism.

The following known insecticidal, fungicidal and acaricidal compounds are suitable for use in such a combined preparation.

Insecticides such as:
1. Chlorinated hydrocarbons, for example, 2,2-bis(p-chlorophenyl)-1,1,1-trichloroethane and hexachloroepoxyoctahydrodimethanonaphthalene;
2. Carbamates, for example N-methyl-1-napththylcarbamate;
3. Dinitropenols, for example 2-methyl-4,6-dinitrophenyl and (2-(2-butyl)-4,6dinitrophenyl-3,3-dimethylacrylate;
4. Organic phosphorus compounds, such as dimethyl-2-methoxy-carbonyl-1-methylvinyl phosphate, 0,0diethyl-O-p-nitrophenylphosphorus thioate; N-monomethylamide of 0,0-dimethyldithiophosphorylacetic acid;
5. Diphenylsulfides, for example p-chlorobenzyl or p-chlorophenyl sulfide and 2,4,4',5tetrachloridiphenylsulfide;
6. Diphenylsulfonates, for example p-chlorophenylbenzenesulfonate;
7. MethylcaRbinols, for example, 4,4-dichloro-1-trichloromethylbenzhydrol;
8. Quinoxaline compounds, such as methylquinoxaline dithiocarbonate;
9. Amidines such as N'-(4-chloro-O-tolyl) N,N-dimethylformamidine;
10. Pyrethroids such as Allethrin;

11. Biologicals such as *Bacillus thuringiensis* preparations;
12. Organic tin compounds such as tricyclohexyltin hydroxide;
13. Synergists such as piperonoyl butoxide;

Fungicides such as:

14. Organic mercury compounds, for example phenylmercuryacetate and methylmercurycyanoguanide;
15. Organic tin compounds, for example triphenyltin hydroxide and triphenyltin acetate;
16. Alkylenebisdithiocarbamates, for example, zinc-ethylenebisthiocarbamate and manganoethylenebisthiocarbamate; and furthermore
17. 2,4dinitro-6-(2octyl-phenylcrotonate), 1-bis(dimethylamino)phosphoryl-3-phenyl-5-amino-1,2-4triazole, 6-methylquinoxaline-2,3-dithiocarbonate, 1,4-dithioantraquinone-2,3-dicarbonitrile, N-trichloromethylthiophthalimide, N-trichloromethylthiotetrahydrophthalimide, N-(1,1,2,2-tetrachloroethylthio)-tetrahydrophthalimide, N-dichlorofluoromethylthio-N-phenyl-N'-dimethylsulfonyldiamide and tetrachloroisophthalonitrile.

Biological Activity

It has been found by biological evaluation that compounds according to the present invention have pesticidal activity and are capable of controlling larvae and adult forms of pests, especially insects from the orders Lepidoptera and Coleoptera. One skilled in the art will know how to determine the activity of a given compound against a given insect and the dosage required to obtain general or selective pesticidal effects. In addition, compounds of the present invention were found active against pyrethroid resistant pests such as the Colorado potato beetle and housefly.

In evaluating the pesticidal activity of the compounds of this invention, the following test procedures were employed.

Evaluations were made on the following insects:

| Common Name | Latin Name |
| --- | --- |
| Mexican Bean Beetle | *Epilachna varivestis* |
| Southern Armyworm | *Spodoptera eridania* |
| Boll Weevil | *Anthonomus grandis grandis* |

A test solution containing 600 parts per million (ppm) was made by dissolving the test compound in a solvent (acetone:methanol, 1:1), adding a surfactant and then water to give an acetone:methanol:water system of 10:10:80. A 1:1 mixture of an alkylarylpolyetheralcohol (sold under the trademark Triton ® X-155) and a modified phthalic glycerol alkyl resin (sold under the trademark Triton ® B-1956) was utilized at the equivalent of 1 ounce per 100 gal. of test solution as a surfactant.

Analogous solutions are made be serially diluting the 600 ppm test solution with water and surfactant to give concentrations of 150, 38, 10, 2.5, 0.6, 0.15, and 0.038 ppm. Not all compounds are tested at each of the several concentrations stated above.

Initial evaluations were carried out on one or more of the stated pest.

For the initial bean beetle and armyworm tests, individual bean (*Phaseolus limensis* var Woods' Prolific) leaves are placed on moistened pieces of filter paper in Petri dishes. The leaves are then sprayed with test solution using a rotating turntable and allowed to dry. The dishes are infested with 10 third instar larvae of Southern armyworm or Mexican bean beetle. The dishes are then covered.

For the boll weevil test ten adult weevils are placed in a 0.5 pint glass Mason jar containing a small cube of apple. The weevils are confined to the jars by fiberglass screen mesh secured by a screw-type rim cap. The jars are then sprayed with the test solution using a rotating turntable, directing the spray through the mesh into the jar.

The percent mortality for the bean beetle, armyworm and boll weevil evaluations are determined 96 hours after treatment. Evaluations are based on a scale of 0–100 percent in which 0 equals no activity and 100 equals total kill.

The rotating turntable consists of a fixed continuously operated spray nozzle under which targets are rotated at a fixed speed and distance. If the target is a Petri dish (such as for the armyworm), the distance from the nozzle is 15 inches. If the target is a Mason jar, the distance between the screened lid and the nozzle is 6 inches (10 inches from the base of the jar to the nozzle). The nozzle is located 8 inches from the rotating shaft. The targets on individual; platforms revolve around the shaft at 1 revolution per 20 seconds but only a brief portion of this time occurs in the spray path. Targets pass only once under the nozzle and then are removed to drying hoods.

The nozzle used is a ¼ JCO Spraying Systems (Wheaton, Ill.) air atomizing nozzle equipped with a No. 2850 fluid cap and No. 70 air cap. At the 10 psig air pressure used with liquid siphon feed 0.5 GPH (gallons per hour) are delivered in a round spray pattern with a 21° spray angle. Targets are misted with spray droplets to the point that the droplets coalesce to form a uniform thin film insufficient to drown test organisms.

All treatments are maintained at 75°–80° F. under continuous fluorescent light in a well-ventilated room. The results of the initial pesticidal evaluations are given in Table II.

For the whole plant Mexican Bean Beetle and Southern Armyworm test, lima bean (*Phaseolus limensis* var. Woods' Prolific) seedlings in 3-inch pots were sprayed to runoff with the test solutions using a DeVilbiss atomizer at 20 psig. When dry, each plant was placed in a plastic box (7.5" long×5.25" wide×3.75" deep). Each box was then infested with 10 third instar larvae of either the Mexican Bean Beetle or the Southern Armyworm. The box was then sealed with a lid equipped with screen ventilation holes.

For the whole plant Boll Weevil, cotton (*Gossypium hirsutum* var. Acala) seedlings are treated in like manner. Ten young adult Boll Weevils are placed in each plastic box containing the treated plant that has been allowed to dry. The boxes are then sealed as noted above.

All treatments are maintained under continuous fluroescent light at 80°±5° F. on open shelves for the course of the exposure period. Plants are watered as needed and replaced with untreated plants if they have been totally consumed as would be the case with ineffective treatments or untreated checks or controls.

Six days after treatment, the percent mortality is determined for each test species and spray concentration. Table III gives the mortality data reported as percentage killed at the stated concentration for whole plant evaluations on compounds of the present invention.

TABLE II

Biological Evaluations[1]

| Example No. | Test Insects | | |
|---|---|---|---|
| | Mexican Bean Beetle | Southern Armyworm | Boll Weevil |
| 1 | 100 | 100 | 100 |
| 2 | 100 | 100 | 100 |
| 3 | 100 | 100 | 100 |
| 4 | 100 | 100 | 100 |
| 5 | 100 | 90 | 60 |
| 6 | 100 | 100 | 20 |
| 7 | 100 | 100 | 0 |
| 8 | 100 | 100 | 0 |
| 9 | 20 | 0 | 40 |
| 10 | 44 | 100 | 20 |
| 11 | 10 | 100 | 0 |
| 12 | 10 | 60 | 0 |
| 13 | 11 | 0 | 0 |
| 14 | 100 | 100 | 100 |
| 15 | 100 | 100 | 100 |
| 16 | 100 | 100 | 100 |
| 17 | 100 | 100 | 100 |
| 18 | 100 | 100 | 100 |
| 19 | 80 | 100 | 100 |
| 20 | 100 | 100 | 40 |
| 21 | 100 | 100 | 60 |
| 22 | 100 | 100 | 80 |
| 23 | 100 | 100 | 20 |
| 24 | 20 | 0 | 0 |
| 25 | 90 | 90 | 20 |
| 26 | 100 | 100 | 100 |
| 27 | 100 | 100 | 80 |
| 28 | 100 | 100 | 100 |
| 29 | 100 | 100 | 100 |
| 30 | 100 | 100 | 40 |
| 31 | 100 | 100 | 100 |
| 32 | 100 | 100 | 100 |
| 33 | 100 | 100 | 100 |
| 34 | 100 | 100 | 100 |
| 35 | 100 | 100 | 80 |
| 36 | 100 | 100 | 100 |
| 37 | 100 | 100 | 20 |
| 38 | 100 | 100 | 100 |
| 39 | 100 | 100 | 100 |
| 40 | 100 | 100 | 100 |
| 41 | 100 | 20 | 20 |
| 42 | 100 | 100 | 0 |
| 43 | 100 | 60 | 100 |
| 44 | 100 | 100 | 80 |
| 45 | 100 | 100 | 80 |
| 46 | 100 | 100 | 100 |
| 47 | 0 | 0 | 40 |
| 48 | 40 | 70 | 60 |
| 49 | 100 | 100 | 100 |
| 50 | 100 | 100 | 20 |
| 51 | 100 | 100 | 60 |
| 52 | 100 | 100 | 100 |
| 53 | 100 | 100 | 100 |
| 54 | 100 | 100 | 40 |
| 55 | 100 | 100 | 100 |
| 56 | 80 | 90 | 0 |
| 57 | 100 | 100 | 0 |
| 58 | 100 | 100 | 40 |
| 59 | 30 | 10 | 0 |
| 60 | 80 | 0 | 0 |
| 61 | 100 | 100 | 100 |
| 62 | 80 | 0 | 0 |
| 63 | 100 | 100 | 40 |
| 64 | 100 | 100 | 0 |
| 65 | 100 | 100 | 60 |
| 66 | 100 | 100 | 80 |
| 67 | 100 | 100 | 100 |
| 68 | 100 | 100 | 0 |
| 69 | 100 | 100 | 0 |
| 70 | 100 | 100 | 100 |
| 71 | 100 | 100 | 100 |
| 72 | 100 | 100 | 100 |
| 73 | 100 | 100 | 100 |
| 74 | 100 | 100 | 100 |
| 75 | 100 | 100 | 100 |
| 76 | 100 | 100 | 100 |
| 77 | 100 | 100 | 100 |
| 78 | 100 | 100 | 60 |
| 79 | 100 | 0 | 60 |
| 80 | 100 | 20 | 0 |
| 81 | 100 | 100 | 100 |
| 82 | 100 | 40 | 0 |
| 83 | 100 | 100 | 100 |
| 84 | 100 | 100 | 100 |
| 85 | 100 | 100 | 100 |
| 86 | 100 | 100 | 100 |
| 87 | 100 | 100 | 100 |
| 88 | 100 | 100 | 100 |
| 89 | 100 | 100 | 100 |
| 90 | 100 | 100 | 100 |
| 91 | 100 | 100 | 60 |
| 92 | 100 | 100 | 100 |
| 93 | 100 | 90 | 60 |
| 94 | 0 | 0 | 20 |
| 95 | 100 | 100 | 100 |
| 96 | 100 | 100 | 80 |
| 97 | 100 | 100 | 100 |
| 98 | 100 | 100 | 100 |
| 99 | 100 | 100 | 100 |
| 100 | 100 | 30 | 0 |
| 101 | 100 | 100 | 80 |
| 102 | 100 | 100 | 100 |
| 103 | 100 | 100 | 100 |
| 104 | 100 | 100 | 40 |
| 105 | 100 | 100 | 100 |
| 106 | 100 | 100 | 100 |
| 107 | 100 | 100 | 100 |
| 108 | 100 | 100 | 100 |
| 109 | 100 | 100 | 80 |
| 110 | 100 | 100 | 100 |
| 111 | 100 | 100 | 100 |
| 112 | 100 | 100 | 80 |
| 113 | 100 | 100 | 100 |
| 115 | 100 | 100 | 100 |
| 116 | 100 | 100 | 100 |
| 117 | 100 | 100 | 100 |
| 118 | 100 | 100 | 60 |
| 119 | 100 | 100 | 100 |
| 120 | 100 | 100 | 100 |
| 121 | 100 | 90 | 100 |
| 122 | 90 | 100 | 80 |
| 123 | 100 | 100 | 100 |
| 124 | 100 | 100 | 100 |
| 125 | 100 | 100 | 100 |
| 126 | 100 | 100 | 100 |
| 127 | 100 | 100 | 100 |
| 128 | 100 | 100 | 100 |
| 129 | 100 | 100 | 100 |
| 130 | 100 | 100 | 100 |
| 131 | 100 | 100 | 100 |
| 132 | 100 | 100 | 100 |
| 133 | 100 | 100 | 100 |
| 134 | 100 | 100 | 100 |
| 135 | 100 | 100 | 100 |
| 136 | 100 | 100 | 100 |
| 137 | 100 | 100 | 100 |
| 138 | 100 | 100 | 80 |
| 139 | 70 | 100 | 100 |
| 140 | 100 | 100 | 100 |
| 141 | 100 | 100 | 100 |
| 142 | 100 | 100 | 100 |
| 143 | 100 | 100 | 100 |
| 144 | 100 | 100 | 100 |
| 145 | 100 | 100 | 100 |
| 146 | 100 | 100 | 100 |
| 147 | 100 | 100 | 100 |
| 148 | 100 | 100 | 100 |
| 149 | 100 | 100 | 100 |
| 150 | 100 | 100 | 100 |
| 151 | 100 | 100 | 100 |
| 152 | 100 | 100 | 100 |
| 153 | 100 | 100 | 100 |
| 154 | 100 | 100 | 100 |
| 155 | 100 | 100 | 100 |

TABLE II-continued

Biological Evaluations[1]

| Example No. | Mexican Bean Beetle | Southern Armyworm | Boll Weevil |
|---|---|---|---|
| 156 | 100 | 100 | 100 |
| 157 | 100 | 100 | 100 |
| 158 | 100 | 100 | 100 |
| 159 | 100 | 100 | 100 |
| 160 | 100 | 100 | 100 |
| 161 | 100 | 100 | 100 |
| 162 | 100 | 100 | 100 |
| 163 | 100 | 100 | 100 |
| 164 | 100 | 0 | 70 |
| 165 | 100 | 100 | 100 |
| 167 | 0 | 0 | 0 |
| 168 | 100 | 100 | 100 |
| 169 | 100 | 100 | 60 |
| 170 | 100 | 100 | 100 |
| 171 | 100 | 0 | 100 |
| 172 | 100 | 0 | 0 |
| 173 | 100 | 100 | 100 |
| 174 | 100 | 100 | 100 |
| 176 | 100 | 100 | 100 |
| 177 | 100 | 100 | 100 |
| 178 | 100 | 100 | 100 |
| 179 | 100 | 100 | 100 |
| 180 | 100 | 100 | 100 |
| 181 | 0 | 0 | 20 |
| 182 | 100 | 0 | 10 |
| 183 | 100 | 100 | 100 |
| 184 | 100 | 0 | 0 |
| 185 | 100 | 100 | 100 |
| 186 | 100 | 100 | 100 |
| 187 | 100 | 100 | 50 |
| 188 | 100 | 100 | 90 |
| 189 | 100 | 100 | 100 |
| 190 | 100 | 100 | 100 |
| 191 | 0 | 0 | 60 |
| 192 | 100 | 100 | 100 |
| 193 | 100 | 0 | 20 |
| 194 | 100 | 100 | 100 |
| 195 | 100 | 100 | 100 |
| 196 | 100 | 100 | 0 |
| 197 | 100 | 100 | 60 |
| 198 | 100 | 100 | 100 |
| 199 | 100 | 100 | 100 |
| 200 | 100 | 100 | 100 |
| 201 | 100 | 100 | 20 |
| 202 | 100 | 100 | 100 |
| 203 | 100 | 100 | 100 |
| 204 | 100 | 100 | 100 |
| 205 | 100 | 100 | 0 |
| 206 | 100 | 100 | 100 |
| 207 | 100 | 100 | 100 |
| 208 | 100 | 100 | 100 |
| 209 | 100 | 100 | 100 |
| 210 | 100 | 100 | 20 |
| 211 | 100 | 100 | 100 |
| 212 | 100 | 100 | 100 |
| 213 | 100 | 100 | 100 |
| 214 | 100 | 100 | 100 |
| 215 | 100 | 100 | 100 |
| 216 | 100 | 100 | 80 |
| 217 | 100 | 100 | 100 |
| 218 | 100 | 100 | 100 |
| 219 | 100 | 100 | 100 |
| 220 | 100 | 100 | 100 |
| 221 | 0 | 0 | 20 |
| 222 | 100 | 100 | 100 |
| 223 | 0 | 0 | 0 |
| 224 | 100 | 100 | 100 |
| 225 | 100 | 0 | 80 |
| 226 | 80 | 0 | 100 |
| 227 | 100 | 100 | 100 |
| 228 | 30 | 0 | 20 |
| 229 | 100 | 100 | 100 |
| 230 | 100 | 100 | 40 |
| 231 | 100 | 100 | 100 |
| 232 | 100 | 100 | 100 |
| 233 | 100 | 100 | 100 |
| 234 | 100 | 100 | 100 |
| 235 | 100 | 100 | 100 |
| 236 | 100 | 100 | 20 |
| 237 | 100 | 100 | 100 |
| 238 | 100 | 100 | 100 |
| 239 | 100 | 100 | 100 |
| 240 | 100 | 100 | 80 |
| 241 | 100 | 100 | 100 |
| 242 | 100 | 100 | 100 |
| 243 | 100 | 100 | 100 |
| 244 | 100 | 100 | 100 |
| 245 | 60 | 0 | 20 |
| 246 | 100 | 100 | 100 |
| 247 | 100 | 30 | 60 |
| 248 | 100 | 100 | 100 |
| 249 | 30 | 0 | 0 |
| 250 | 100 | 100 | 100 |
| 251 | 100 | 40 | 20 |
| 252 | 100 | 100 | 100 |
| 253 | 100 | 100 | 100 |
| 254 | 100 | 100 | 100 |
| 255 | 100 | 100 | 100 |
| 256 | 100 | 100 | 100 |
| 257 | 100 | 100 | 100 |
| 258 | 100 | 100 | 60 |
| 259 | 100 | 100 | 40 |
| 260 | 100 | 100 | 20 |
| 261 | 40 | 0 | 40 |
| 262 | 100 | 100 | 100 |
| 263 | 100 | 100 | 100 |
| 264 | 100 | 100 | 100 |
| 265 | 100 | 1100 | 100 |
| 266 | 100 | 100 | 0 |
| 267 | 100 | 40 | 0 |
| 268 | 100 | 100 | 80 |
| 269 | 100 | 100 | 100 |
| 270 | 100 | 60 | 0 |
| 271 | 100 | 100 | 100 |
| 272 | 100 | 100 | 100 |
| 273 | 40 | 0 | 0 |
| 274 | 100 | 100 | 100 |
| 275 | 100 | 0 | 0 |
| 276 | 100 | 100 | 100 |
| 277 | 100 | 100 | 0 |
| 278 | 100 | 100 | 100 |
| 279 | 100 | 100 | 100 |
| 280 | 100 | 100 | 100 |
| 281 | 100 | 100 | 60 |
| 282 | 100 | 100 | 80 |
| 283 | 100 | 100 | 100 |
| 284 | 100 | 100 | 100 |
| 285 | 50 | 0 | 20 |

[1]Percent Control 600 ppm after 96 hours.

TABLE III

Whole Plant Biological Evaluations

| Example No. | Mexican Bean Beetle | | Southern Armyworm | | Boll Weevil | |
|---|---|---|---|---|---|---|
| | 10 ppm | 2.5 ppm | 38 ppm | 10 ppm | 38 ppm | 10 ppm |
| 2 | 100 | 70 | 100 | 100 | 100 | 100 |
| 16 | 60 | 40 | 90 | 0 | 100 | 90 |
| 66 | 100 | 10 | 100 | 100 | 100 | 80 |
| 77 | 100 | 90 | —[a] | 100 | 100 | 100 |
| 84 | 90 | 80 | 100 | 90 | 90 | 20 |
| 92 | — | 100 | 100 | 20 | 100 | 90 |
| 105 | 100 | 100 | 100 | 90 | 100 | 100 |
| 114 | 100 | 100 | 100 | 80 | 100 | 100 |
| 123 | 100 | 80 | — | 70 | 100 | 100 |
| 124 | 100 | 100 | 100[b] | 100[b] | 100 | 100 |
| 141 | — | 100 | 100 | 100 | 100 | 100 |
| 143 | — | 100 | — | 100 | — | 100 |
| 149 | — | 100 | — | 100 | — | —[c] |
| 152 | — | 100 | 100 | 100 | 100 | 100 |

TABLE III-continued

| | Whole Plant Biological Evaluations | | | | | |
|---|---|---|---|---|---|---|
| | Test Insect | | | | | |
| | Mexican Bean Beetle | | Southern Armyworm | | Boll Weevil | |
| Example No. | 10 ppm | 2.5 ppm | 38 ppm | 10 ppm | 38 ppm | 10 ppm |
| 186 | — | 100 | — | 100 | 100 | 90 |

*Not tested at the stated concentration.
*The maximum concentration originally applied was 2.5 ppm and failed to elicit kill. The Southern Armyworm assay was repeated giving the results shown and again gave 0% kill at 2.5 ppm.
*The maximum concentration applied was 2.5 ppm and elicited 100% kill.

It should be understood that the instant specification and examples are set forth by way of illustration and not limitation, and that various modifications and changes may be made without departing from the spirit and scope of the present invention as defined by the appended claims.

I claim:
1. A compound of the formula

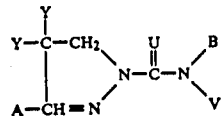

wherein
A is unsubstituted or substituted aryl;
B is unsubstituted or substituted aryl;
U is O, S or N—Q;
V is ($C_3$-$C_6$)cycloalkyl or $R^4$—Q;
Y is ($C_1$-$C_6$) straight or branched chain unsubstituted or substituted alkyl where the alkyl substituents are selected from Q, unsubstituted or substituted aryl, or a group having the formula

where X is N—$R^1$ or $CR^1R^2$;
Z is ($C_3$-$C_6$)cycloalkyl or $R^4$—Q provided that Z is not hydrogen when Y is alkyl or aryl and Z is not methyl when Y is methyl;
Q is hydrogen, halogen, cyano, nitro, —$OR^1$, —$R^4OR^1$, —$CO_2R^1$, —$OR^4OR^1$, —$CR^1R^2R^3$, —$CONR^1R^2$, —$NR^1R^2$, —$NR^1COR^2$, —$N(COR^1)COR^2$, —$CSR^1$, —$SR^1$, —$SOR^1$, —$SO_2R^1$, —$NR^1SOR^2$, —$R^4SR^1$, —$OR^4SR^1$, —$SR^4SR^1$, —$SNHSR^1$, —$SNHSO_2R^1$, —$CONHSR^1$, —$OCOR^1$, —$R^1$, —$C(=NR^1)R^2$, —$COR^1$, —$N_3$, —$OSO_2R^1$, —$NR^1SO_2R^2$, —$NR^1CSR^2$, alkenyl (—$CR^1=CR^2R^3$), alkynyl (—C≡$CR^1$), unsubstituted or substituted aryl, pyrrolidin-1-yl, piperidin-1-yl or morpholin-1-yl;
$R^1$, $R^2$ and $R^3$ are, independently, hydrogen, halogen, cyano, nitro, hydroxy, an alkoxy group (—OR) having up to four carbon atoms, an aryloxy group, an amino group (—$NH_2$), and alkylamino group (—NHR) having up to six carbon atoms, a dialkylamino group (—$NR_2$) having, independently, up to six carbon atoms in each alkyl moiety, alkylideneamino group (—N=$CR_2$) having, independently, up to six carbon atoms in each alkyl moiety, a carboxy group (—$CO_2H$), a carbalkoxy group (—$CO_2R$) having up to six carbon atoms in the alkyl moiety, an alkylcarbonyl group (—COR) having up to six carbon atoms in the alkyl moiety, a formyl group (—CHO), an alkanoyloxy group (—OCOR) having up to six carbon atoms in the alkyl moiety, a formate group (—OCHO), a carboxamido group (—$CONH_2$), an N-alkylcarboxamido group (—CONHR) having up to six carbon atoms in the alkyl moiety, an N,N-dialkylcarboxamido group (—$CONR_2$) having, independently, up to six carbon atoms in each alkyl moiety, a carbamoyloxy group (—$OCONH_2$), an N-alkylcarbamoyloxy group (—OCONHR) having up to six carbon atoms in the alkyl moiety, an N,N-dialkylcarbamoyloxy group (—$OCONR_2$) having, independently, up to six carbon atoms in each alkyl moiety, a sulfhydril group (—SH), an alkylsulfinyl group (—SOR) having up to six carbon atoms, an alkylsulfonyl group (—$SO_2R$) having up to six carbon atoms, an alkylsulfonato group (—$OSO_2R$) having up to six carbon atoms, an alkylthio group (—SR) having up to six carbon atoms, a sulfonamido group (—$SO_2NH_2$), an N-alkysulfonamido group (—$SO_2NHR$), having up to six carbon atoms, an N,N-dialkylsulfonamido group (—$SO_2NR_2$) having, independently, up to six carbon atoms in each alkyl moiety, an acylamino group (—NHCOR) having up to six carbon atoms in the alkyl moiety, an N-alkyl-N-acylamino group (—NRCOR) having independently, up to six carbon atoms in each alkyl moiety, an alkylsulfonamido group (—$NHSO_2R$) having up to six carbon atoms, an N-alkyl-N-alkylsulfonylamino group (—$NRSO_2R$) having, independently, up to six carbon atoms in each alkyl moiety, a thioformyl group (—CHS), an alkylthiocarbonyl group (—CSR) having up to six carbon atoms in the alkyl moiety, a thioformamido group (—NHCHS), an N-alkyl-N-thioformylamino group (—NRCHS) having up to six carbon atoms in the alkyl moiety, a thioacylamino group (—NHCSR) having up to six carbon atoms in the alkyl moiety, an N-alkyl-N-thioacylamino group (—NRCSR) having independently, up to six carbon atoms in each alkyl moiety, a thioureido group (—$NHCSNH_2$), an alkylsulfinamido group (—NRSOR) having, independently, up to six carbon atoms, an N-alkyl-N-alkylsulfinylamino group (—NHSOR) having, independently, up to six carbon atoms in each alkyl moiety, an N,N-diacylamino group (—N(COR)COR) having, independently, up to six carbon atoms in each alkyl moiety, an unsubstituted or substituted straight or branched chain ($C_1$-$C_6$)alkyl, ($C_2$-$C_6$)alkenyl, ($C_2$-$C_6$)alkynyl, ($C_3$-$C_6$)cycloalkyl or aryl where the substituent on the alkyl, alkenyl or alkynyl moiety can be one or more of the same or different halogen, cyano, nitro, hydroxy, and alkoxy group (—OR) having up to four carbon atoms, an aryloxy group, an amino group (—$NH_2$), an alkylamino group (—NHR) having up to six carbon atoms, a dialkylamino group (—$NR_2$) having, independently, up to six carbon atoms in each alkyl moiety, alkylideneamino group (—N=$CR_2$) having, independently, up to six carbon atoms in each alkyl moiety, a carboxy group (—$CO_2H$), a carbalkoxy group (—$CO_2R$) having up to six carbon atoms in the alkyl moiety, an alkylcarbonyl group (—COR) having up to six carbon atoms in the alkyl moiety, a formyl group (—CHO), an alkanoyloxy group (—OCOR) having up to six carbon atoms in the alkyl moiety, a formate group (—OCHO), a carboxamido group (—CONH₂), an N-alkylcarboxamido group (—CONHR) having up to six carbon atoms in the alkyl moiety, an N,N-dialkylcarboxamido group (—CONR₂) having, independently, up to six carbon atoms in each alkyl moiety, a carbamoyloxy group (—OCONH₂), an N-alkylcarbamoyloxy group (—OCONHR) having up to six carbon atoms in the alkyl moiety, an N,N-dialkylcarbamoyloxy group (—OCONR₂) having, independently, up to six carbon atoms in each alkyl moiety, a sulhydril group (—SH), an alkylsulfinyl group (—SOR) having up to six carbon atoms, an alkylsulfonyl group (—SO₂R) having up to six carbon atoms, an alkylsulfonato group (—OSO₂R) having up to six carbon atoms, an alkylthio group (—SR) having up to six carbon atoms, a sulfonamido group (—SO₂NH₂), an N-alkylsulfonamido group (—SO₂NHR), having up to six carbon atoms, an N,N-dialkylsulfonamido group (—SO₂NR₂) having, independently, up to six carbon atoms in each alkyl moiety, an acylamino group (—NHCOR) having up to six carbon atoms in the alkyl moiety, an N-alkyl-N-acylamino group (—NRCOR) having, independently, up to six carbon atoms in each alkyl moiety, an alkylsulfonamido group (—NHSO₂R) having up to six carbon atoms an N-alkyl-N-alkylsulfonylamino group (—NRSO₂R) having, independently, up to six carbon atoms in each alkyl moiety, a thioformyl group (—CHS), an alkylthiocarbonyl group (—CSR) having up to six carbon atoms in the alkyl moiety, a thioformamido group (—NHCHS), an N-alkyl-N-thioformylamino group (—NRCHS) having up to six carbon atoms in the alkyl moiety, a thioacylamino group (—NHCSR) having up to six carbon atoms in the alkyl moiety, an N-alkyl-N-thioacylamino group (—NRCSR) having, independently, up to six carbon atoms in each alkyl moiety, a thioureido group (—NHCSNH₂), an alkylsulfinamido group (—NHSOR) having up to six carbon atoms, an N-alkyl-N-alkyl-sulfinylamino group (—NRSOR) having, independently, up to six carbon atoms in each alkyl moiety, an N,N-diacylamino group (—N(COR)COR) having, independently, up to six carbon atoms in each alkyl moiety, or an unsubstituted or substituted aryl group, where R is an alkyl group having the stated number of carbon atoms;

$R^4$ is

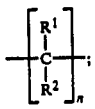

G is ($C_3$–$C_6$)cycloalkyl or $R^4$—Q; and
n is an integer from 0 to 10; or
an agronomically acceptable salt thereof;
wherein unsubstituted or substituted aryl is phenyl, optionally substituted with 1 to 5 substituents independently chosen from W; methylenedioxyphenyl; naphthyl, optionally substituted with 1 to 7 substituents independently chosen from W; a pyrryl; furyl; thienyl; imidazolyl; oxazolyl; thiazolyl; pyrazolyl; pyridyl or pyrimidyl optionally substituted with 1 to 4 substituents independently chosen from W; where W is halogen, cyano, nitro, $R^1$, $CO_2R^1$, $CONR^1R^2$, $CR^1=CR^2R^3$, $C≡CR^1$, $SR^1$, $OR^1$, $NR^1R^2$, $SOR^1$, $SO_2R^1$, $OSO_2R^1$, $NR^1COR^2$, $SF_5$, $CF_3$, $OCF_3$, $OCF_2H$, $SCF_3$, $OCF_2Br$, $SCF_2Br$, $SCF_2Cl$, $SCF_2H$, $NR^1SO_2R^2$ or $N(COR^1)COR^2$.

2. The compound according to claim 1 wherein A, B, U, V, Q, R, $R^1$, $R^2$, $R^3$, $R^4$, G and n are as defined in claim 1 and
Y is a group having the formula

where X is N—$R^1$ or $CR^1R^2$; and
Z is ($C_3$–$C_6$)cycloalkyl, or $R^4$—Q; or
an agronomically acceptable salt thereof.

3. The compound according to claim 2 wherein R, $R^1$, $R^2$, $R^3$ and $R^4$, G, Q and n are as defined in claim 2 and
A is unsubstituted or substituted phenyl;
B is unsubstituted or substituted phenyl;
U is O or S;
V is ($C_3$–$C_6$)cycloalkyl or $R^4$—Q;
Y is a group having the formula

where X is $NR^1$ or $CR^1R^2$ and
Z is ($C_3$–$C_6$)cycloalkyl, or $R^4$—Q; or
an agronomically acceptable salt thereof.

4. The compound according to claim 3 wherein A, U, Y, Z, Q, R, $R^1$, $R^2$, $R^3$, $R^4$, G and n are as defined in claim 3 and
B is substituted phenyl; and
V is $R^4$—Q; or
an agronomically acceptable salt thereof.

5. The compound according to claim 4 wherein U, Y, Q, R, $R^1$, $R^2$, $R^3$, $R^4$, G and n are as defined in claim 4 and
A is unsubstituted or monosubstituted or disubstituted phenyl;
B is monosubstituted or disubstituted phenyl;
V is $R^413$ Q; and
Z is $R^4$—Q; or
an agronomically acceptable salt thereof.

6. The compound according to claim 1 wherein A, B, U, V, Q, R, $R^1$, $R^2$, $R^3$, $R^4$ and n are as defined in claim 1 and
Y is lower ($C_1$–$C_6$) straight or branched chain unsubstituted or substituted alkyl or unsubstituted or substituted aryl; and
Z is ($C_3$–$C_6$)cycloalkyl, or $R^4$—Q provided that Z is not hydrogen and Z is not methyl when Y is methyl; or
an agronomically acceptable salt thereof.

7. The compound according to claim 6 wherein V, Y, Z, Q, R, $R^1$, $R^2$, $R^3$, $R^4$ and n are as defined in claim 6 and
A is unsubstituted or substituted phenyl;
B is unsubstituted or substituted phenyl; and
U is O or S; or
an agronomically acceptable salt thereof.

8. The compound according to claim 7 wherein U, Y, Q, R, $R^1$, $R^2$, $R^3$, $R^4$ and n are as defined in claim 7 and A is substituted phenyl;
B is substituted phenyl;
V is $R^4$—Q; and
Z is $R^4$—Q, provided that Z is not hydrogen and Z is not methyl when Y is methyl; or
an agronomically acceptable salt thereof.

9. The compound according to claim 8 wherein U, Y, Z, Q, R, $R^1$, $R^2$, $R^3$, $R^4$ and n are as defined in claim 8 and
A is monosubstituted or disubstituted phenyl;
B is monosubstituted or disubstituted phenyl; and
V is $R^4$—Q; or
an agronomically acceptable salt thereof.

10. The compound according to claim 9 wherein V, Y, Q, R, $R^1$, $R^2$, $R^3$, $R^4$ and n are as defined in claim 8 and
A is monosubstituted phenyl;
B is monosubstituted phenyl;
U is O; and
Z is $R^4$—Q, provided that Z is not hydrogen and Z is not methyl when Y is methyl; or
an agronomically acceptable salt thereof.

11. The compound according to claim 10 wherein
A is monosubstituted phenyl where the substituent is fluoro, chloro, bromo, trifluoromethyl, trifluoromethoxy, difluoromethoxy or methyl;
B is monosubstituted phenyl where the substituent is fluoro, chloro, bromo, trifluoromethyl, trifluoromethoxy, difluoromethoxy, carbomethoxy, carboethoxy, carboisopropoxy, methylthio or methylsulfonyl;
U is O;
V is hydrogen, ($C_1$-$C_6$) straight or branched chain unsubstituted or substituted alkyl, ($C_1$-$C_6$)alkoxy, ($C_1$-$C_6$)alkylthio, unsubstituted or substituted arylthio, $COR^1$ or $CSR^1$ where $R^1$ is as in claim 10, or cyano;
Y is ($C_1$-$C_6$) straight or branched chain unsubstituted or substituted alkyl, or unsubstituted or substituted phenyl, and
Z is ($C_1$-$C_4$)alkyl, or unsubstituted or substituted phenyl, provided that Z is not methyl when Y is methyl.

12. The compound according to claim 11 wherein
A is 4-chlorophenyl, 4-bromophenyl, 4-trifluoromethylphenyl, 4-trifluoromethoxyphenyl or 4-difluoromethoxyphenyl;
B is 4-chlorophenyl, 4-bromophenyl, 4-carbomethoxyphenyl, 4-carboethoxyphenyl, 4-carboisopropoxyphenyl, 4-difluoromethoxyphenyl, 4-trifluoromethoxyphenyl, 4-trifluoromethylphenyl, 4-methylthiophenyl or 4-methylsulfonylphenyl;
U is O;
V is hydrogen, methyl, methysulfenyl, 2-nitrophenylsulfenyl, carbomethoxy, acetyl, trifluoroacetyl, formyl or methoxalyl;
Y is ethyl, n-propyl, n-butyl, 3-chloropropyl, 4-bromopropyl or phenyl; and
Z is methyl, ethyl, n-propyl, n-butyl or phenyl.

13. The compound according to claim 12 wherein
A is 4-chlorophenyl;
B is 4-chlorophenyl;
U is O;
V is hydrogen;
Y is phenyl; and
Z is methyl.

14. The compound according to claim 12 wherein
A is 4-chlorophenyl;
B is 4-chlorophenyl;
U is O;
V is hydrogen;
Y is n-butyl; and
Z is methyl.

15. The compound according to claim 12 wherein
A is 4-chlorophenyl;
B is 4-chlorophenyl;
U is O;
V is hydrogen;
Y is 3-chloropropyl; and
Z is methyl.

16. The compound according to claim 5 wherein V, Z, Q, R, $R^1$, $R^2$, $R^3$, G and n are as defined in claim 5 and
A is monosubstituted phenyl;
B is monosubstituted phenyl;
U is O; and
Y is $$-\overset{\overset{CR^1R^2}{\|}}{C}-G;$$

an agronomically acceptable salt thereof.

17. The compound according to claim 16 wherein
A is monosubstituted phenyl where the substituent is fluoro, chloro, bromo, methoxy, ethoxy, n-propoxy, isopropoxy, trifluoromethyl, trifluoromethoxy, difluoromethoxy or methyl;
B is monosubstituted phenyl where the substituent is fluoro, chloro, bromo, trifluoromethyl, trifluoromethoxy, difluoromethoxy, carbomethoxy, carboethoxy, carboisopropoxy, methylthio or methylsulfonyl;
U is O;
V is hydrogen, ($C_1$-$C_6$) straight or branched chain unsubstituted or substituted alkyl, ($C_1$-$C_6$)alkoxy, ($C_1$-$C_6$)alkylthio, as unsubstituted or substituted arylthio, cyano, —$COR^1$ or —$CSR^1$ where $R^1$ is as defined in claim 1;
Y is $$-\overset{\overset{CR^4R^5}{\|}}{C}-G;$$

Z is hydrogen, ($C_1$-$C_4$)alkyl or unsubstituted or substituted phenyl;
G is hydrogen, hydroxy, ($C_1$-$C_4$)alkyl, ($C_1$-$C_4$)alkoxy, ($C_1$-$C_4$)alkylamino, dialkylamino having independently one to four carbon atoms in each alkyl moiety, or phenyl; and
$R^3$ and $R^4$ are independently hydrogen, halogen, —CN, —$NO_2$, ($C_1$-$C_4$)alkyl group, ($C_1$-$C_4$)carbalkoxy group (—$CO_2R$), ($C_1$-$C_4$)alkylcarbonyl group (—COR), trifluoromethyl group, ($C_1$-$C_4$)alkylthio group (—SR), phenylthio group, carboxamido group (—$CONH_2$), ($C_1$-$C_4$) N-alkylcarboxamido group (—CONHR), or ($C_1$-$C_4$) N,N-dialkylcarboxamido group (—$CONR_2$) where each alkyl group independently contains the stated number of carbon atoms and R is an alkyl group containing up to six carbon atoms.

18. The compound according to claim 17 wherein
A is 4-chlorophenyl, 4-bromophenyl, 4-methoxyphenyl, 4-ethoxyphenyl, 4-n-propoxyphenyl, 4-isopropoxyphenyl, 4-trifluoromethylphenyl, B is 4-chlorophenyl, 4-bromophenyl, 4-carbomethoxyphenyl, 4-carboethoxyphenyl, 4-carboisopropoxyphenyl, 4-difluoromethoxyphenyl, 4-trifluoromethylphenyl, 4-methylthiophenyl or 4-methylsufonylphenyl;
U is O;
V is hydrogen, methyl, methylsulfenyl, 2-nitrophenylsulfenyl, carbomethoxy, acetyl, trifluoroacetyl, formyl or methoxalyl;
Y is

Z is hydrogen, methyl, phenyl, 4-chlorophenyl, 4-trifluoromethylphenyl, 4-trifluoromethoxyphenyl, 4-trifluorothiomethoxyphenyl, 4-difluoromethoxyphenyl or 4-difluorobromothiomethoxyphenyl;
G is hydrogen, hydroxy, methyl, ethyl, methoxy, ethoxy, dimethylamino or phenyl; and
$R^1$ and $R^2$ are chloro or bromo.

19. The compound according to claim 18 wherein
A is 4-chlorophenyl;
B is 4-trifluoromethyl phenyl
U is O;
V is hydrogen
Y is

Z is methyl;
G is hydrogen; and
$R^1$ and $R^2$ are chloro.

20. The compound according to claim 18 wherein
A is 4-chlorophenyl;
B is 4-trifluoromethoxyphenyl;
U is O;
V is hydrogen
Y is

Z is methyl;
G is hydrogen; and
$R^1$ and $R^2$ are chloro.

21. The compound according to claim 18 wherein
A is 4-n-propoxyphenyl;
B is 4-trifluoromethylphenyl;
U is O;
V is hydrogen;
Y is

Z is methyl;
G is hydrogen; and
$R^1$ and $R^2$ are chloro.

22. The compound according to claim 18 wherein
A is 4-n-propoxyphenyl;
B is 4-trifluoromethoxyphenyl;
U is O;
V is hydrogen;
Y is

Z is methyl;
G is hydrogen; and
$R^1$ and $R^2$ are chloro.

23. The compound according to claim 18 wherein
A is 4-isopropoxyphenyl;
B is 4-trifluoromethylphenyl;
U is O;
V is hydrogen;
Y is

Z is methyl;
G is hydrogen; and
$R^1$ and $R^2$ are chloro.

24. The compound according to claim 18 wherein
A is 4-isopropoxyphenyl;
B is 4-trifluoromethoxyphenyl;
U is O;
V
Y is

Z is methyl;
G is hydrogen; and
$R^1$ and $R^2$ are chloro.

25. The compound according to claim 18 wherein
A is 4-methoxyphenyl;
B is 4-trifluoromethylphenyl;
U is O;
V
Y is

Z is methyl;
G is hydrogen; and
$R^1$ and $R^2$ are chloro.

26. The compound according to claim 18 wherein
A is ethoxyphenyl;
B is 4-trifluoromethylphenyl;
U is O;
V
Y is

Z is methyl;
G is hydrogen; and
$R^1$ and $R^2$ are chloro.

27. A compound of the formula

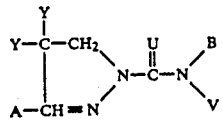

wherein

A is an alkoxy substituted phenyl having up to six carbon atoms in the alkoxy substituent;

B is unsubstituted or substituted aryl;

U is O, S or N—Q;

V is $(C_3-C_6)$cycloalkyl or $R^4$—Q;

Y is $(C_1-C_6)$ straight or branched chain unsubstituted or substituted alkyl where the alkyl substituents are selected from Q, unsubstituted or substituted aryl, or a group having the formula

where X is N—$R^1$ or $CR^1R^2$;

Z is $(C_3-C_6)$cycloalkyl or $R^4$—Q provided that Z is not hydrogen when Y is alkyl or aryl and Z is not methyl when Y is methyl;

Q is hydrogen, halogen, cyano, nitro, —$OR^1$, —$R^4OR^1$, —$COR^1$, —$OR^4OR^1$, —$CR^1R^2R^3$, —$CONR^1R^2$, —$NR^1R^2$, —$NR^1COR^2$, —$N(COR^1)COR^2$, —$CSR^1$, —$SR^1$, —$SOR^1$, —$SO_2R^1$, —$NR^1SOR^2$, —$R^4SR^1$, —$OR^4SR^1$, —$SR^4SR^1$, —$SNHSR^1$, —$SNHSO_2R^1$, —$CONHSR^1$, —O-$COR^1$, —$R^1$, —$C(=NR^1)R^2$, —$COR^1$, —$N_3$, —O-$SO_2R^1$, —$NR^1SO_2R^2$, —$NR^1CSR^2$, alkenyl (—$CR^1=CR^2R^3$), alkynyl (—C≡$CR^1$), unsubstituted or substituted aryl, pyrrolidin-1-yl, piperidin-1-yl or morpholin-1-yl;

$R^1$, $R^2$ and $R^3$ are, independently, hydrogen, halogen, cyano, nitro, hydroxy, an alkoxy group (—OR) having up to four carbon atoms, an aryloxy group, an amino group (—$NH_2$), an alkylamino group (—NHR) having up to six carbon atoms, a dialkylamino group (—$NR_2$) having, independently, up to six carbon atoms in each alkyl moiety, alkylideneamino group (—N=$CR_2$) having, independently, up to six carbon atoms in each alkyl moiety, a carboxy group (—$CO_2H$), a carbalkoxy group (—$CO_2R$) having up to six carbon atoms in the alkyl moiety, an alkylcarbonyl group (—COR) having up to six carbon atoms in the alkyl moiety, a formyl group (—CHO), an alkanoyloxy group (—OCOR) having up to six carbon atoms in the alkyl moiety, a formate group (—OCHO), a carboxamide group (—$CONH_2$), an N-alkylcarboxamido group (—CONHR) having up to six carbon atoms in the alkyl moiety, an N,N-dialkylcarboxamido group (—$CONR_2$) having, independently, up to six carbon atoms in each alkyl moiety, a carbamoyloxy group (—$OCONH_2$), an N-alkylcarbamoyloxy group (—OCONHR) having up to six carbon atoms in the alkyl moiety, an N,N-dialkylcarbamoyloxy group (—$OCONR_2$) having, independently, up to six carbon atoms in each alkyl moiety, a sulfhydril group (—SH), an alkylsulfinyl group (—SOR) having up to six carbon atoms, an alkylsulfonyl group (—$SO_2R$) having up to six carbon atoms, an alkylsulfonato group (—$OSO_2R$) having up to six carbon atoms, an alkylthio group (—SR) having up to six carbon atoms, a sulfonamido group (—$SO_2NH_2$), an N-alkylsulfonamido group (—$SO_2NHR$), having up to six carbon atoms, an N,N-dialkylsulfonamido group (—$SO_2NR_2$) having, independently, up to six carbon atoms in each alkyl moiety, an acylamino group (—NHCOR) having up to six carbon atoms in the alkyl moiety, an N-alkyl-N-acylamino group (—NRCOR) having independently, up to six carbon atoms in each alkyl moiety, an alkylsulfonamido group (—$NHSO_2R$) having up to six carbon atoms, an N-alkyl-N-alkylsulfonylamino group (—$NRSO_2R$) having, independently, up to six carbon atoms in each alkyl moiety, a thioformyl group (—CHS), an alkylthiocarbonyl group (—CSR) having up to six carbon atoms in the alkyl moiety, a thiofromamido group (—NHCHS), an N-alkyl-N-thioformylamino group (—NRCHS) having up to six carbon atoms in the alkyl moiety, a thiochylamino group (—NHCSR) having up to six carbon atoms in the alkyl moiety, an N-alkyl-N-thioacylamino group (—NRCSR) having independently, up to six carbon atoms in each alkyl moiety, a thioureido group (—$NHCSNH_2$), an alkylsulfinamido group (—NHSOR) having up to six carbon atoms, an N-alkyl-N-alkylsulfinylamino group (—NRSOR) having, independently, up to six carbon atoms in each alkyl moiety, an N,N-diacylamino group (—N(COR)COR) having, independently, up to six carbon atoms in each alkyl moiety, an unsubstituted or substituted straight or branched chain $(C_1-C_6)$alkyl, $(C_2-C_6)$alkenyl, $(C_2-C_6)$alkynyl, $(C_3-C_6)$cycloalkyl or aryl where the substituent on the alkyl, alkenyl or alkynyl moiety can be one or more of the same or different halogen, cyano, nitro, hydroxy, an alkoxy group (—OR) having up to four carbon atoms, an aryloxy group, an amino group (—$NH_2$), an alkylamino group (—NHR) having up to six carbon atoms, a dialkylamino group (—$NR_2$) having, independently, up to six carbon atoms in each alkyl moiety, alkylideneamino group (—N=$CR_2$) having, independently, up to six carbon atoms in each alkyl moiety, a carboxy group (—$CO_2H$), a carbalkoxy group (—$CO_2R$) having up to six carbon atoms in the alkyl moiety, an alkylcarbonyl group (—COR) having up to six carbon atoms in the alkyl moiety, a formyl group (—CHO), an alkanoyloxy group (—OCOR) having up to six carbon atoms in the alkyl moiety, a formate group (—OCHO), a carboxamide group (—$CONH_2$), an N-alkylcarboxamido group (—CONHR) having up to six carbon atoms in the alkyl moiety, an N,N-dialkylcarboxamido group (—$CONR_2$) having independently, up to six carbon atoms in each alkyl moiety, a carbamoyloxy group (—$OCONH_2$), an N-alkylcarbamoyloxy group (—OCONHR) having up to six carbon atoms in the alkyl moiety, an N,N-dialkylcarbamoyloxy group (—$OCONR_2$) having, independently, up to six carbon atoms in each alkyl moiety, a sulhydril group (—SH), an alkylsulfinyl group (—SOR) having up to six carbon atoms, an alkylsulfonyl group (—$SO_2R$) having up to six carbon atoms, an alkylsulfonato group (—$OSO_2R$) having up to six carbon atoms, an alkylthio group (—SR) having up to six carbon atoms, a sulfonamido group (—$SO_2NH_2$), an N-alkylsulfonamido group (—SO$_2$NHR), having up to six carbon atoms, an N,N-dialkylsulfonamido group (—SO$_2$NR$_2$) having, independently, up to six carbon atoms in each alkyl moiety, an acylamino group (—NHCOR) having up to six carbon atoms in the alkyl moiety, an N-alkyl-N-acylamino group (—NRCOR) having, independently, up to six carbon atoms in each alkyl moiety, an alkylsulfonamido group (—NHSO$_2$R) having up to six carbon atoms, an N-alkyl-N-alkylsulfonylamino group (—NRSO$_2$R) having, independently, up to six carbon atoms in each alkyl moiety, a thioformyl group (—CHS), an alkylthiocarbonyl group (—CSR) having up to six carbon atoms in the alkyl moiety, a thioformamido group (—NHCHS), an N-alkyl-N-thioformylamino group (—NRCHS) having up to six carbon atoms in the alkyl moiety, a thioacylamino group (—NHCSR) having up to six carbon atoms in the alkyl moiety, an N-alkyl-N-thioacylamino group (NRCSR) having, independently, up to six carbon atoms in each alkyl moiety, a thioureido group (—NHCSNH$_2$), an alkylsulfinamido group (—NHSOR) having up to six carbon atoms, an N-alkyl-N-alkylsulfinylamino group (—NRSOR) having, independently, up to six carbon atoms in each alkyl moiety, an N,N-diacylamino group (—N(COR)COR) having, independently, up to six carbon atoms in each alkyl moiety, or an unsubstituted or substituted aryl group, where R is an alkyl group having the stated number of carbon atoms;

R$^4$ is

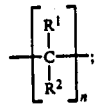

G is (C$_3$–C$_6$)cycloalkyl or R$^4$—Q; and n is an integer from 0 to 10; or an agronomically acceptable salt thereof;

wherein unsubstituted or substituted aryl is phenyl, optionally substituted with 1 to 5 substituents independently chose from W; methylenedioxyphenyl; naphthyl, optionally substituted with 1 to 7 substituents independently chosen from W; a pyrryl; furyl; thienyl; imidazolyl; oxazolyl; thiazolyl; pyrazolyl; pyridyl or pyrimidyl optionally substituted with 1 to 4 substituents independently chosen from W; where W is halogen, cyano, nitro, R$^1$, CO$_2$R$^1$, CONR$^1$R$^2$, CR$^1$=CR$^2$R$^3$, C≡CR$^1$, SR$^1$, OR$^1$, NR$^1$R$^2$, SOR$^1$, SO$_2$R$^1$, OSO$_2$R$^1$, NR$^1$COR$^2$, SF$_5$, CF$_3$, OCF$_3$, OCF$_2$H, SCF$_3$, OCF$_2$Br, SCF$_2$Br, SCF$_2$Cl, SCF$_2$H, NR$^1$SO$_2$R$^2$ or N(COR$^1$)COR$^2$.

28. A compound of the formula

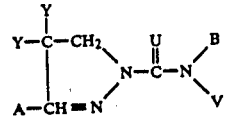

wherein

A is unsubstituted or substituted aryl;
B is unsubstituted or substituted aryl;

U is O, S or N—Q;

V is R$^4$–R$^5$ where R$^5$ is alkenyl, alkynyl or alkylideneamino each having up to six carbon atoms;

Y is (C$_1$–C$_6$) straight or branched chain unsubstituted or substituted alkyl where the alkyl substituents are selected from Q, unsubstituted or substituted aryl Z is (C$_3$–C$_6$)cycloalkyl or R$^4$—Q provided that Z is not hydrogen when Y is alkyl or aryl and Z is not methyl when Y is methyl;

Q is hydrogen, halogen, cyano, nitro, —OR$^1$, —R$^4$OR$^1$, —CO$_2$R$^1$, —OR$^4$OR$^1$, —CR$^1$R$^2$R$^3$, —CONR$^1$R$^2$, —NR$^1$R$^2$, —NR$^1$COR$^2$, —N(COR$^1$)COR$^2$, —CSR$^1$, —SR$^1$, —SOR$^1$, —SO$_2$R$^1$, —SO$_2$R$^1$, —NR$^1$SOR$^2$, —R$^4$SR$^1$, —OR$^4$SR$^1$, —SR$^4$SR$^1$, —SNHSR$^1$, —SNHSO$_2$R$^1$, —CONHSR$^1$, —OCOR$^1$, —R$^1$, —C(=NR$^1$)R$^2$, —COR$^1$, —N$_3$, —OSO$_2$R$^1$, —NR$^1$SO$_2$R$^2$, —NR$^1$CSR$^2$, alkenyl (—CR$^1$=CR$^2$R$^3$), alkynyl (—C≡CR$^1$), unsubstituted or substituted aryl, pyrrolidin-1-yl, piperidin-1-yl or morpholin-1-yl;

R$^1$, R$^2$ and R$^3$ are, independently, hydrogen, halogen, cyano, nitro, hydroxy, an alkoxy group (—OR) having up to four carbon atoms, an aryloxy group, an amino group (—NH$_2$), an alkylamino group (—NHR) having up to six carbon atoms, a dialkylamino group (—NR$_2$) having, independently, up to six carbon atoms in each alkyl moiety, alkylideneamino group (—N=CR$_2$) having, independently, up to six carbon atoms in each alkyl moiety, a carboxy group (—CO$_2$H), a carbalkoxy group (—CO$_2$R) having up to six carbon atoms in the alkyl moiety, an alkylcarbonyl group (—COR) having up to six carbon atoms in the alkyl moiety, a formyl group (—CHO), an alkanoyloxy group (—OCOR) having up to six carbon atoms in the alkyl moiety, a formate group (—OCHO), a carboxamido group (—CONH$_2$), an N-alkylcarboxamido group (—CONHR) having up to six carbon atoms in the alkyl moiety, an N,N-dialkylcarboxamido group (—CONR$_2$) having, independently, up to six carbon atoms in each alkyl moiety, a carbamoyloxy group (—OCONH$_2$), an N-alkylcarbamoyloxy group (—OCONHR) having up to six carbon atoms in the alkyl moiety, an N,N-dialkylcarbamoyloxy group (—OCONR$_2$) having, independently, up to six carbon atoms in each alkyl moiety, a sulfhydril group (—SH), an alkylsulfinyl group (—SOR) having up to six carbon atoms, an alkylsulfonyl group (—SO$_2$R) having up to six carbon atoms, an alkylsulfonato group (—OSO$_2$R) having up to six carbon atoms, an alkylthio group (—SR) having up to six carbon atoms, a sulfonamido group (—SO$_2$NH$_2$), an N-alkylsulfonamido group (—SO$_2$NHR), having up to six carbon atoms, an N,N-dialkylsulfonamido group (—SO$_2$NR$_2$) having, independently, up to six carbon atoms in each alkyl moiety, an acylamino group (—NHCOR) having up to six carbon atoms in the alkyl moiety, an N-alkyl-N-acylamino group (—NRCOR) having independently, up to six carbon atoms in each alkyl moiety, an alkylsulfonamido group (—NHSO$_2$R) having up to six carbon atoms, an N-alkyl-N-alkylsulfonylamino group (—NRSO$_2$R) having, independently, up to six carbon atoms in each alkyl moiety, a thioformyl group (—CHS), an alkylthiocarbonyl group (—CSR) having up to six carbon atoms in the alkyl moiety, a thioformamido group (—NHCHS), an N-alkyl- N-thioformylamino group (—NRCHS) having up to six carbon atoms in the alkyl moiety, a thioacylamino group (—NHCSR) having up to six carbon atoms in the alkyl moiety, an N-alkyl-N-thioacylamino group (—NRCSR) having independently, up to six carbon atoms in each alkyl moiety, a thioureido group (—NHCSNH$_2$), an alkylsulfinamido group (—NHSOR) having up to six carbon atoms, an N-alkyl-N-alkylsulfinylamino group (—NRSOR) having, independently, up to six carbon atoms in each alkyl moiety, an N,N-diacylamino group (—N(COR)COR) having, independently, up to six carbon atoms in each alkyl moiety, an unsubstituted or substituted straight or branched chain (C$_1$–C$_6$)alkyl, (C$_2$–C$_6$)alkenyl, (C$_2$–C$_6$)-alkynyl, (C$_3$–C$_6$)cycloalkyl or aryl where the substituent on the alkyl, alkenyl or alkynyl moiety can be one or more of the same or different halogen, cyano, nitro, hydroxy, an alkoxy group (—OR) having up to four carbon atoms, an aryloxy group, an amino group (—NH$_2$), an alkylamino group (—NHR) having up to six carbon atoms, a dialkylamino group (—NR$_2$) having, independently, up to six carbon atoms in each alkyl moiety, alkylideneamino group (—N═CR$_2$) having, independently, up to six carbon atoms in each alkyl moiety, a carboxy group (—CO$_2$H), a carbalkoxy group (—CO$_2$R) having up to six carbon atoms in the alkyl moiety, an alkylcarbonyl group (—COR) having up to six carbon atoms in the alkyl moiety, a formyl group (—CHO), an alkanoyloxy group (—OCOR) having up to six carbon atoms in the alkyl moiety, a formate group (—OCHO), a carboxamido group (—CONH$_2$), an N-alkylcarboxamido group (—CONHR) having up to six carbon atoms in the alkyl moiety, an N,N-dialkylcarboxamido group (—CONR$_2$) having independently, up to six carbon atoms in each alkyl moiety, a carbamoyloxy group (—OCONH$_2$), an N-alkylcarbamoyloxy group (—OCONHR) having up to six carbon atoms in the alkyl moiety, an N,N-dialkylcarbamoyloxy group (—OXONR$_2$) having, independently, up to six carbon atoms in each alkyl moiety, a sulhydril group (—SH), an alkylsulfinyl group (—SOR) having up to six carbon atoms, an alkylsulfonyl group (—SO$_2$R) having up to six carbon atoms, an alkylsulfonato group (—OSO$_2$R) having up to six carbon atoms, an alkylthio group (—SR) having up to six carbon atoms, a sulfonamido group (—SO$_2$NH$_2$), an N-alkylsulfonamido group (—SO$_2$NHR), having up to six carbon atoms, an N,N-dialkylsulfonamido group (—SO$_2$NR$_2$) having, independently, up to six carbon atoms in each alkyl moiety, an acylamino group (—NHCOR) having up to six carbon atoms in the alkyl moiety, an N-alkyl-N-acylamino group (—NRCOR) having, independently, up to six carbon atoms in each alkyl moiety, an alkylsulfonamido group (—NHSO$_2$R) having up to six carbon atoms, an N-alkyl-N-alkylsulfonylamino group (—NRSO$_2$R) having, independently, up to six carbon atoms in each alkyl moiety, a thioformyl group (—CHS), an alkylthiocarbonyl group (—CSR) having up to six carbon atoms in the alkyl moiety, a thioformamido group (—NHCHS), an N-alkyl-N-thioformylamino group (—NRCHS) having up to six carbon atoms in the alkyl moiety, a thioacylamino group (—NHCSR) having up to six carbon atoms in the alkyl moiety, an N-alkyl-N-thioacylamino group (NRCSR) having, independently, up to six carbon atoms in each alkyl moiety, a thioureido group (—NHCSNH$_2$), an alkylsulfinamido group (—NHSOR) having up to six carbon atoms, an N-alkyl-N-alkylsulfinylamino group (—NRSOR) having, independently, up to six carbon atoms in each alkyl moiety, an N,N-diacylamino group (—N(COR)COR) having, independently, up to six carbon atoms in each alkyl moiety, or an unsubstituted or substituted aryl group, where R is an alkyl group having the stated number of carbon atoms;

R$^4$ is

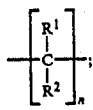

G is (C$_3$–C$_6$)cycloalkyl or R$^4$—Q; and
n is an integer from 0 to 10; or
an agronomically acceptable salt thereof;
wherein unsubstituted or substituted aryl is phenyl, optionally substituted with 1 to 5 substituents independently chose from W; methylenedioxyphenyl; naphthyl, optionally substituted with 1 to 7 substituents independently chose from W; a pyrryl; furyl; thienyl; imidazolyl; oxazolyl, thiazolyl; pyrazolyl, pyridyl or pyrimidyl optionally substituted with 1 to 4 substituents independently chosen from W; where W is halogen, cyano, nitro, R$^1$, CO$_2$R$^1$, CONR$^1$R$^2$, CR$^1$═CR$^2$R$^3$, C≡CR$^1$, SR$^1$, OR$^1$, NR$^1$R$^2$, SOR$^1$, SO$_2$R$^1$, OSO$_2$R$^1$, NR$^1$COR$^2$, SF$_5$, CF$_3$, OCF$_3$, OCF$_2$H, SCF$_3$, OCF$_2$Br, SCF$_2$Br, SCF$_2$Cl, SCF$_2$H, NR$^1$SO$_2$R$^2$ or N(COR$^1$)COR$^2$.

29. A compound of the formula

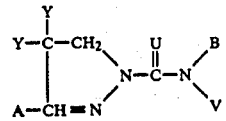

wherein
A is unsubstituted or substituted aryl;
B is unsubstituted or substituted aryl;
U is O, S or N—Q;
V is (C$_3$–C$_6$)cycloalkyl or R$^4$—Q;
Y is (C$_1$–C$_6$) straight or branched chain unsubstituted or substituted alkyl where the alkyl substituents are selected from Q, unsubstituted or substituted aryl;
Z is (C$_3$–C$_6$)cycloalkyl or R$^4$—Q provided that Z is not hydrogen when Y is alkyl or aryl and Z is not methyl when Y is methyl;
Q is hydrogen, halogen, cyano, nitro, —OR$^1$, —R$^4$OR$^1$, —CO$_2$R$^1$, —OR$^4$OR$^1$, —CR$^1$R$^2$R$^3$, —CONR$^1$R$^2$, —NR$^1$R$^2$, —NR$^1$COR$^2$, —N(COR$^1$)COR$^2$, —CSR$^1$, —SR$^1$, —SOR$^1$, —SO$_2$R$^1$, —NR$^1$SOR$^2$, —R$^4$SR$^1$, —OR$^4$SR$^1$, —SR$^4$SR$^1$, —SNHSR$^1$, —SNHSO$_2$R$^1$, —CONHSR$^1$, —OCOR$^1$, —R$^1$, —C(═NR$^1$)R$^2$, —COR$^1$, —N$_3$, —OSO$_2$R$^1$, —NR$^1$SO$_2$R$^2$, —NR$^1$CSR$^2$, alkenyl (—CR$^1$═CR$^2$R$^3$), alkynyl (—C≡CR$^1$), unsubstituted or substituted aryl, pyrrolidin-1-yl, piperidin-1-yl or morpholin-1-yl;

$R^1$, $R^2$ and $R^3$ are, independently, hydrogen, halogen, cyano, nitro, hydroxy, an alkoxy group (—OR) having up to four carbon atoms, an aryloxy group, an amino group (—NH$_2$), an alkylamino group (—NHR) having up to six carbon atoms, a dialkylamino group (—NR$_2$) having, independently, up to six carbon atoms in each alkyl moiety, alkylideneamino group (—N=CR$_2$) having, independently, up to six carbon atoms in each alkyl moiety, a carboxy group (—CO$_2$H), a carbalkoxy group (—CO$_2$R) having up to six carbon atoms in the alkyl moiety, an alkylcarbonyl group (—COR) having up to six carbon atoms in the alkyl moiety, a formyl group (—CHO), an alkanoyloxy group (—OCOR) having up to six carbon atoms in the alkyl moiety, a formate group (—OCHO), a carboxamido group (—CONH$_2$), an N-alkylcarboxamido group (—CONHR) having up to six carbon atoms in the alkyl moiety, an N,N-dialkylcarboxamido group (—CONR$_2$) having, independently, up to six carbon atoms in each alkyl moiety, a carbamoyloxy group (—OCONH$_2$), an N-alkylcarbamoyloxy group (—OCONHR) having up to six carbon atoms in the alkyl moiety, an N,N-dialkylcarbamoyloxy group (—OCONR$_2$) having, independently, up to six carbons atoms in each alkyl moiety, a sulfhydril group (—SH), an alkylsulfinyl group (—SOR) having up to six carbon atoms, an alkylsulfonyl group (—SO$_2$R) having up to six carbon atoms, an alkylsulfonato group (—OSO$_2$R) having up to six carbon atoms, an alkylthio group (—SR) having up to six carbon atoms, a sulfonamido group (—SO$_2$NH$_2$), an N-alkylsulfonamido group (—SO$_2$NHR), having up to six carbon atoms, an N,N-dialkylsulfonamido group (—SO$_2$NR$_2$) having, independently, up to six carbon atom in each alkyl moiety, an acylamino group (—NHCOR) having up to six carbon atoms in the alkyl moiety, an N-alkyl-N-acylamino group (—NRCOR) having, independently, up to six carbon atoms in each alkyl moiety, an alkylsulfonamido group (—NHSO$_2$R) having up to six carbon atoms, an N-alkyl-N-alkylsulfonylamino group (—NRSO$_2$R) having, independently, up to six carbon atoms in each alkyl moiety, a thioformyl group (—CHS), an alkylthiocarbonyl group (—CSR) having up to six carbon atoms in the alkyl moiety, a thioformamido group (—NHCHS), an N-alkyl-N-thioformylamino group (—NRCHS) having up to six carbon atoms in the alkyl moiety, a thioacylamino group (—NHCSR) having up to six carbon atoms in the alkyl moiety, an N-alkyl-N-thioacylamino group (—NRCSR) having independently, up to six carbon atoms in each alkyl moiety, a thioureido group (—NHCSNH$_2$), an alkylsulfinamido group (—NHSOR) having up to six carbon atoms, an N-alkyl-N-alkylsulfinylamino group (—NRSOR) having, independently, up to six carbon atoms in each alkyl moiety, an N,N-diacylamino group (—N(COR)COR) having, independently, up to six carbon atoms in each alkyl moiety, an unsubstituted or substituted straight or branched chain (C$_1$-C$_6$)alkyl, (C$_2$-C$_6$)alkenyl, (C$_2$-C$_6$)alkynyl, (C$_3$-C$_6$)cycloalkyl or aryl where the substituent on the alkyl, alkenyl or alkynyl moiety can be one or more of the same or different halogen, cyano, nitro, hydroxy, an alkoxy group (—OR) having up to four carbon atoms, an aryloxy group, an amino group (—NH$_2$), an alkylamino group (—NHR) having up to six carbon atoms, a dialkylamino group (—NR$_2$) having, independently, up to six carbon atoms in each alkyl moiety, alkylideneamino group (—N=CR$_2$) having, independently, up to six carbon atoms in each alkyl moiety, a carboxy group (—CO$_2$H), a carbalkoxy group (—CO$_2$R) having up to six carbon atoms in the alkyl moiety, an alkylcarbonyl group (—COR) having up to six carbon atoms in the alkyl moiety, a formyl group (13 CHO), an alkanoyloxy group (—OCOR) having up to six carbon atoms in the alkyl moiety, a formate group (—OCHO), a carboxamido group (—CONH$_2$), an N-alkylcarboxamido group (—CONHR) having up to six carbon atoms in the alkyl moiety, an N,N-dialkylcarboxamido group (—CONR$_2$) having independently, up to six carbon atoms in each alkyl moiety, a carbamoyloxy group (—OCONH$_2$), an N-alkylcarbamoyloxy group (—OCONHR) having up to six carbon atoms in the alkyl moiety, an N,N-dialkylcarbamoyloxy group (—OCONR$_2$) having, independently, up to six carbon atoms in each alkyl moiety, a sulhydril group (—SH), an alkylsulfinyl group (—SOR) having up to six carbon atoms, an alkylsulfonyl group (—SO$_2$R) having up to six carbon atoms, an alkylsulfonato group (—OSO$_2$R) having up to six carbon atoms, an alkylthio group (—SR) having up to six carbon atoms, a sulfonamido group (—SO$_2$NH$_2$), an N-alkylsulfonamido group (—SO$_2$NHR), having up to six carbon atoms, an N,N-dialkylsulfonamido group (—SO$_2$NR$_2$) having, independently, up to six carbon atoms in each alkyl moiety, an acylamino group (—NHCOR) having up to six carbon atoms in the alkyl moiety, an N-alkyl-N-acylamino group (—NRCOR) having, independently, up to six carbon atoms in each alkyl moiety, an alkylsulfonamido group (—NHSO$_2$R) having up to six carbon atoms, an N-alkyl-N-alkylsulfonylamino group (—NRSO$_2$R) having, independently, up to six carbon atoms in each alkyl moiety, a thioformyl group (—CHS), an alkylthiocarbonyl group (—CSR) having up to six carbon atoms in the alkyl moiety, a thioformamido group (—NHCHS), an N-alkyl-N-thioformylamino group (—NRCHS) having up to six carbon atoms in the alkyl moiety, a thioacylamino group (—NHCSR) having up to six carbon atoms in the alkyl moiety, an N-alkyl-N-thioacylamino group (NRCSR) having, independently, up to six carbon atoms in each alkyl moiety, a thioureido group (—NHCSNH$_2$), an alkylsulfinamido group (—NHSOR) having up to six carbon atoms, an N-alkyl-N-alkylsulfinylamino group (—NRSOR) having, independently, up to six carbon atoms in each alkyl moiety, an N,N-diacylamino group (—N(COR)COR) having, independently, up to six carbon atoms in each alkyl moiety, or an unsubstituted or substituted aryl group, where R is an alkyl group having the stated number of carbon atoms;

$R^4$ is

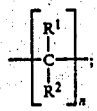

G is $R^4$-$R^5$ where $R^5$ is alkenyl, alkynyl or alkylideneamino each having up to six carbon atoms; and n is an integer from 0 to 10; or an agronomically acceptable salt thereof;

wherein unsubstituted or substituted aryl is phenyl, optionally substituted with 1 to 5 substituents independently chosen from W; methylenedioxyphenyl; naphthyl, optionally substituted with 1 to 7 substituents independently chosen from W; a pyrryl; furyl; thienyl; imidazolyl; oxazolyl; thiazolyl; pyrazolyl; pyridyl or pyrimidyl optionally substituted with 1 to 4 substituents independently chosen from W; where W is halogen, cyano, nitro, $R^1$, $CO_2R^1$, $CONR^1R^2$, $CR^1=CR^2R^3$, $C\equiv CR^1$, $SR^1$, $OR^1$, $NR^1R^2$, $SOR^1$, $SO_2R^1$, $OSO_2R^1$, $NR^1COR^2$, $SF_5$, $CF_3$, $OCF_3$, $OCF_2H$, $SCF_3$, $OCF_2Br$, $SCF_2Br$, $SCF_2Cl$, $SCF_2H$, $NR^1SO_2R^2$ or $N(COR^1)COR^2$.

30. An insecticidal composition comprising a compound according to claim 6 and an agronomically acceptable carrier.

31. The composition according to claim 30 wherein said compound is present at from about 0.00001 to about 99% by weight of the composition.

32. The composition according to claim 31 wherein said compound is present at from about 0.00005 to about 90% by weight of the composition.

33. The composition according to claim 30 wherein said compound is N,3-bis-(4-chlorophenyl)-4-methyl-4-phenyl-4,5-dihydro-1H-pyrazole-1-carboxamide.

34. The composition according to claim 30 wherein said compound is N,3-bis-(4-chlorophenyl)-4-butyl-4-methyl-4,5-dihydro-1H-pyrazole-1-carboxamide.

35. The composition according to claim 30 wherein said compound is N,3-bis-(4-chlorophenyl)-4-(3-chloropropyl)-4-methyl-4,5-dihydro-1H-pyrazole-1-carboxamide.

36. An insecticidal composition which comprises an insecticidally effective amount of the compound of claim 16 and an agronomically acceptable carrier.

37. An insecticidal composition comprising a compound according to claim 2 and an agronomically acceptable carrier.

38. The composition according to claim 37 wherein said compound is present at from about 0.00001 to about 99% by weight of the composition.

39. The composition according to claim 55 wherein said compound is present at from about 0.00005 to about 90% by weight of the composition.

40. A method of controlling insects which comprises applying to the insects or to the loci to be freed or protected from attack by insects an insecticidally effective amount of the compound of claim 16.

41. The method of claim 40 wherein the compound is applied at from about 0.1 to about 1,000 grams per hectare.

42. The method of claim 41 where the compound is applied at from about 5 to about 200 grams per hectare.

43. A method of controlling insects which comprises applying to the insects or to the loci to be freed or protected from attack by insects an insecticidally effective amount of a compound according to claim 6.

44. The method of claim 43 wherein said compound is applied at from about 0.1 to about 1000 grams per hectare.

45. The method of claim 44 wherein said compound is applied at from about 5 to about 200 grams per hectare.

46. The method of claim 43 wherein the compound is N,3-bis-(4-chlorophenyl)-4-methyl-4-phenyl-4,5-dihydro-1H-pyrazole-1-carboxamide.

47. The method of claim 43 wherein the compound is N,3-bis-(4-chlorophenyl)-4-butyl-4-methyl-4,5-dihydro-1H-pyrazole-1-carboxamide.

48. The method of claim 43 wherein the compound is N,3-bis-(4-chlorophenyl)-4-(3-chloropropyl)-4-methyl-4,5-dihydro-1H-pyrazole-1-carboxamide.

* * * * *